(12) United States Patent
Kwong et al.

(10) Patent No.: US 10,109,799 B2
(45) Date of Patent: *Oct. 23, 2018

(54) ORGANIC ELECTROLUMINESCENT MATERIALS AND DEVICES

(71) Applicant: Universal Display Corporation, Ewing, NJ (US)

(72) Inventors: Raymond Kwong, Hong Kong (CN); Sze Kui Lam, Hong Kong (CN)

(73) Assignee: Universal Display Corporation, Ewing, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/359,597

(22) Filed: Nov. 22, 2016

(65) Prior Publication Data
US 2017/0077409 A1    Mar. 16, 2017

Related U.S. Application Data

(63) Continuation-in-part of application No. 14/718,299, filed on May 21, 2015.

(51) Int. Cl.
| | |
|---|---|
| *H01L 51/00* | (2006.01) |
| *C07D 209/88* | (2006.01) |
| *C07D 471/04* | (2006.01) |
| *C09K 11/06* | (2006.01) |
| *C09K 11/02* | (2006.01) |
| *C07D 333/76* | (2006.01) |
| *C07D 209/86* | (2006.01) |
| *C07D 333/54* | (2006.01) |
| *C07D 519/00* | (2006.01) |
| *H01L 51/50* | (2006.01) |

(52) U.S. Cl.
CPC ........ *H01L 51/0055* (2013.01); *C07D 209/86* (2013.01); *C07D 209/88* (2013.01); *C07D 333/54* (2013.01); *C07D 333/76* (2013.01); *C07D 471/04* (2013.01); *C07D 519/00* (2013.01); *C09K 11/025* (2013.01); *C09K 11/06* (2013.01); *H01L 51/0072* (2013.01); *H01L 51/0074* (2013.01); *C09K 2211/1007* (2013.01); *C09K 2211/1044* (2013.01); *C09K 2211/185* (2013.01); *H01L 51/5016* (2013.01)

(58) Field of Classification Search
CPC .. C07D 209/86; C07D 209/88; C07D 471/04; H01L 51/055
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,416,887 B1 * | 7/2002 | Tokito | C07C 211/61 313/504 |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,468,212 B2 * | 12/2008 | Ogasawara | C07C 15/20 257/40 |
| 7,534,505 B2 | 5/2009 | Lin et al. | |
| 7,740,956 B2 * | 6/2010 | Igarashi | C09K 11/06 313/504 |
| 7,858,211 B2 | 12/2010 | Ogasawara et al. | |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 1, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).

(Continued)

*Primary Examiner* — Rita J Desai
(74) *Attorney, Agent, or Firm* — Duane Morris LLP

(57) ABSTRACT

Novel substituted tetraphenylene compounds useful as host for phosphorescent emitters in OLEDs is disclosed.

19 Claims, 2 Drawing Sheets

(56) References Cited

U.S. PATENT DOCUMENTS

| | | | |
|---|---|---|---|
| 2001/0006741 A1* | 7/2001 | Ishikawa | H01L 51/0057 428/690 |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Pakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |

FOREIGN PATENT DOCUMENTS

| | | | |
|---|---|---|---|
| EP | 2034538 | | 3/2009 |
| JP | 2001167884 | * | 6/2001 |
| JP | 200511610 | | 1/2005 |
| JP | 2007123392 | | 5/2007 |
| JP | 2007254297 | | 10/2007 |
| JP | 2008074939 | | 4/2008 |
| WO | 01/39234 | | 5/2001 |
| WO | 02/02714 | | 1/2002 |
| WO | 02015645 | | 2/2002 |
| WO | 03040257 | | 5/2003 |
| WO | 03060956 | | 7/2003 |
| WO | 2004093207 | | 10/2004 |
| WO | 04107822 | | 12/2004 |
| WO | 2005014551 | | 2/2005 |
| WO | 2005019373 | | 3/2005 |
| WO | 2005030900 | | 4/2005 |
| WO | 2005089025 | | 9/2005 |
| WO | 2005123873 | | 12/2005 |
| WO | 2006009024 | | 1/2006 |
| WO | 2006056418 | | 6/2006 |
| WO | 2006072002 | | 7/2006 |
| WO | 2006082742 | | 8/2006 |
| WO | 2006/098120 | * | 9/2006 |
| WO | 2006098120 | | 9/2006 |
| WO | 2006100298 | | 9/2006 |
| WO | 2006103874 | | 10/2006 |
| WO | 2006114966 | | 11/2006 |
| WO | 2006132173 | | 12/2006 |
| WO | 2007002683 | | 1/2007 |
| WO | 2007004380 | | 1/2007 |
| WO | 2007063754 | | 6/2007 |
| WO | 2007063796 | | 6/2007 |
| WO | 2008056746 | | 5/2008 |
| WO | 2008101842 | | 8/2008 |
| WO | 2008132085 | | 11/2008 |
| WO | 2009000673 | | 12/2008 |
| WO | 2009003898 | | 1/2009 |
| WO | 2009008311 | | 1/2009 |
| WO | 2009018009 | | 2/2009 |
| WO | 2009021126 | | 2/2009 |
| WO | 2009050290 | | 4/2009 |
| WO | 2009062578 | | 5/2009 |
| WO | 2009063833 | | 5/2009 |
| WO | 2009066778 | | 5/2009 |
| WO | 2009066779 | | 5/2009 |
| WO | 2009086028 | | 7/2009 |
| WO | 2009100991 | | 8/2009 |

OTHER PUBLICATIONS

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Kai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1)162-164 (2002).

(56) References Cited

OTHER PUBLICATIONS

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of $\alpha$-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5''-Bis(dimesitylboryl)-2,2'5',2''-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91: 209-215 (1997).

Shirota, Yasuhiko et al., "Starburst Molecules Based on pi-Electron Systems as Materials for Organic Electroluminescent Devices," Journal of Luminescence, 72-74:985-991 (1997).

Sotoyama, Wataru et al., "Efficient Organic LIght-Emitting Diodes with Phosphorescent Platinum Complexes Containing N^C^N-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 88:171-177 (1997).

Takizawa, Shin-ya et al., "Phosphorescent Iridium Complexes Based on 2-Phenylimidazo[1,2-$\alpha$]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69 (15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

ORGANIC ELECTROLUMINESCENT MATERIALS AND DEVICES

CROSS-REFERENCE TO RELATED APPLICATIONS

This application is a continuation-in-part of U.S. patent application Ser. No. 14/718,299, filed May 21, 2015, the contents of which are incorporated herein by reference.

PARTIES TO A JOINT RESEARCH AGREEMENT

The claimed invention was made by, on behalf of, and/or in connection with one or more of the following parties to a joint university corporation research agreement: The Regents of the University of Michigan, Princeton University, University of Southern California, and Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and to organic materials used in such devices. More specifically, the present invention relates to novel organic materials for use as support layers in OLEDs, in particular as hosts and electron-blocking layer materials, but not limited as such. The materials are based on tetraphenylene moiety. The compounds are expected to improve phosphorescent OLED performance.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

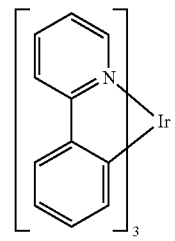

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment, a compound is disclosed, the compound having a formula

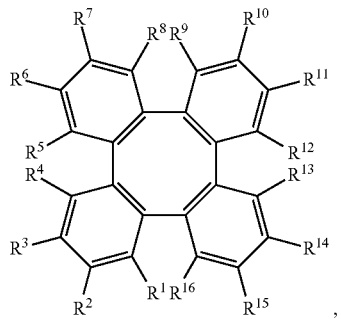

Formula 1, wherein $R^1$-$R^{16}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;
wherein at least one of $R^1$-$R^{16}$ comprises a chemical group selected from the group consisting of carbazole, dibenzofuran, dibenzothiophene, dibenzoselenophene, triphenylene, fluorene, aza-carbazole, aza-dibenzofuran, aza-dibenzothiophene, aza-dibenzoselenophene, aza-triphenylene, and aza-fluorene; and
wherein the compound has the highest symmetry of $C_1$.

According to another embodiment, a device comprising one or more organic light emitting devices is also provided. At least one of the one or more organic light emitting devices can include an anode, a cathode, and an organic layer, disposed between the anode and the cathode, wherein the organic layer can include a compound of Formula I including all of the variations disclosed herein. The device can be a consumer product, an electronic component module, an organic light-emitting device, and/or a lighting panel.

According to yet another embodiment, a formulation containing the compound of Formula I, including all of the variations, is also provided.

The substituted tetraphenylene compounds disclosed herein can be used as the host for phosphorescent emitters in organic light emitting devices resulting in enhanced device external quantum efficiency and lifetime. Furthermore, tetraphenylene substituted with oligomeric carbazoles and/or aza-carbazoles may be used as host for phosphorescent emitters in organic light emitting diodes.

According to some embodiments, a compound having a formula

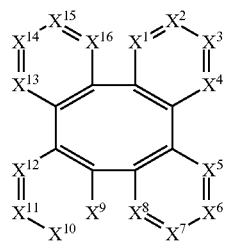

Formula 2 is disclosed, wherein $X^1$-$X^{16}$ are each independently selected from the group consisting of CR and N;
wherein each R is independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein at least one of $X^1$-$X^{16}$ is CR;
wherein R is

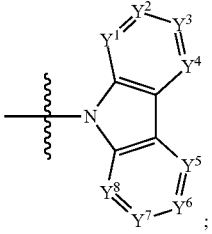

wherein $Y^1$-$Y^8$ are independently selected from the group consisting of CR' and N;
wherein each R' is independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, aza-carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein at least one of $Y^1$ to $Y^8$ is CR' whose R' is a group containing at least one carbazole or aza-carbazole.

According to some other embodiments, a device comprising one or more organic light emitting devices incorporating the compound of Formula 2 is also provided. At least one of the one or more organic light emitting devices can include an anode, a cathode, and an organic layer, disposed between the anode and the cathode, wherein the organic layer can include a compound of Formula 2 including all of the variations disclosed herein. The device can be a consumer product, an electronic component module, an organic light-emitting device, and/or a lighting panel.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
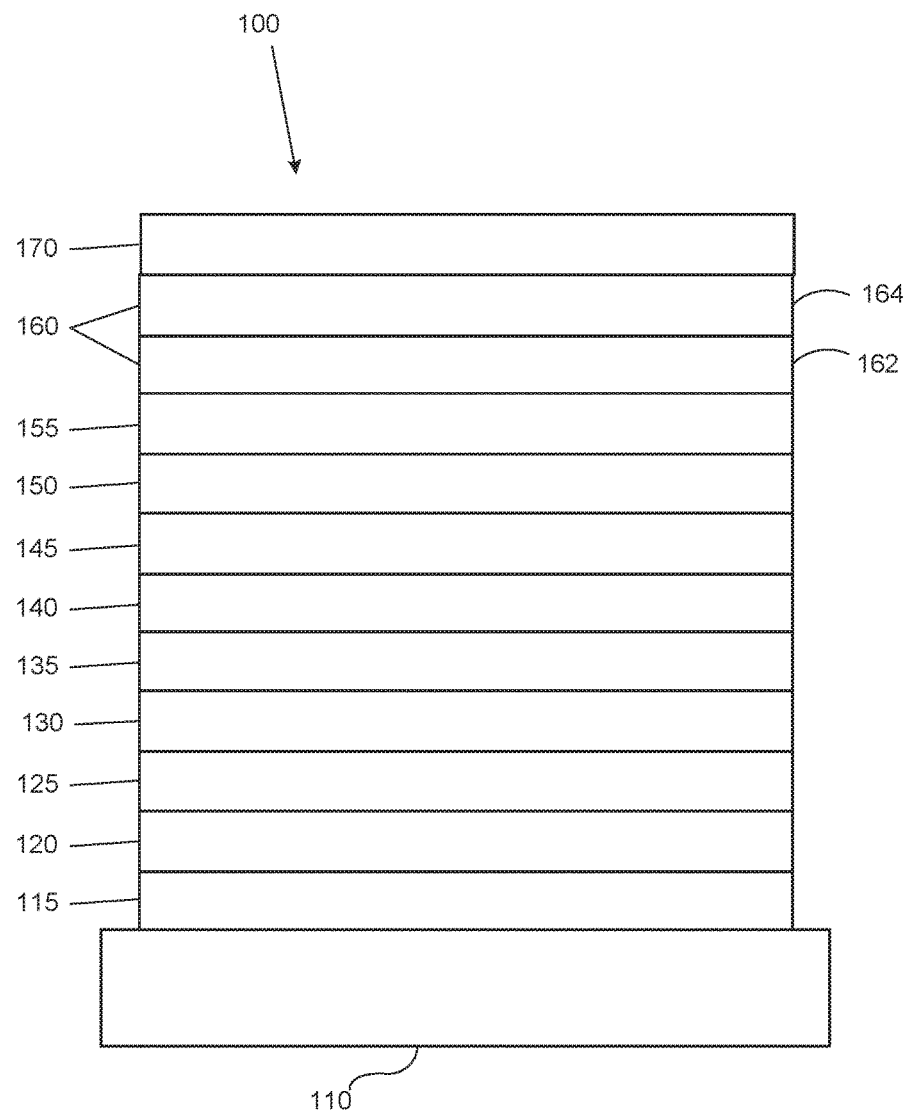
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
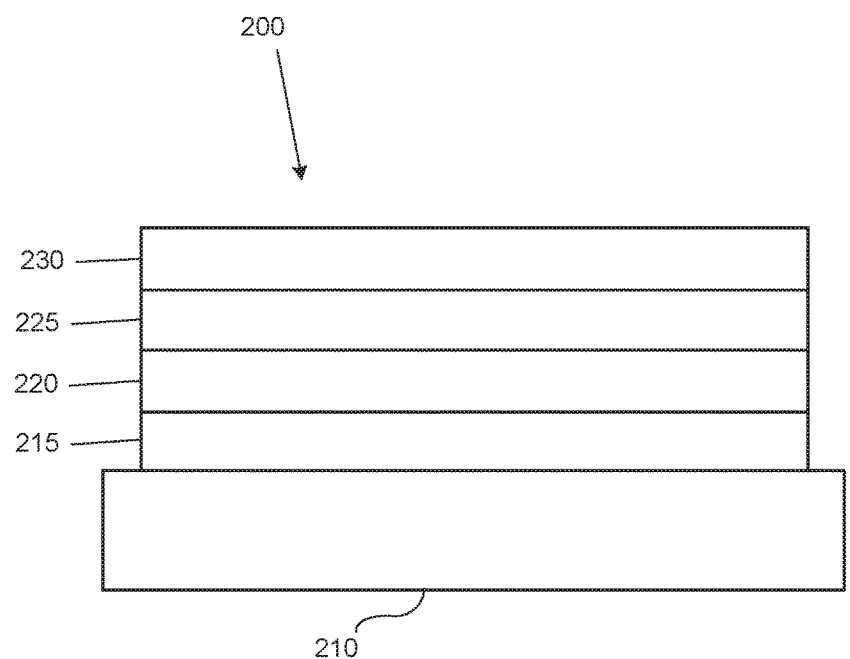
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

The inventors have found that substituted tetraphenylene compounds when used as hosts for phosphorescent emitters in organic light emitting devices, yields good external quantum efficiency particularly in blue and green light emitting devices. Substituents include N-carbazole and dibenzothiophene which are the key to stabilizing the charges and achieve good device lifetime. Tetraphenylene has a unique saddle-shaped structure in which all the phenyl groups are orientated above and below the average plane of the molecule and have minimum conjugation. With this distinct structure, tetraphenylene can be envisioned as a phenyl group and has high triplet energy. For this reason, novel substituted tetraphenylene compounds are useful as high triplet energy hosts in organic light emitting devices with good external quantum efficiency in the blue and green devices.

According to an aspect of the present disclosure, a compound is disclosed, the compound having a formula

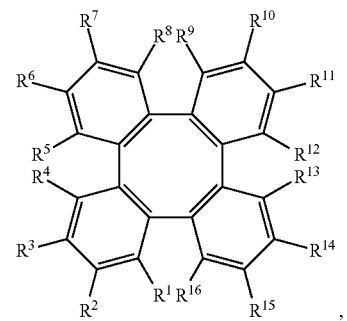

Formula 1, wherein $R^1$-$R^{16}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

wherein at least one of $R^1$-$R^{16}$ comprises a chemical group selected from the group consisting of carbazole, dibenzofuran, dibenzothiophene, dibenzoselenophene, triphenylene, fluorene, aza-carbazole, aza-dibenzofuran, aza-dibenzothiophene, aza-dibenzoselenophene, aza-triphenylene, and aza-fluorene; and wherein the compound has the highest symmetry of $C_1$.

Tetraphenylene is a non-planar sterically cumbersome compound. Its triplet energy by DFT calculation is 361 nm. Benzene's triplet energy by comparison is 330 nm. The very high triplet energy of tetraphenylene suggests there is limited electronic communication among the four benzene rings. Due to its high triplet energy, it is particularly useful for use as a building block for phosphorescence OLED hosts. Low symmetry substituted tetraphenylene compounds such as compounds with $C_1$ symmetry (mono substitution or di/tri substitution with different substituents) are especially attractive because they cannot pack well in the solid state (such as in the thin film form in OLED) and can reduce π stacking between host-host molecules and host-dopant molecules, leading to reduction in luminescence quenching and improvement in luminescence efficiency. The tetraphenylene block can therefore be viewed as a "heavy benzene," meaning it has electronic characteristic like benzene, but the molecular weight and its steric bulk is much higher than benzene. It can become very useful when it is connected to more conjugated (electrochemically active) high triplet energy chromophores such as carbazole, dibenzofuran and dibenzothopehene because the electronic characteristic of carbazole, dibenzofuran and dibenzothopehene will not be much affected and their high triplet energy can be retained and become useful for hosting blue and green PHOLED. At the same time, since tetraphenylene is much heavier than benzene, it can increase the glass transition temperature ($T_g$) of the tetraphenylen-carbazole/dibenzofuran/dibenzothopehene compounds, rendering them even more suitable for OLED applications. On the contrary, if only a benzene ring is connected to carbazole/dibenzofuran/dibenzothopehene, the high triplet energy may be retained, but the $T_g$ would be too low for OLED applications.

According to another aspect of the present disclosure, a device comprising one or more organic light emitting devices is disclosed. At least one of the one or more organic light emitting devices comprise: an anode; a cathode; and an organic layer, disposed between the anode and the cathode. In one embodiment, the organic layer comprises a compound having the formula

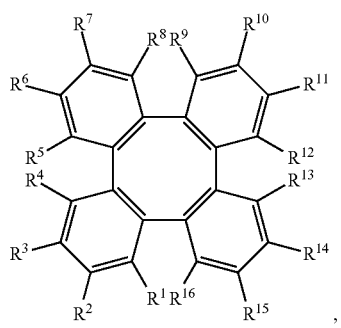

Formula 1, wherein $R^1$-$R^{16}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

wherein at least one of $R^1$-$R^{16}$ comprises a chemical group selected from the group consisting of carbazole, dibenzofuran, dibenzothiophene, dibenzoselenophene, triphenylene, fluorene, aza-carbazole, aza-dibenzofuran, aza-dibenzothiophene, aza-dibenzoselenophene, aza-triphenylene, and aza-fluorene; and wherein the compound has the highest symmetry of $C_1$.

In some embodiments of the compound, at least one of $R^1$-$R^{16}$ comprises a chemical group selected from the group consisting of dibenzofuran, dibenzothiophene, dibenzoselenophene, aza-dibenzofuran, aza-dibenzothiophene, and aza-dibenzoselenophene.

In other embodiments, at least one of $R^1$-$R^{16}$ comprises a chemical group selected from the group consisting of triphenylene, and aza-triphenylene.

In other embodiments, at least one of $R^1$-$R^{16}$ comprises a chemical group selected from the group consisting of dibenzofuran, dibenzothiophene, dibenzoselenophene, triphenylene, fluorene, aza-carbazole, aza-dibenzofuran, aza-dibenzothiophene, aza-dibenzoselenophene, aza-triphenylene, and aza-fluorene.

In other embodiments, at least one of $R^1$-$R^{16}$ comprises a chemical group selected from the group consisting of carbazole and aza-carbazole.

In other embodiments, at least two of $R^1$-$R^{16}$ comprises a chemical group independently selected from the group consisting of carbazole, dibenzofuran, dibenzothiophene, dibenzoselenophene, triphenylene, fluorene, aza-carbazole, aza-dibenzofuran, aza-dibenzothiophene, aza-dibenzoselenophene, aza-triphenylene, and aza-fluorene.

In some other embodiments, at least two of $R^1$-$R^{16}$ comprises different chemical groups selected from the group consisting of carbazole, dibenzofuran, dibenzothiophene, dibenzoselenphene, triphenylene, fluorene, aza-carbazole, aza-dibenzofuran, aza-dibenzothiophene, aza-dibenzoselenphene, aza-triphenylene, and aza-fluorene.

In other embodiments, the compound comprises at least two different chemical groups selected from the group consisting of carbazole, dibenzofuran, dibenzothiophene, dibenzoselenophene, triphenylene, fluorene, aza-carbazole, aza-dibenzofuran, aza-dibenzothiophene, aza-dibenzoselenophene, aza-triphenylene, and aza-fluorene.

In some embodiments, at least one of $R^1$-$R^{16}$ is selected from the group consisting of carbazole, dibenzofuran, dibenzothiophene, dibenzoselenophene, triphenylene, fluorene, aza-carbazole, aza-dibenzofuran, aza-dibenzothiophene, aza-dibenzoselenophene, aza-triphenylene, and aza-fluorene.

In some embodiments, the compound is selected from the group consisting of:

Compound 1

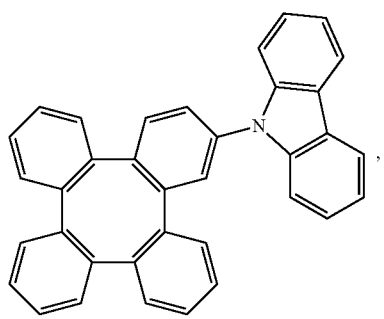

Compound 2

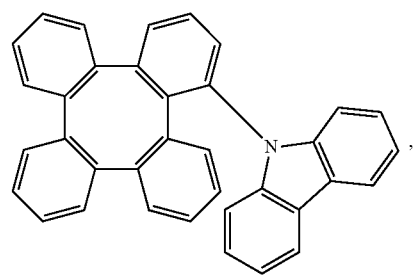

Compound 3

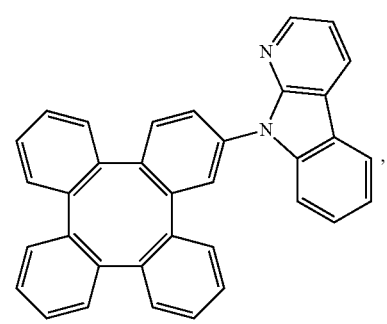

Compound 4
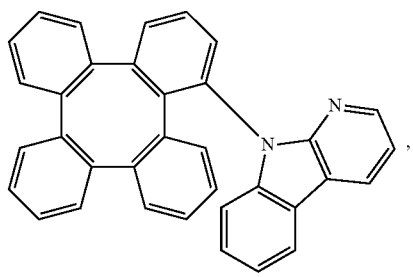
Compound 5
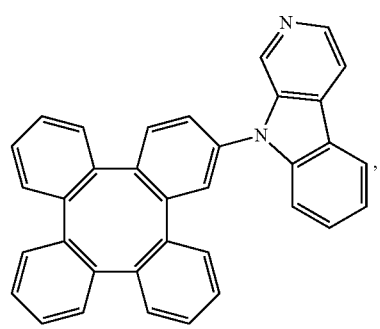
Compound 6
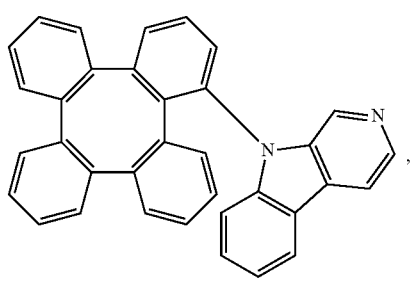
Compound 7
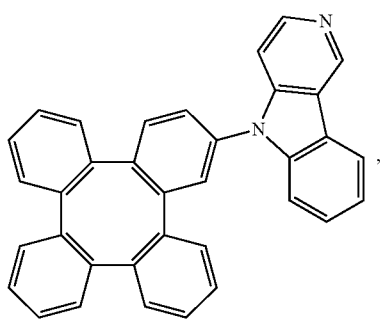
Compound 8
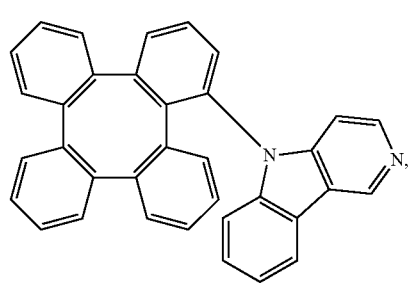
Compound 9
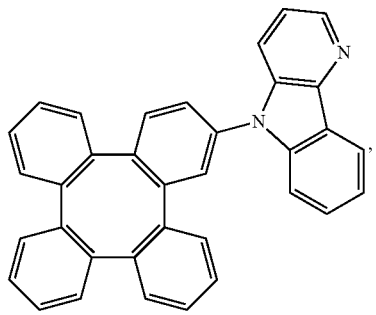
Compound 10
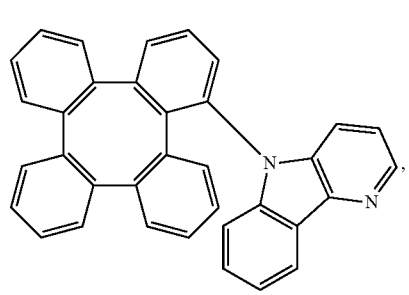
Compound 11
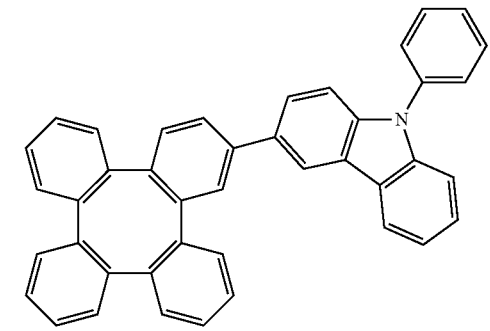
Compound 12
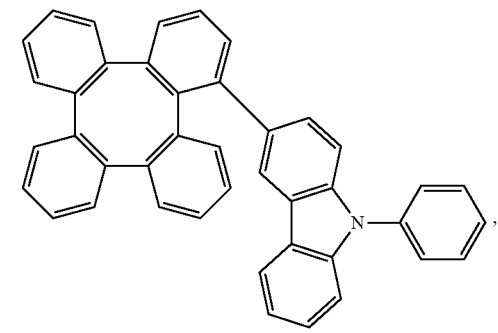

-continued
Compound 13
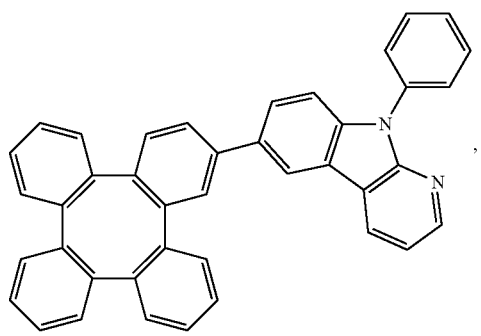
Compound 14
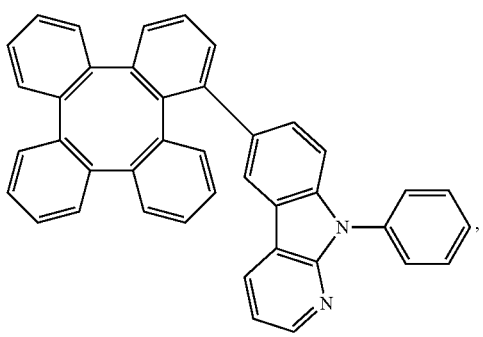
Compound 15
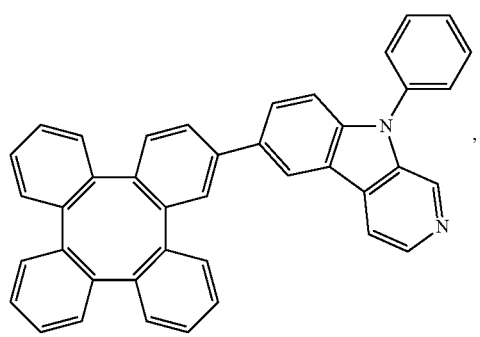
Compound 16
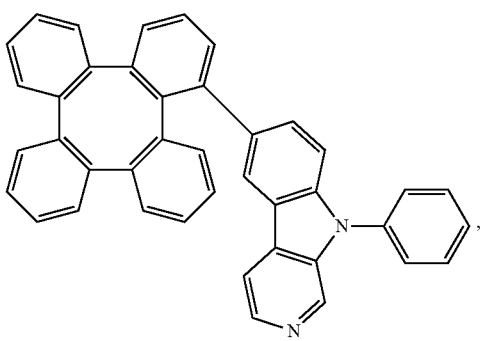
Compound 17
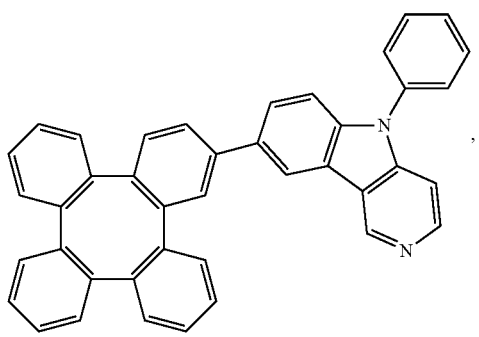
Compound 18
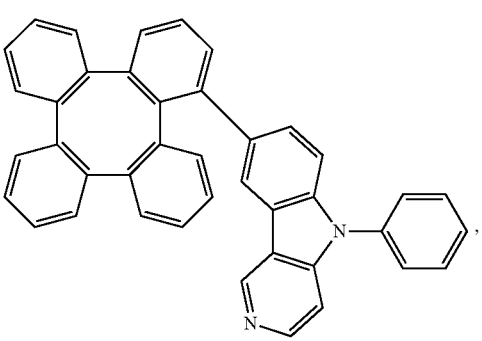
Compound 19
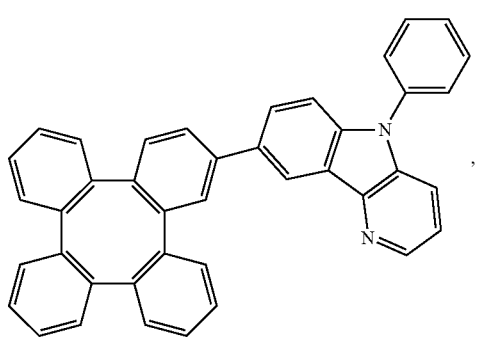
Compound 20
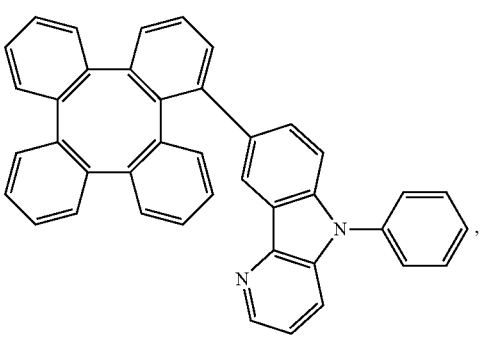

Compound 21
Compound 22
Compound 23
Compound 24
Compound 25
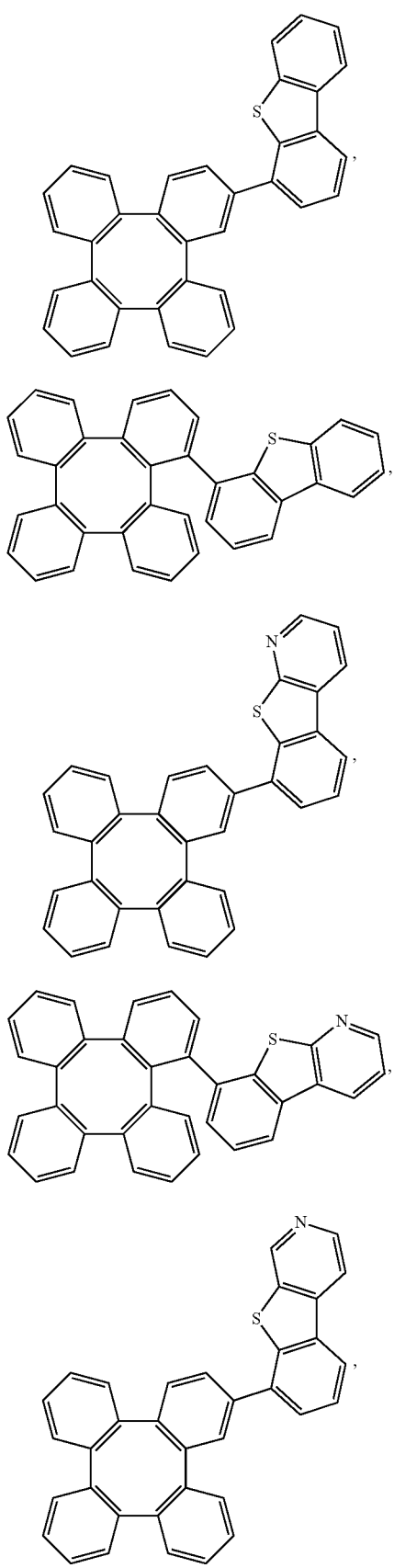
Compound 26
Compound 27
Compound 28
Compound 29
Compound 30
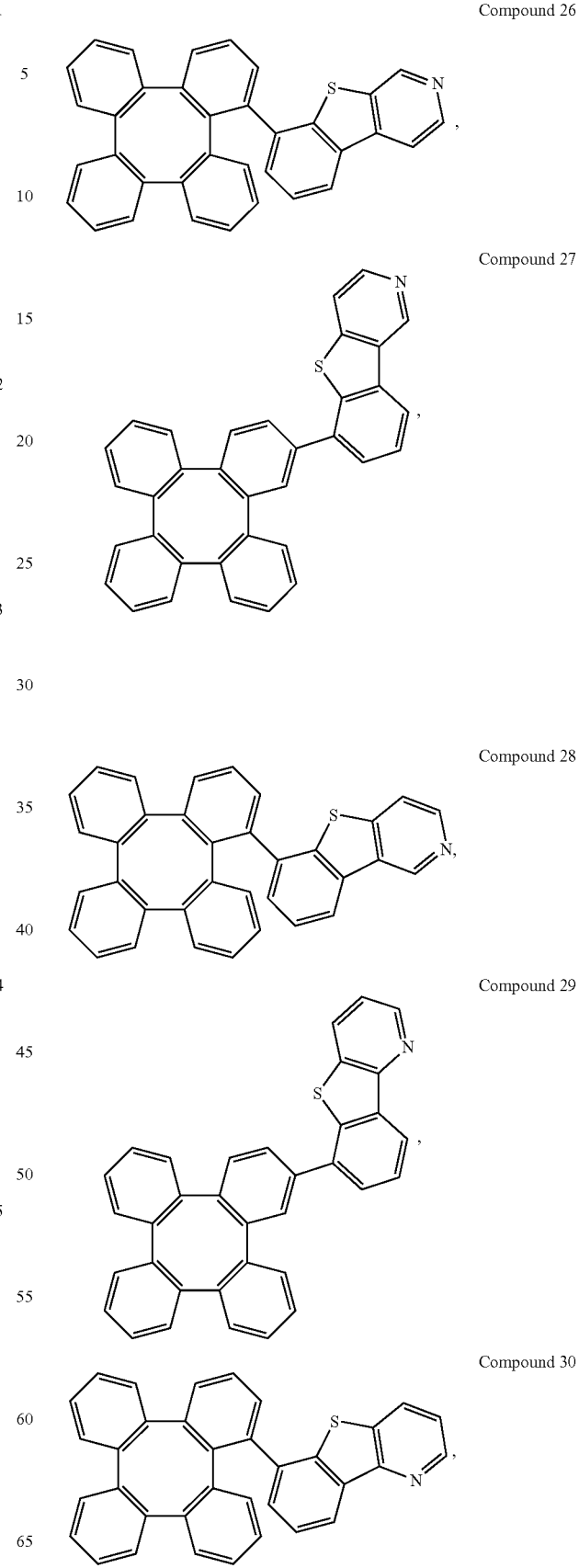

Compound 31
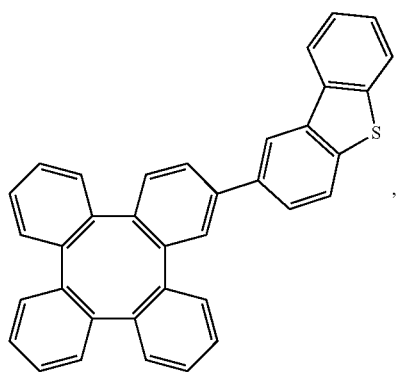
Compound 32
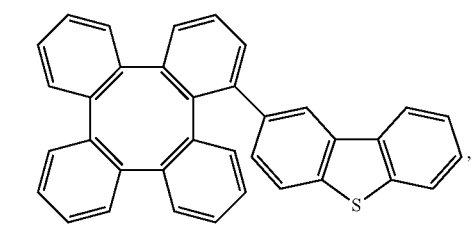
Compound 33
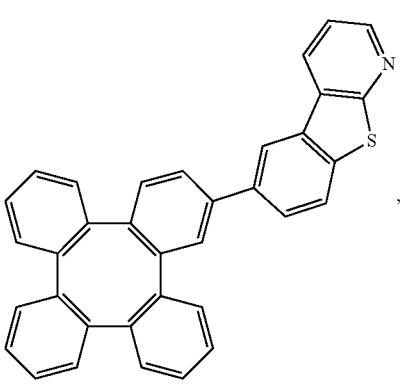
Compound 34
Compound 35
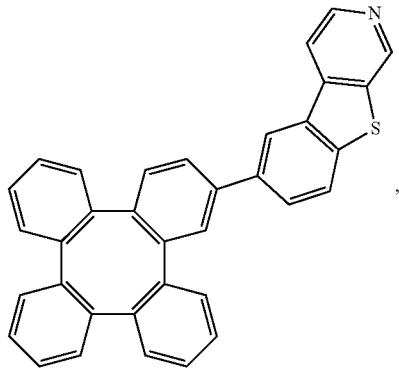
Compound 36
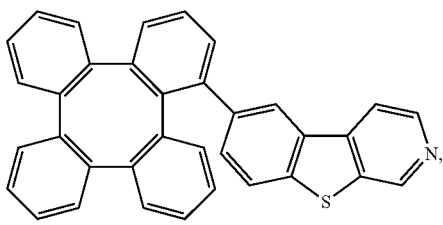
Compound 37
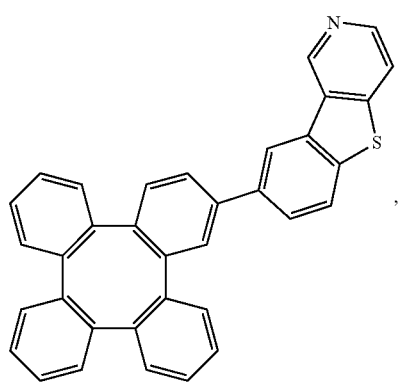
Compound 38
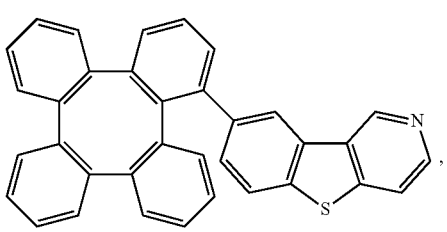

-continued
Compound 39
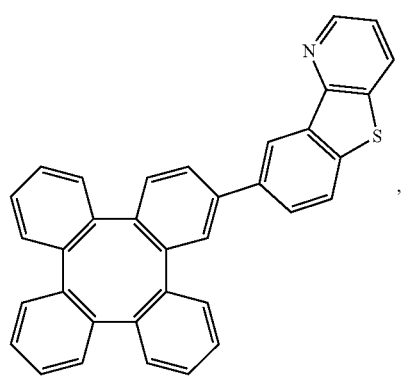
Compound 40
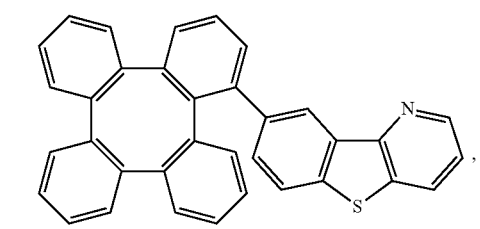
Compound 41
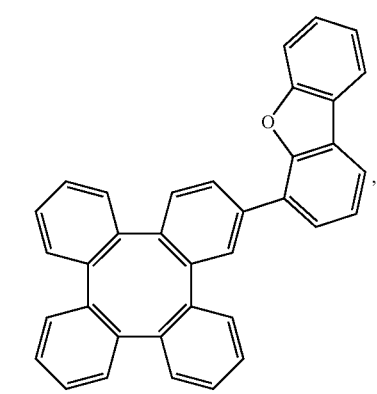
Compound 42
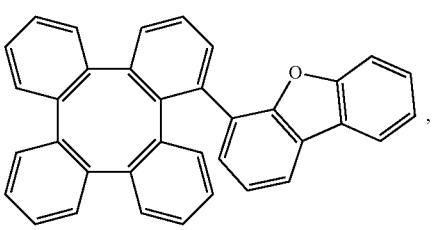
-continued
Compound 43
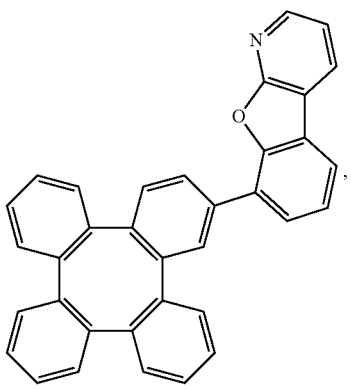
Compound 44
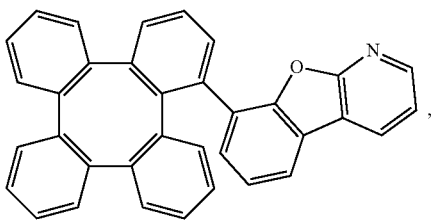
Compound 45
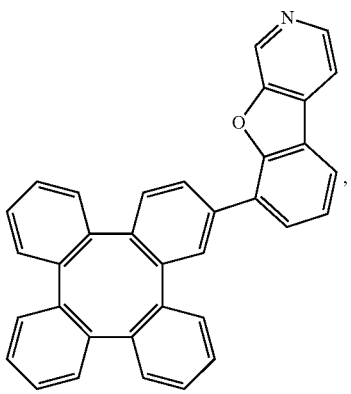
Compound 46
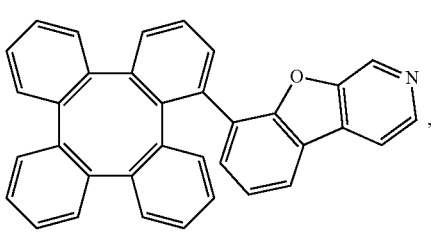

Compound 47
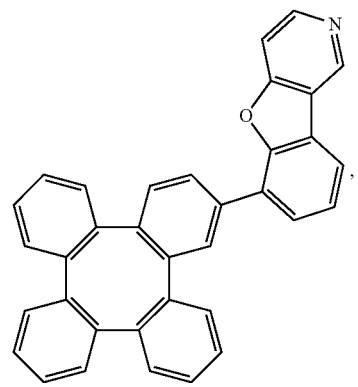
Compound 48
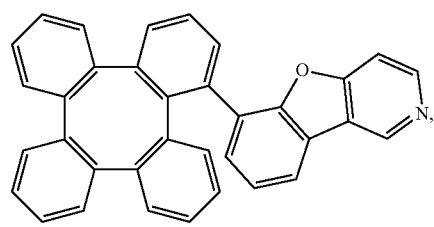
Compound 49
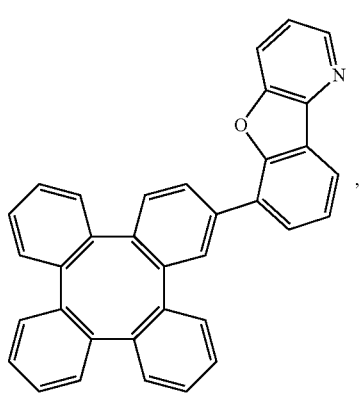
Compound 50
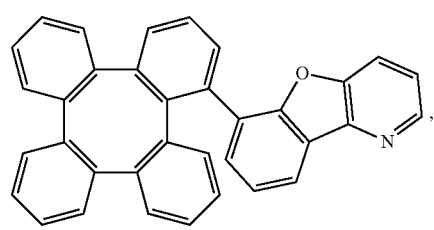
Compound 51
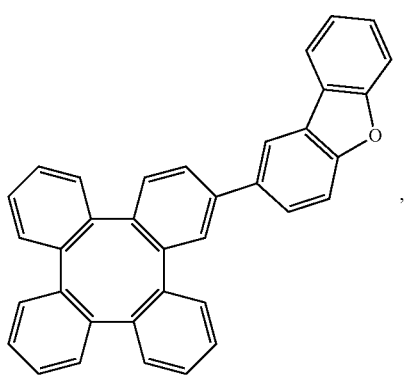
Compound 52
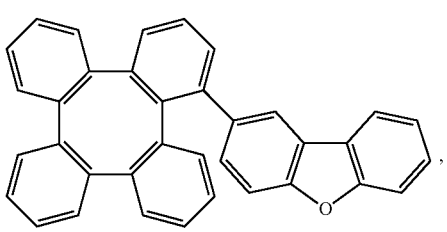
Compound 53
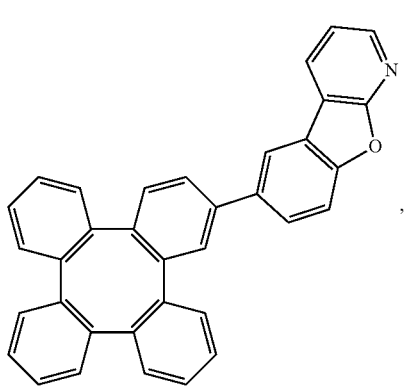
Compound 54
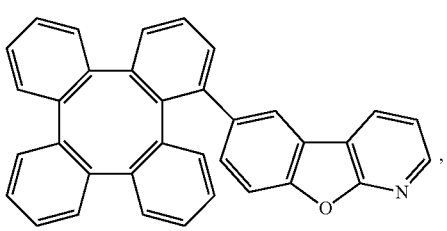

Compound 55
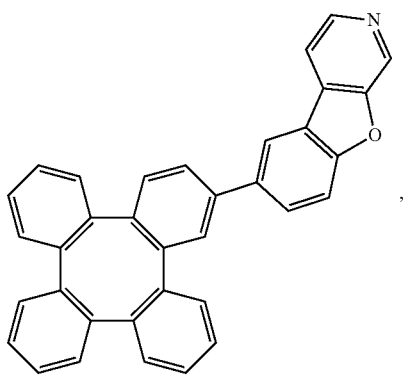
Compound 56
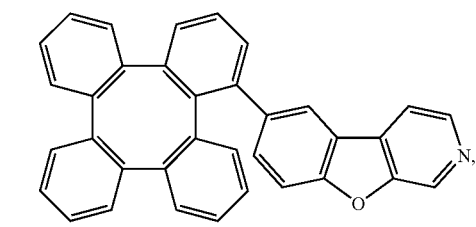
Compound 57
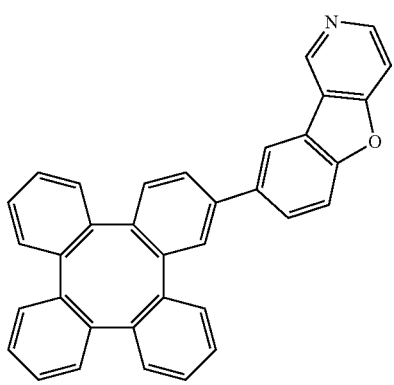
Compound 58
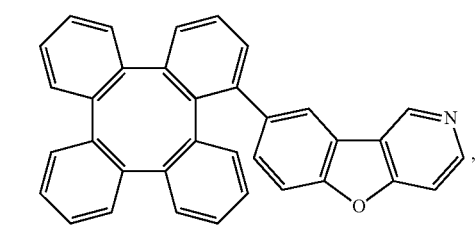
Compound 59
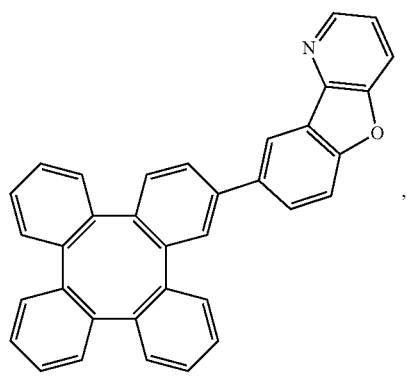
Compound 60
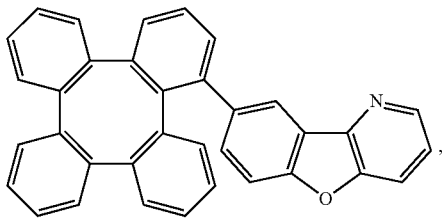
Compound 61
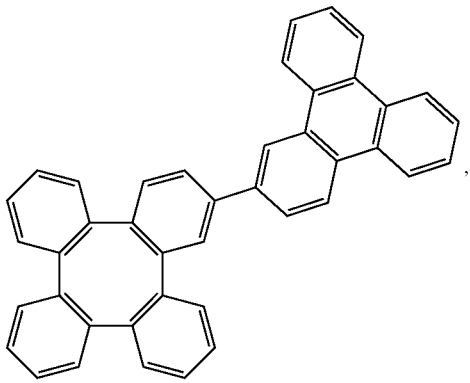
Compound 62
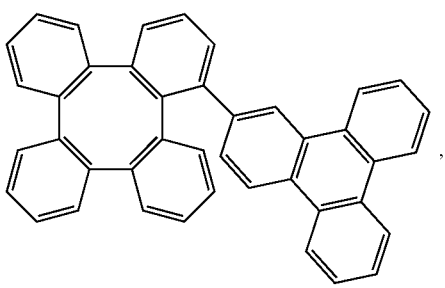

Compound 63
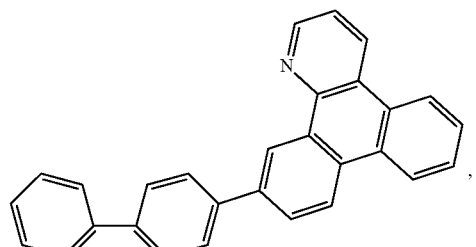
Compound 64
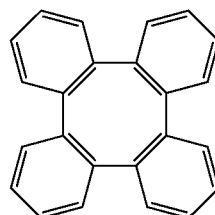
Compound 65
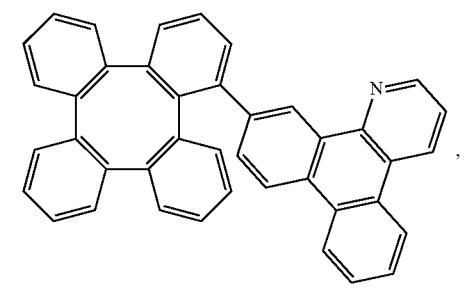
Compound 66
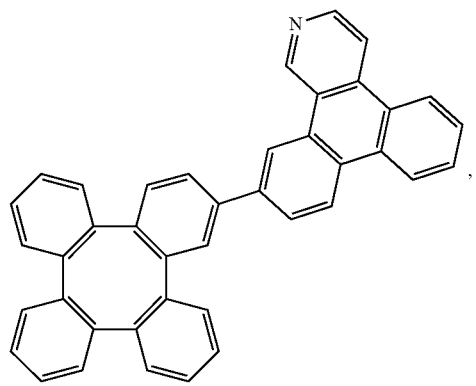
Compound 67
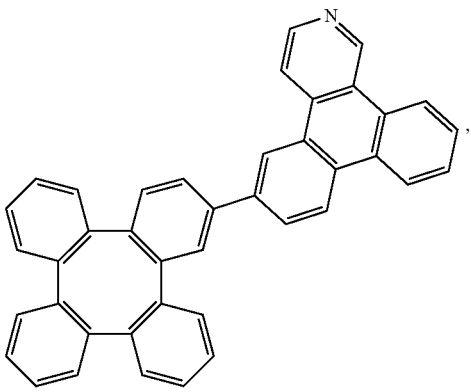
Compound 68
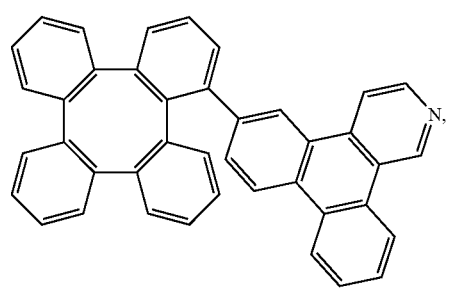
Compound 69
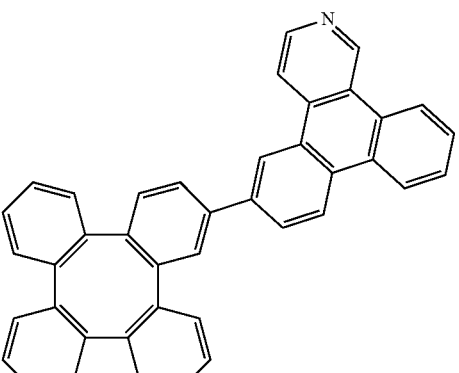
Compound 70
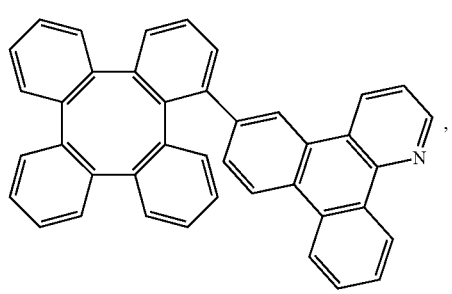

Compound 71
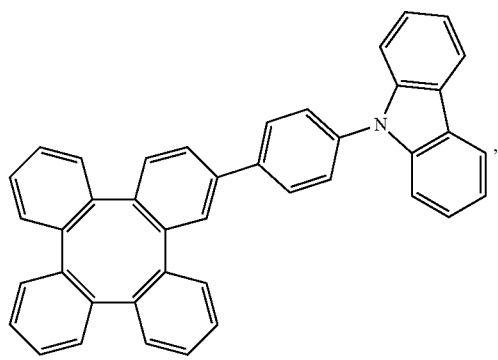
Compound 72
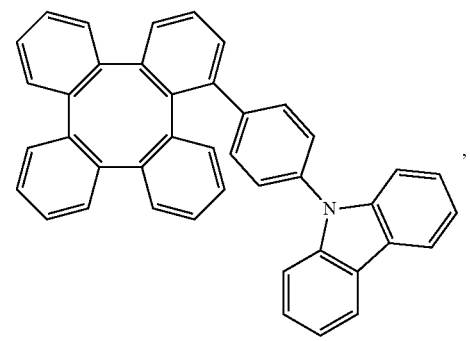
Compound 73
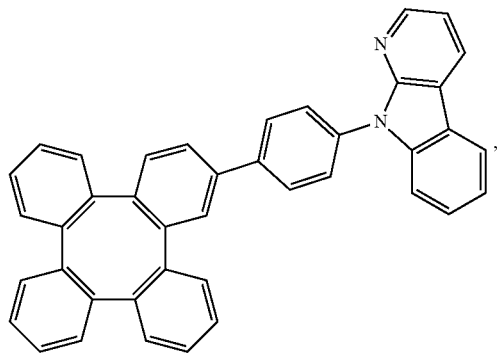
Compound 74
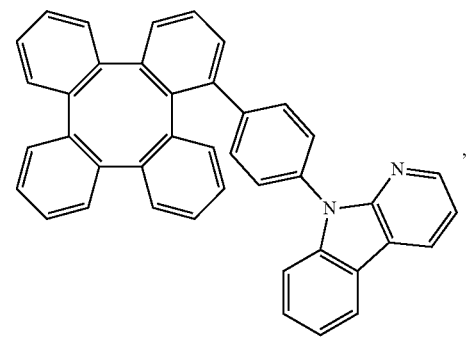
Compound 75
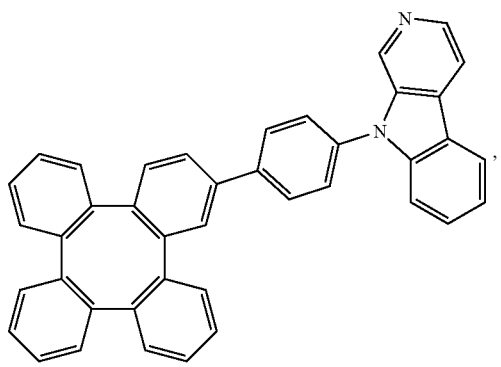
Compound 76
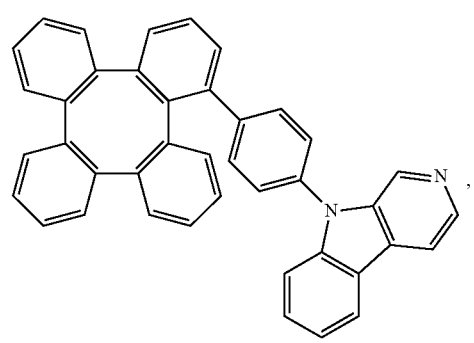
Compound 77
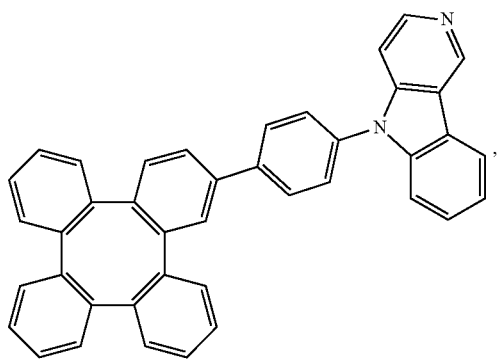
Compound 78
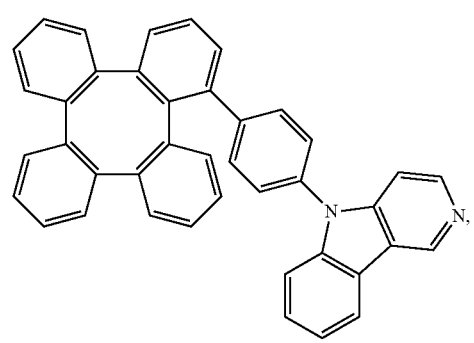

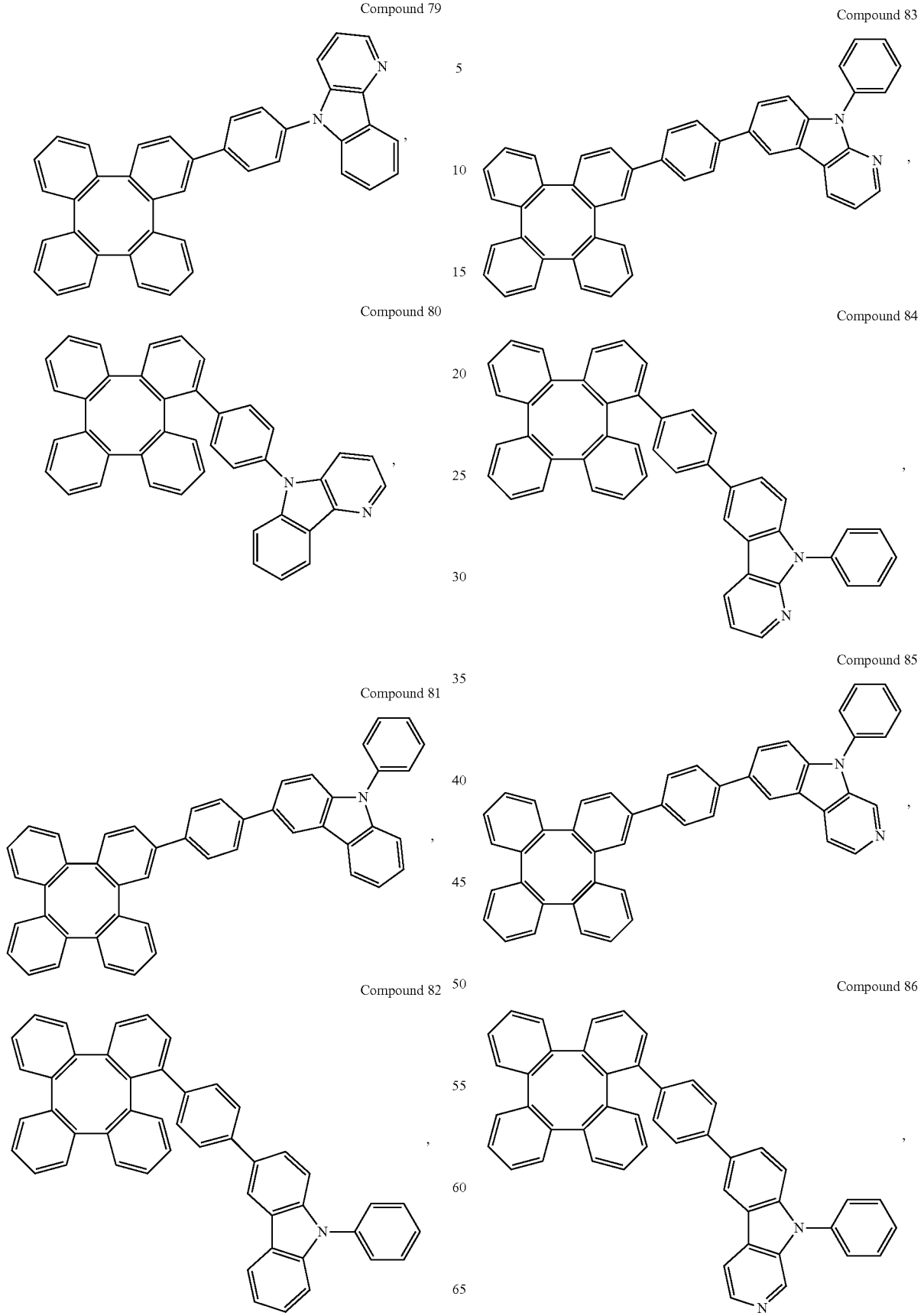

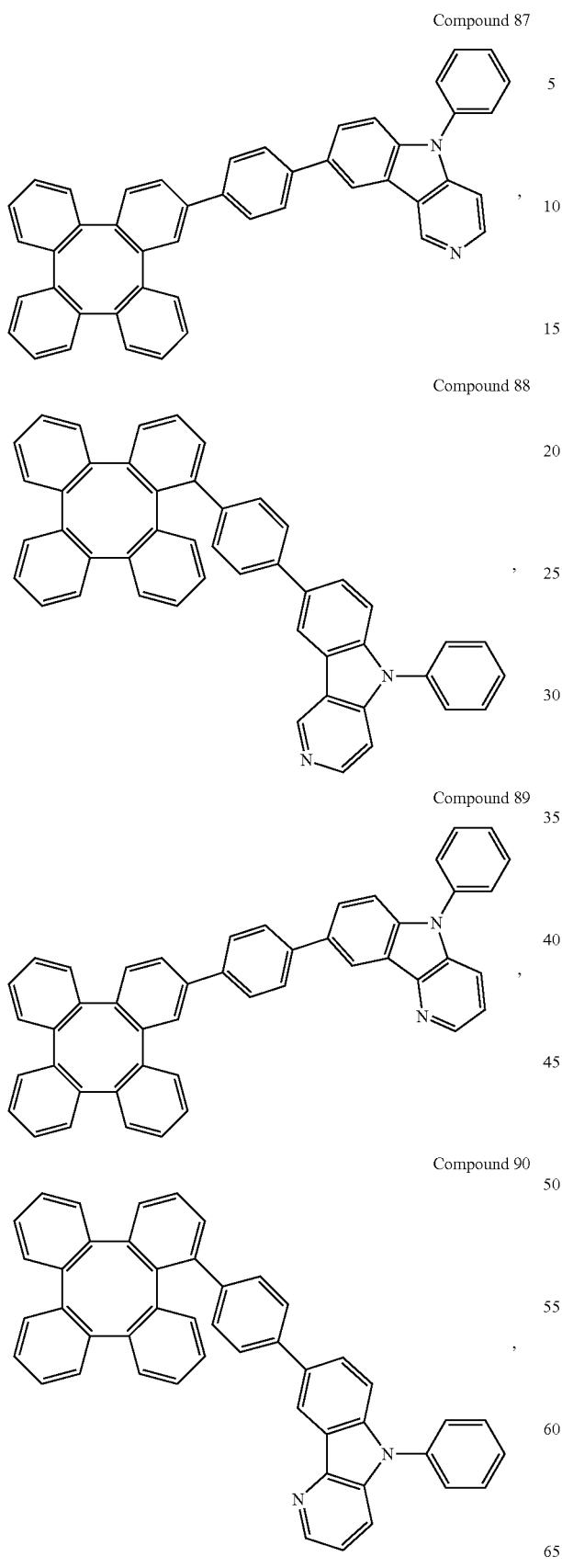
Compound 87
Compound 88
Compound 89
Compound 90
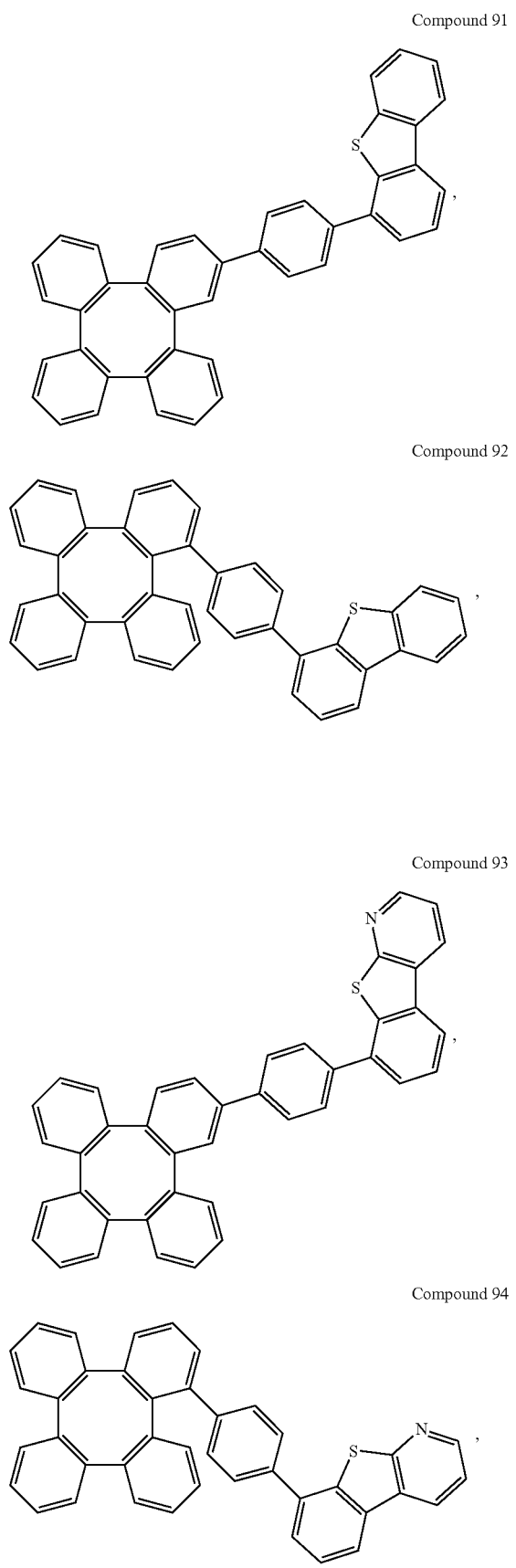
Compound 91
Compound 92
Compound 93
Compound 94

Compound 95
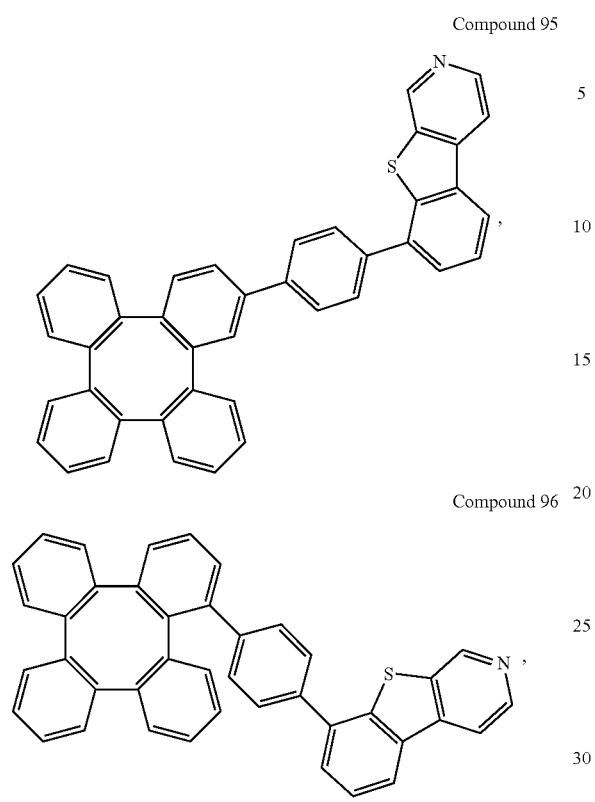
Compound 96
Compound 97
Compound 98
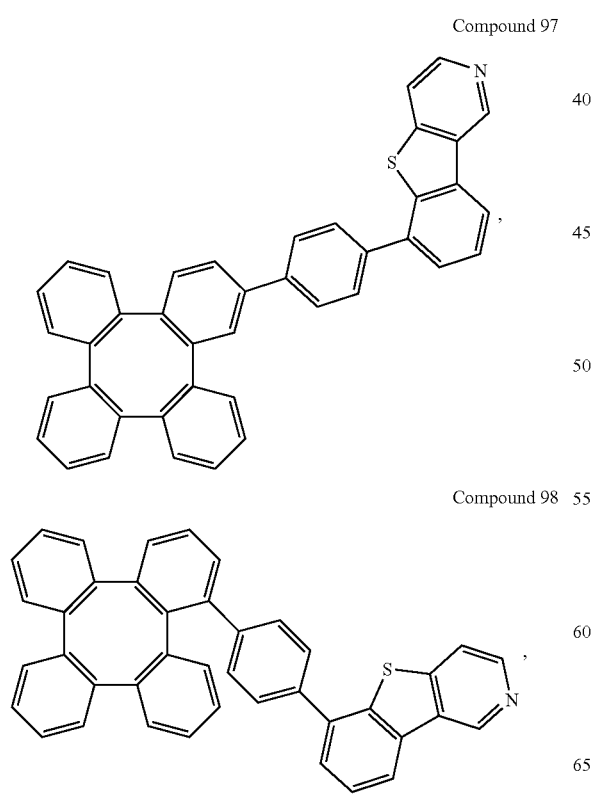
Compound 99
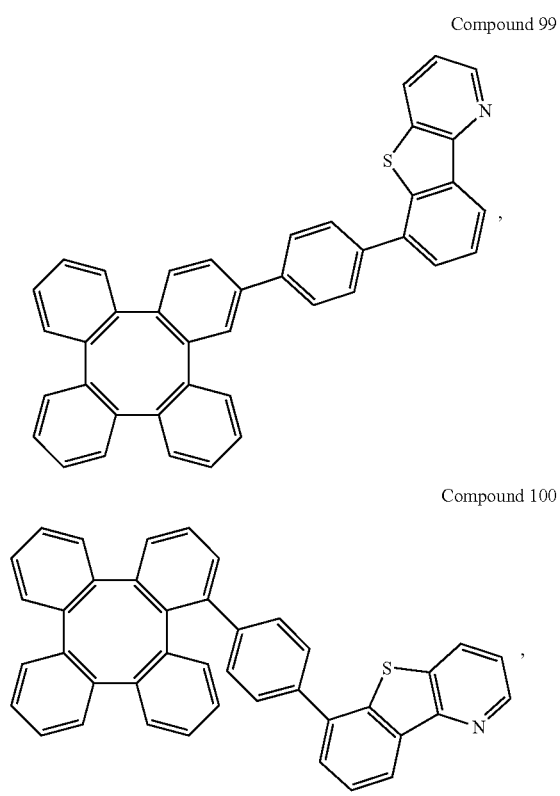
Compound 100
Compound 101
Compound 102
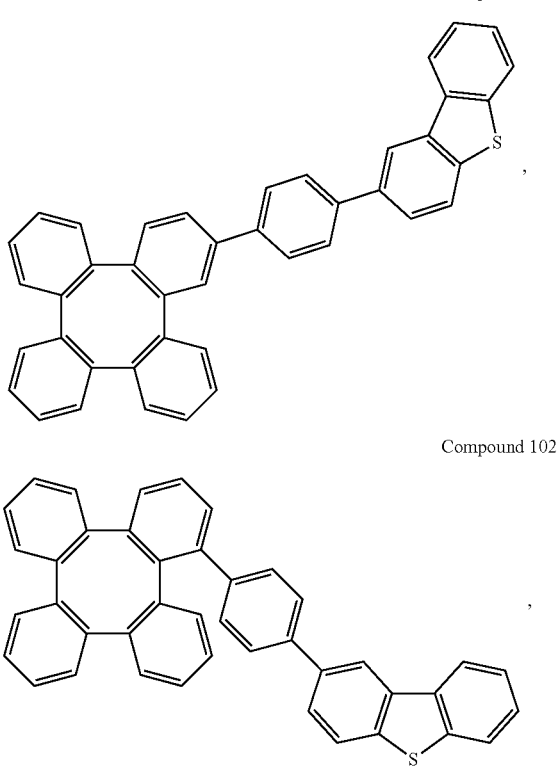

Compound 103
Compound 104
Compound 105
Compound 106
Compound 107
Compound 108
Compound 109
Compound 110
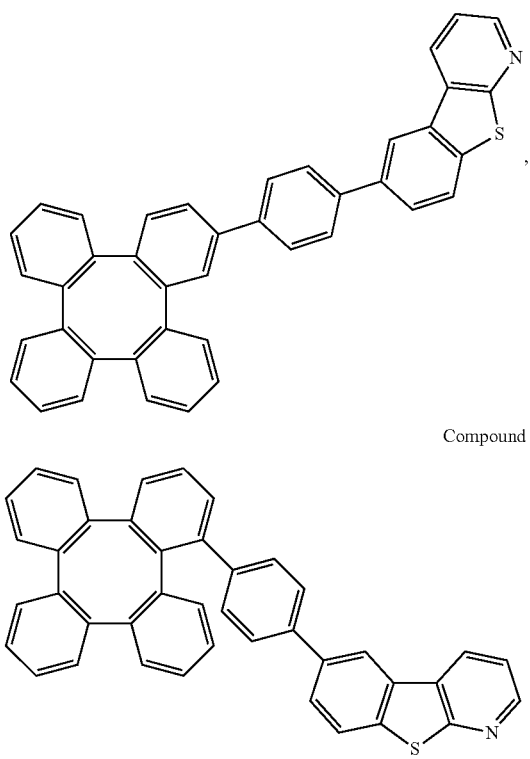

Compound 111
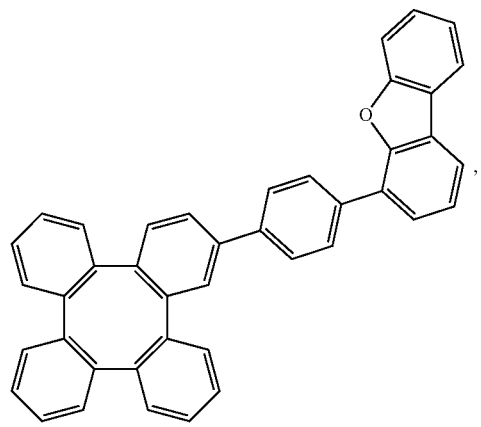
Compound 112
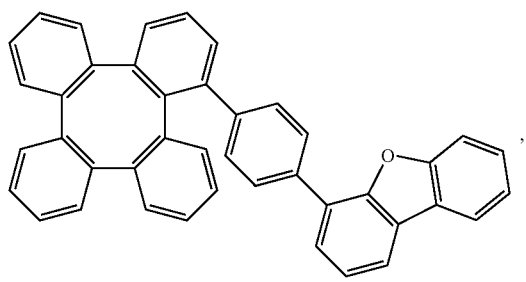
Compound 113
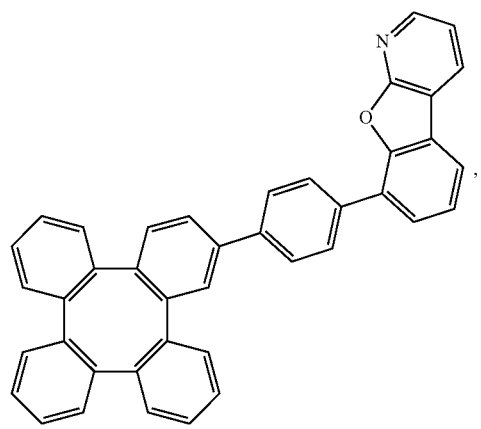
Compound 114
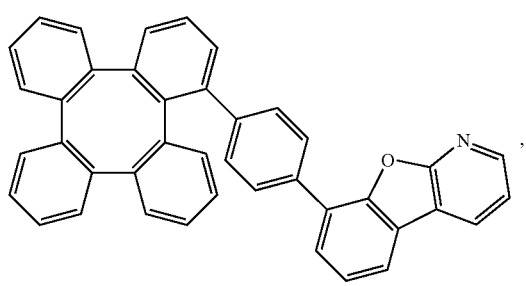
Compound 115
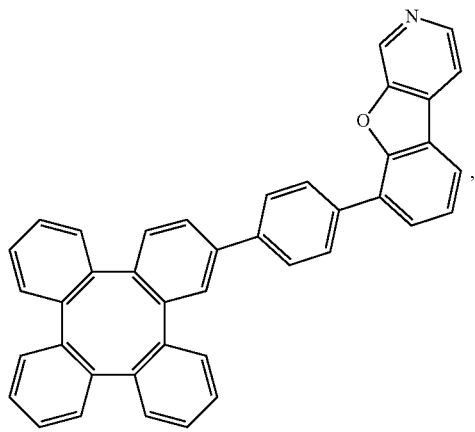
Compound 116
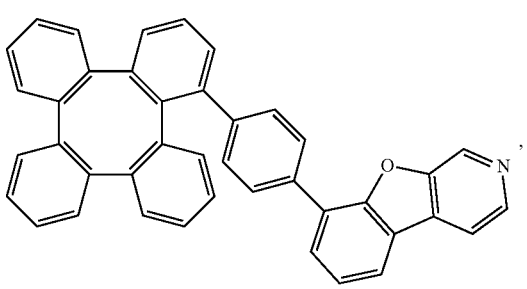
Compound 117
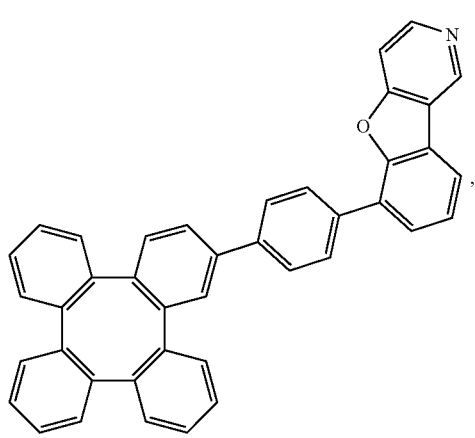
Compound 118
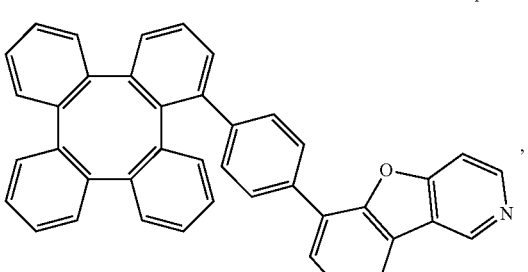

Compound 119
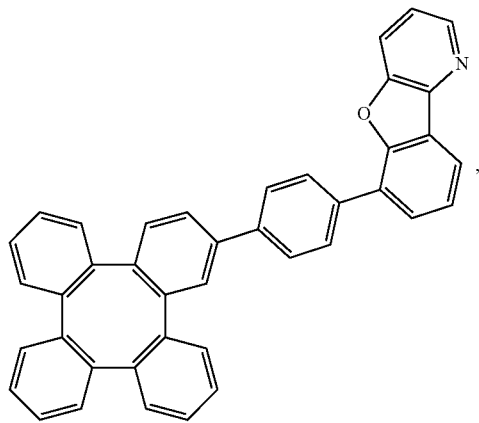
Compound 120
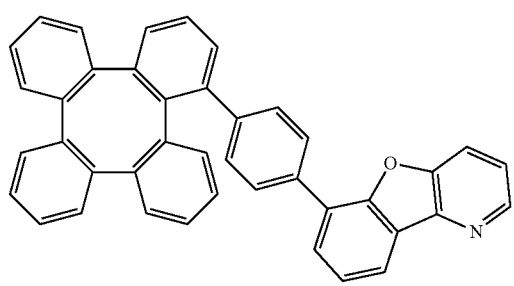
Compound 121
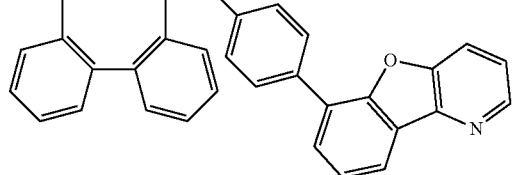
Compound 122
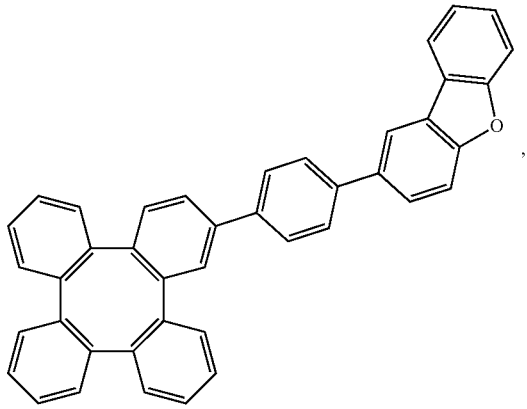
Compound 123
Compound 124
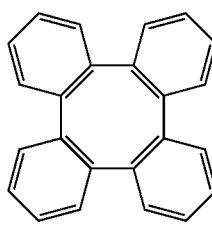
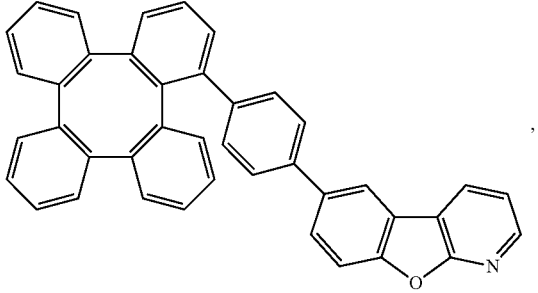
Compound 125
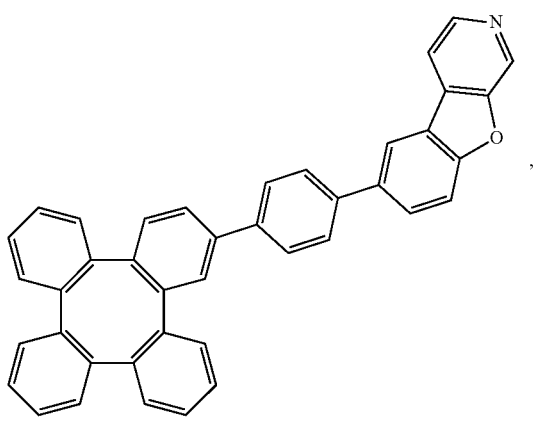
Compound 126
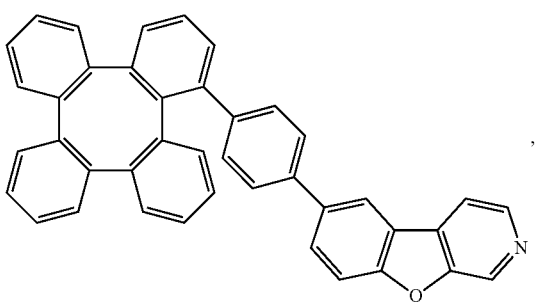

Compound 127
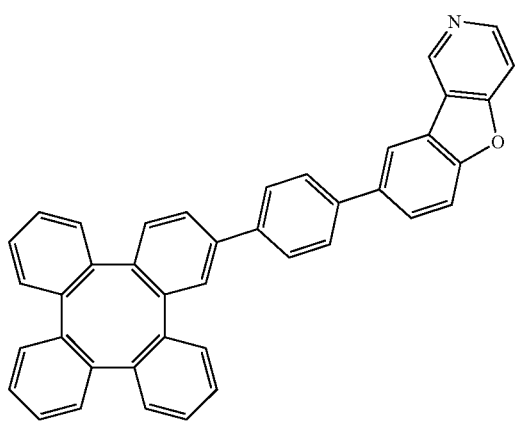
Compound 128
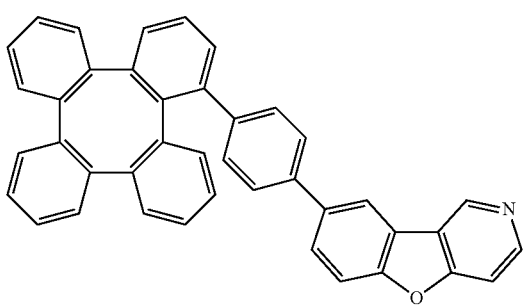
Compound 129
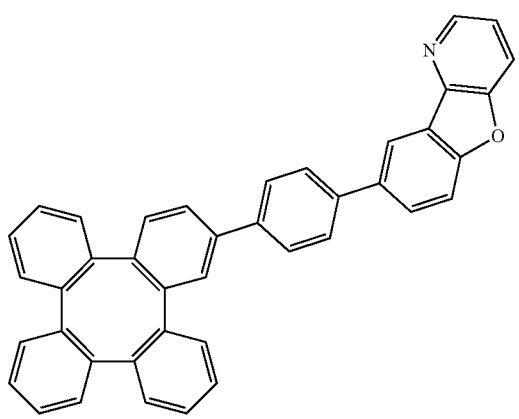
Compound 130
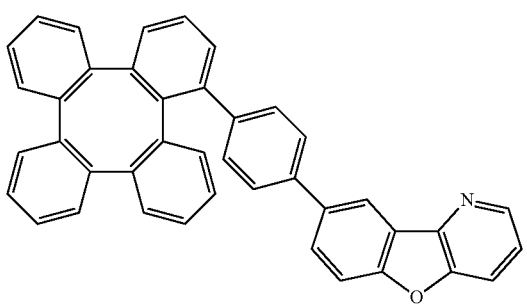
Compound 131
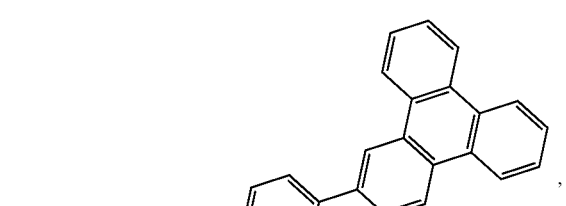
Compound 132
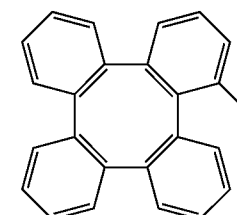
Compound 133
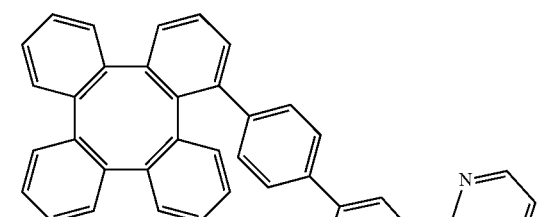
Compound 134
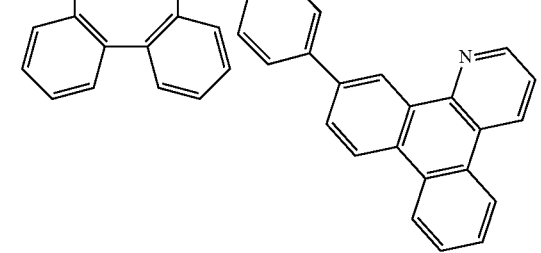

Compound 135
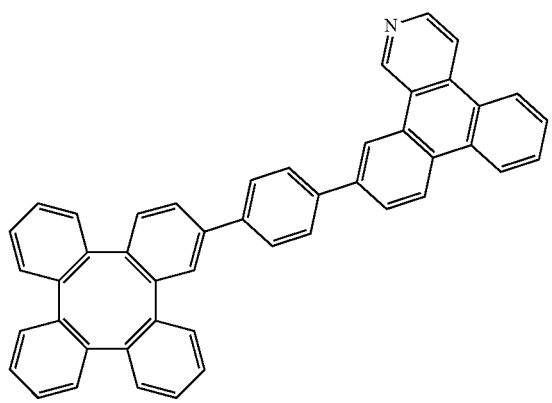
Compound 136
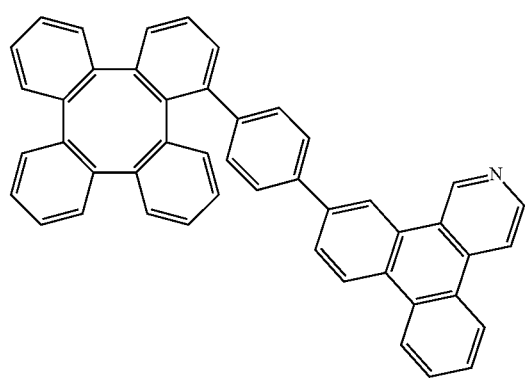
Compound 137
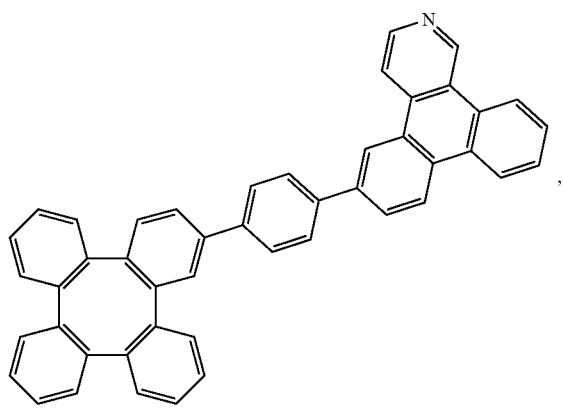
Compound 138
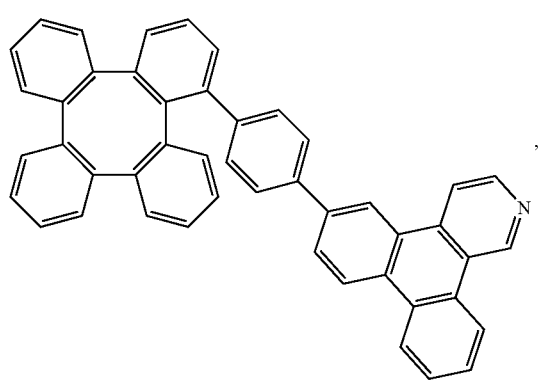
Compound 139
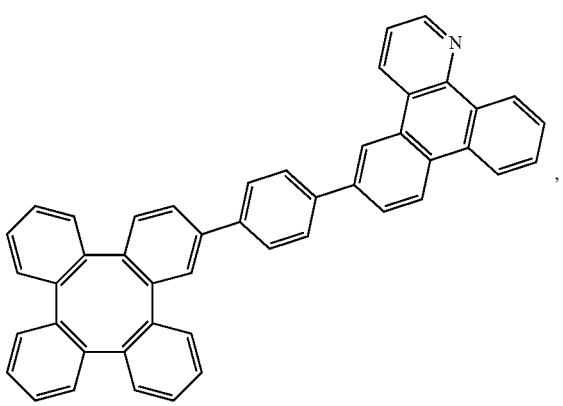
Compound 140
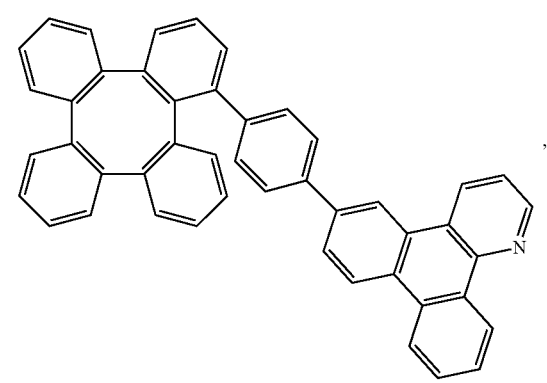
Compound 141
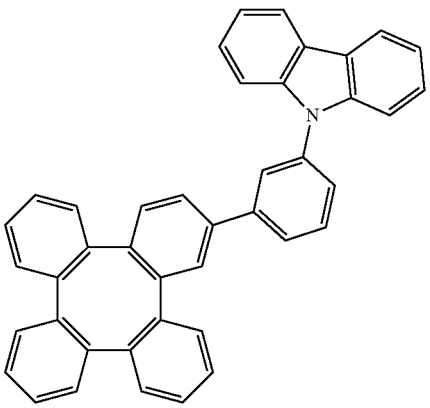
Compound 142
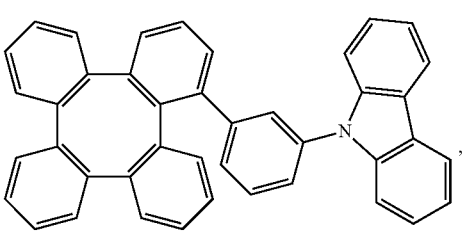

Compound 143
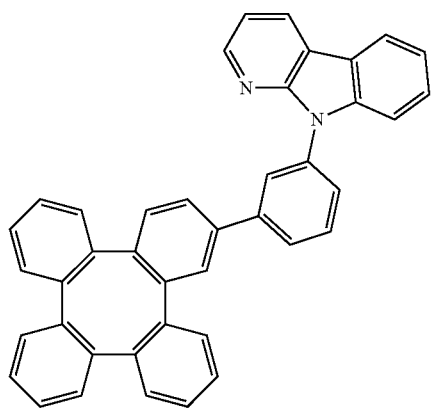
Compound 144
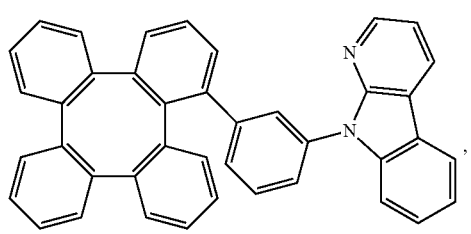
Compound 145
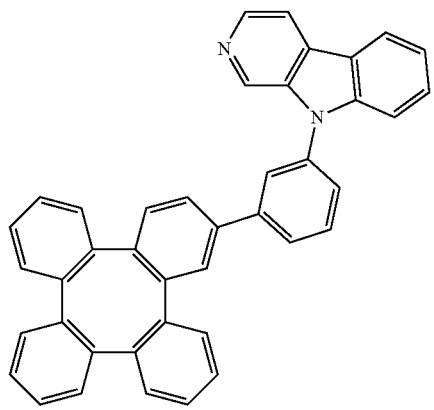
Compound 146
Compound 147
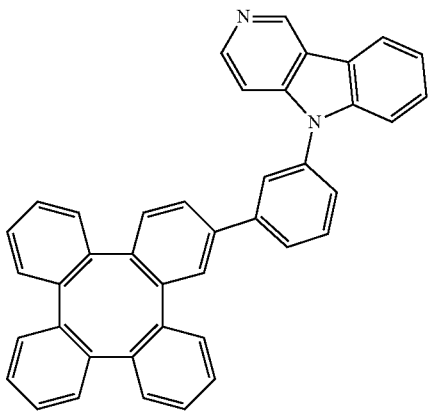
Compound 148
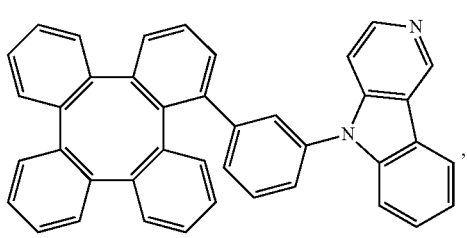
Compound 149
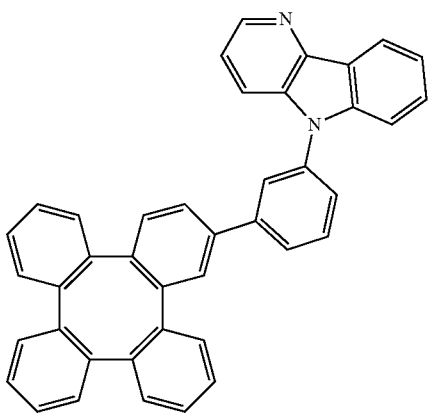
Compound 150
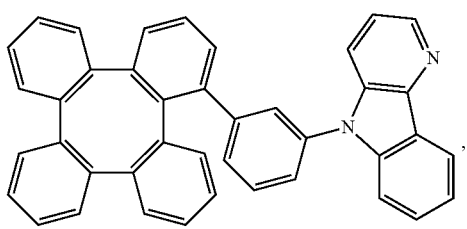

Compound 151
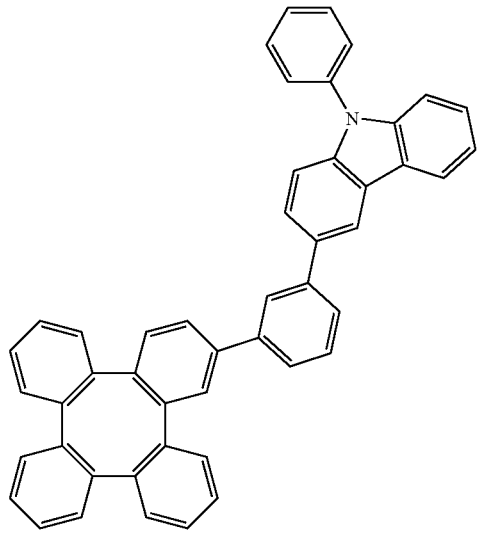
Compound 152
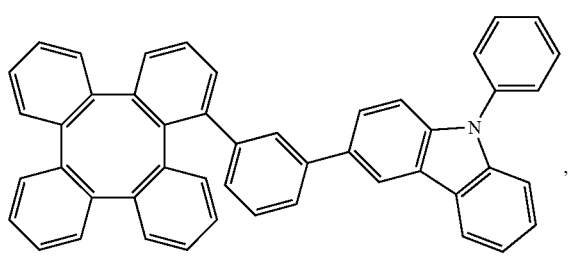
Compound 153
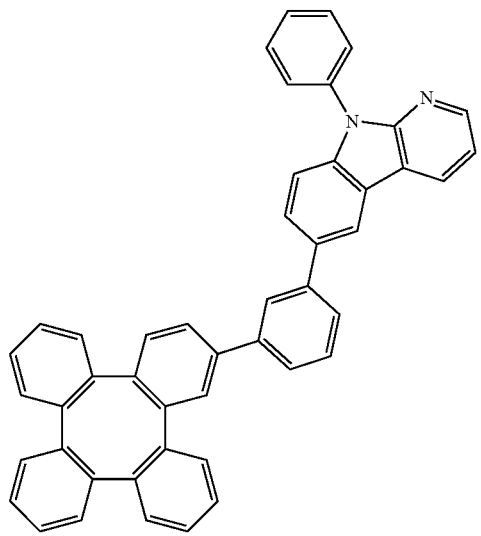
Compound 154
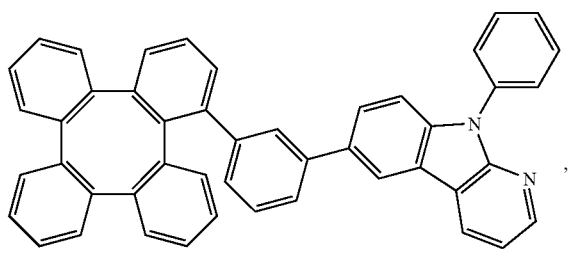
Compound 155
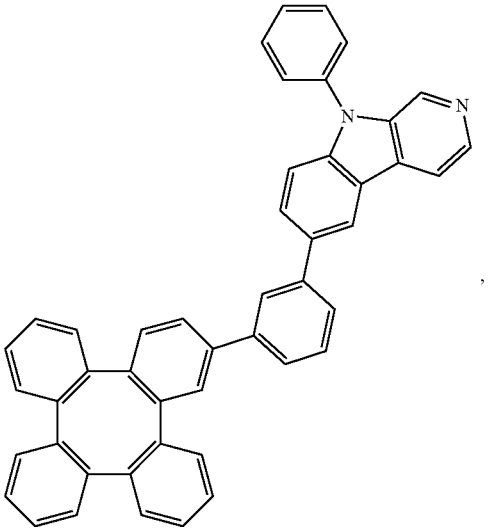
Compound 156
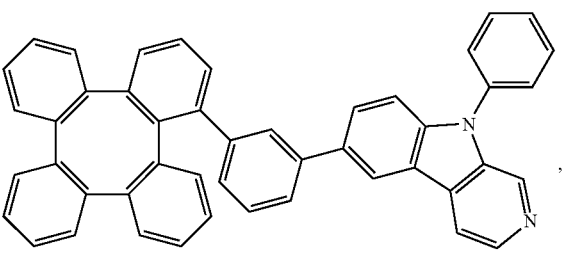
Compound 157
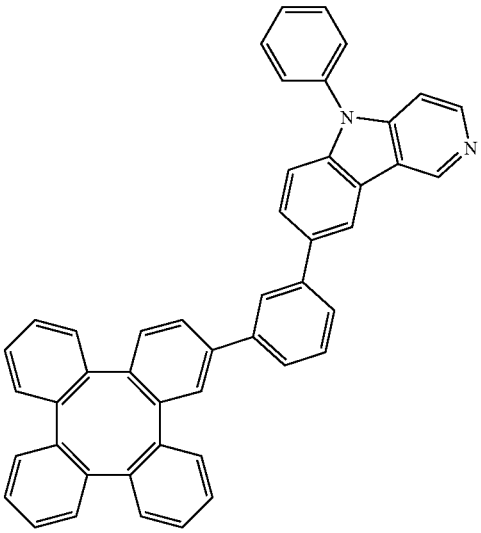
Compound 158
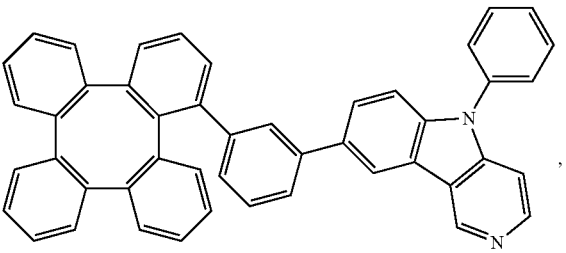

Compound 159
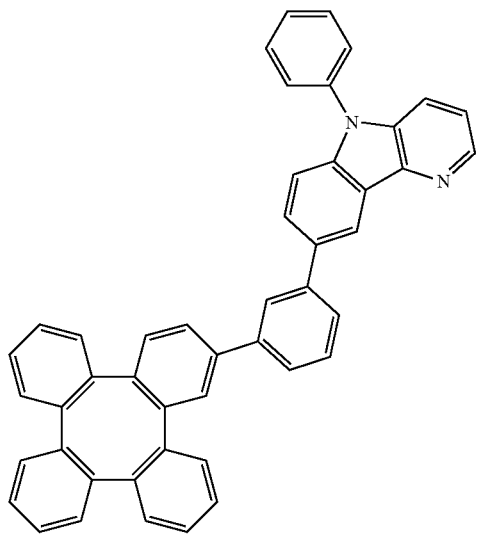
Compound 160
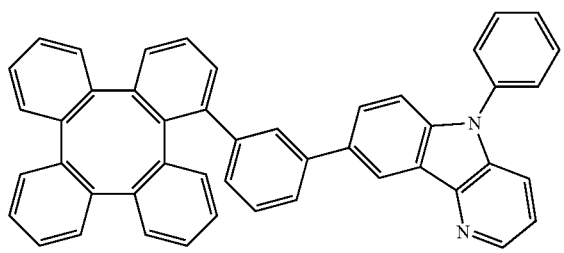
Compound 161
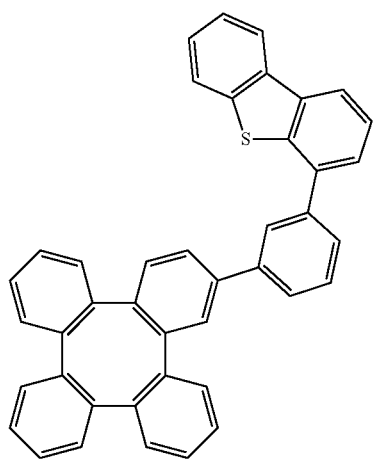
Compound 162
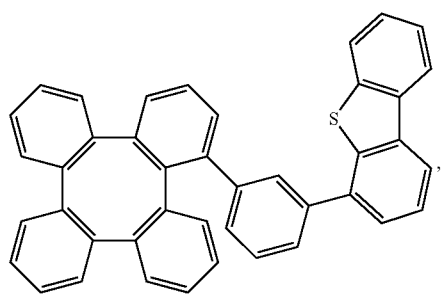
Compound 163
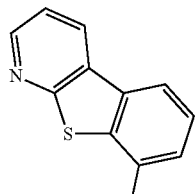
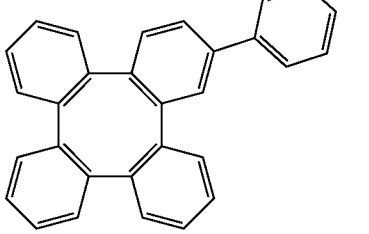
Compound 164
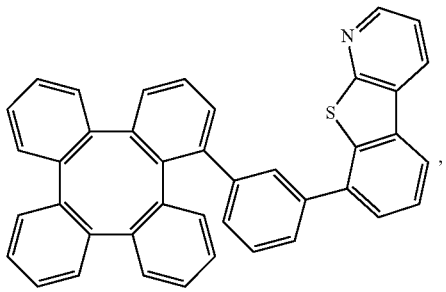
Compound 165
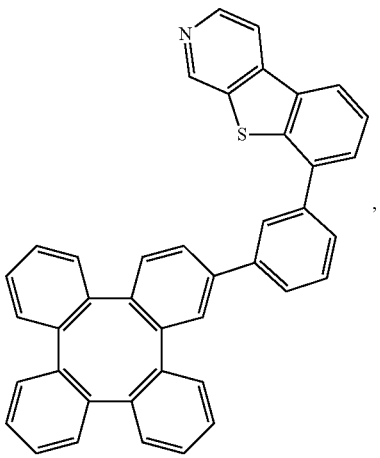
Compound 166
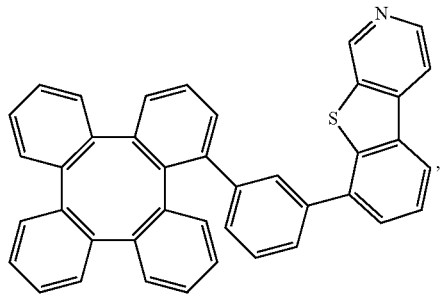

-continued
Compound 167
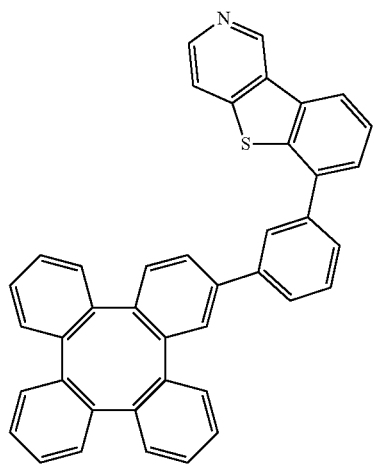
Compound 168
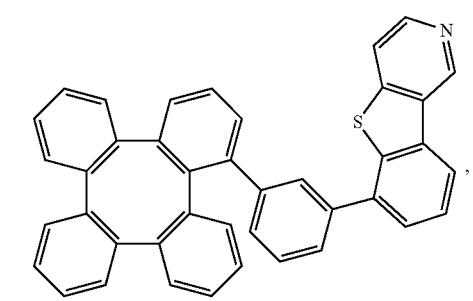
Compound 169
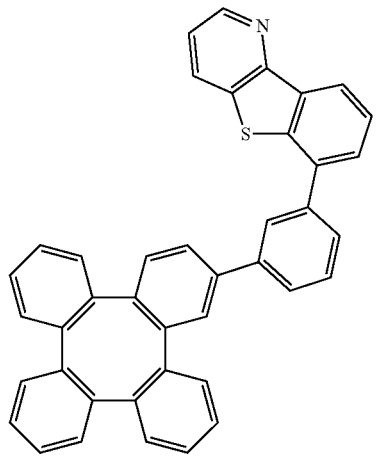
Compound 170
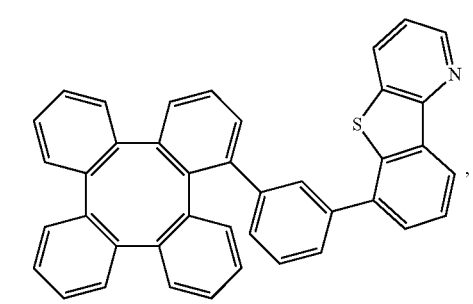
Compound 171
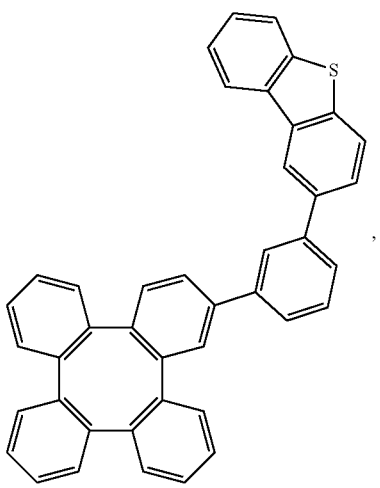
Compound 172
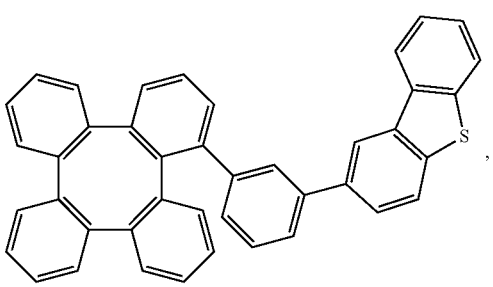
Compound 173
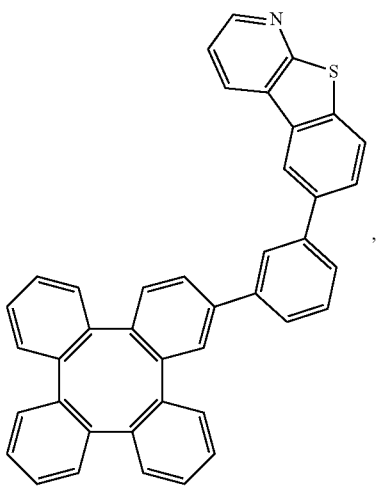
Compound 174
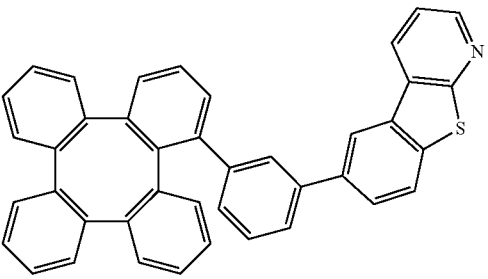

Compound 175
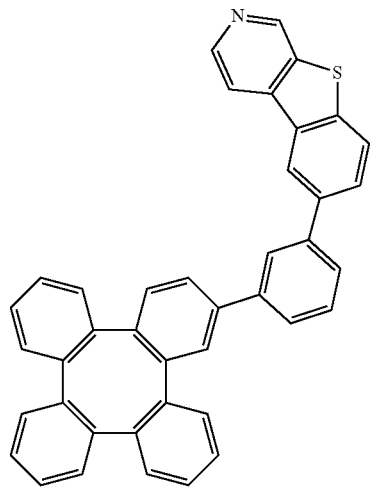
Compound 176
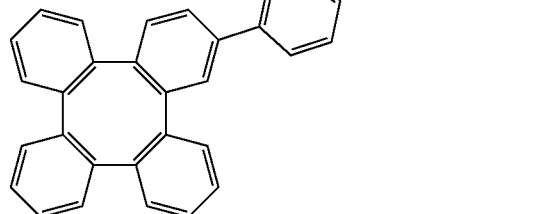
Compound 177
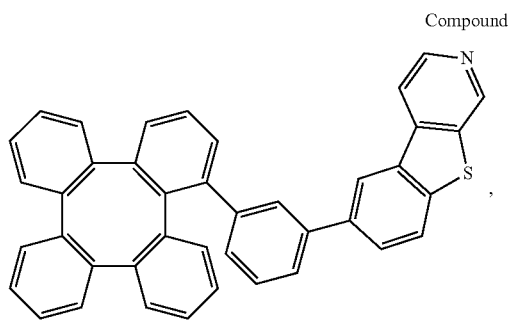
Compound 178
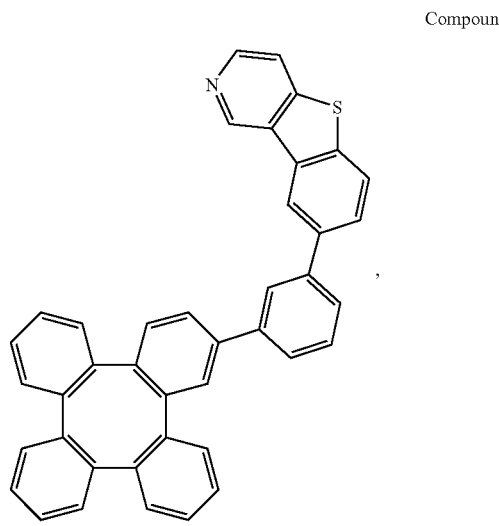
Compound 179
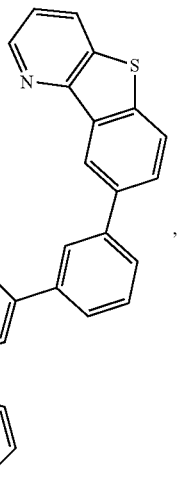
Compound 180
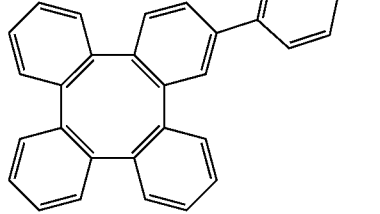
Compound 181
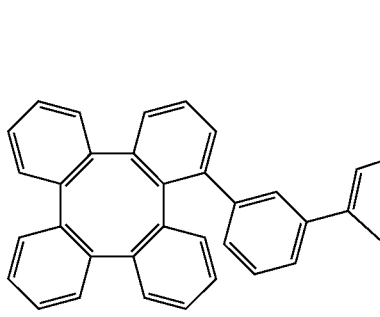
Compound 182
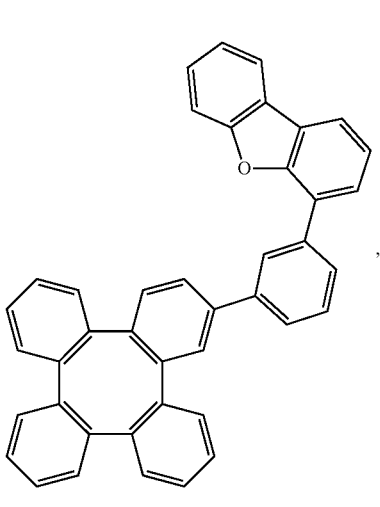

Compound 183
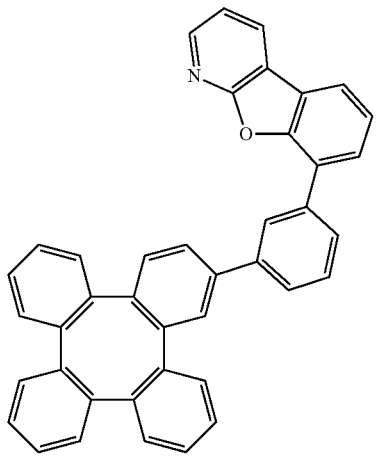
Compound 184
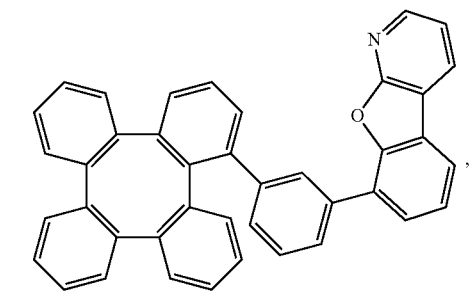
Compound 185
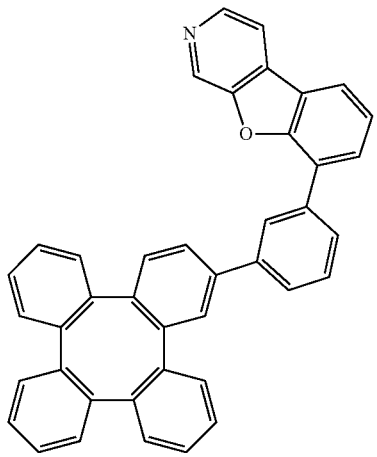
Compound 186
Compound 187
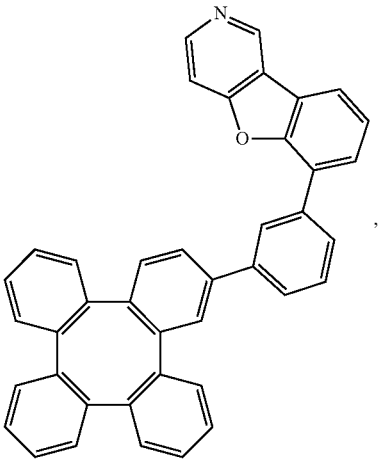
Compound 188
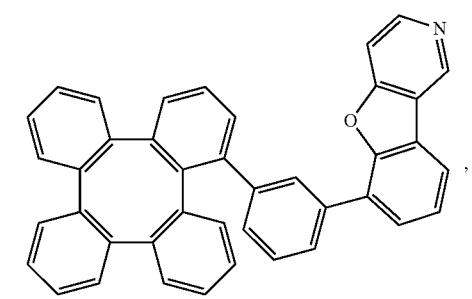
Compound 189
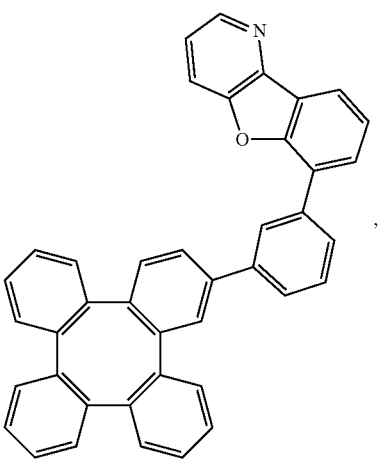
Compound 190
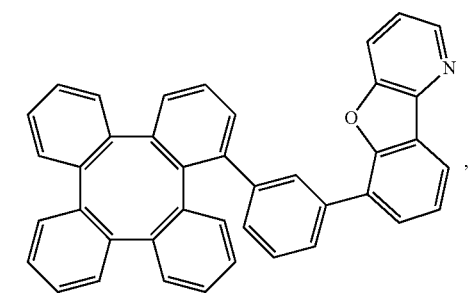

Compound 191
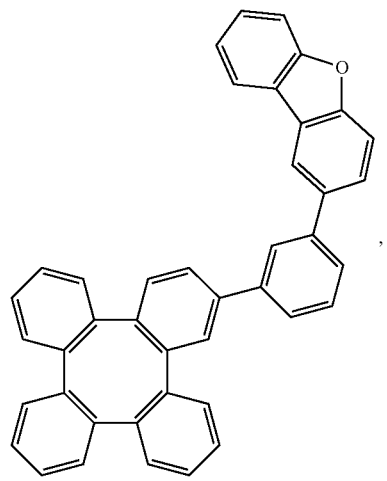
Compound 192
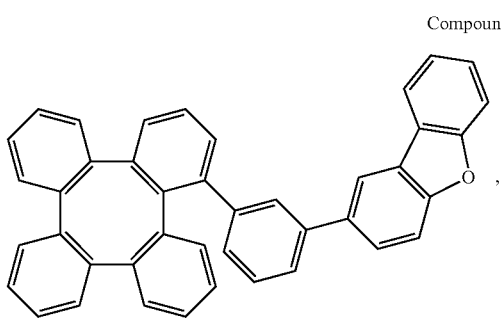
Compound 193
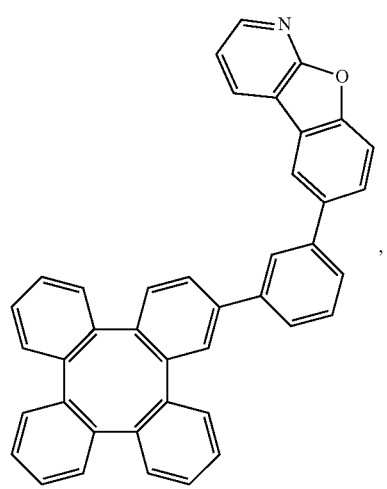
Compound 194
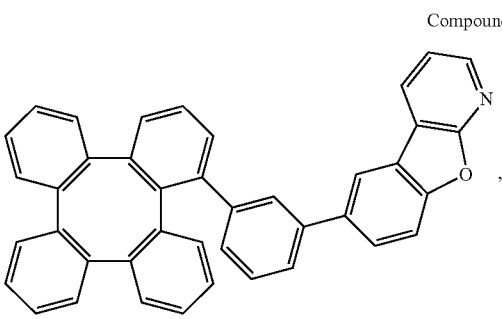
Compound 195
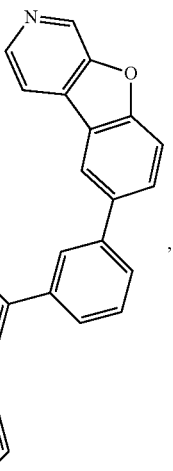
Compound 196
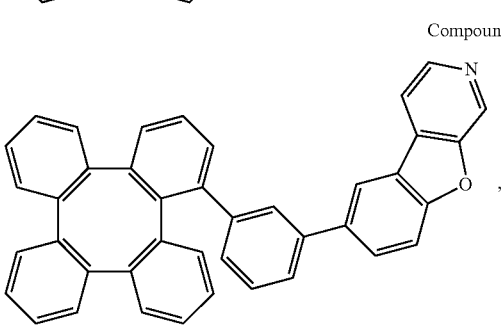
Compound 197
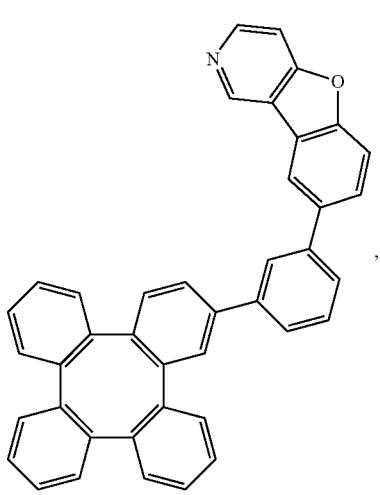
Compound 198
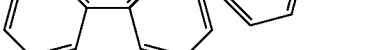

Compound 199
Compound 200
Compound 201
Compound 202
Compound 203
Compound 204
Compound 205
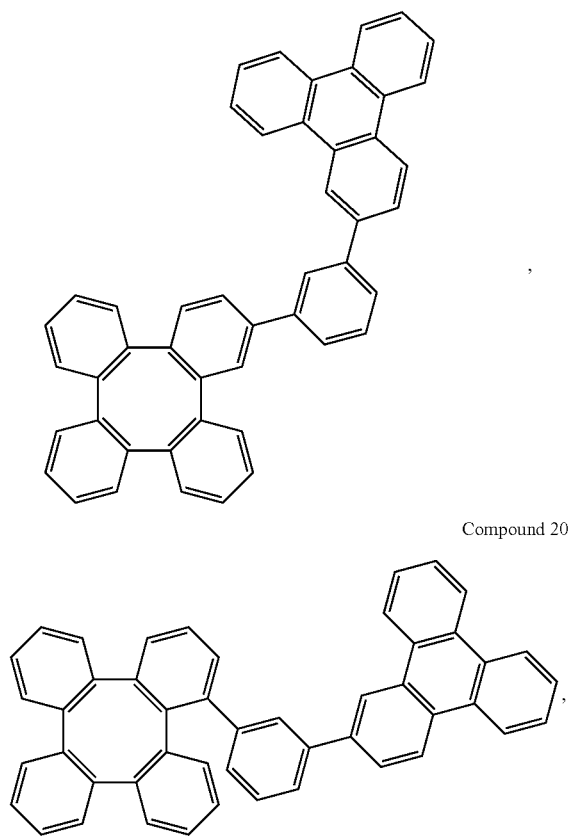

Compound 206
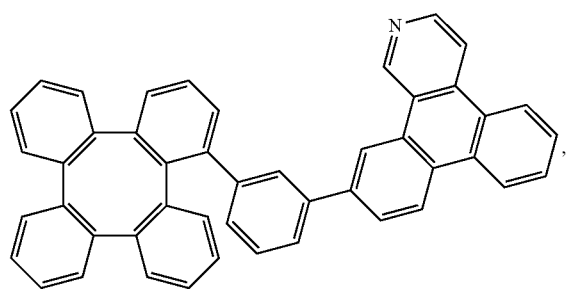
Compound 207
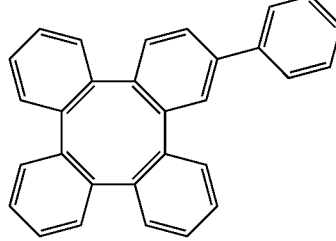
Compound 208
Compound 209
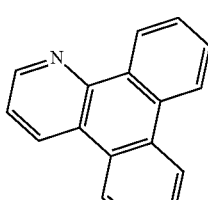
Compound 210
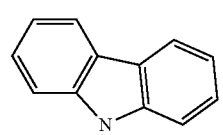
Compound 211
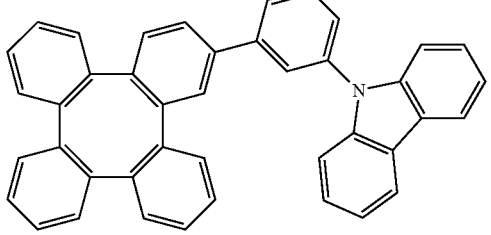
Compound 212
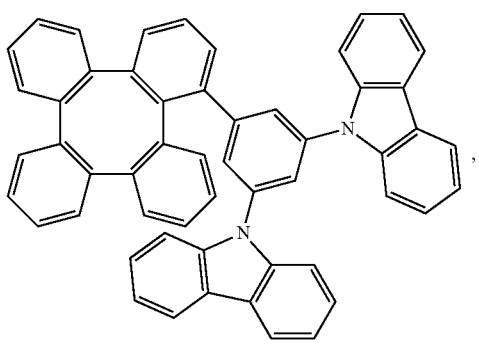

-continued
Compound 213
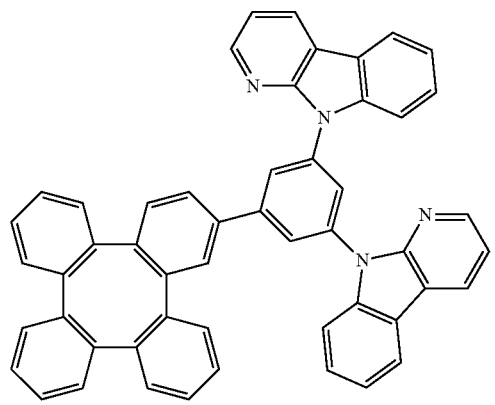
Compound 214
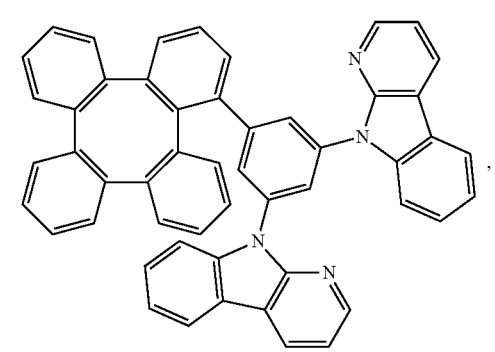
Compound 215
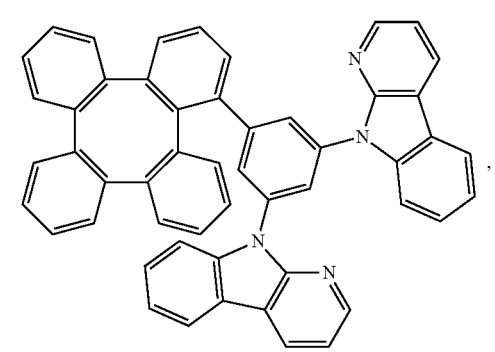
Compound 216
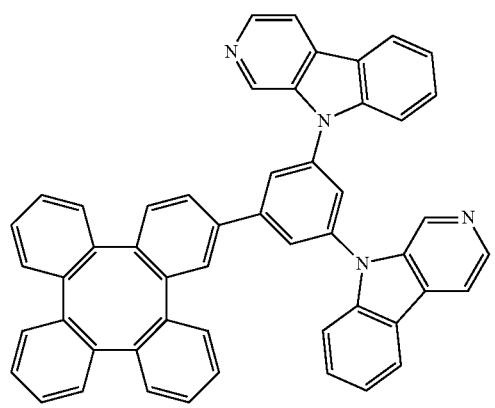
Compound 217
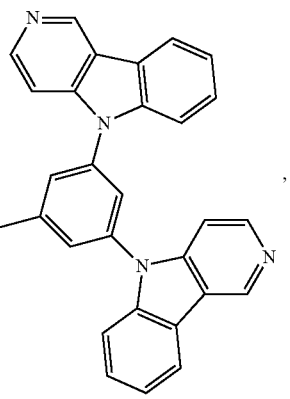
Compound 218
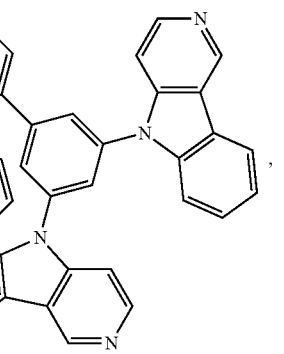
Compound 219
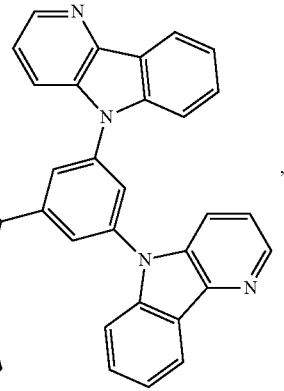
Compound 220
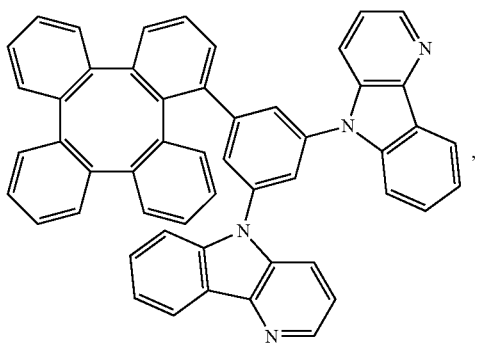

Compound 221
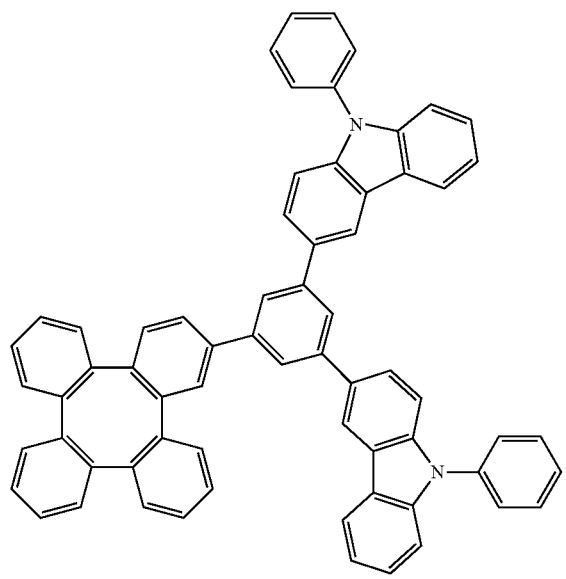
Compound 222
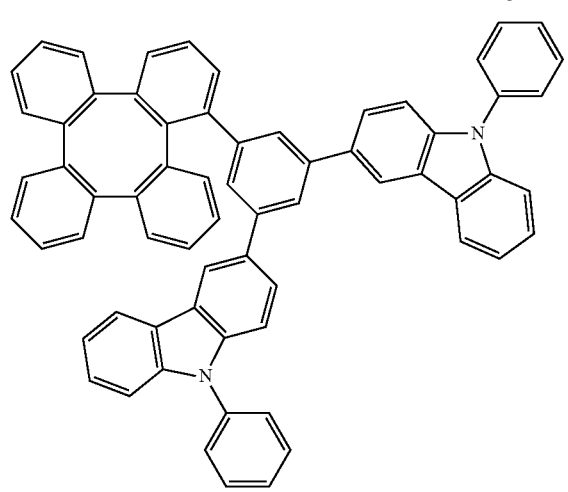
Compound 223
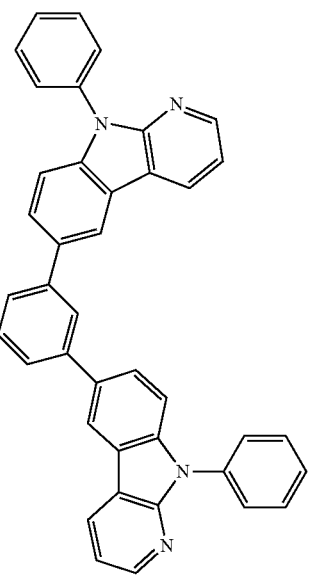
Compound 224
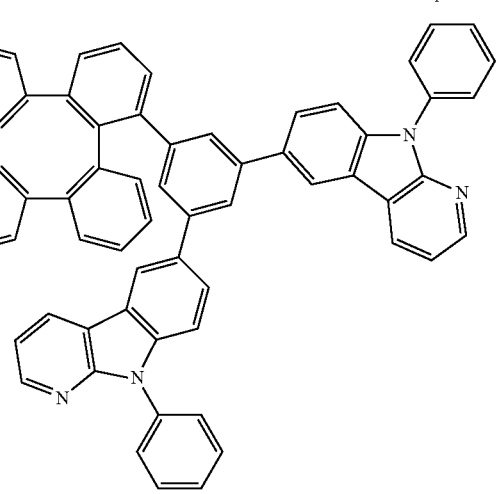

Compound 225
Compound 227
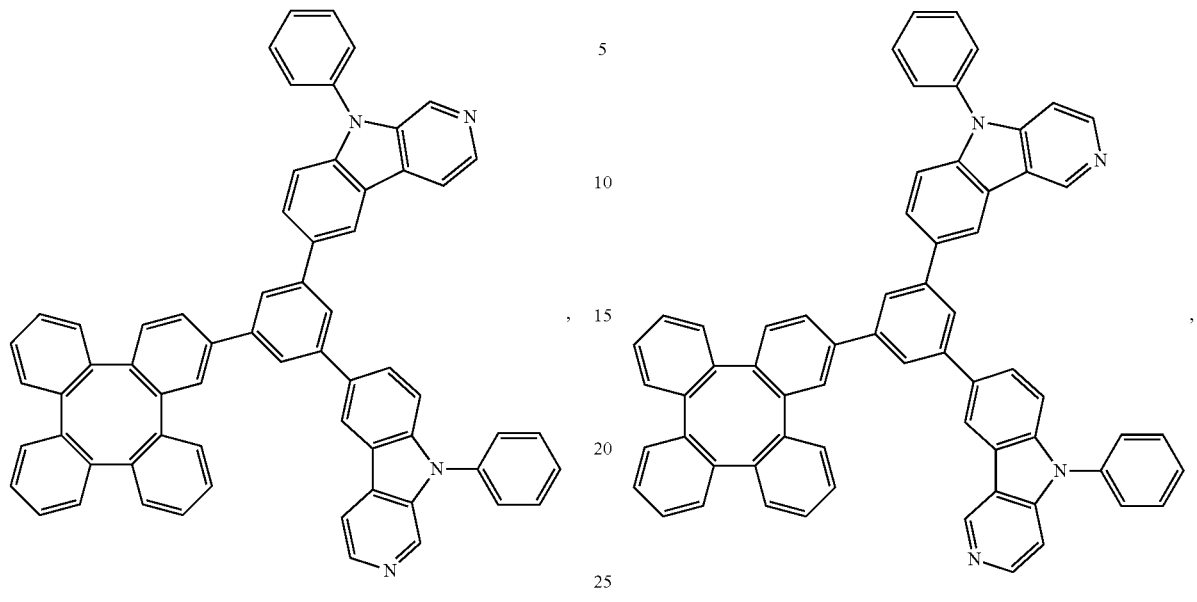
Compound 226
Compound 228
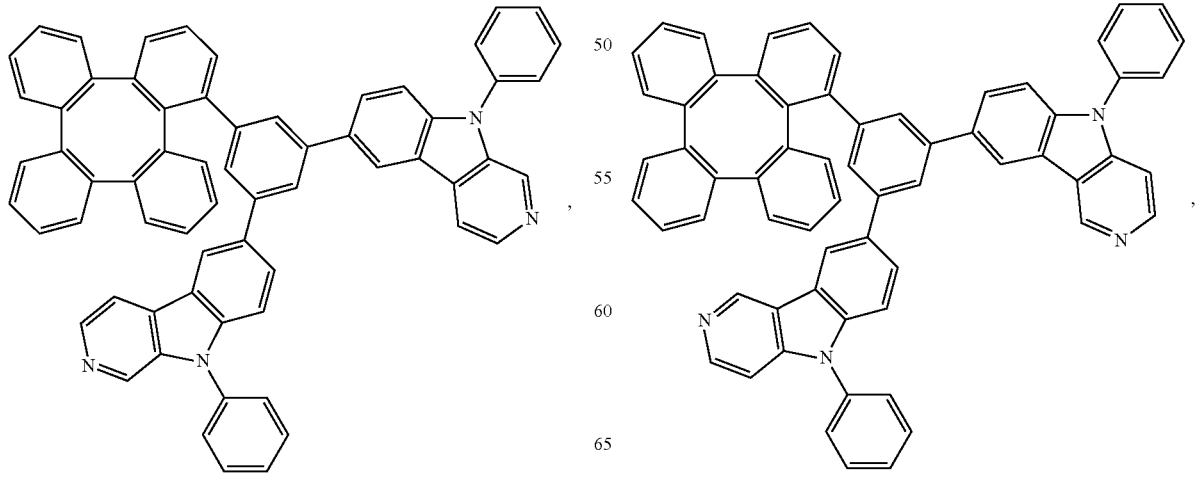

Compound 229
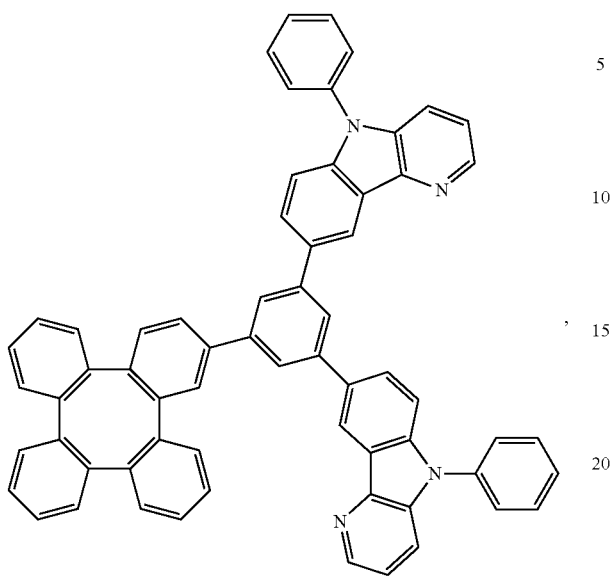
Compound 230
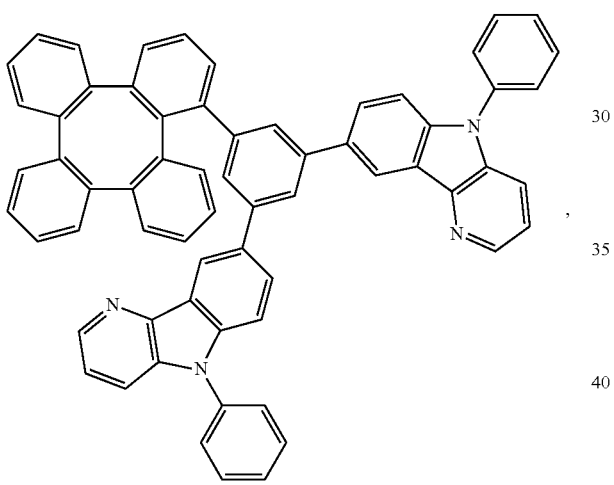
Compound 231
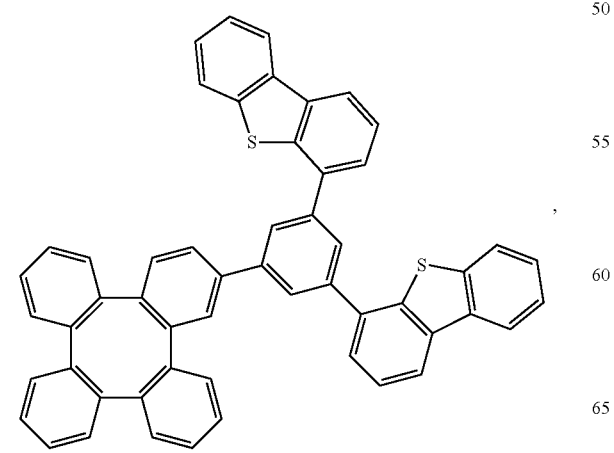
Compound 232
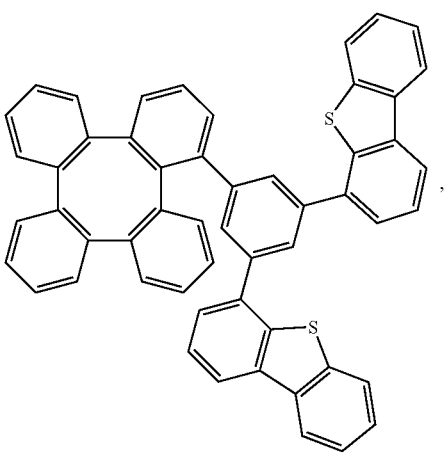
Compound 233
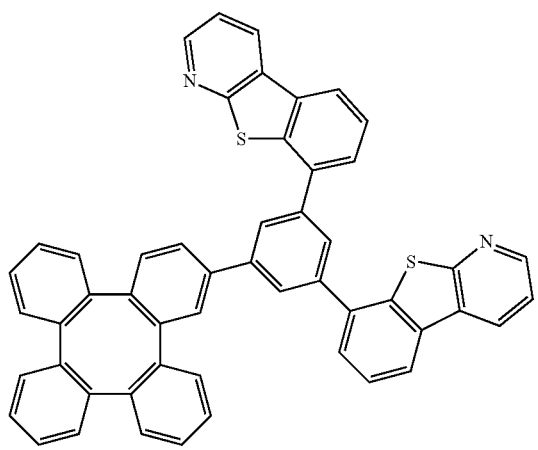
Compound 234
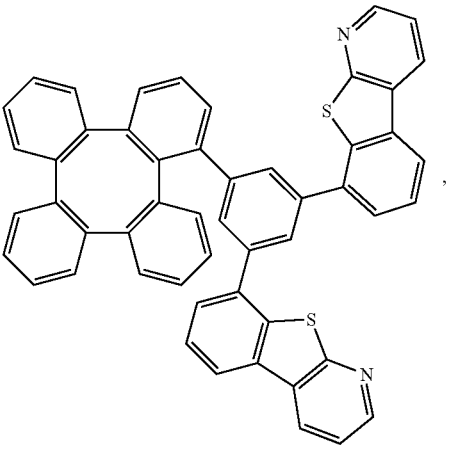

Compound 235
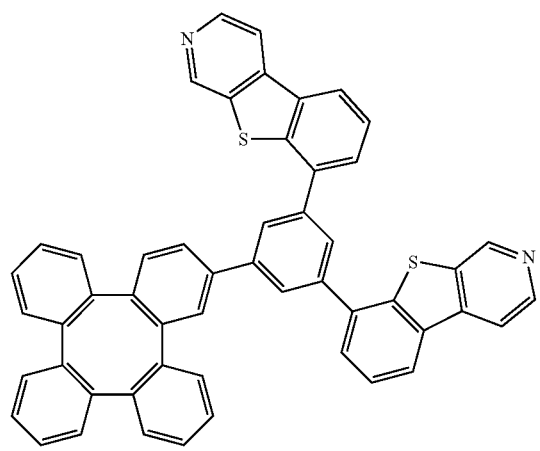
Compound 236
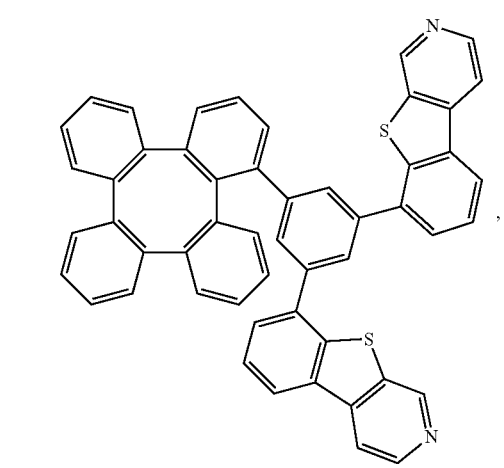
Compound 237
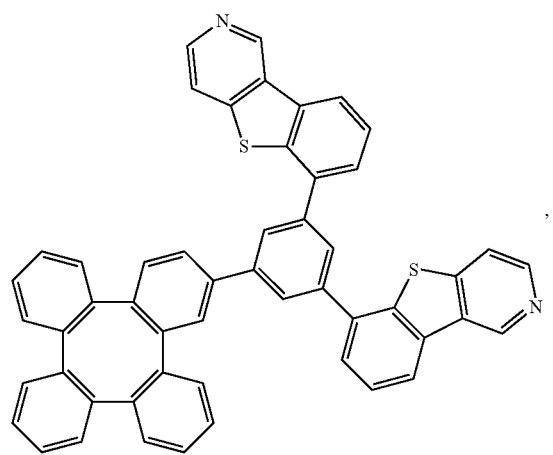
Compound 238
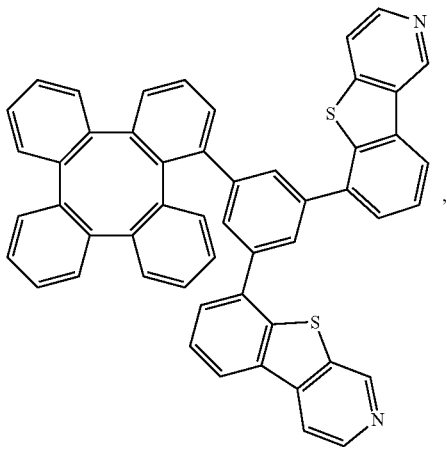
Compound 239
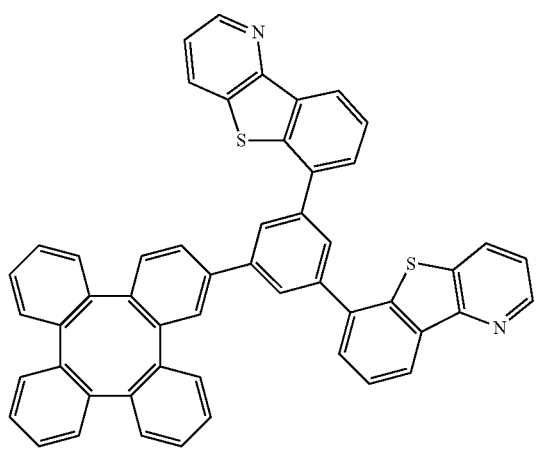
Compound 240
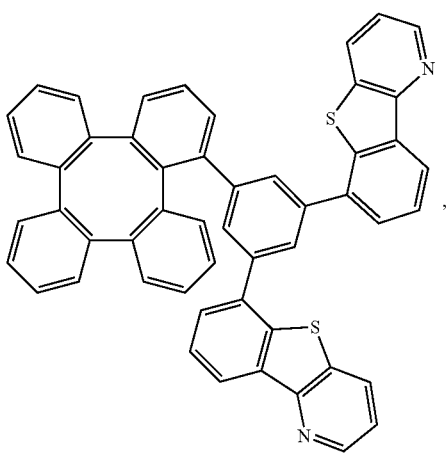

Compound 241
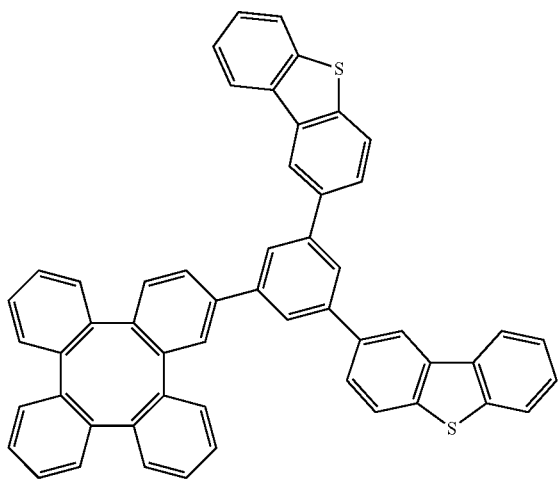
Compound 242
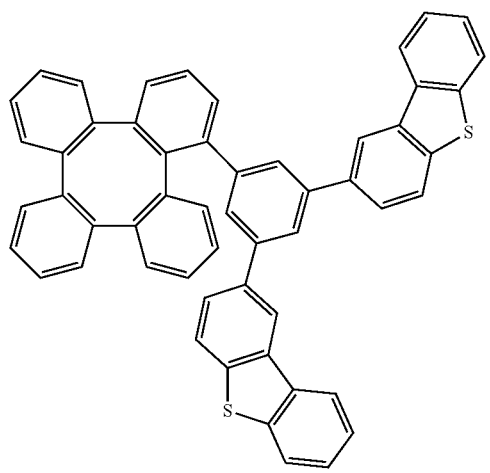
Compound 243
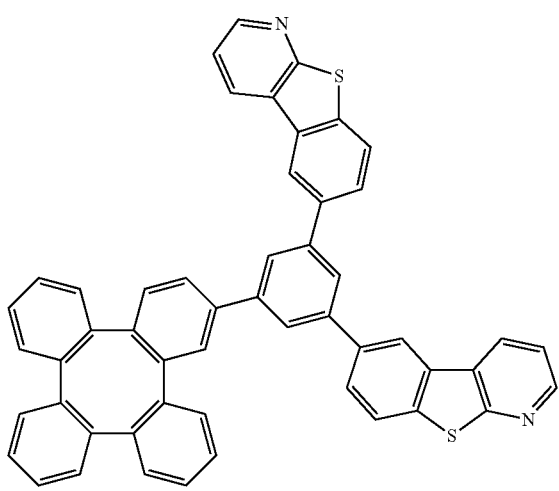
Compound 244
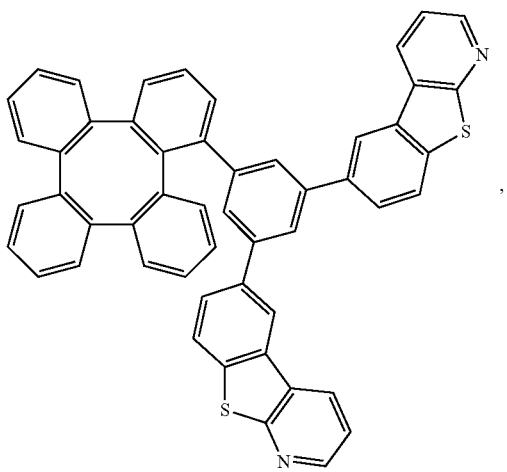
Compound 245
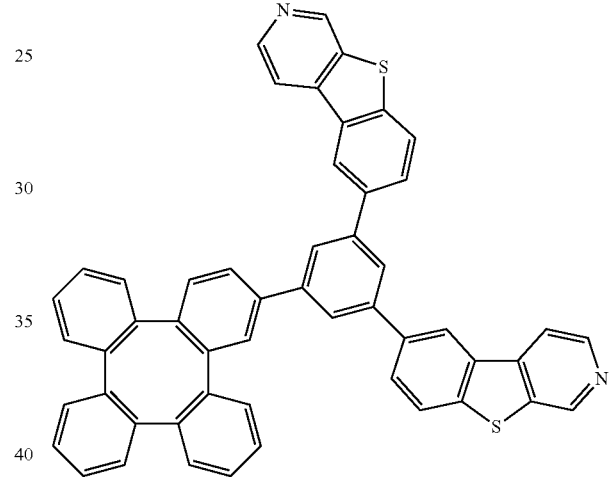
Compound 246
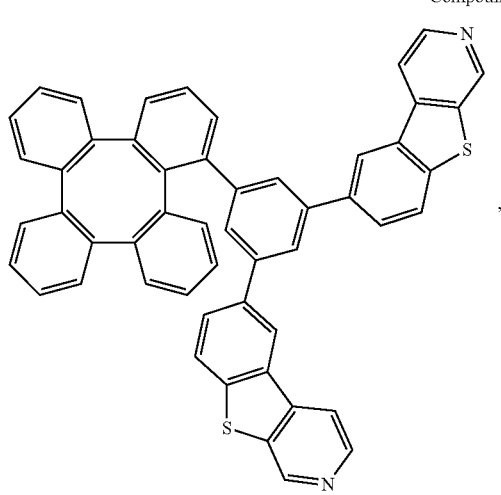

Compound 247
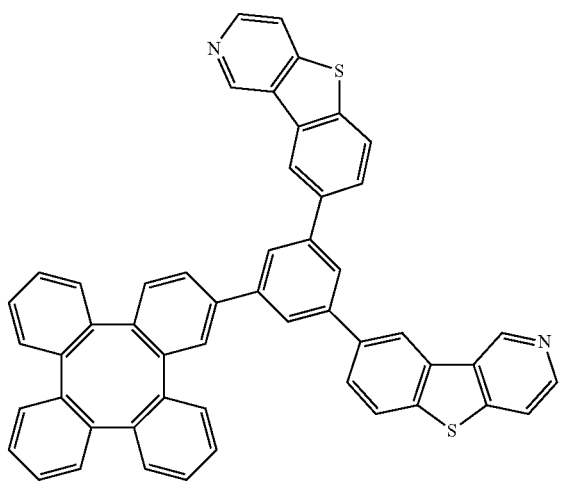
Compound 248
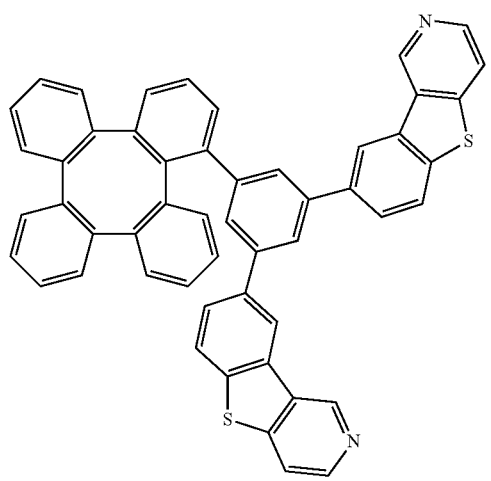
Compound 249
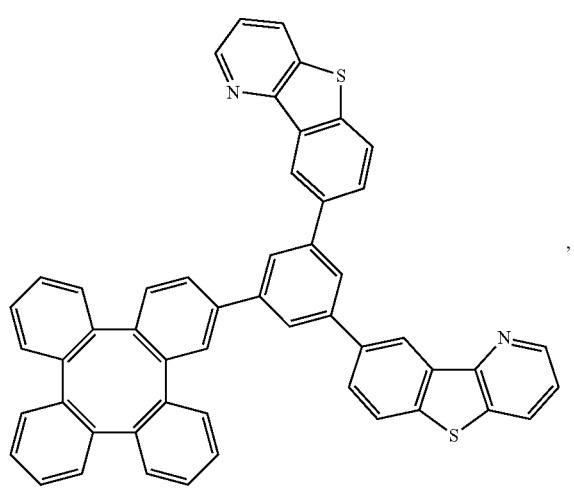
Compound 250
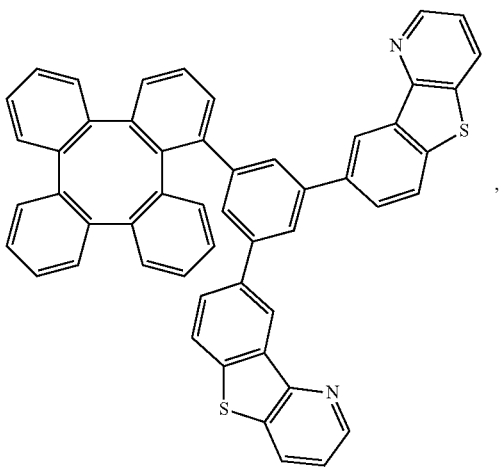
Compound 251
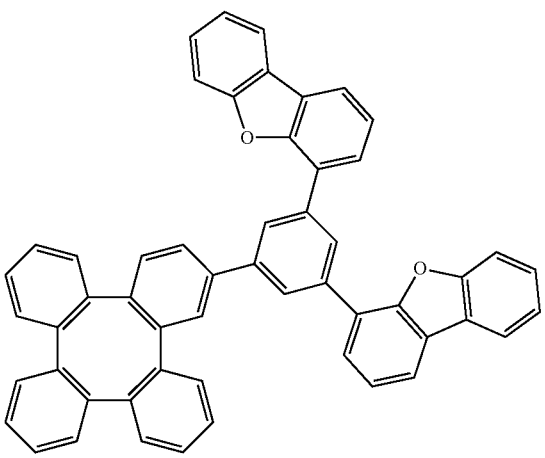
Compound 252
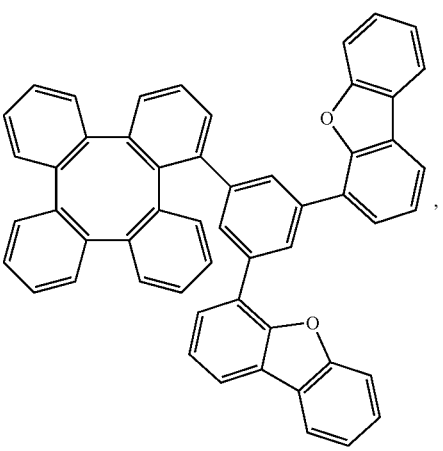

Compound 253
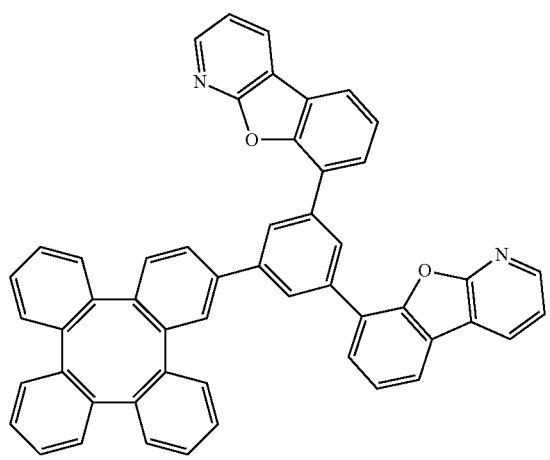
Compound 254
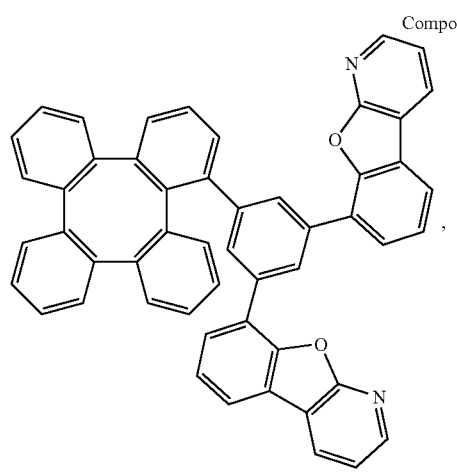
Compound 255
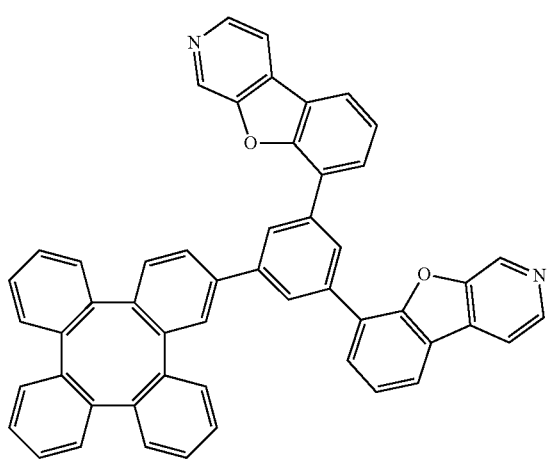
Compound 256
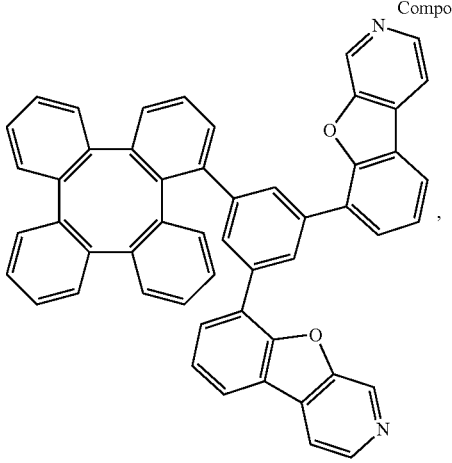
Compound 257
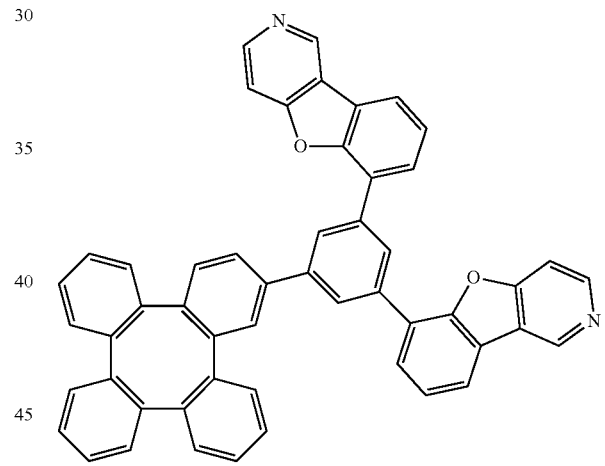
Compound 258
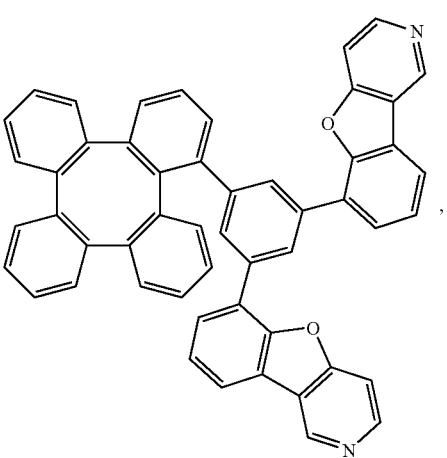

Compound 259
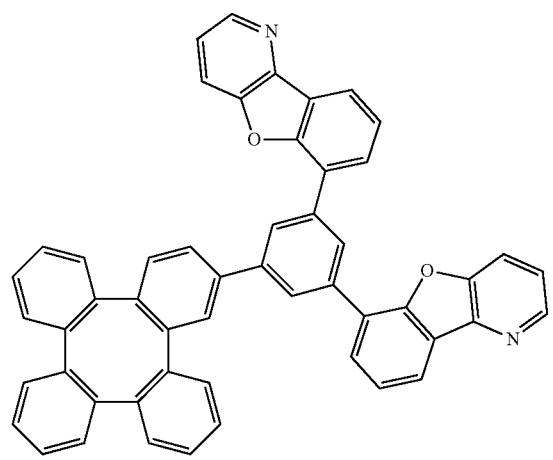
Compound 260
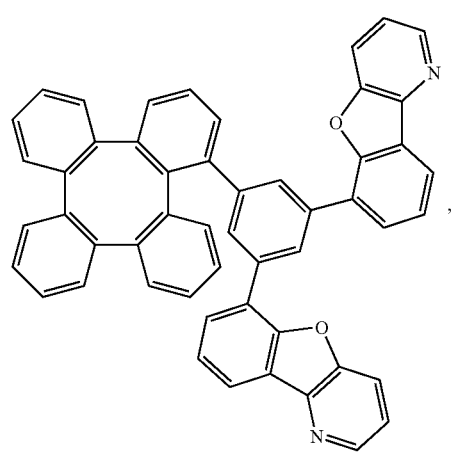
Compound 261
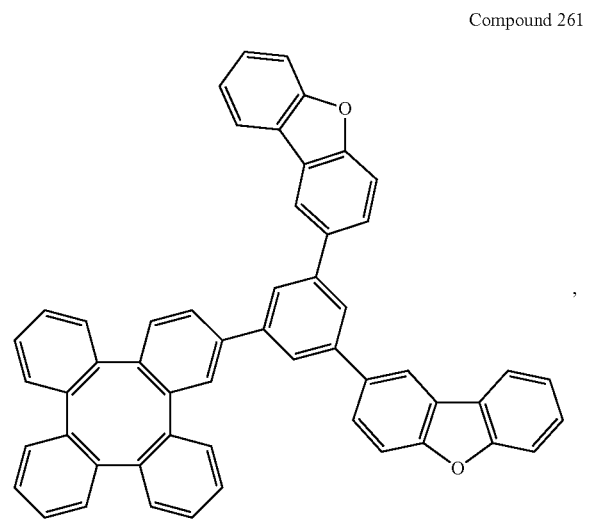
Compound 262
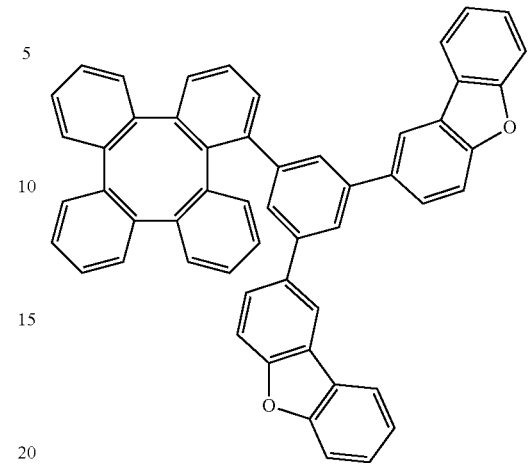
Compound 263
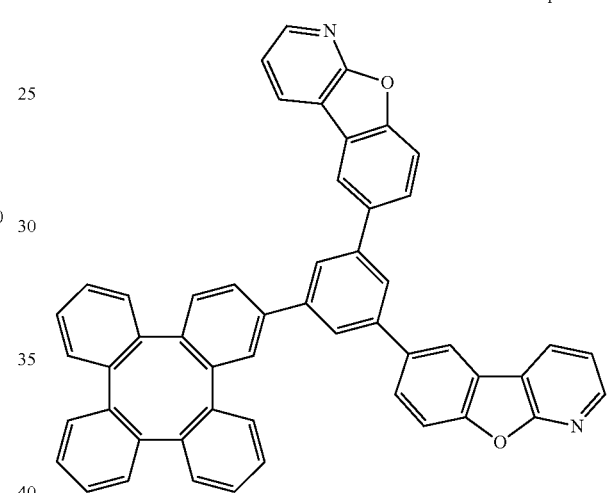
Compound 264
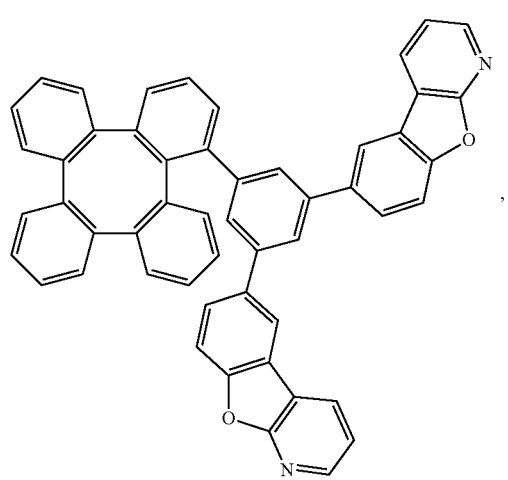

Compound 265
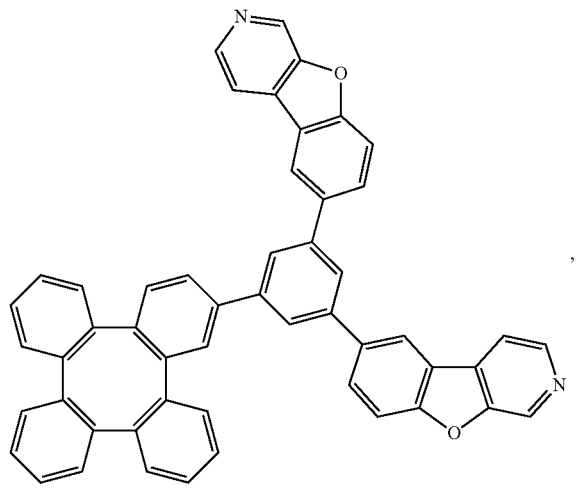
Compound 266
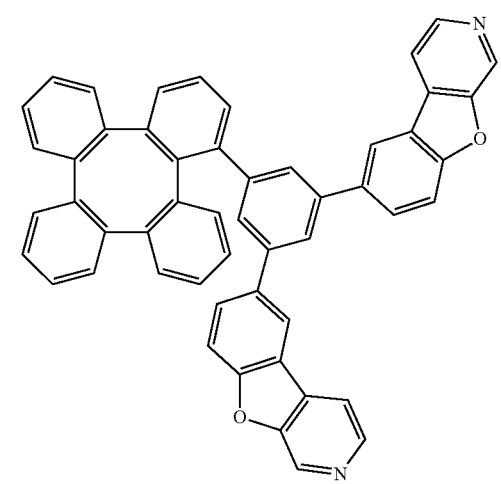
Compound 267
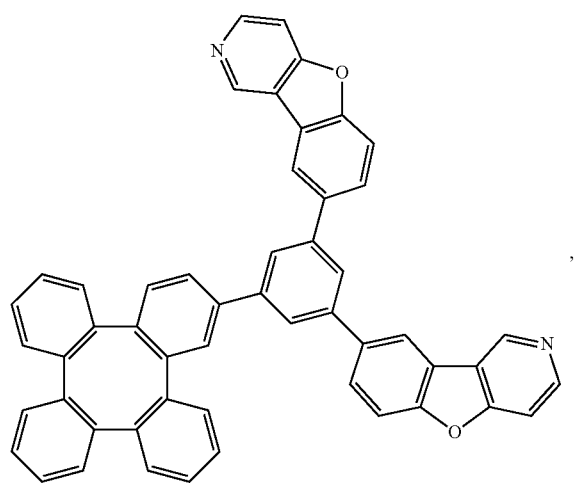
Compound 268
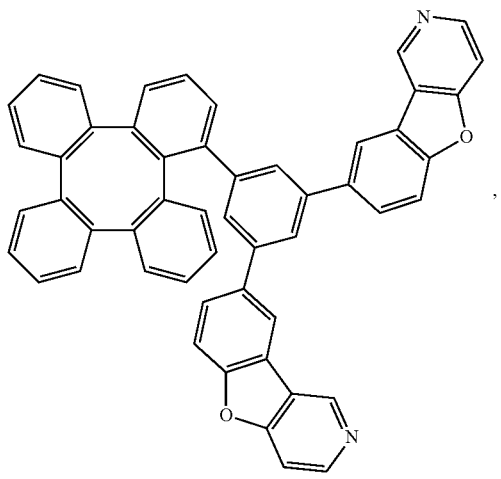
Compound 269
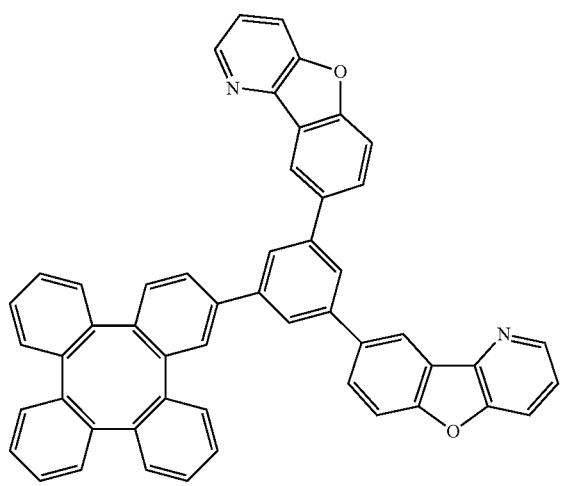
Compound 270
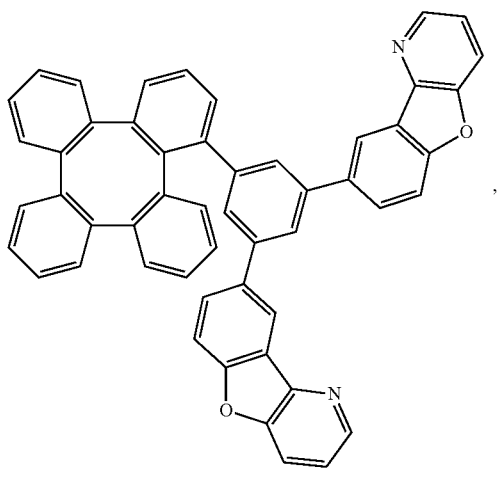

Compound 271
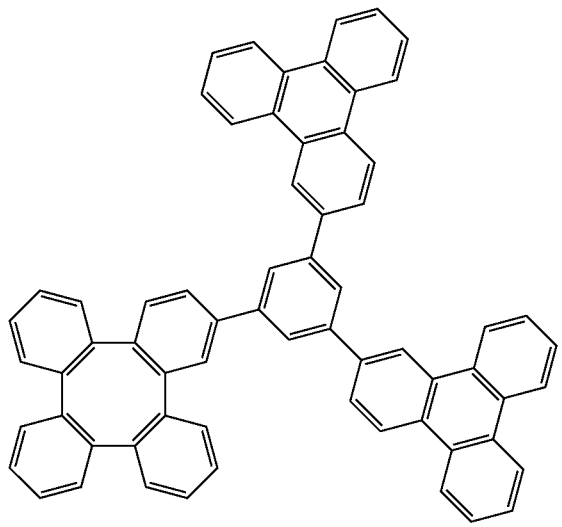
Compound 272
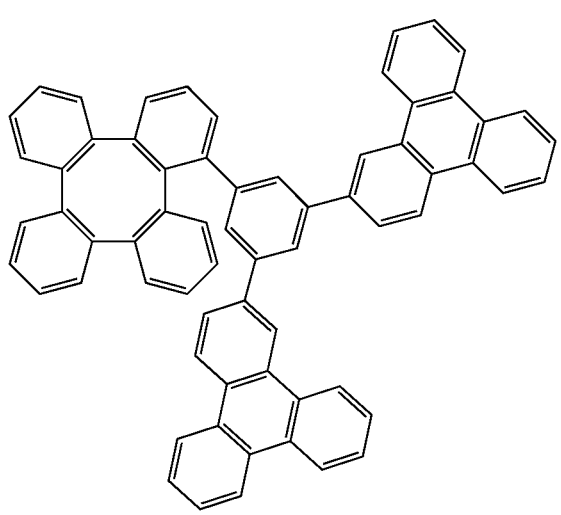
Compound 273
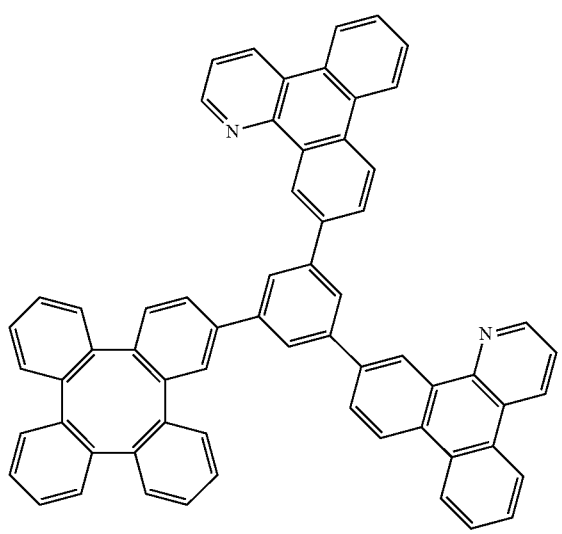
Compound 274
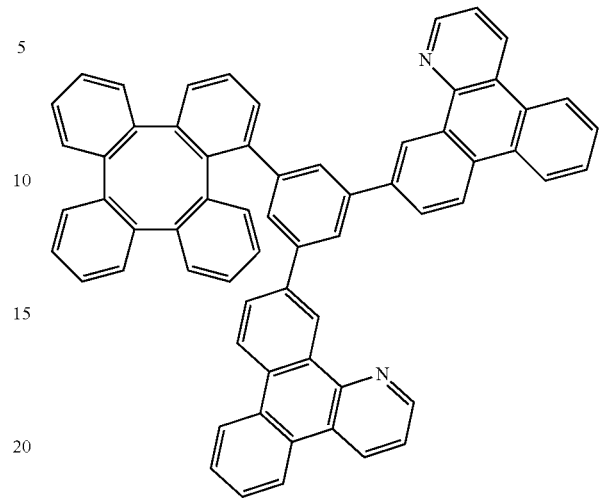
Compound 275
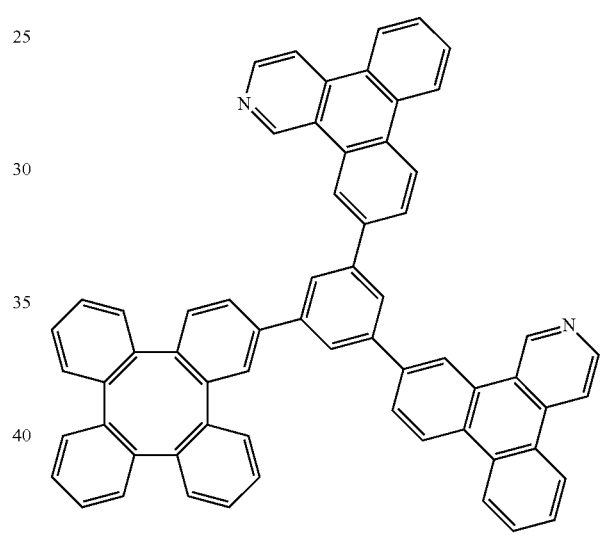
Compound 276
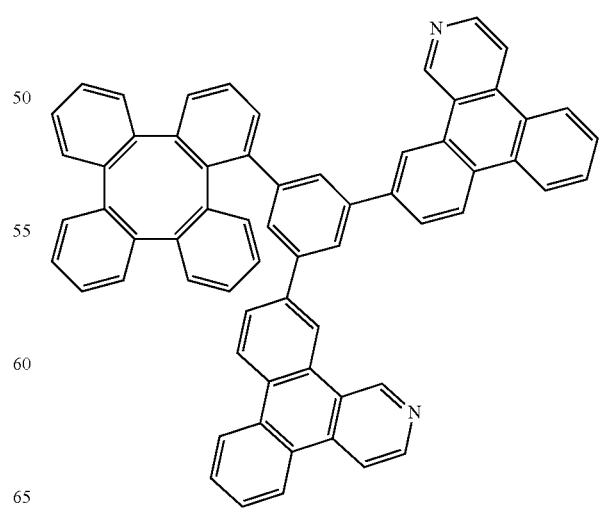

Compound 277
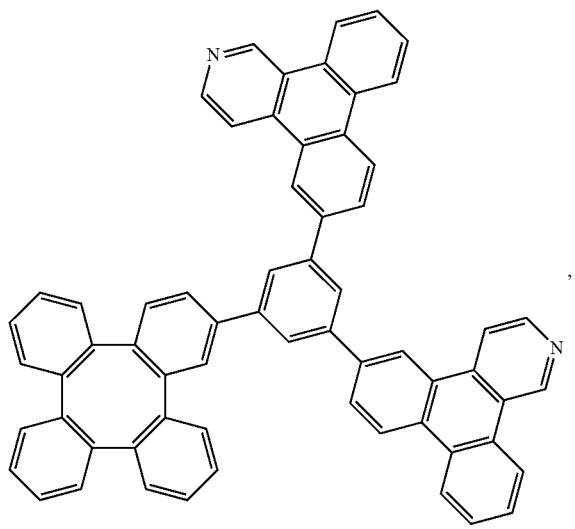
Compound 278
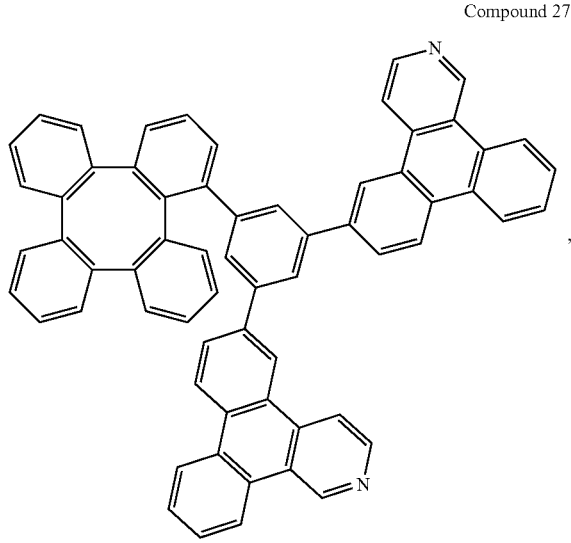
Compound 279
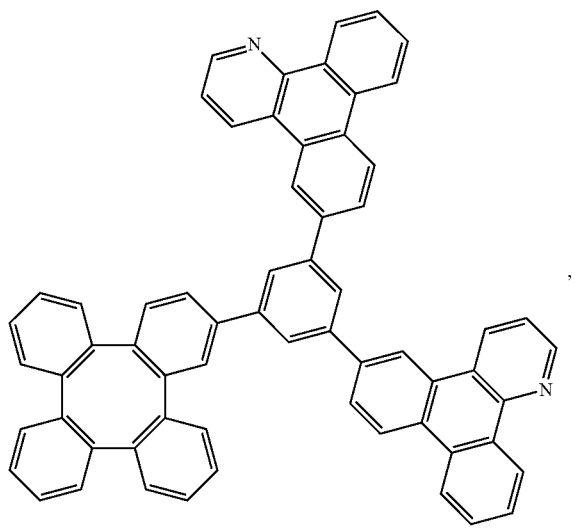
Compound 280
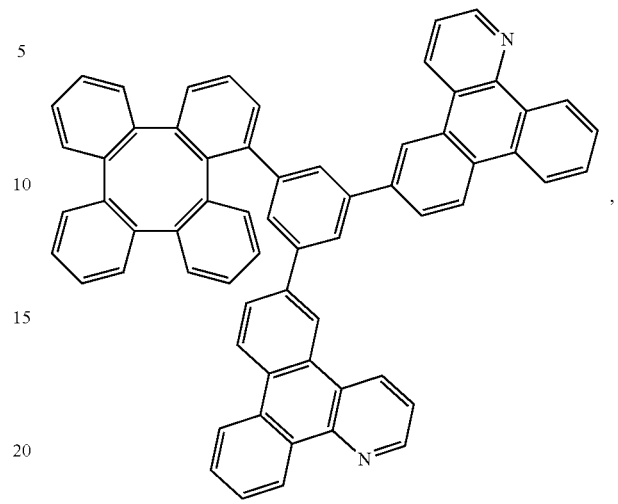
Compound 281
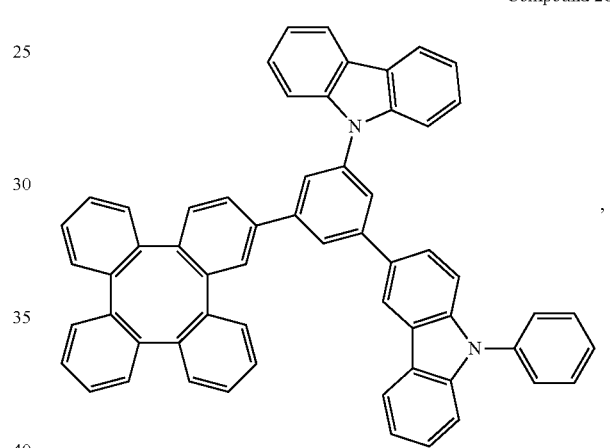
Compound 282

Compound 283
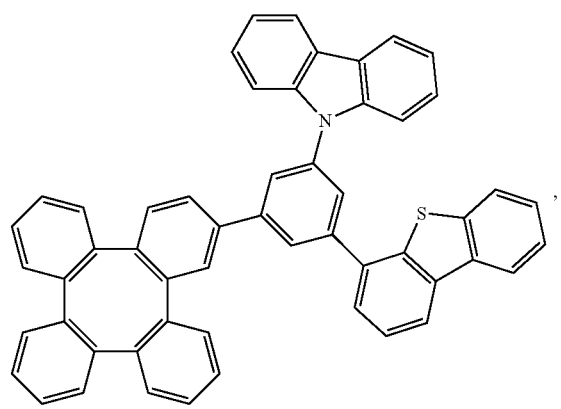
Compound 284
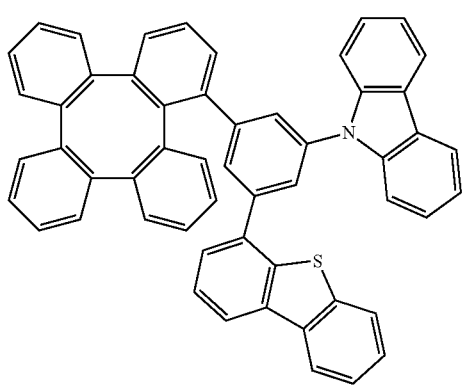
Compound 285
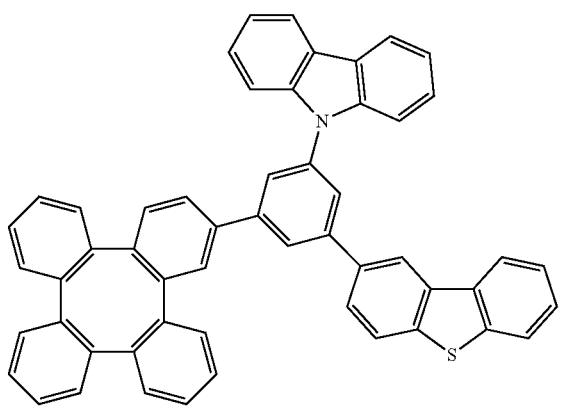
Compound 286
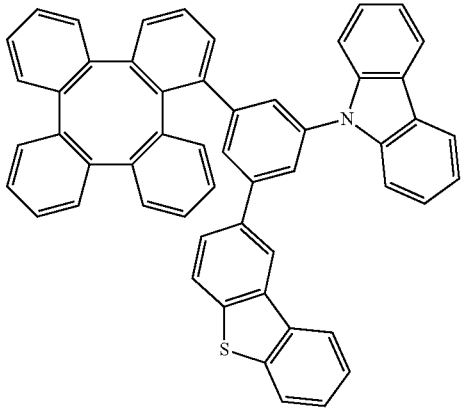
Compound 287
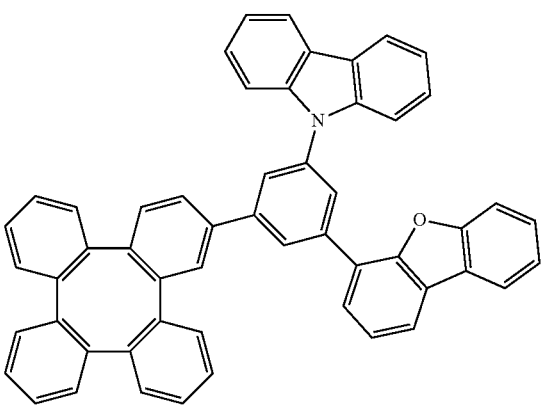
Compound 288
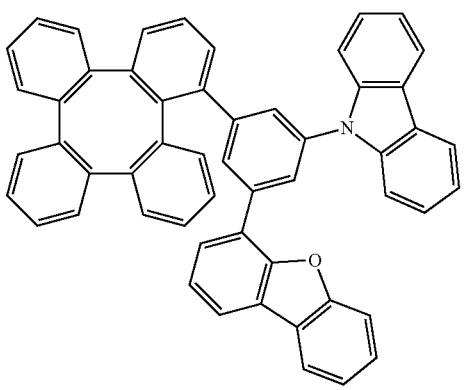

Compound 289
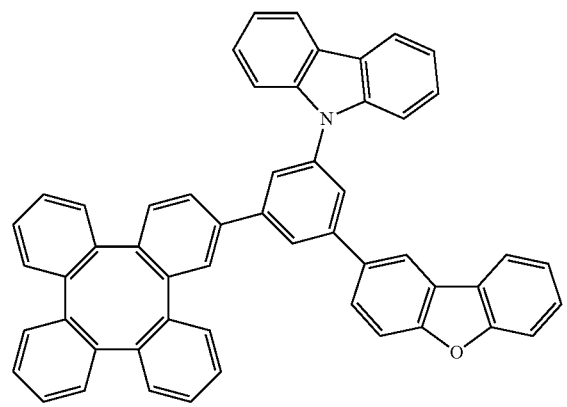
Compound 290
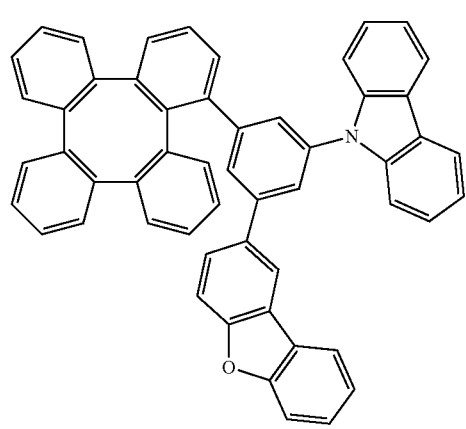
Compound 291
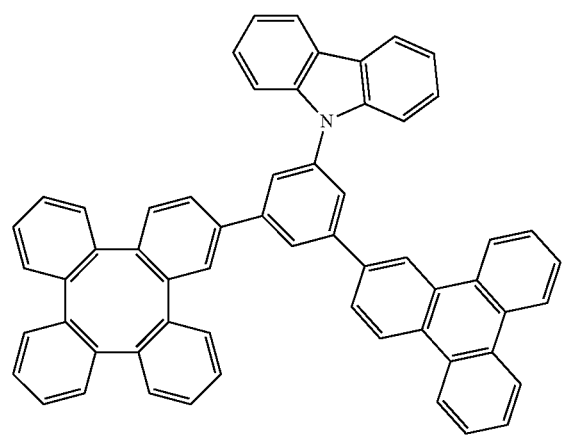
Compound 292
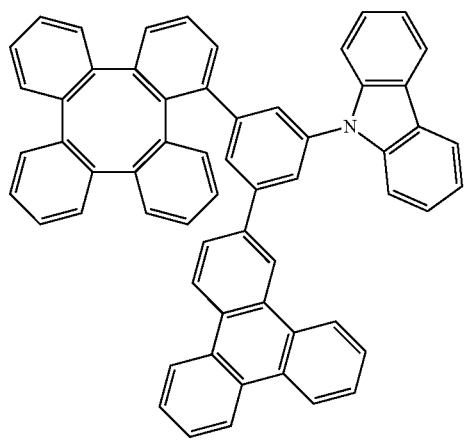
Compound 293
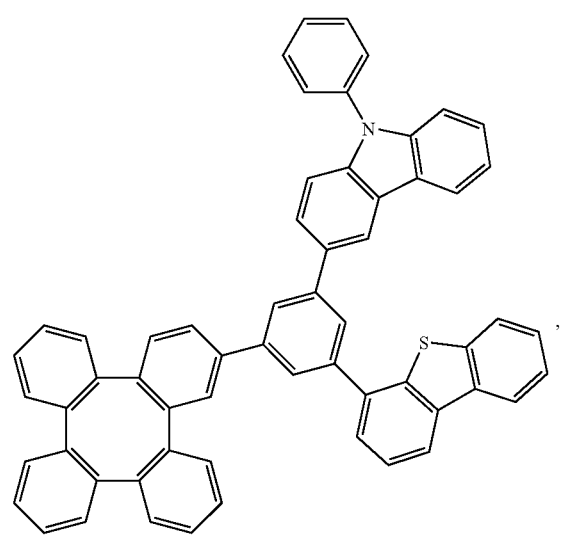
Compound 294
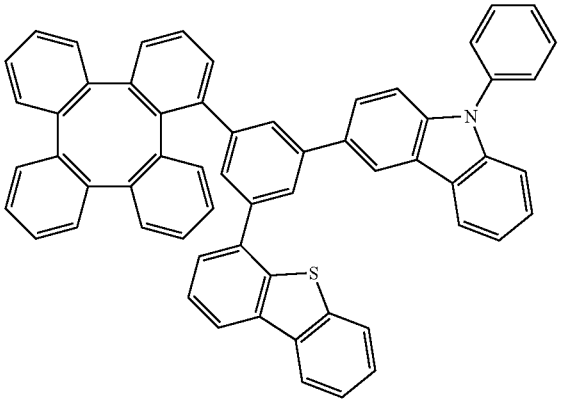

Compound 295
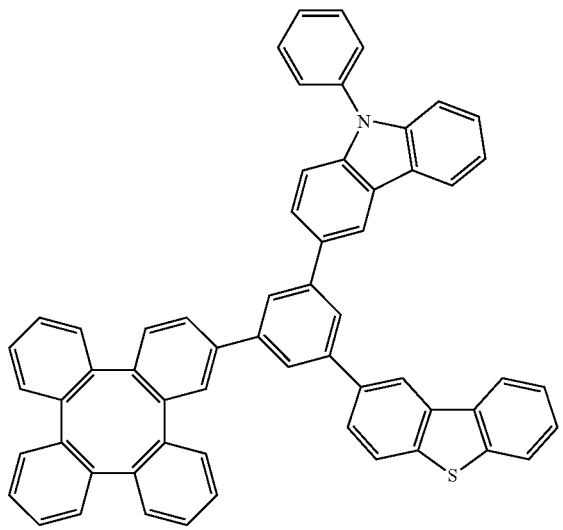
Compound 296
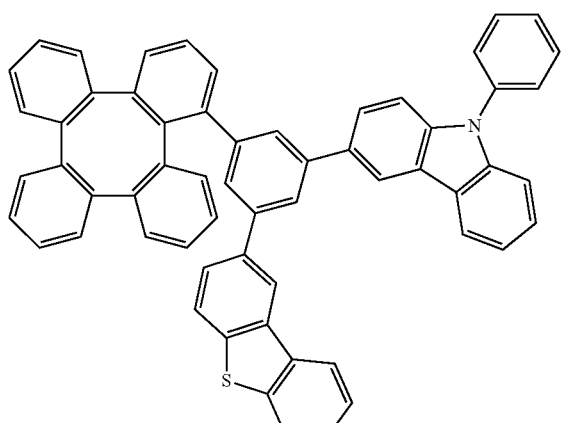
Compound 297
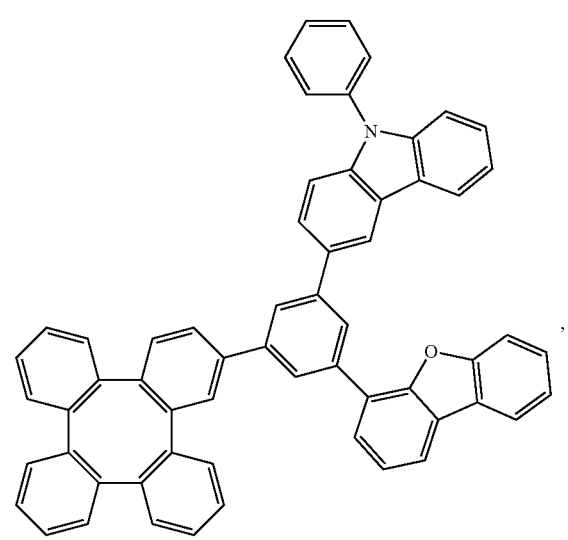
Compound 298
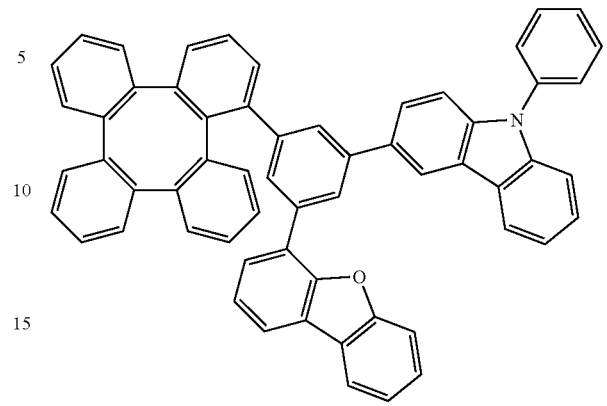
Compound 299
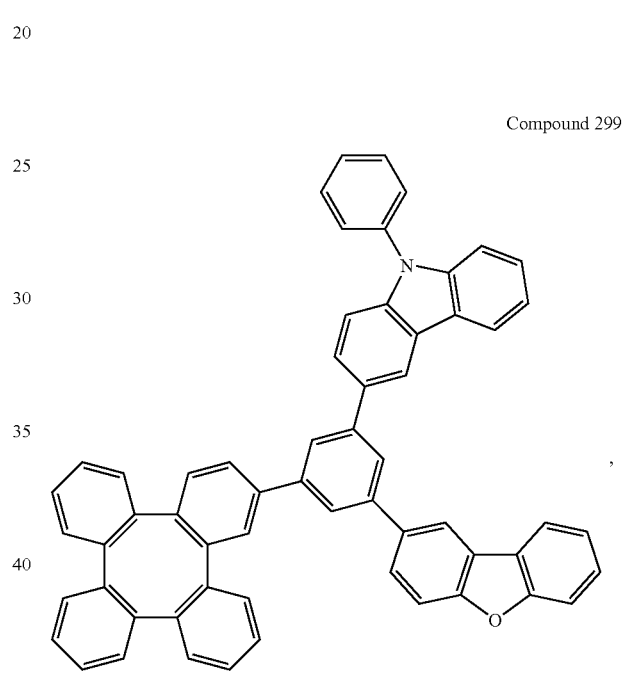
Compound 300
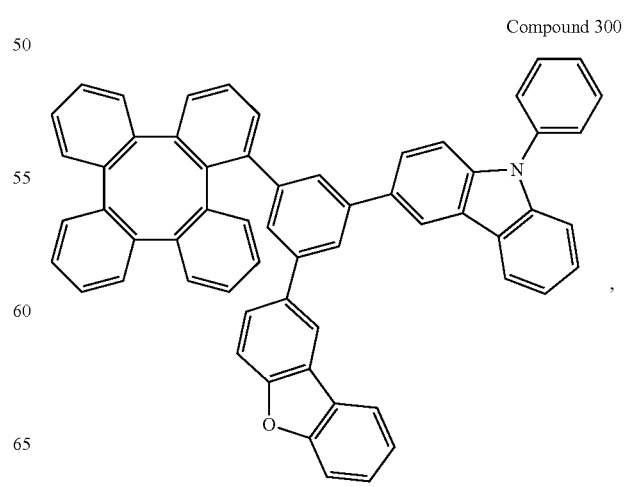

Compound 301
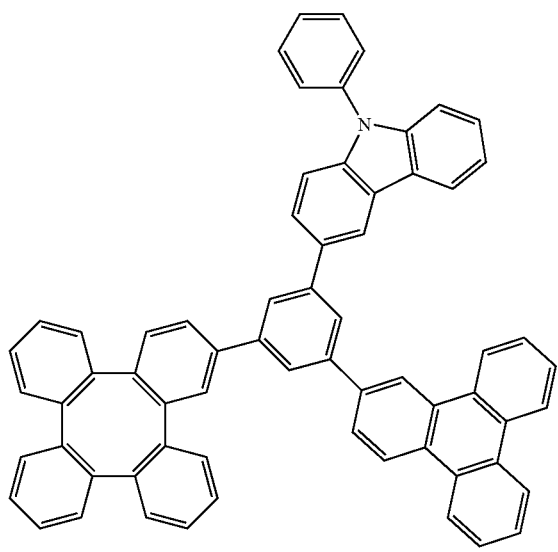
Compound 302
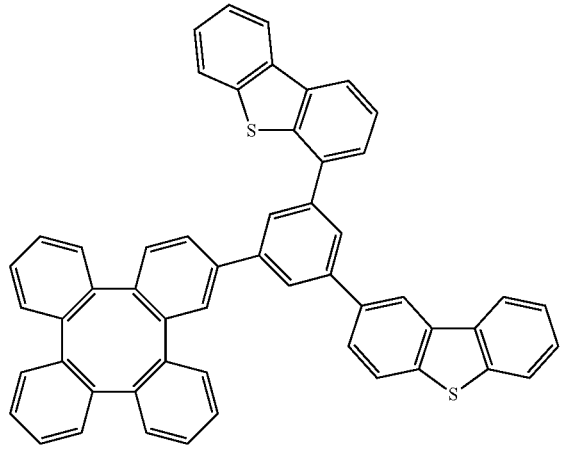
Compound 303
Compound 304
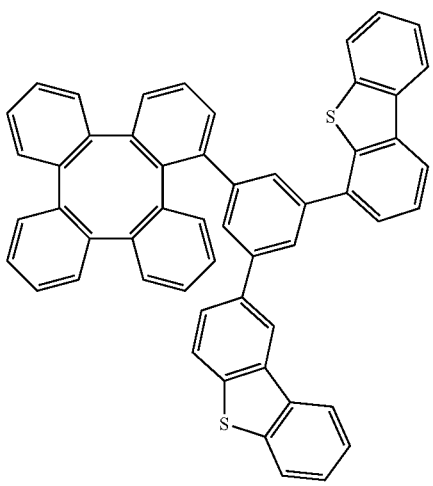
Compound 305
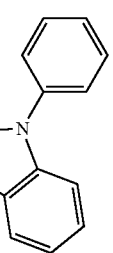
Compound 306
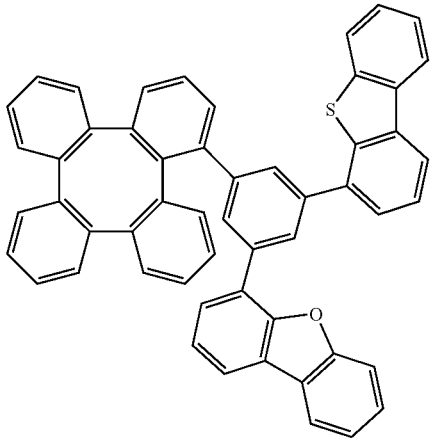

Compound 307
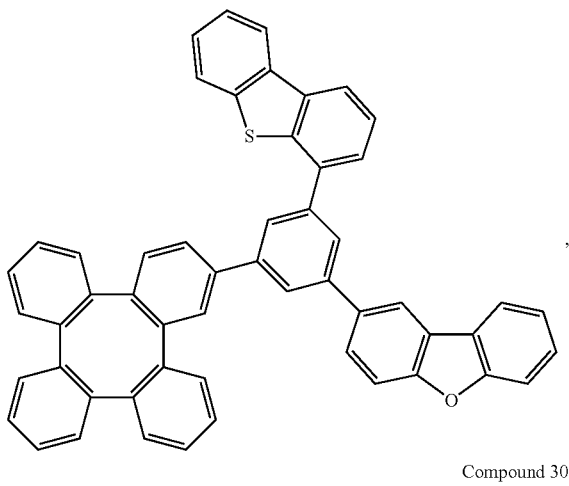
Compound 308
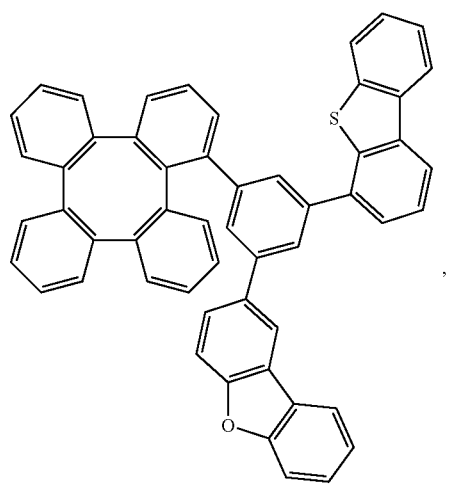
Compound 309
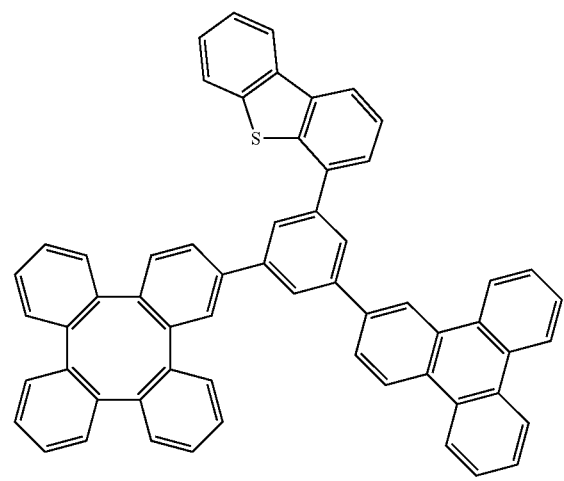
Compound 310
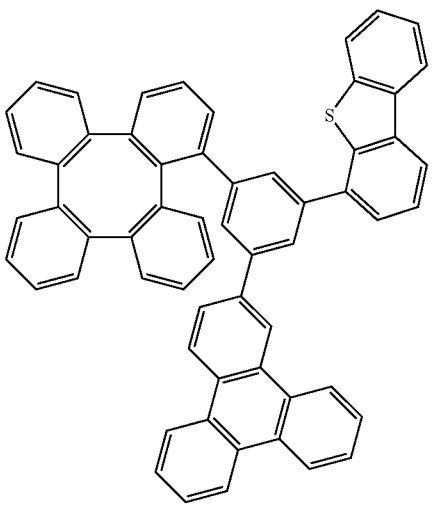
Compound 311
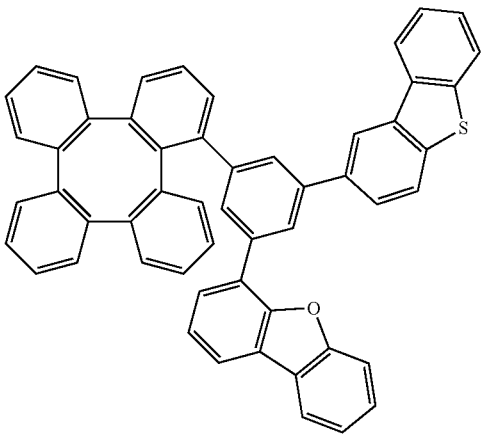
Compound 312

Compound 313
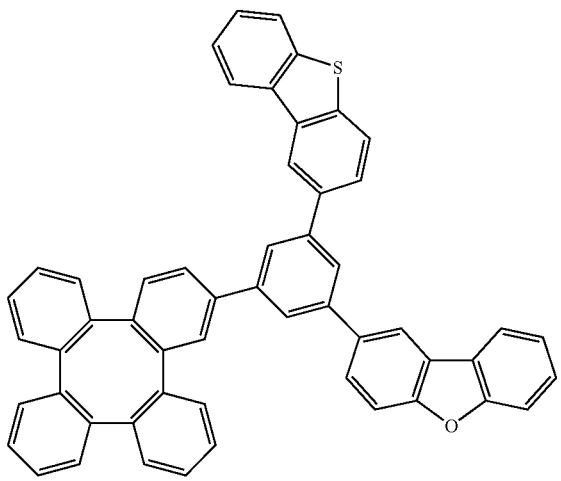
Compound 314
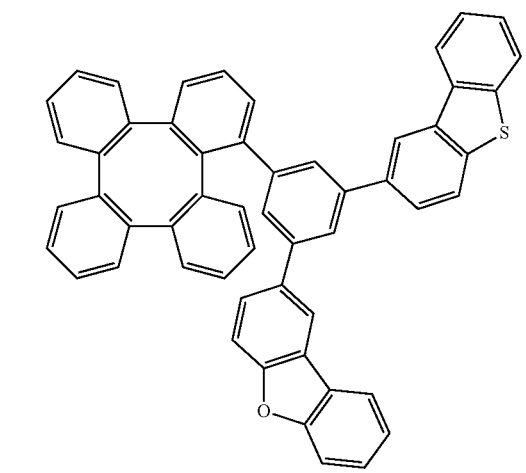
Compound 315
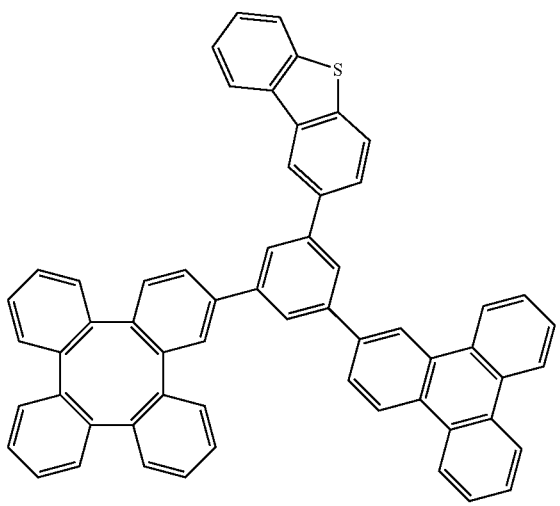
Compound 316
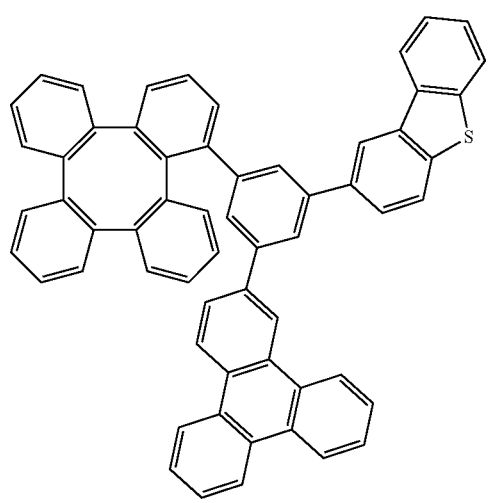
Compound 317
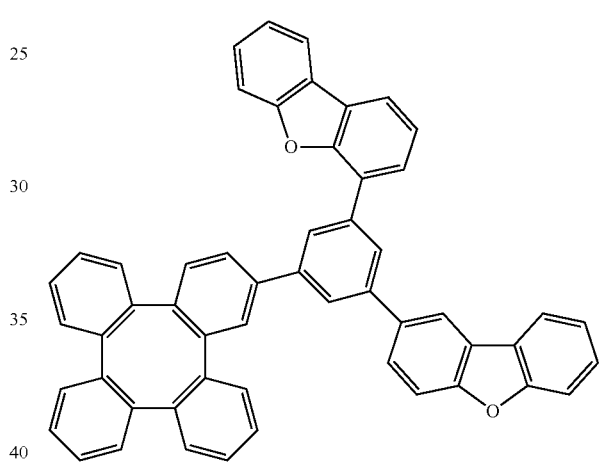
Compound 318
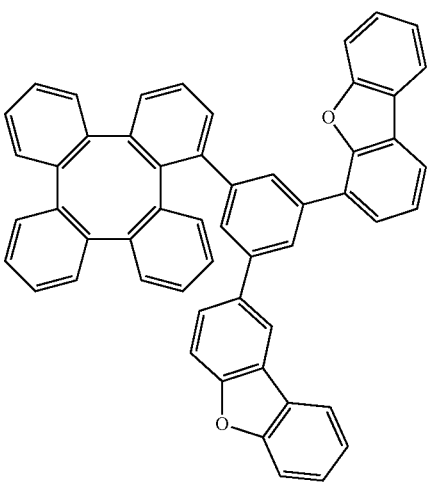

Compound 319
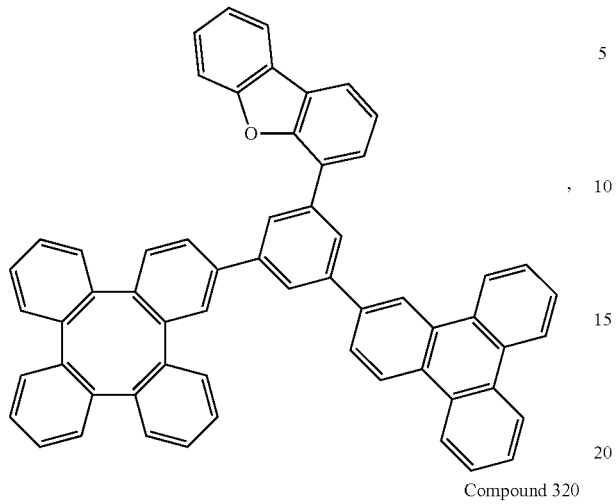
Compound 320
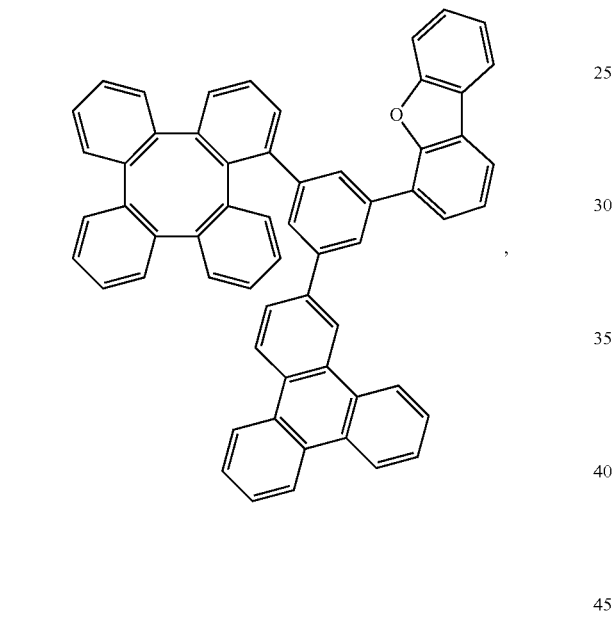
Compound 321
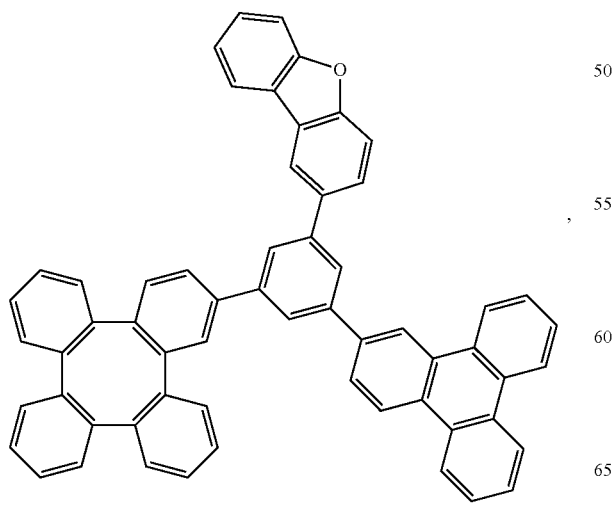
Compound 322
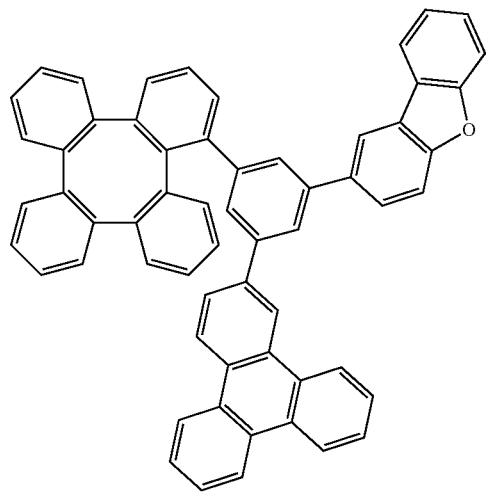
Compound 323
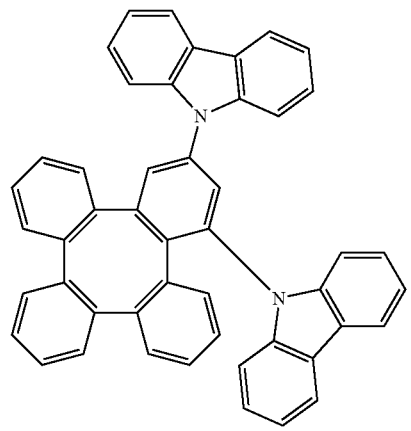
Compound 324
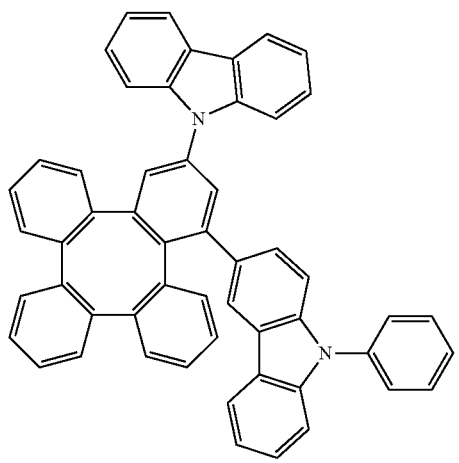

Compound 325
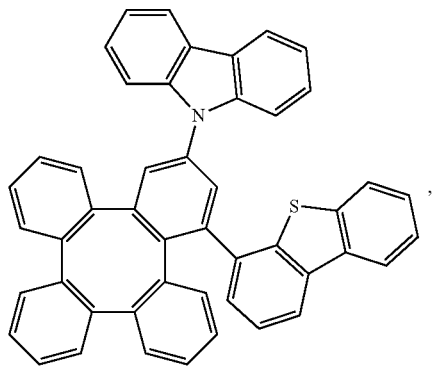
Compound 326
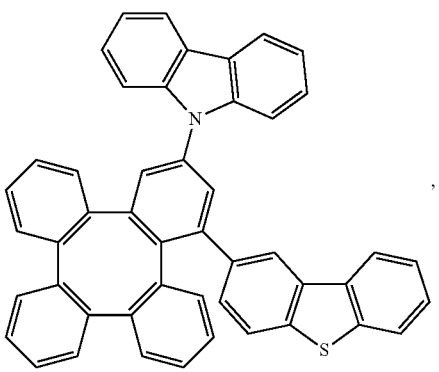
Compound 327
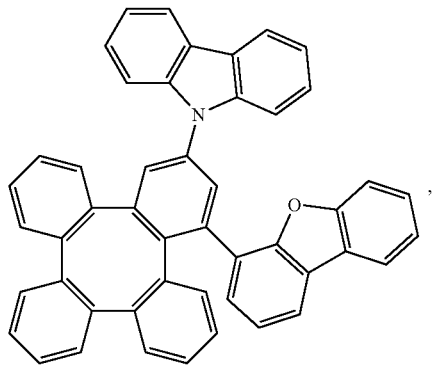
Compound 328
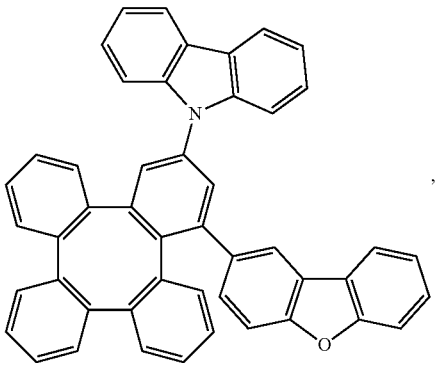
Compound 329
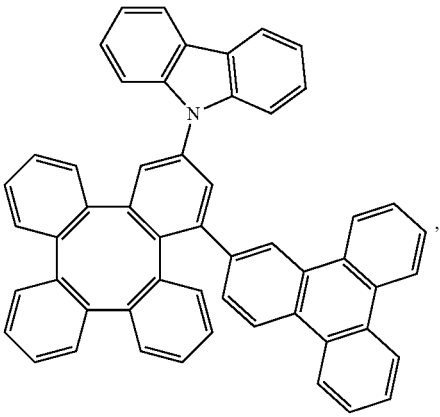
Compound 330
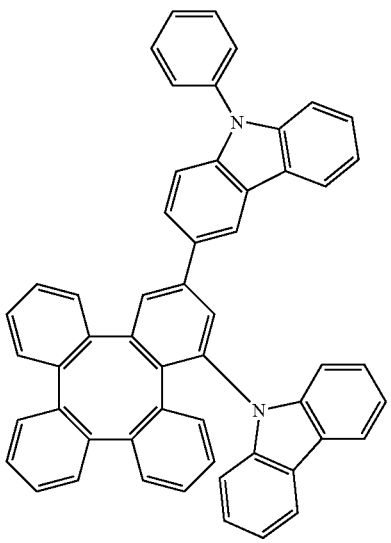
Compound 331
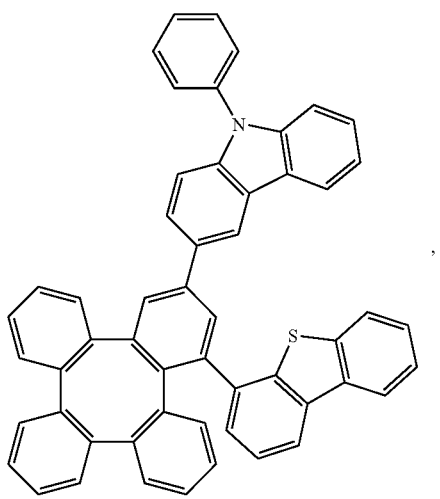

Compound 332
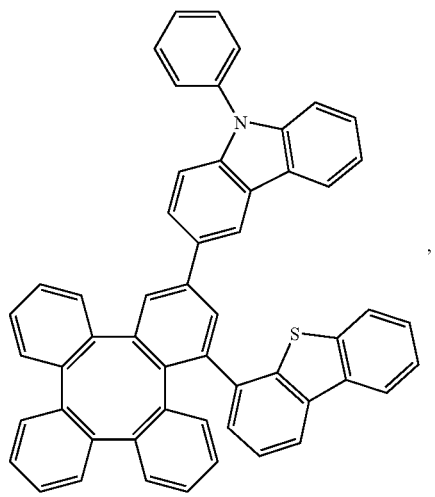
Compound 333
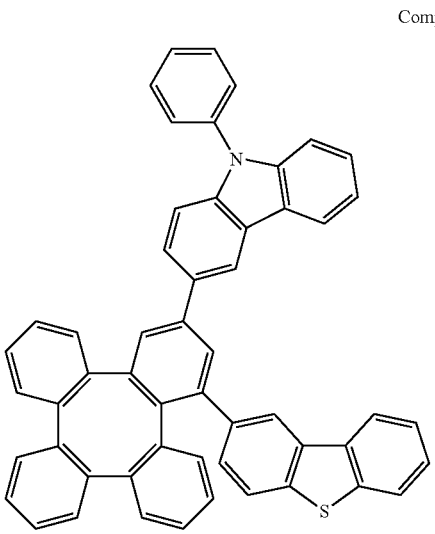
Compound 334
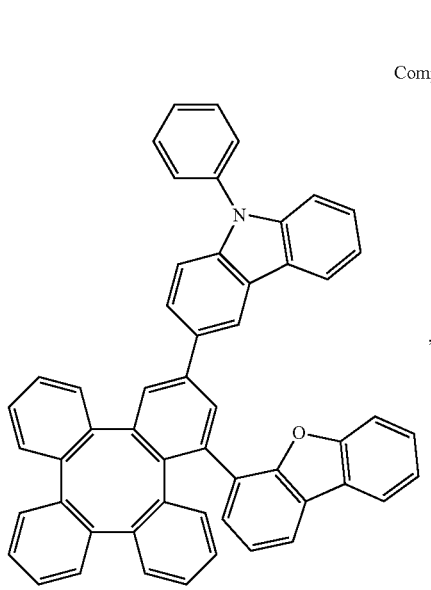
Compound 335
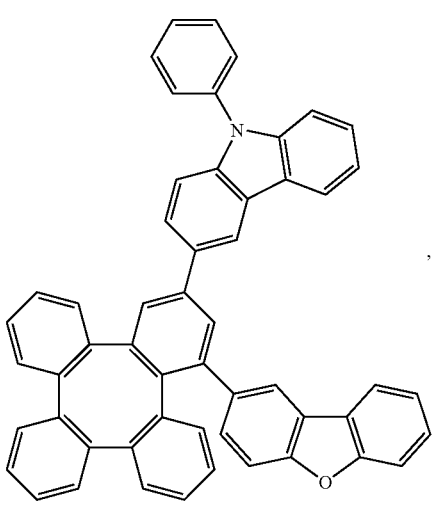
Compound 336
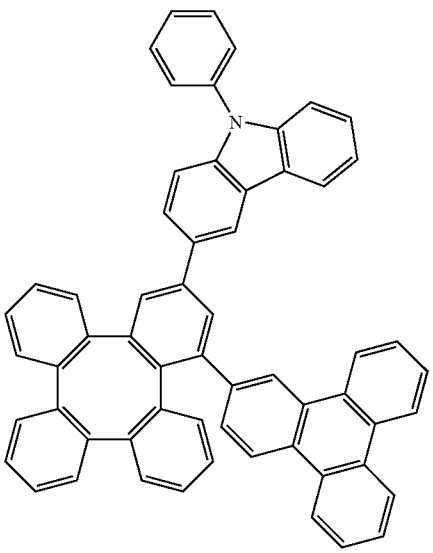
Compound 337
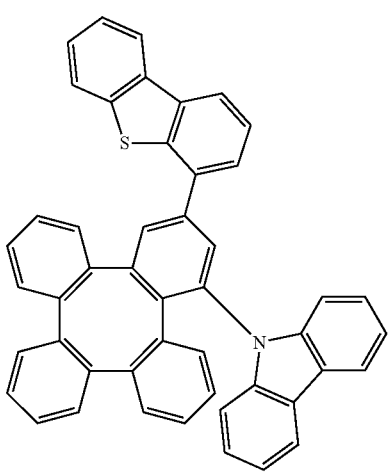

Compound 338
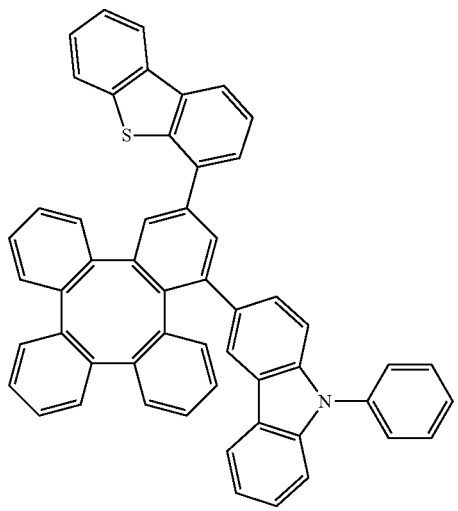
Compound 339
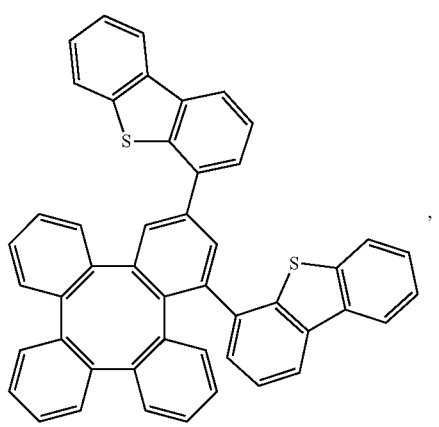
Compound 340
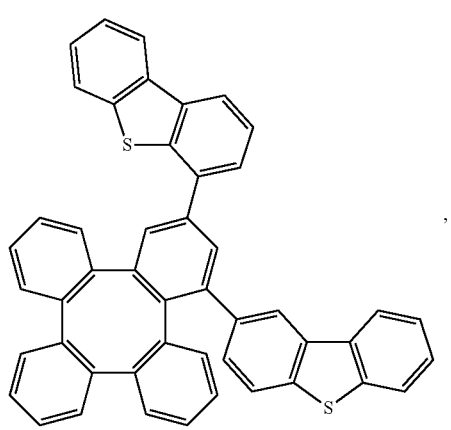
Compound 341
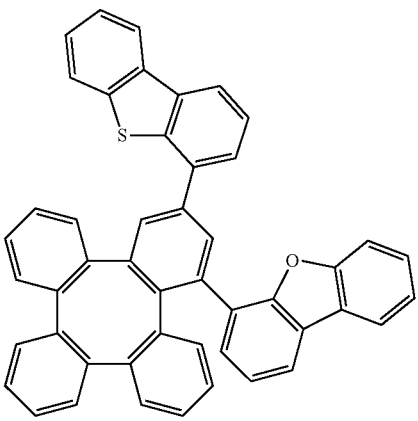
Compound 342
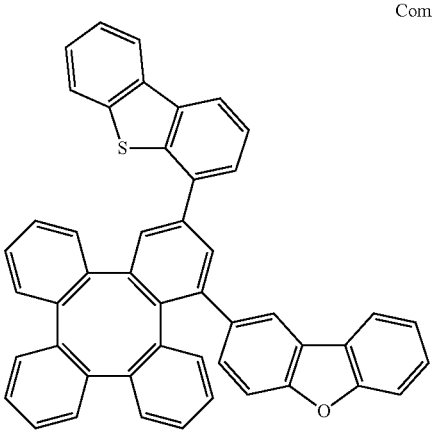
Compound 343

Compound 344
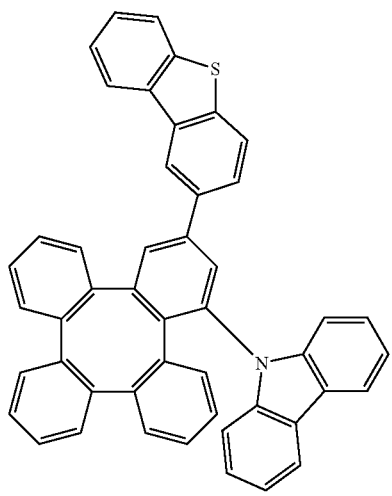
Compound 345
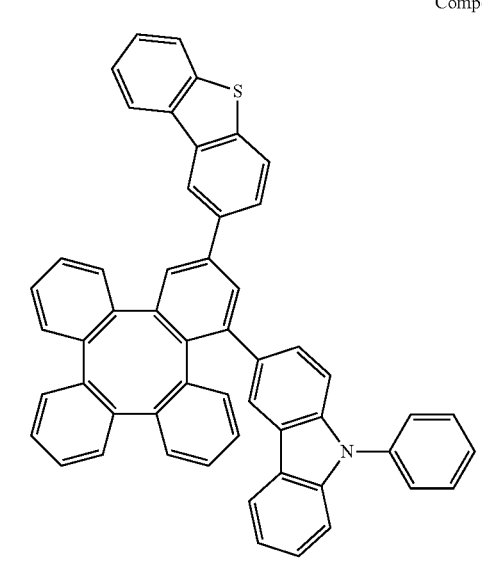
Compound 346
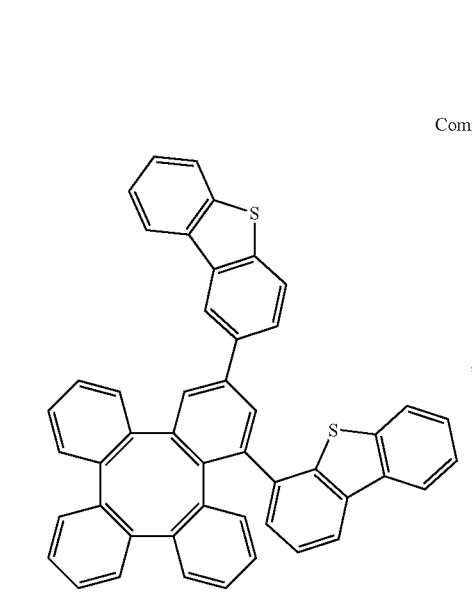
Compound 347
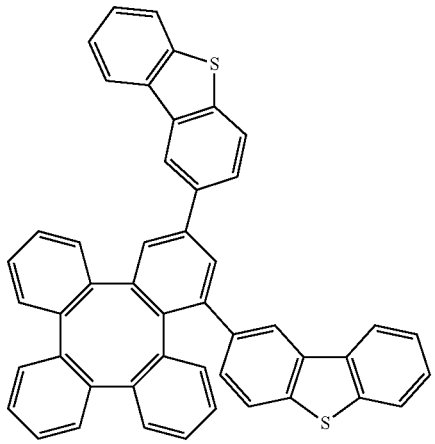
Compound 348
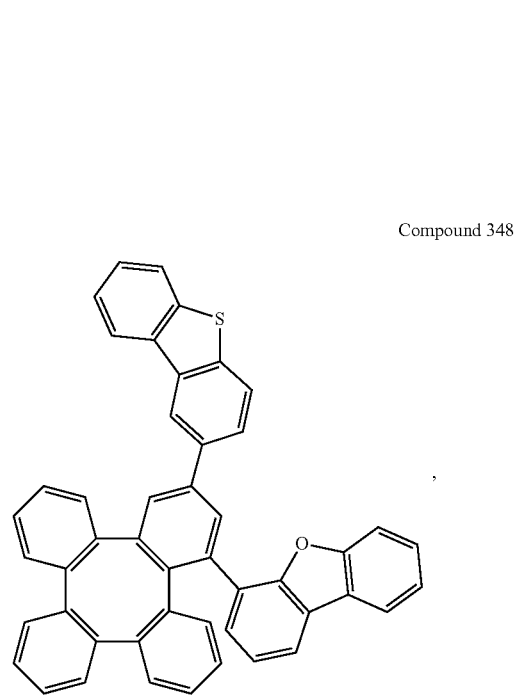
Compound 349
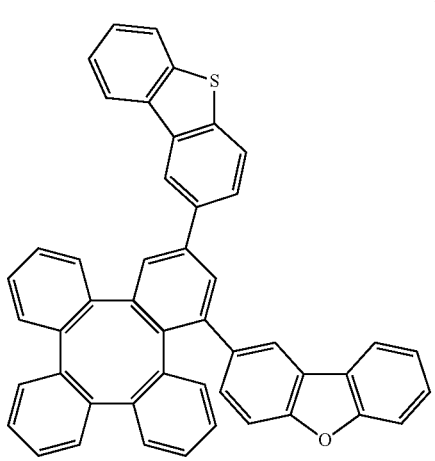

Compound 350
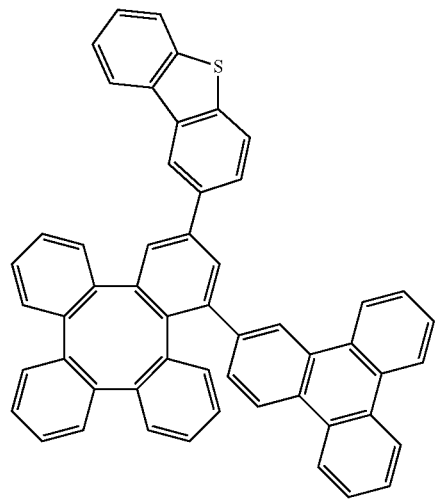
Compound 351
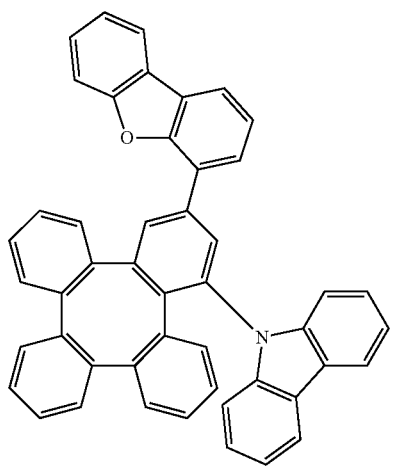
Compound 352
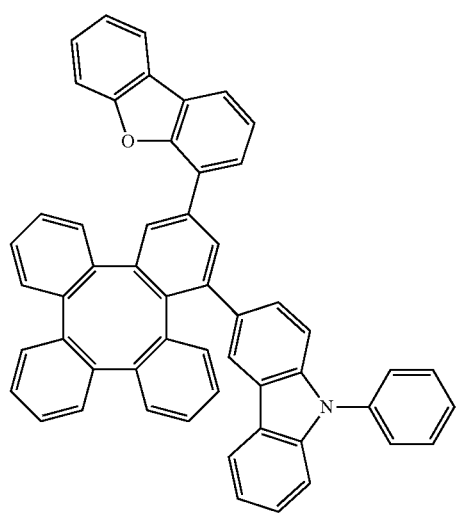
Compound 353
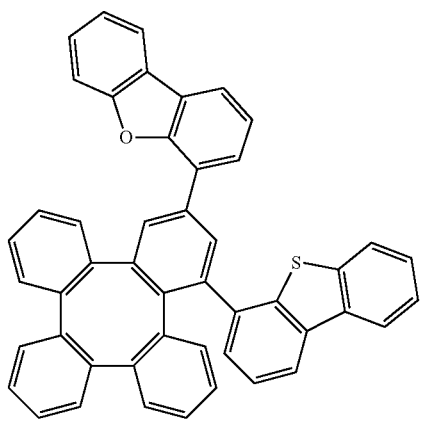
Compound 354
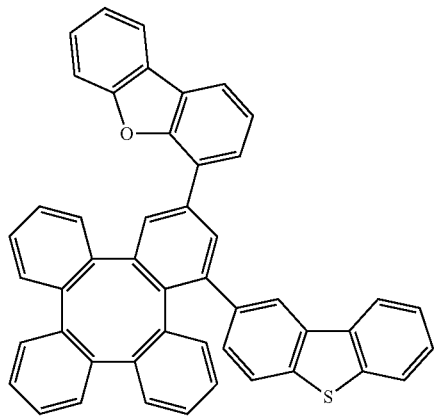
Compound 355
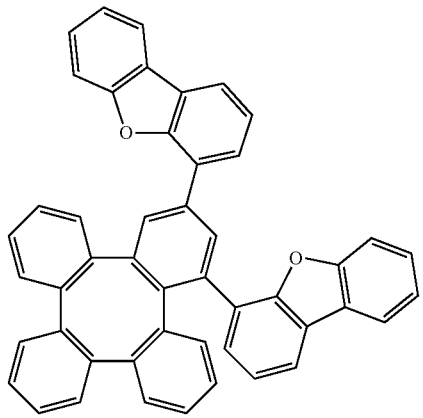

Compound 356
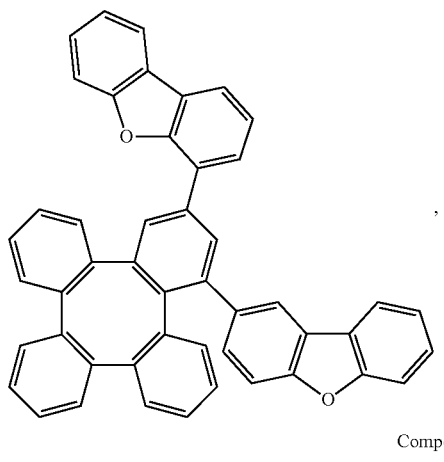
Compound 357
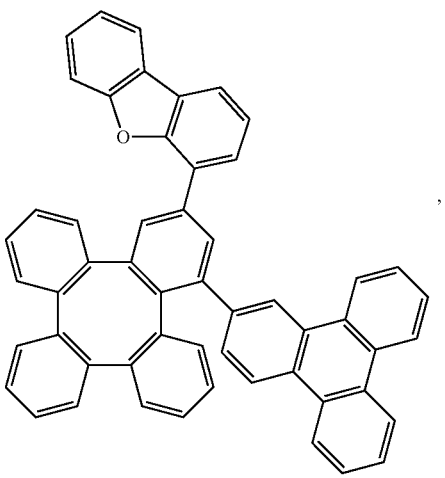
Compound 358
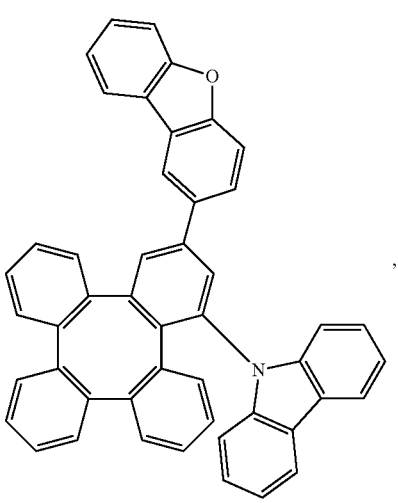
Compound 359
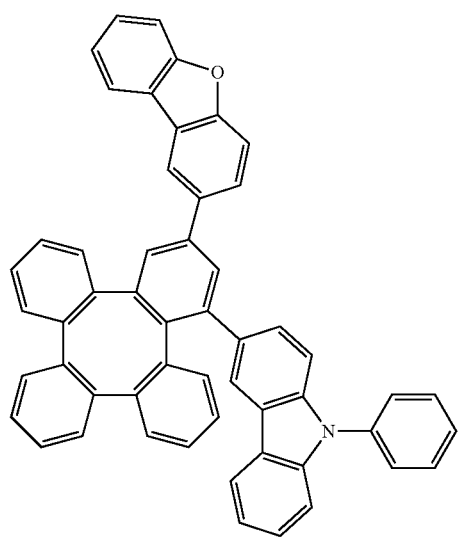
Compound 360
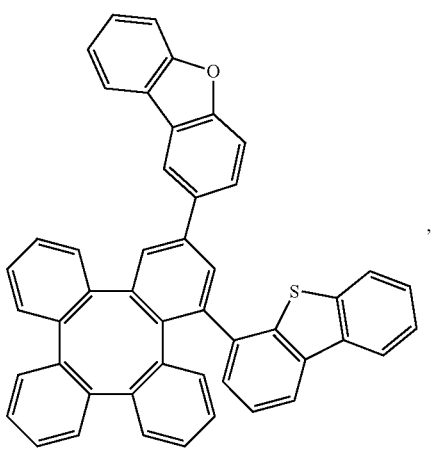
Compound 361
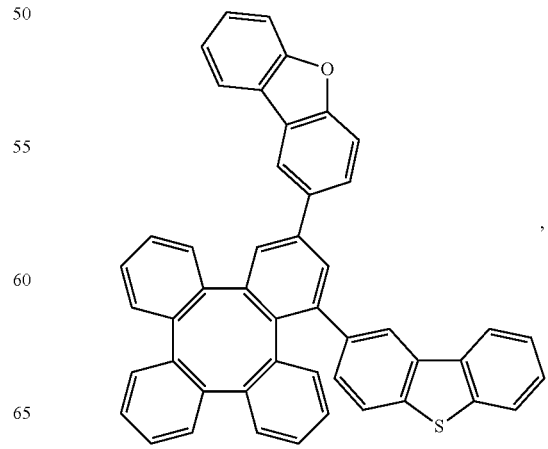

Compound 362
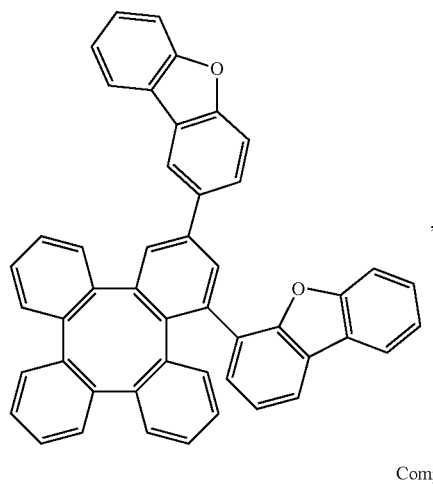
Compound 363
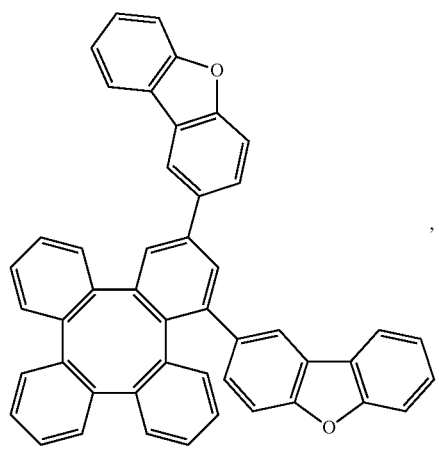
Compound 364
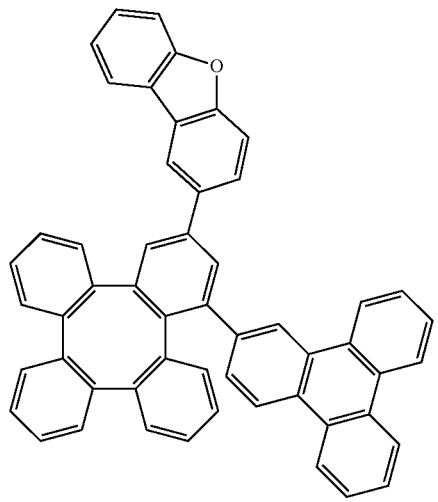
Compound 365
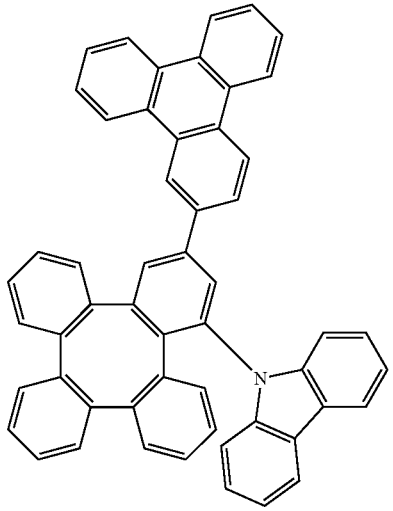
Compound 366
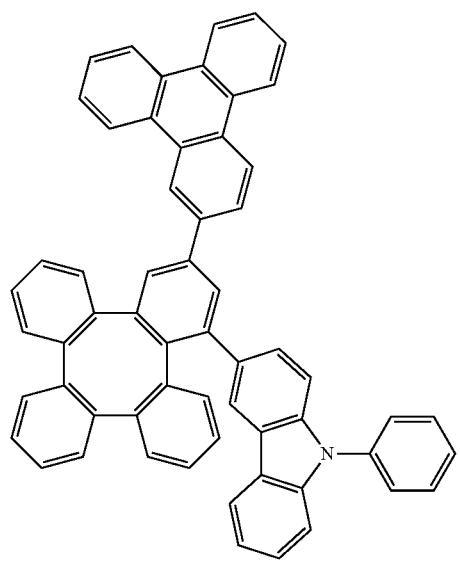
Compound 367
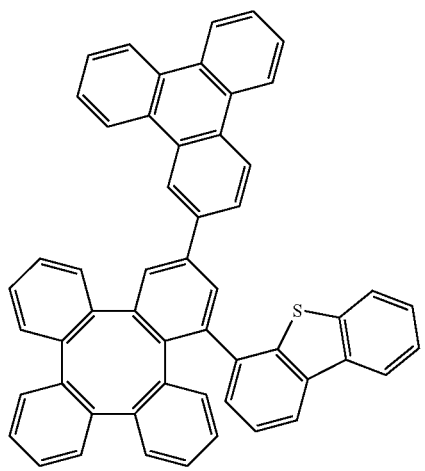

Compound 368
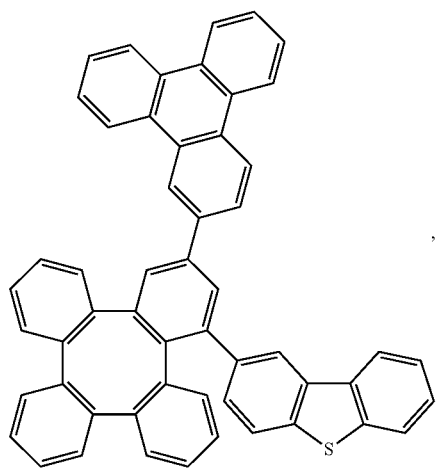
Compound 369
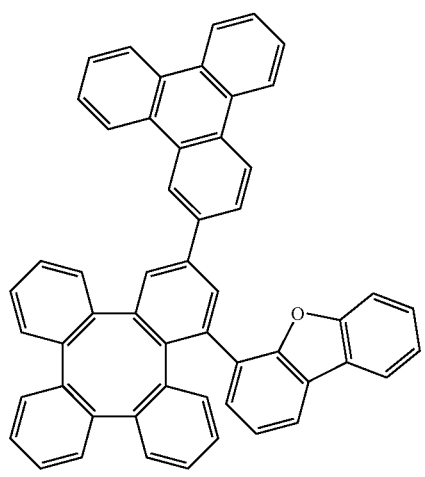
Compound 370
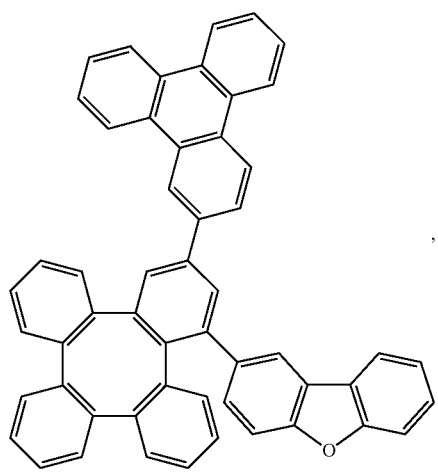
Compound 371
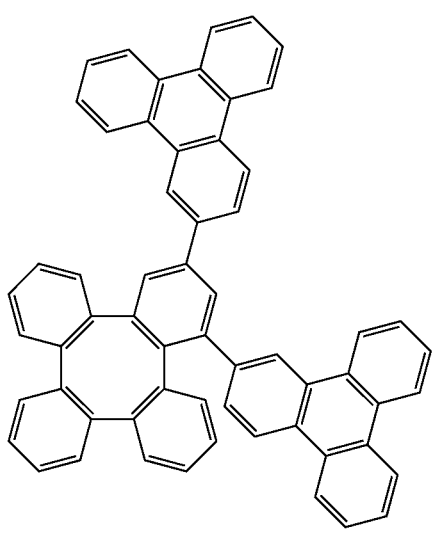
Compound 372
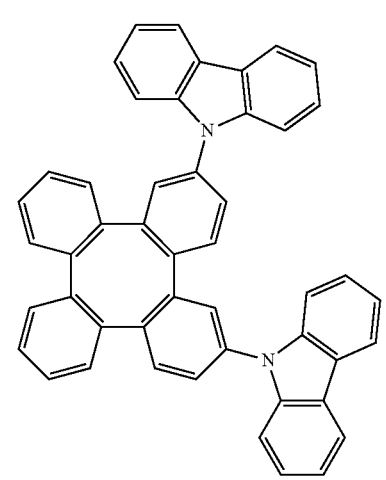
Compound 373

119
-continued
Compound 374
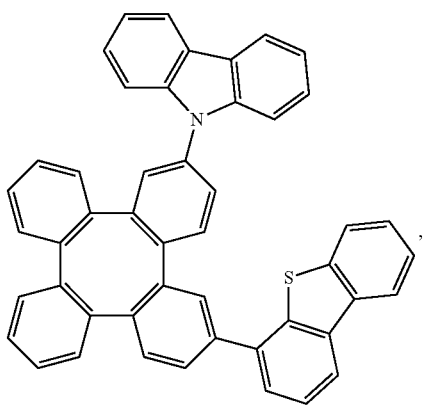
Compound 375
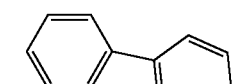
Compound 376
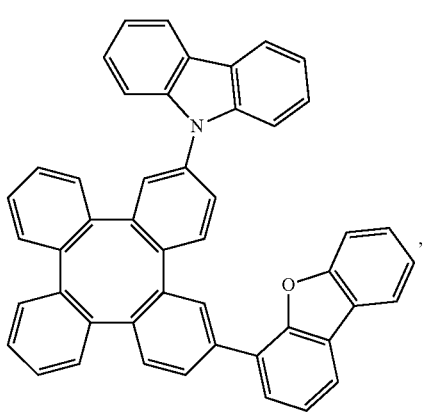
120
-continued
Compound 377
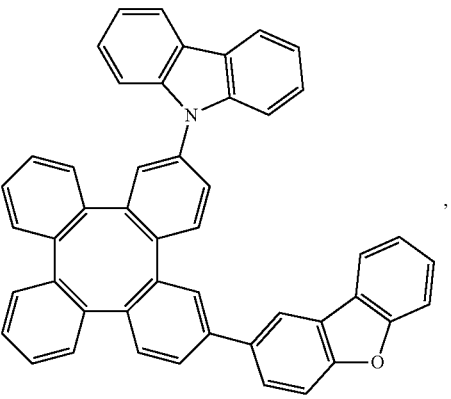
Compound 378
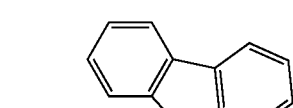
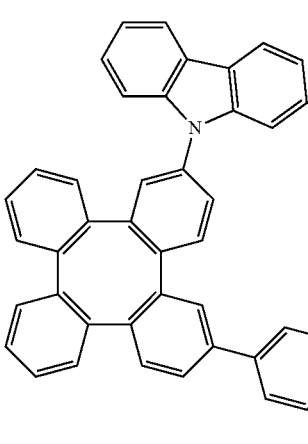
Compound 379
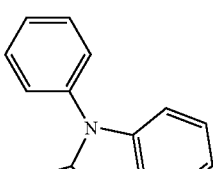

Compound 380
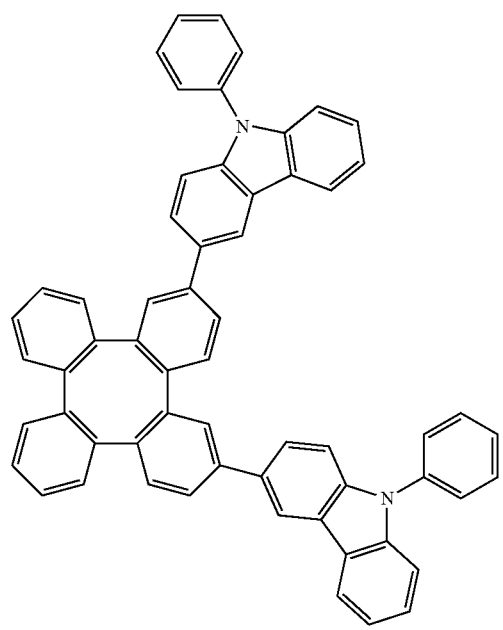
Compound 381
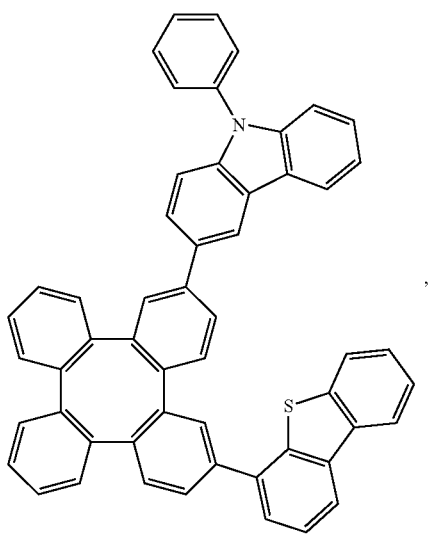
Compound 382
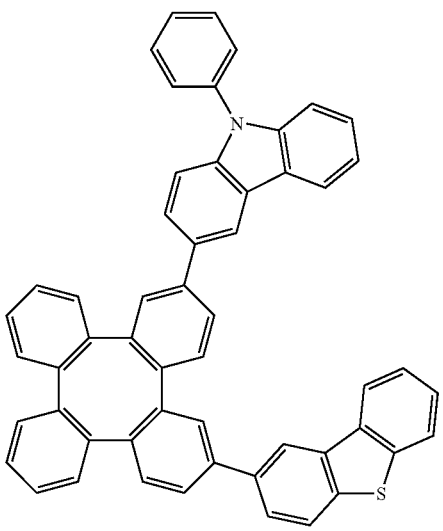
Compound 383
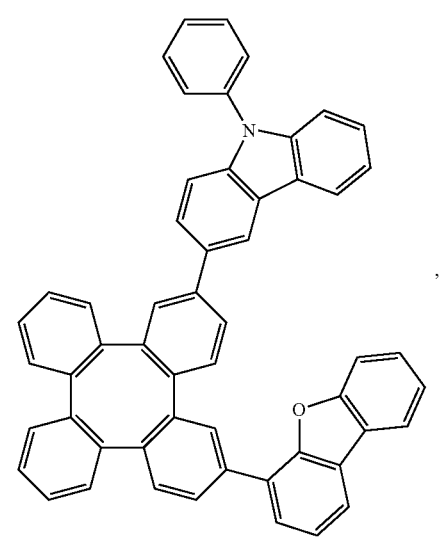
Compound 384
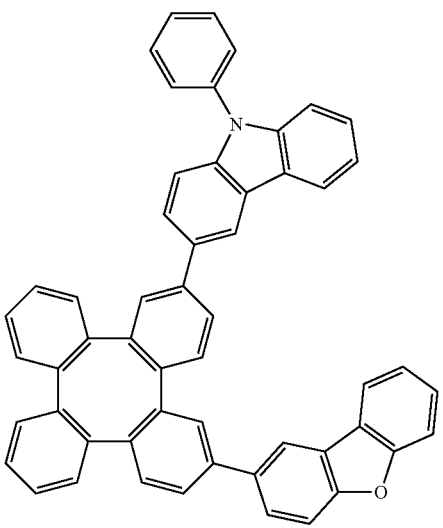

Compound 385
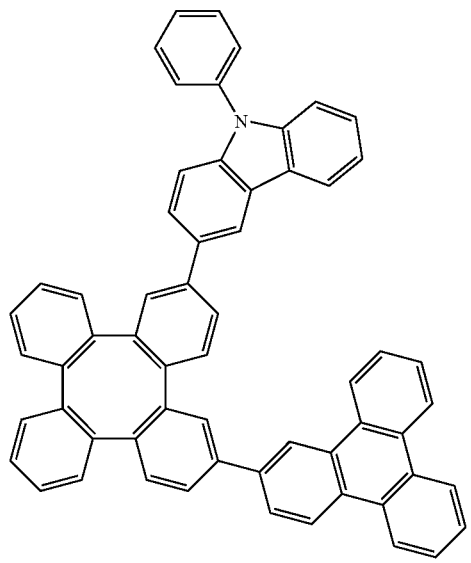
Compound 386
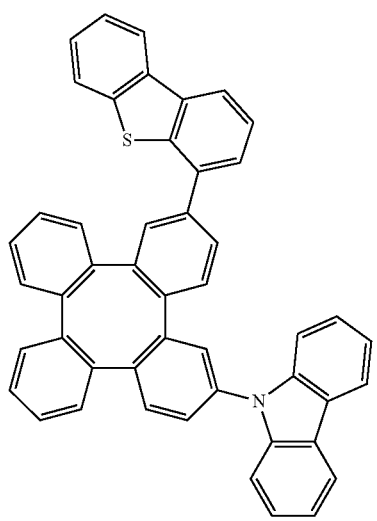
Compound 387
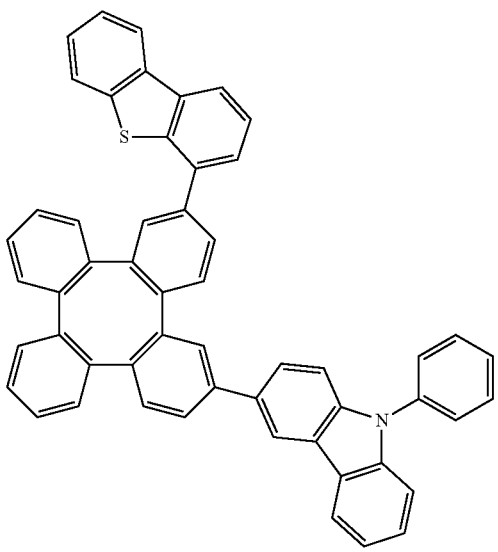
Compound 388
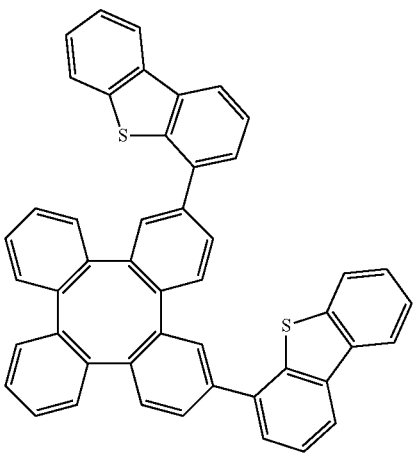
Compound 389
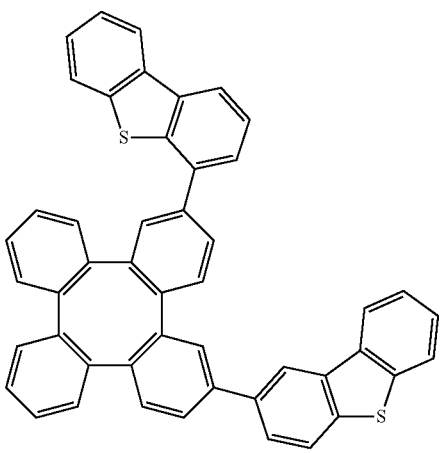
Compound 390
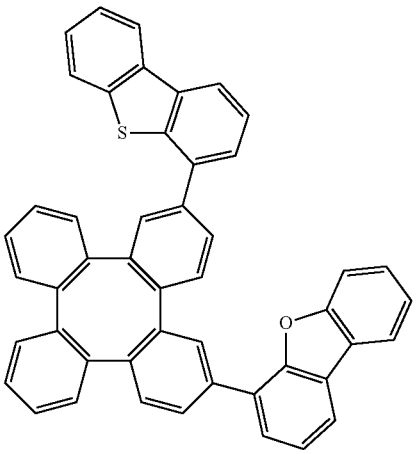

Compound 391
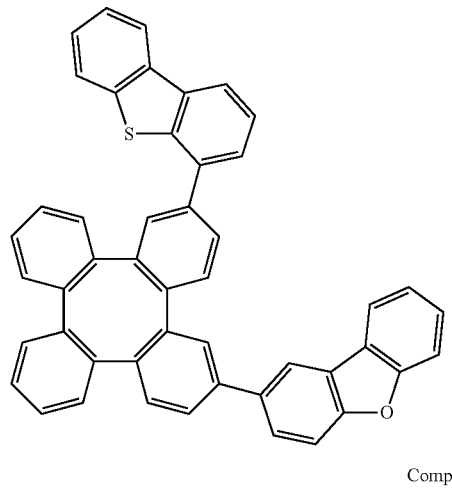
Compound 392
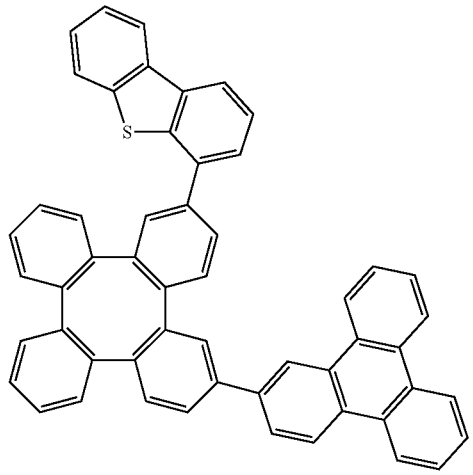
Compound 393
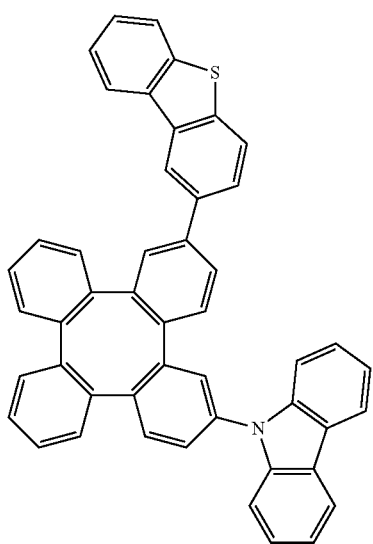
Compound 394
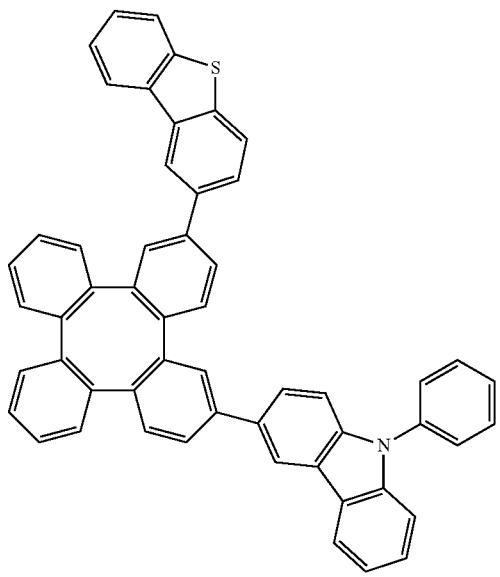
Compound 395
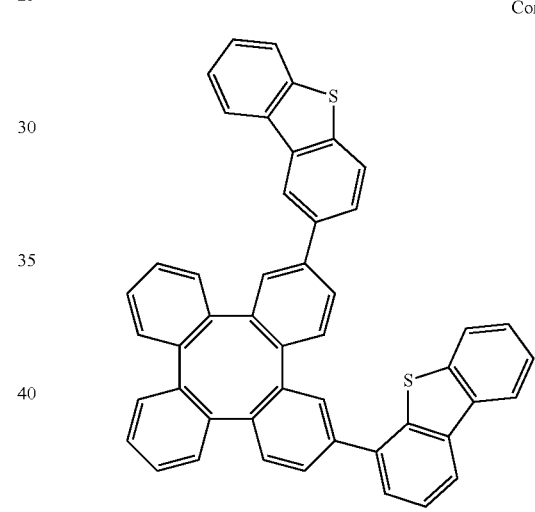
Compound 396
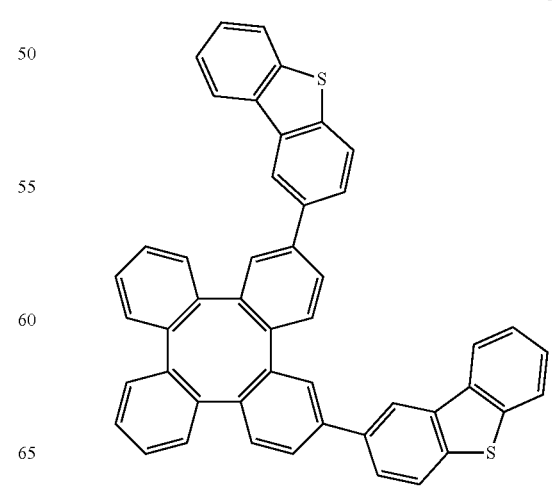

Compound 397
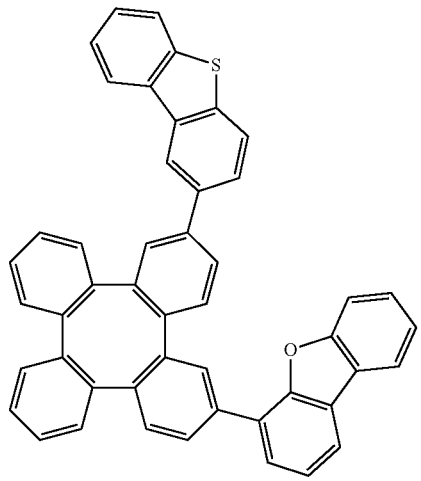
Compound 398
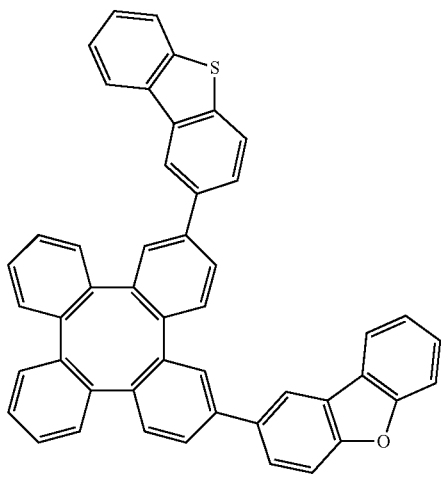
Compound 399
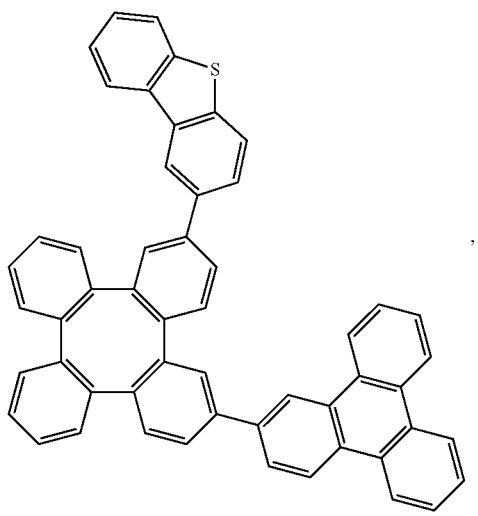
Compound 400
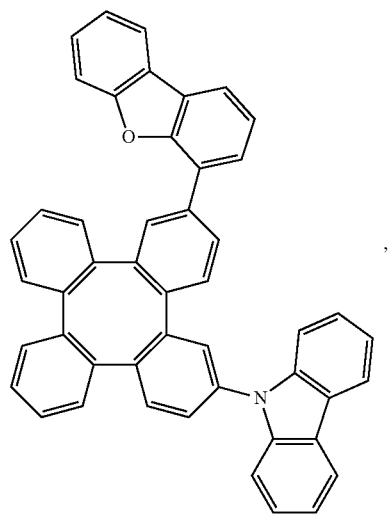
Compound 401
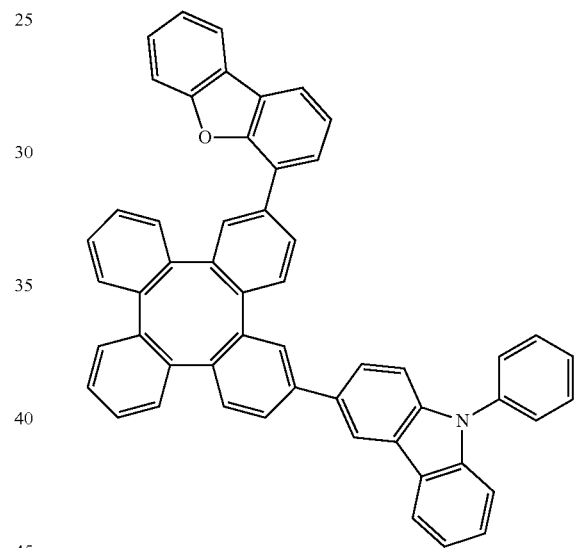
Compound 402
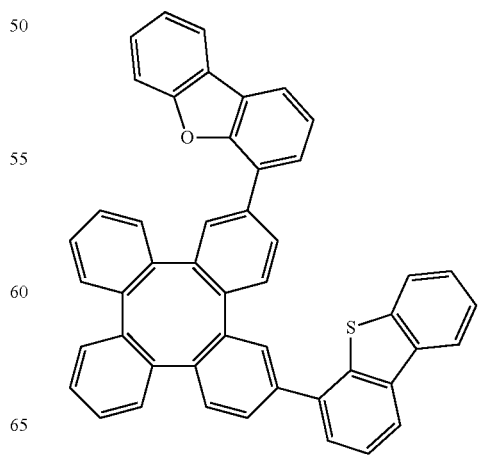

Compound 403
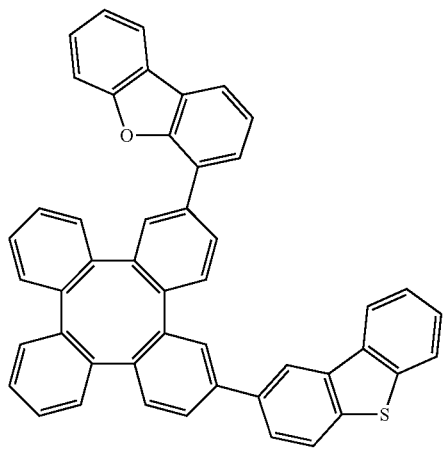
Compound 404
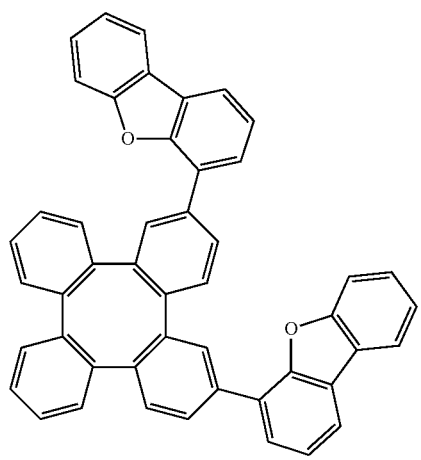
Compound 405
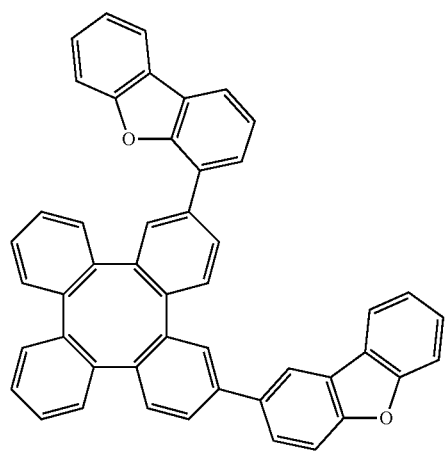
Compound 406
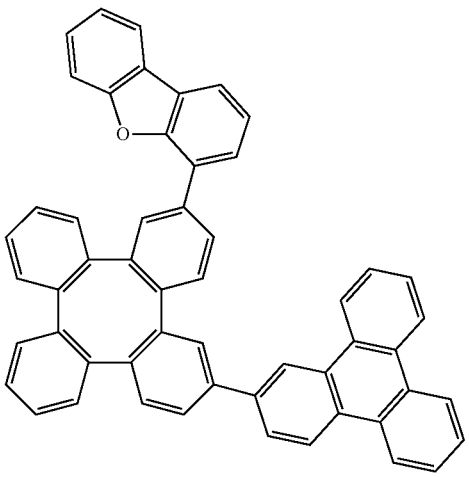
Compound 407
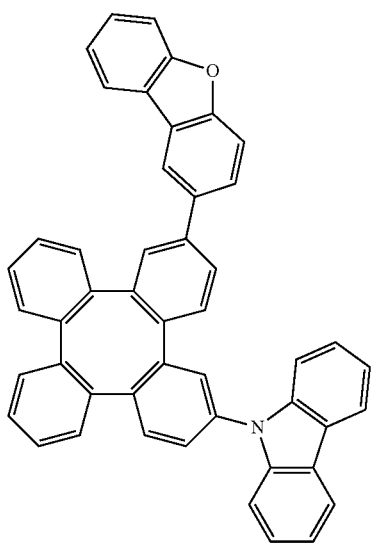
Compound 408
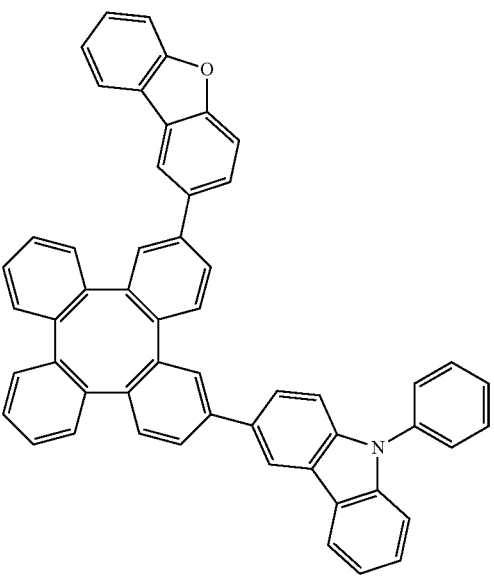

Compound 409
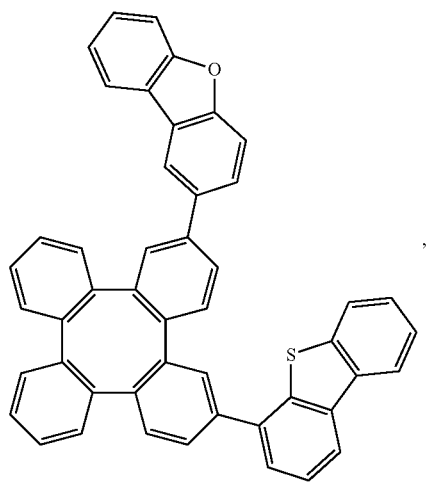
Compound 410
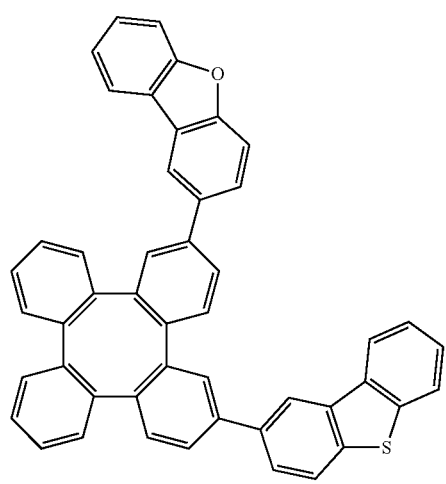
Compound 411
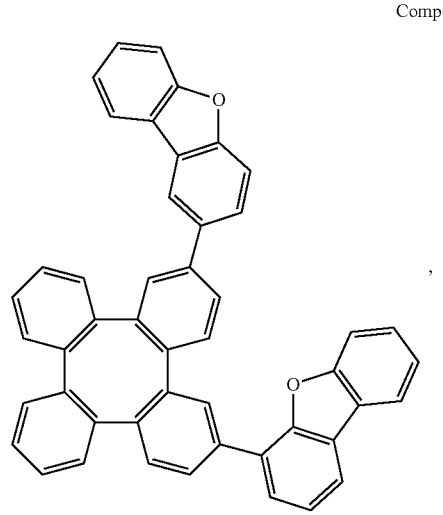
Compound 412
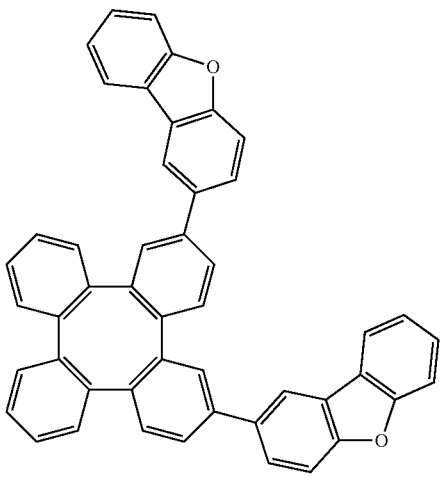
Compound 413
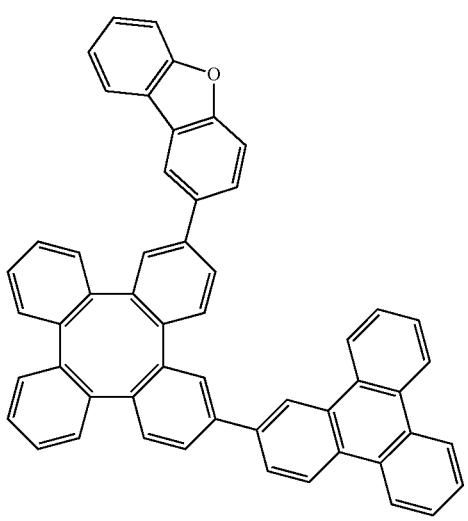
Compound 414
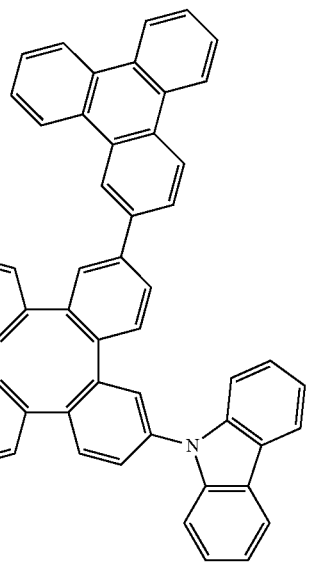

Compound 415
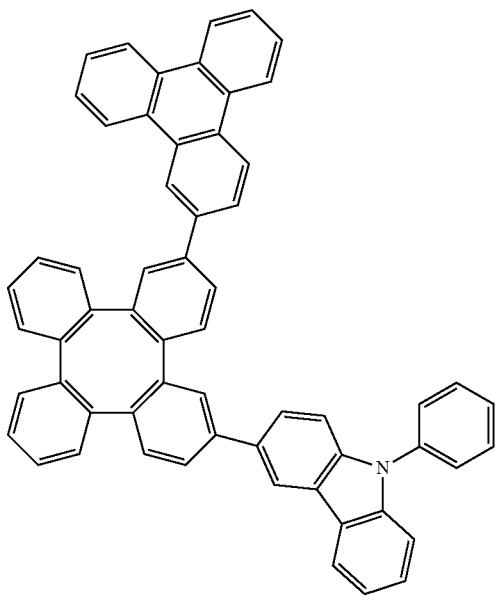
Compound 416
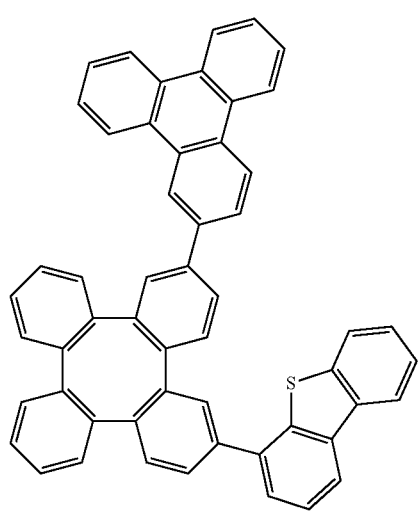
Compound 417
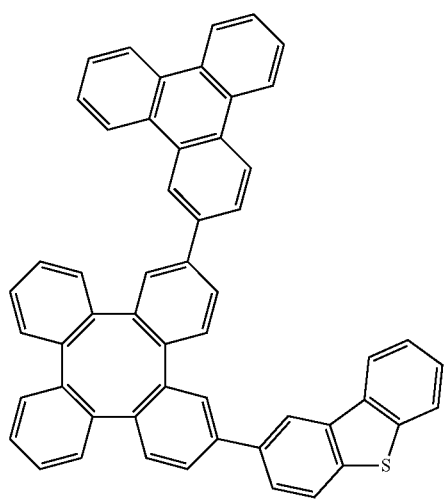
Compound 418
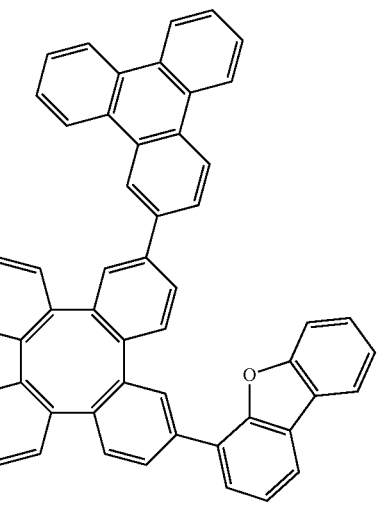
Compound 419
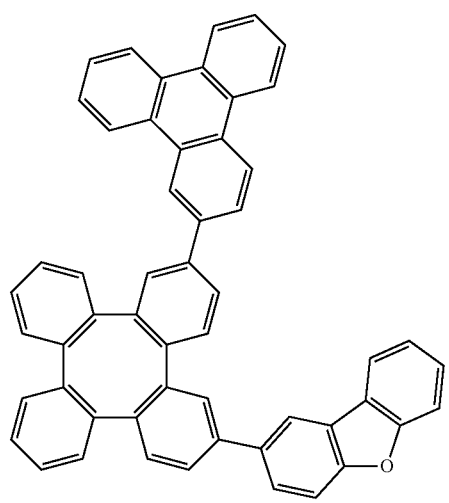
Compound 420
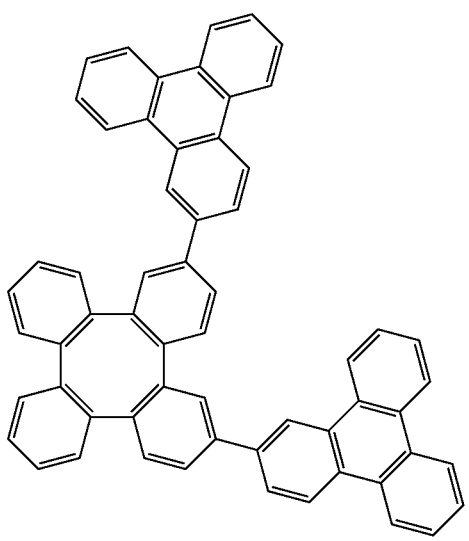

Compound 421
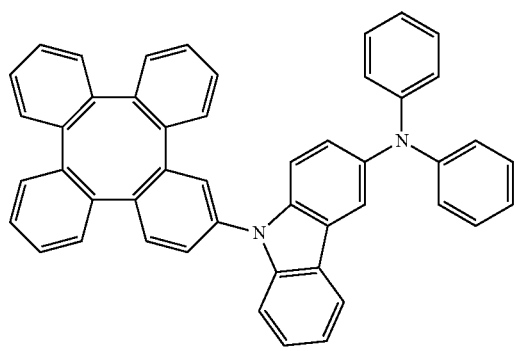
Compound 422
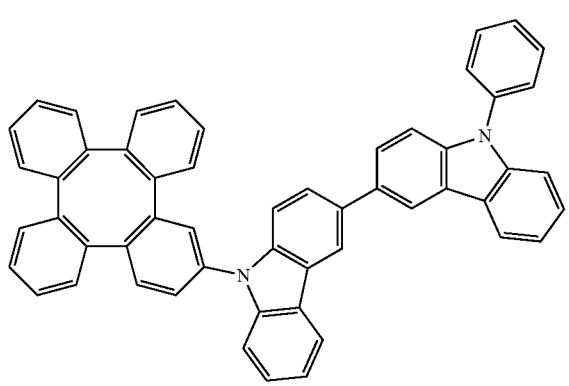
Compound 423
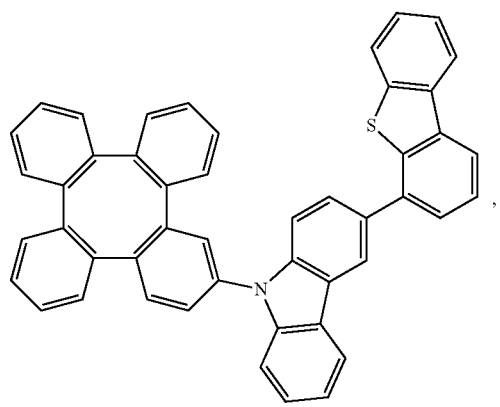
Compound 424
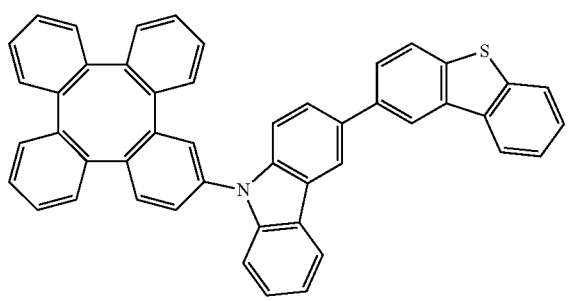
Compound 425
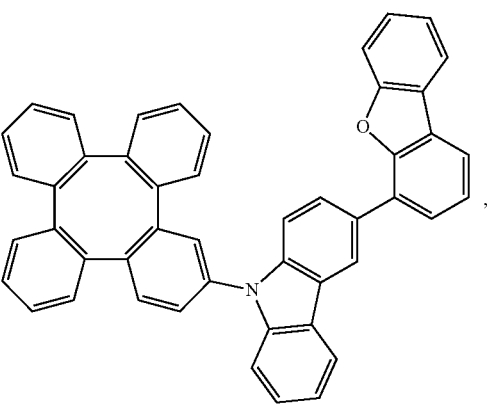
Compound 426
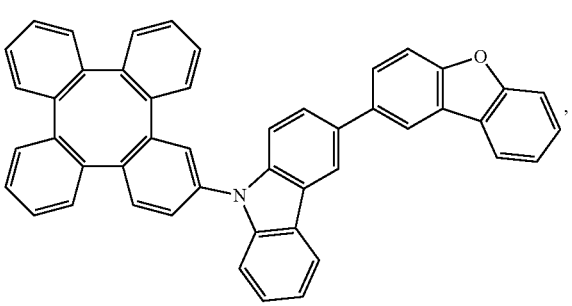
Compound 427
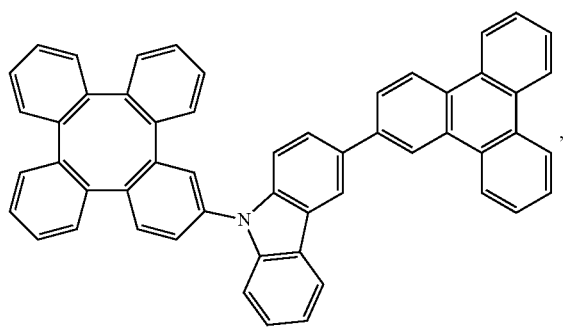
Compound 428
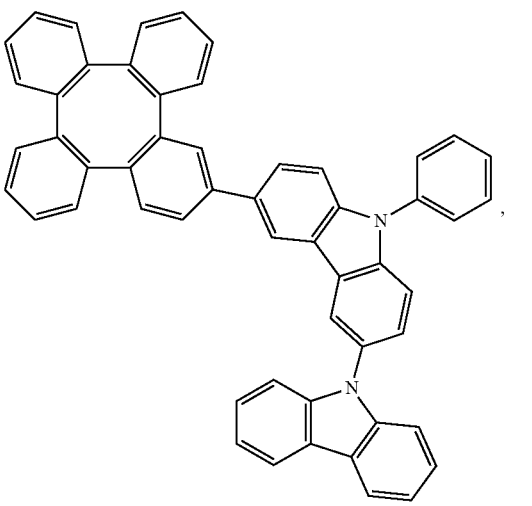

Compound 429
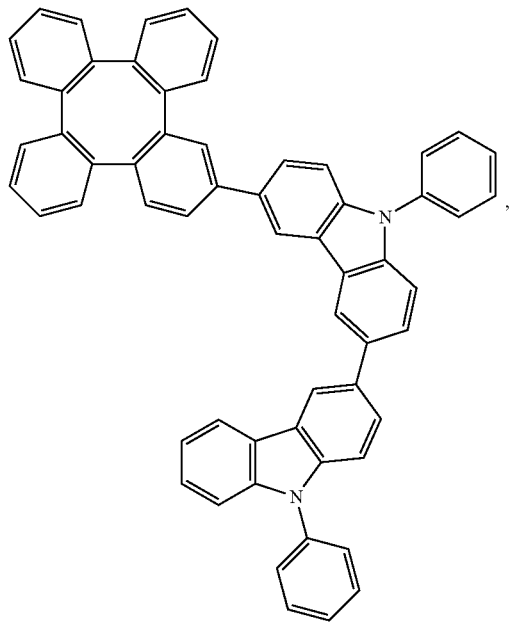
Compound 430
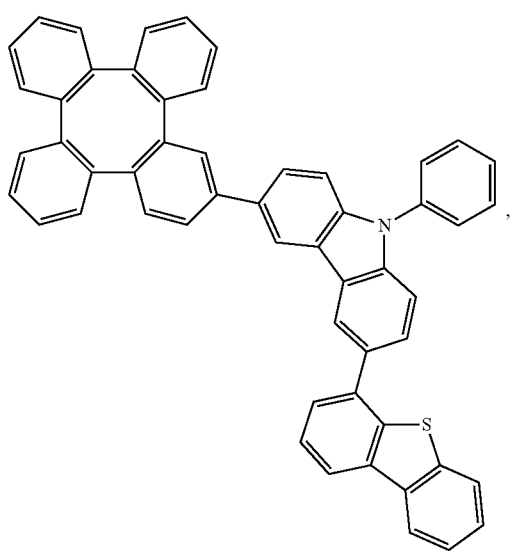
Compound 431
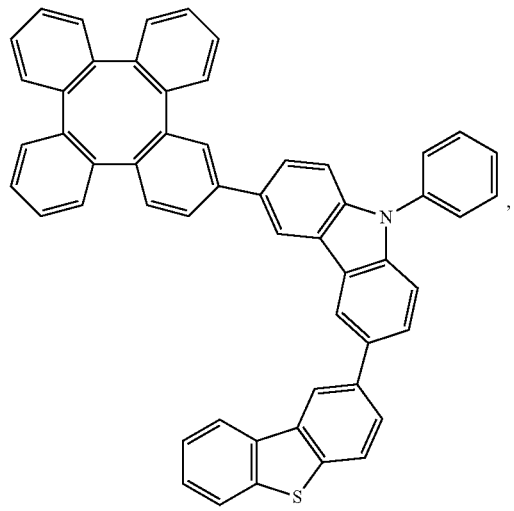
Compound 432
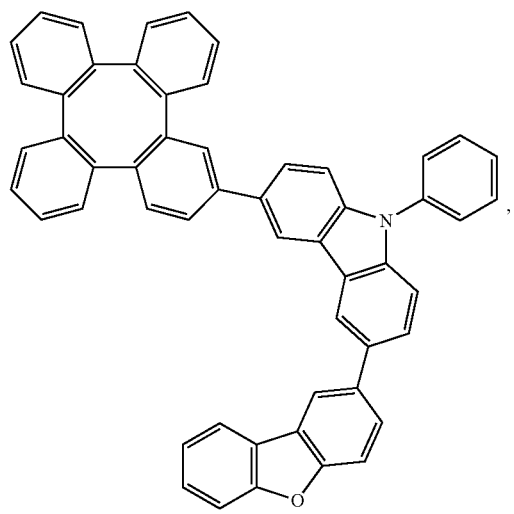
Compound 433

Compound 434
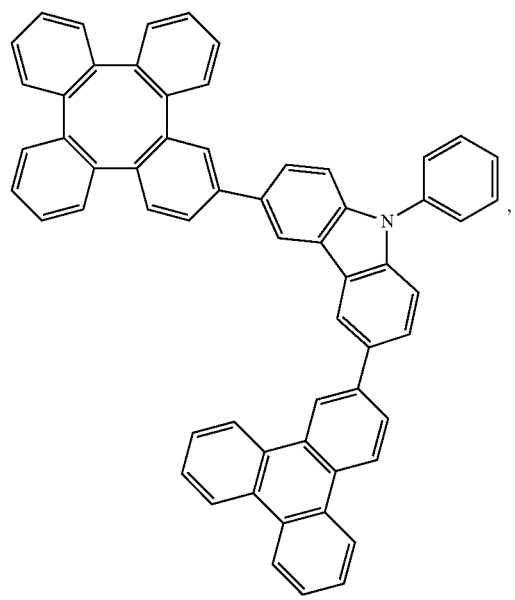
Compound 435
Compound 436
Compound 437
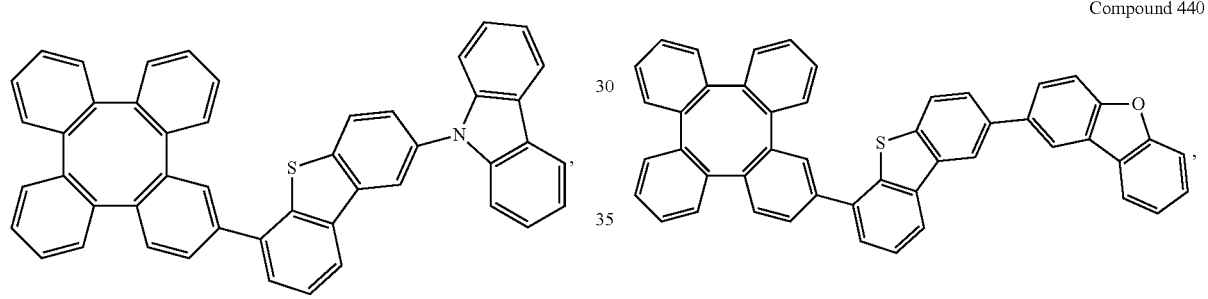
Compound 438
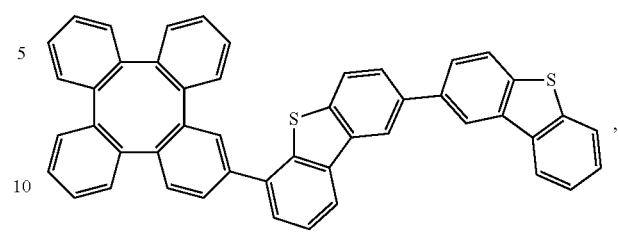
Compound 439
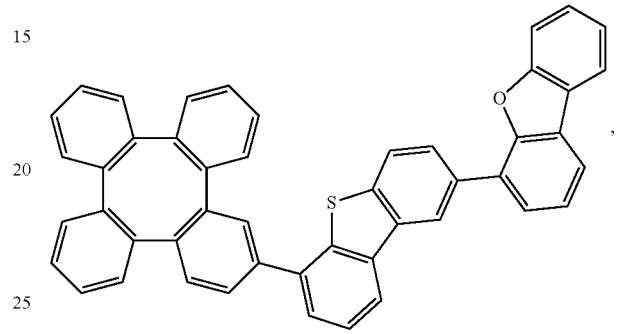
Compound 440
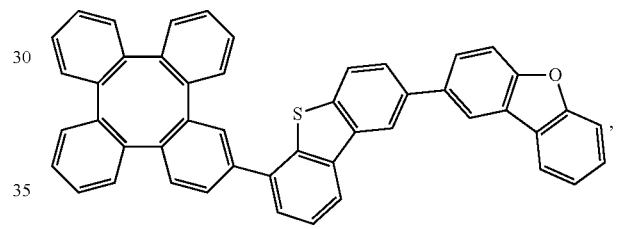
Compound 441
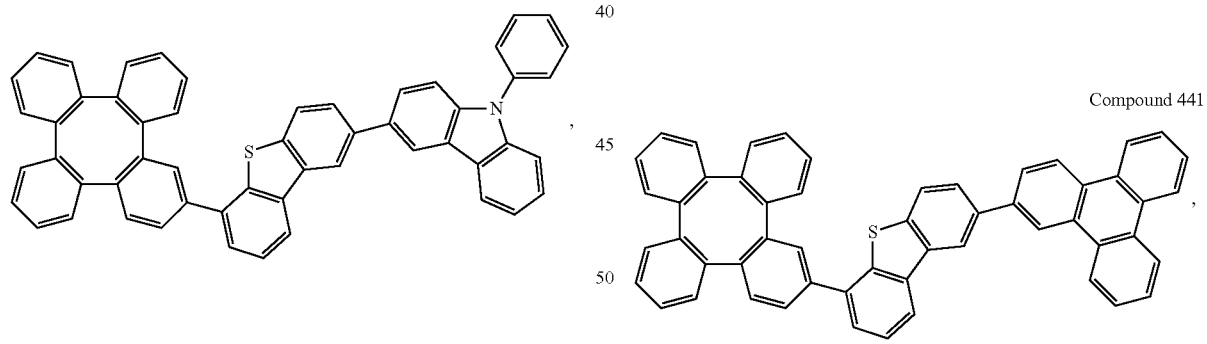
Compound 442
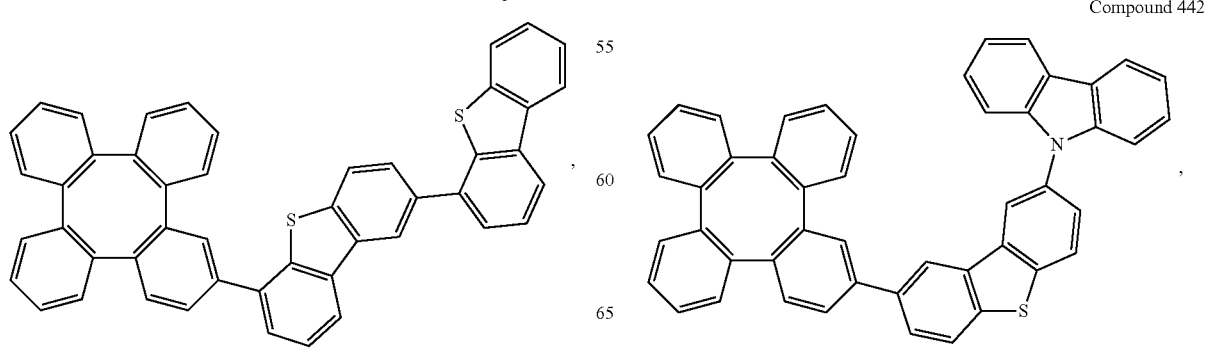

Compound 443
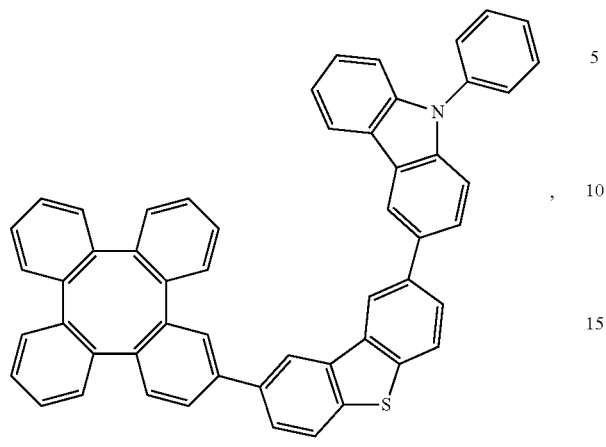
Compound 444
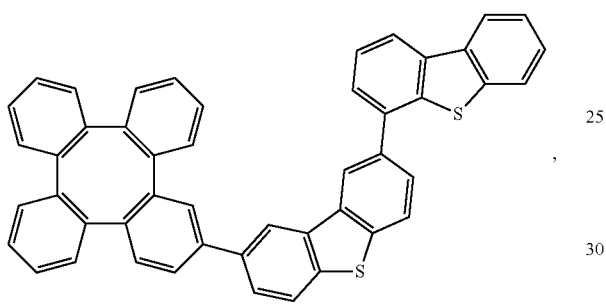
Compound 445
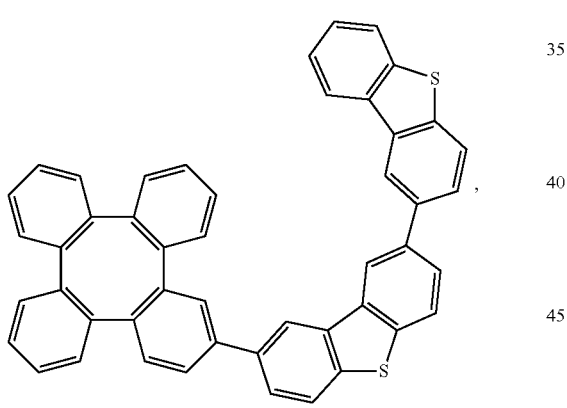
Compound 446
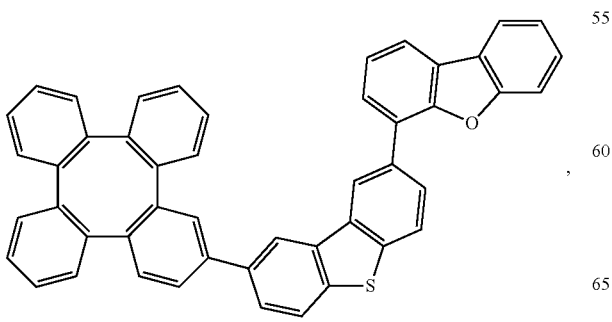
Compound 447
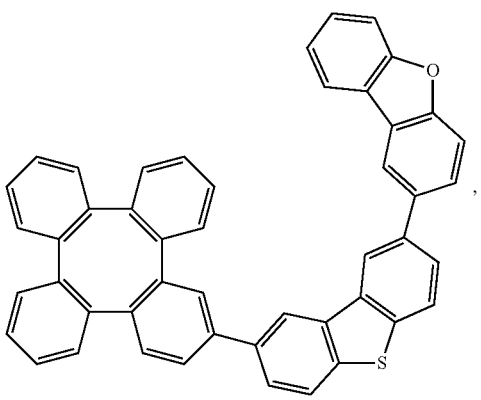
Compound 448
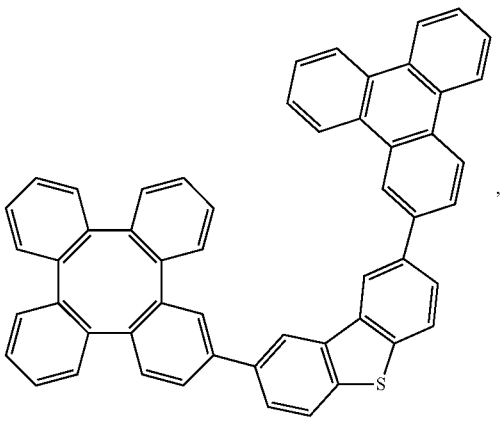
Compound 449
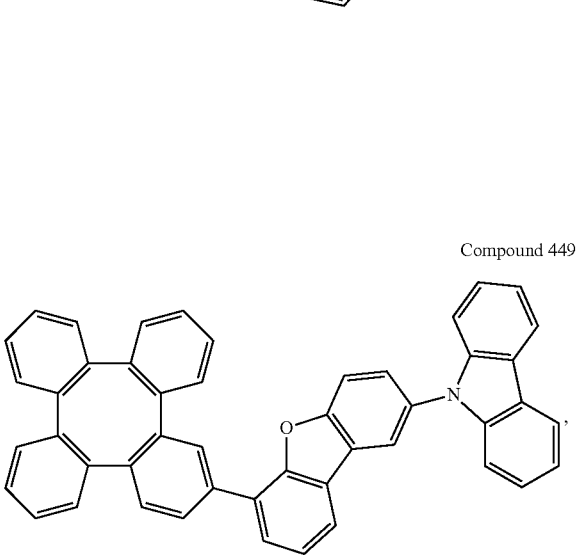
Compound 450
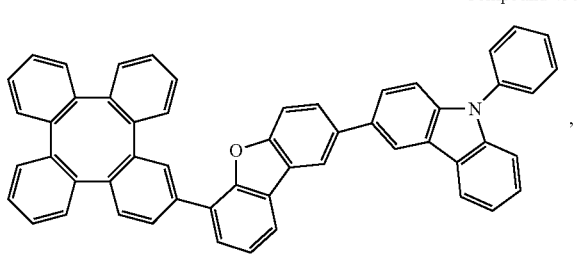

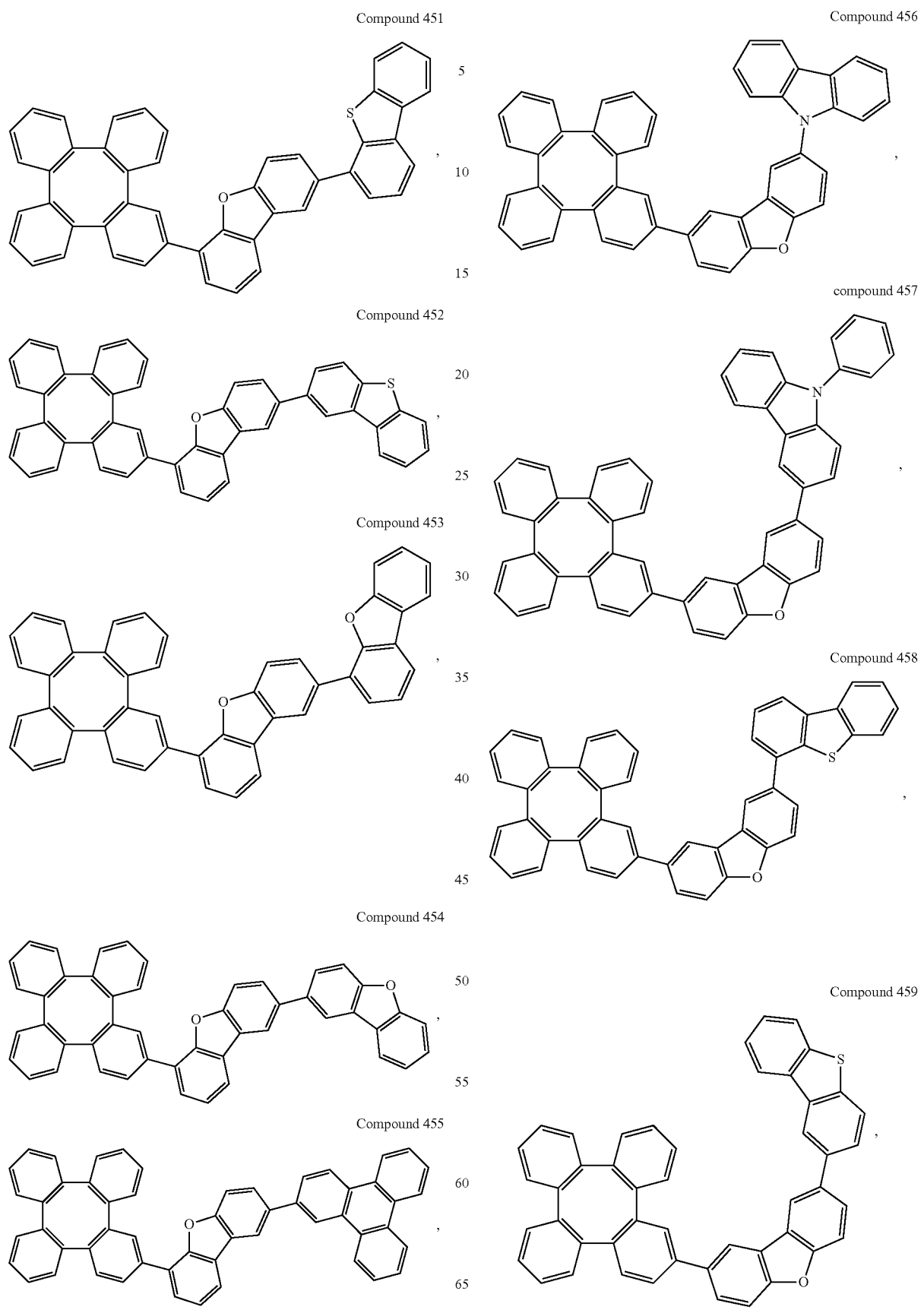

Compound 460
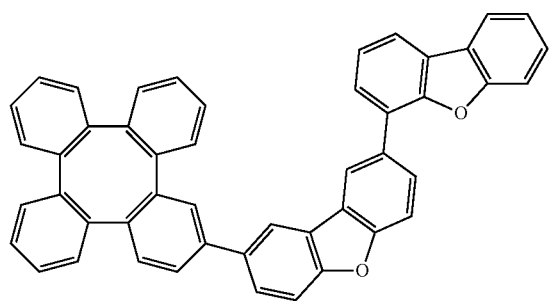
Compound 461
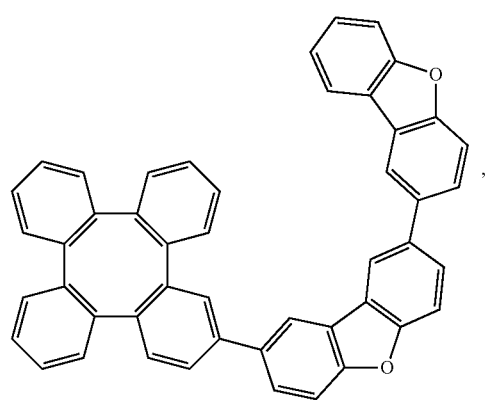
Compound 462
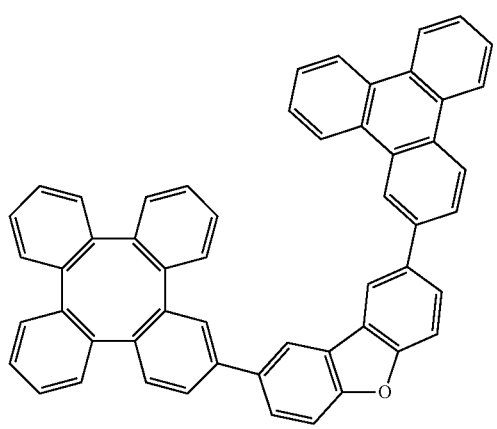
Compound 463
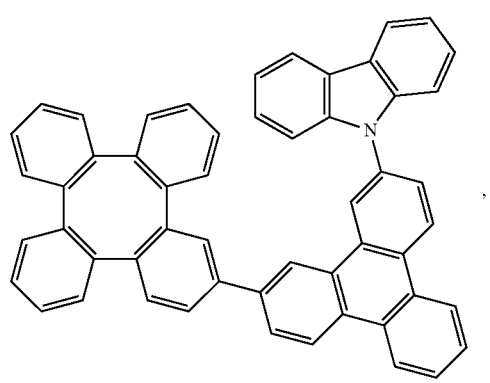
Compound 464
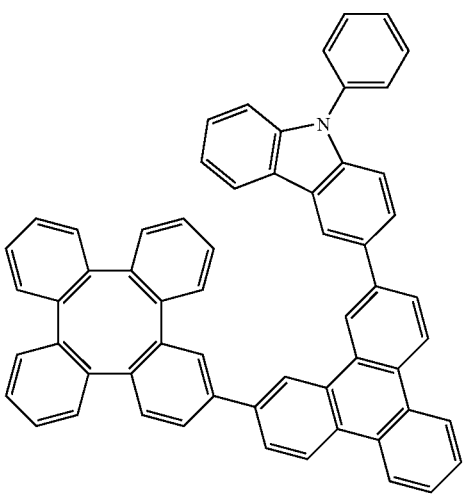
Compound 465
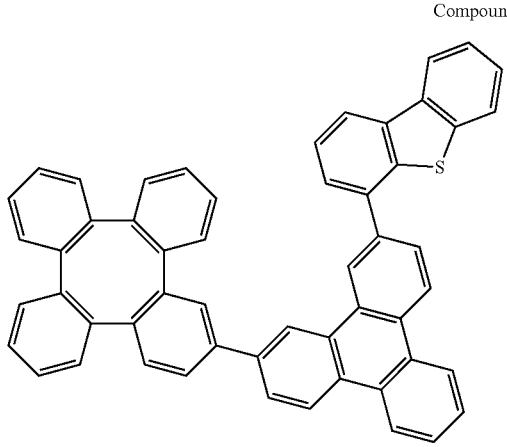
Compound 466
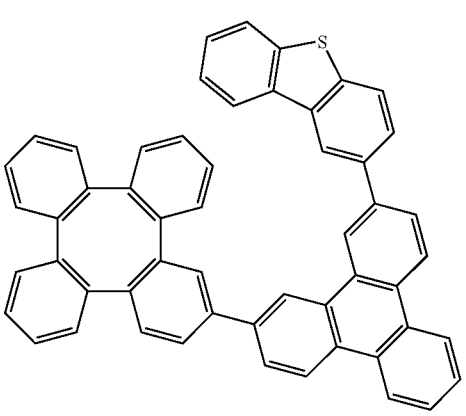

Compound 467

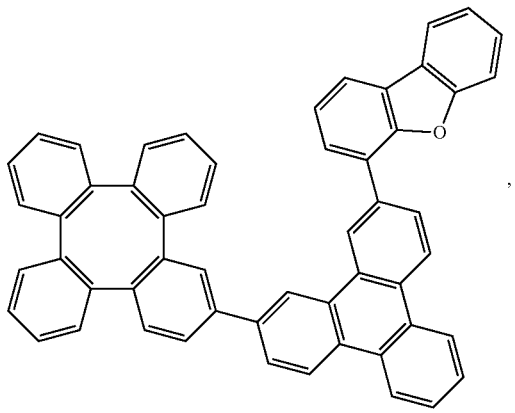

Compound 468

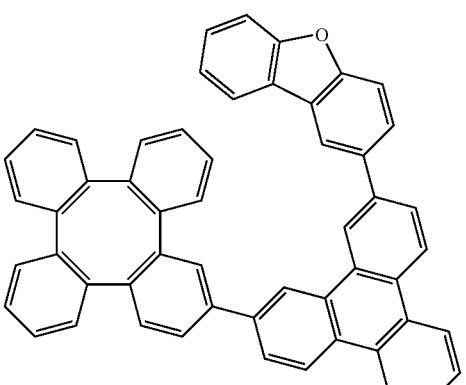
, and,

Compound 469

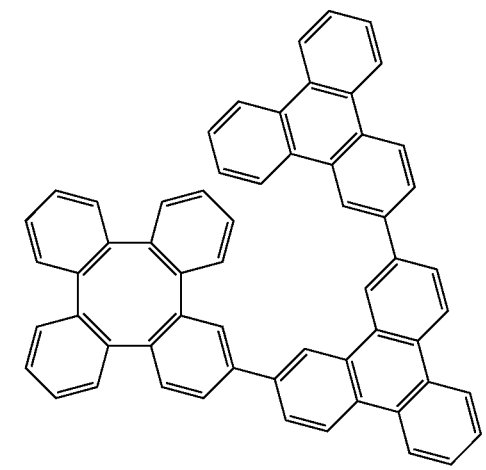
.

According to another aspect of the present disclosure, a device comprising one or more organic light emitting devices is disclosed. At least one of the organic light emitting devices comprises an anode, a cathode, and an organic layer, disposed between the anode and the cathode, wherein the organic layer comprises the compound of Formula I, including all of the variations disclosed herein.

In one embodiment of the device, the organic layer is an emissive layer and the compound is a host.

In other embodiments of the device, the organic layer can further comprise a phosphorescent emissive dopant.

In other embodiments of the device, the organic layer can be an emissive layer and the compound is a host.

In another embodiment, the organic layer further comprises a phosphorescent emissive dopant. The phosphorescent emissive dopant can be a transition metal complex having at least one ligand or part of the ligand if the ligand is more than bidentate, selected from the group consisting of:

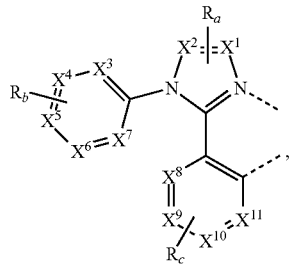

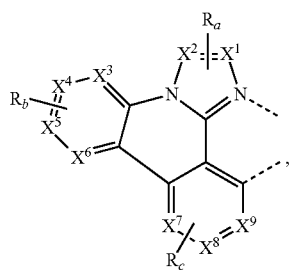

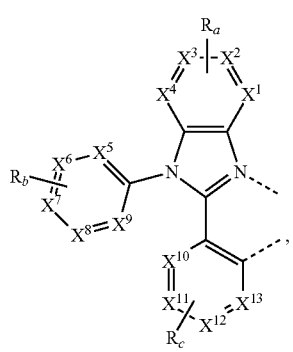

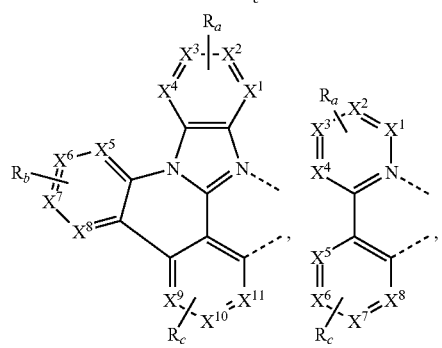

-continued

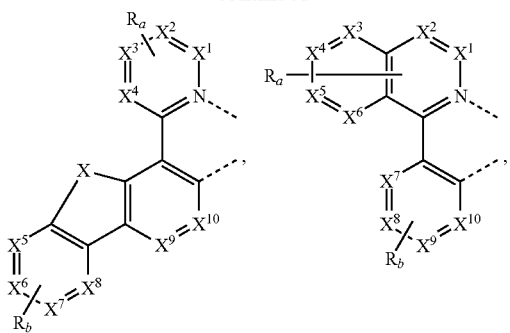

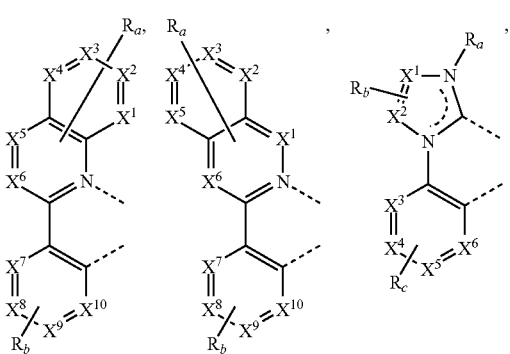

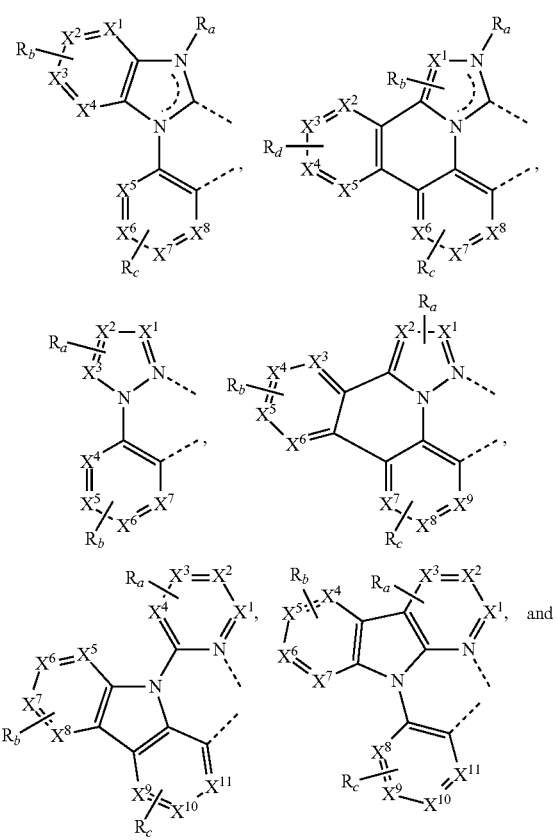

-continued

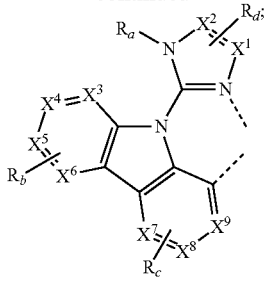

wherein each $X^1$ to $X^{13}$ are independently selected from the group consisting of carbon and nitrogen;

wherein X is selected from the group consisting of BR', NR', PR', O, S, Se, C=O, S=O, $SO_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substitutents of $R_a$, $R_b$, $R_c$, and $R_d$ are optionally fused or joined to form a ring or form a multidentate ligand.

In another embodiment of the device, the organic layer is a charge carrier blocking layer and the compound having Formula I is a charge carrier blocking material in the organic layer.

In another embodiment of the device, the organic layer is a charge carrier transporting layer and the compound having Formula I is a charge carrier transporting material in the organic layer.

In another embodiment, the device is selected from the group consisting of a consumer product, an electronic component module, an organic light-emitting device, and a lighting panel.

In yet another aspect of the present disclosure, a formulation that comprises a compound according to Formula I, and its variations as described herein, is described. The formulation can include one or more components selected from the group consisting of a solvent, a host, a hole injection material, hole transport material, and an electron transport layer material, disclosed herein.

According to another aspect of the present disclosure, tetraphenylene compounds substituted with oligomeric carbazoles and/or aza-carbazoles are potential high triplet hosts with good external quantum efficiency in the blue emitting devices. Substituents with oligomeric carbazoles and/or aza-carbazoles are believed to stabilize the charges and achieve good device lifetime.

According to some embodiments, a compound having a formula:

Formula 2

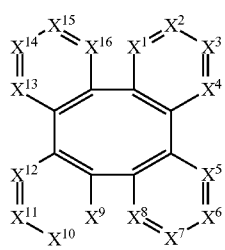

is disclosed, wherein $X^1$-$X^{16}$ are each independently selected from the group consisting of CR and N;

wherein each R is independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein at least one of $X^1$-$X^{16}$ is CR;
wherein R is

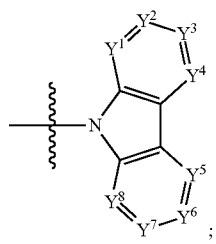

wherein $Y^1$-$Y^8$ are independently selected from the group consisting of CR' and N;

wherein each R' is independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, aza-carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein at least one of $Y^1$ to $Y^8$ is CR' whose R' is a group containing at least one carbazole or aza-carbazole.

In some embodiments of the compound of Formula 2, each of $X^1$ to $X^{16}$ is CR. In some embodiments of the compound, at least one of $X^1$ to $X^{16}$ is N. In some embodiments, each of $Y^1$ to $Y^8$ is CR'. In some embodiments of the compound, at least one of $Y^1$ to $Y^8$ is N. In some embodiments of the compound, at least one of $Y^1$ to $Y^8$ is CR' whose R' is a group containing at least one carbazole. In some embodiments of the compound, at least one of $Y^1$ to $Y^8$ is CR' whose R' is a group containing at least one aza-carbazole.

In some other embodiments of the compound, the compound of Formula 2 is selected from the group consisting of:

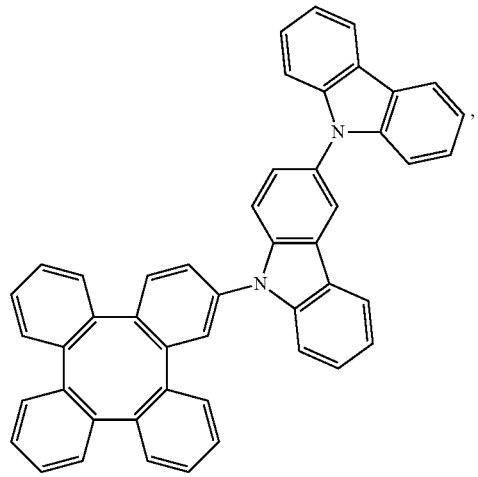

Compound 470

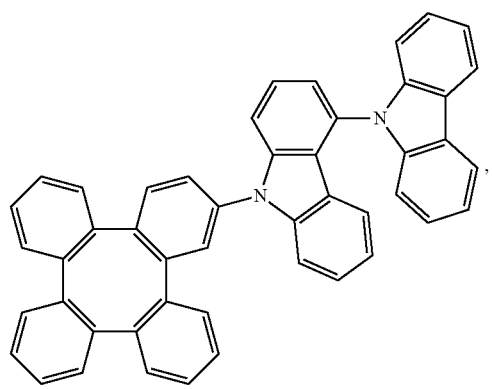

Compound 471

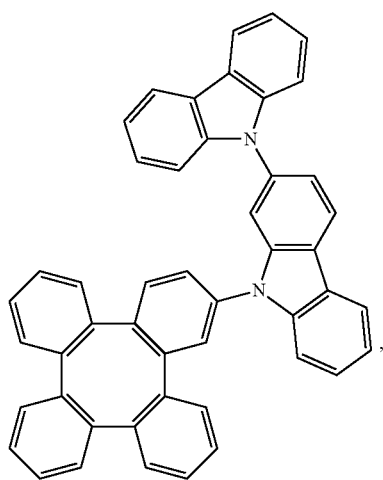

Compound 472

Compound 473
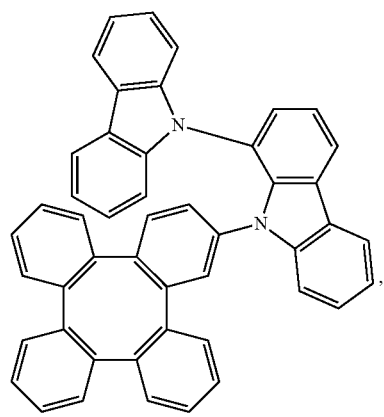
Compound 474
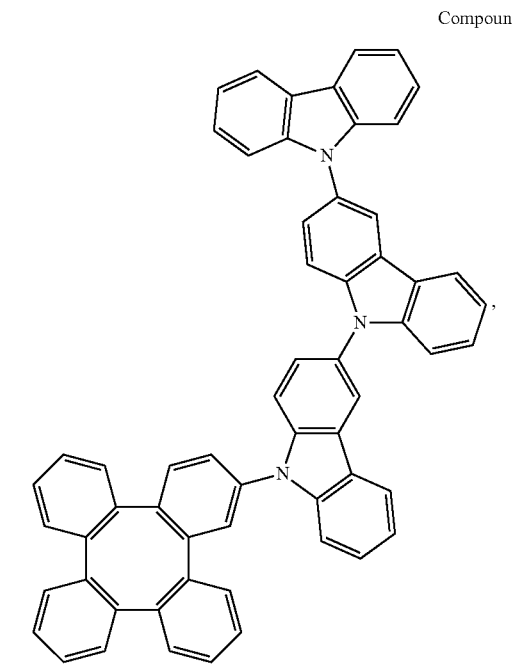
Compound 475
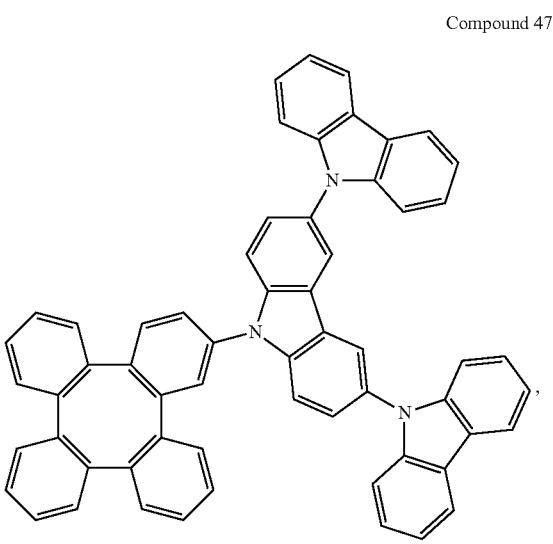
Compound 476
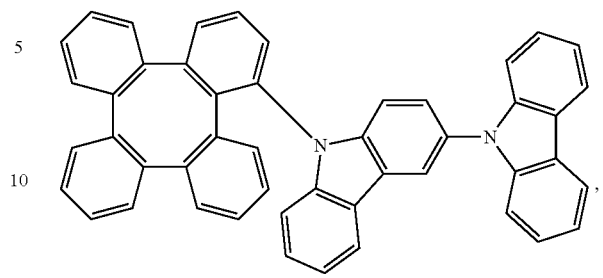
Compound 477
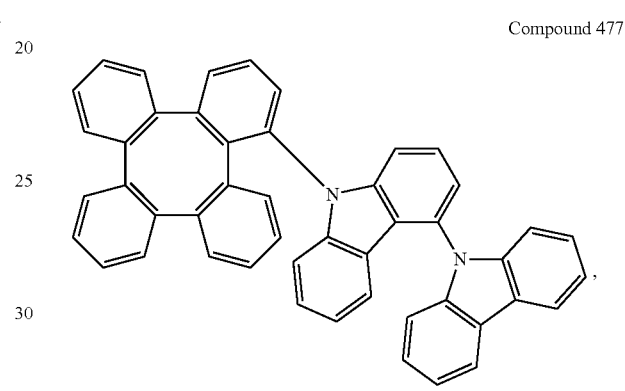
Compound 478
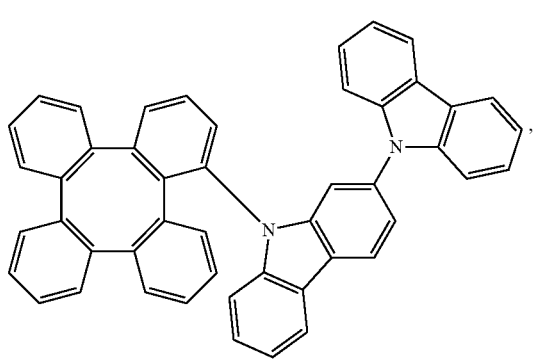
Compound 479
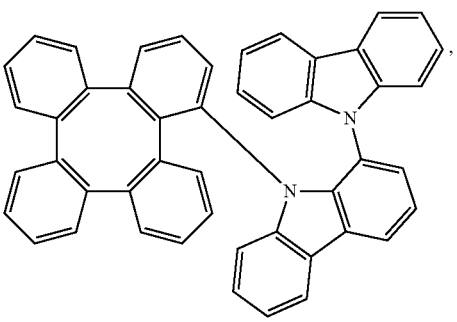

Compound 480
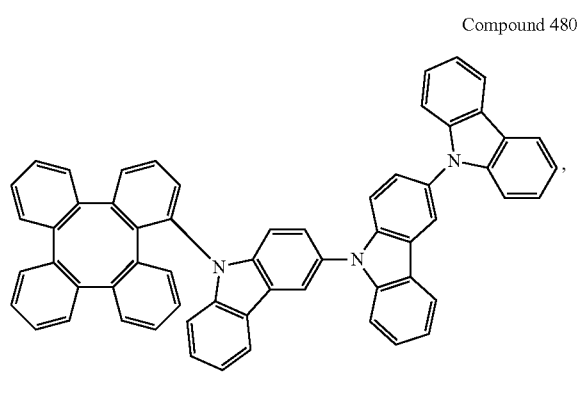
Compound 481
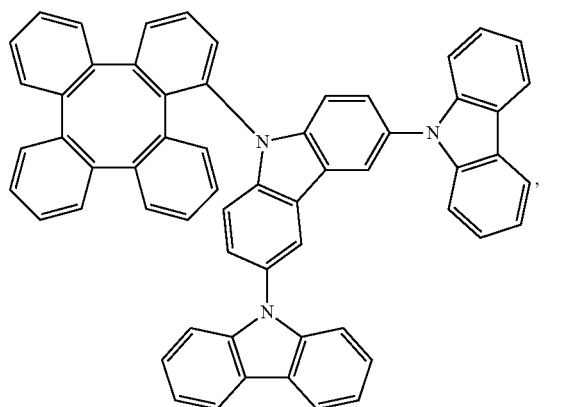
Compound 482
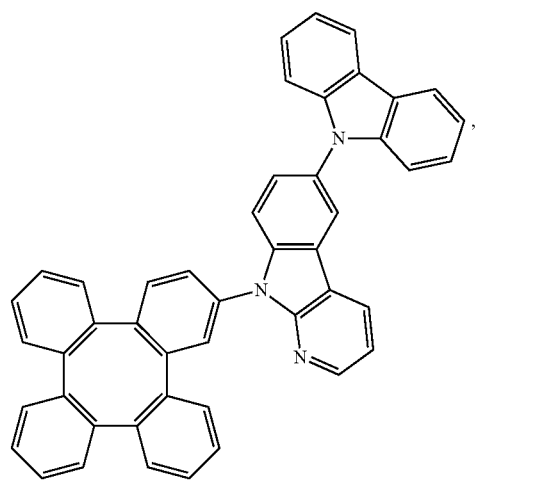
Compound 483
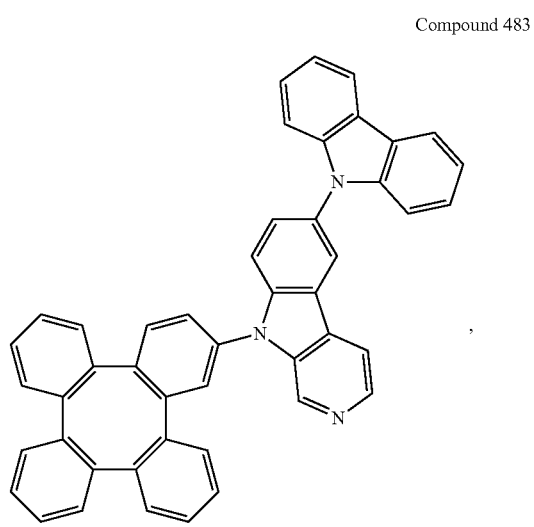
Compound 484
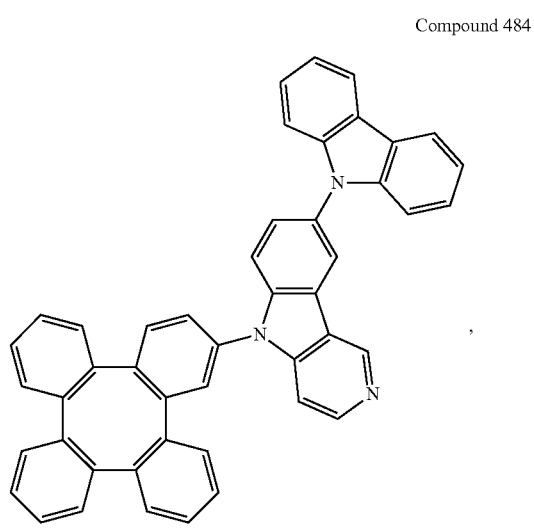
Compound 485
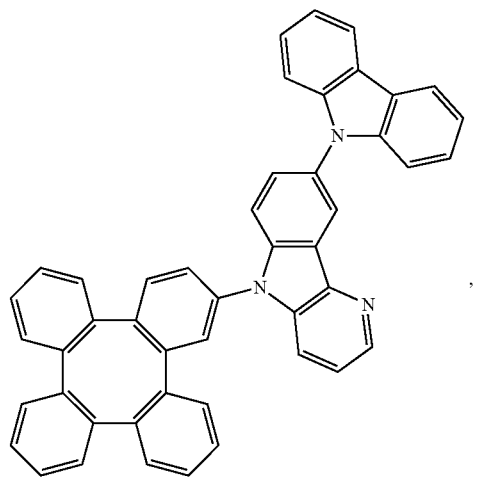

Compound 486
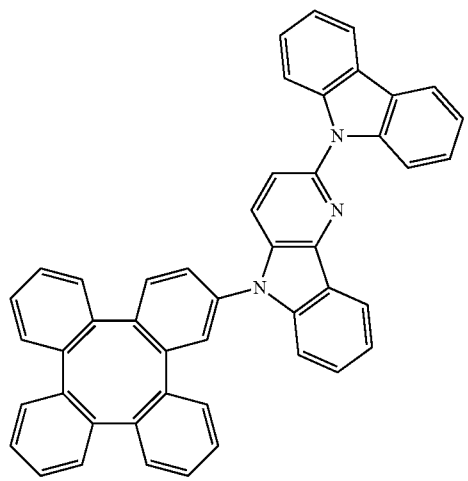
Compound 487
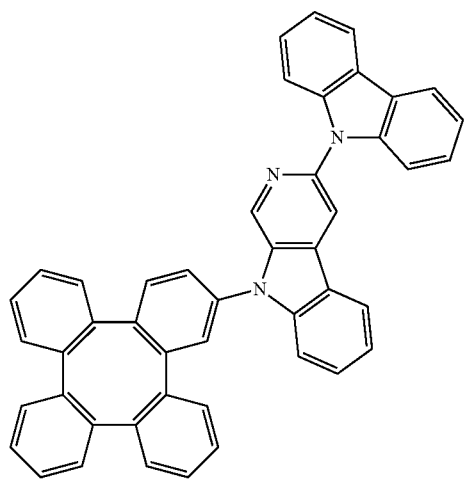
Compound 488
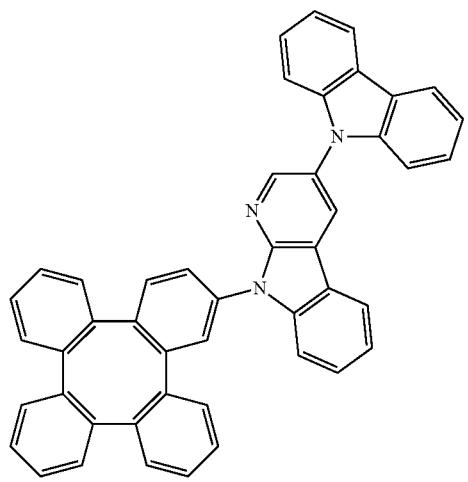
Compound 489
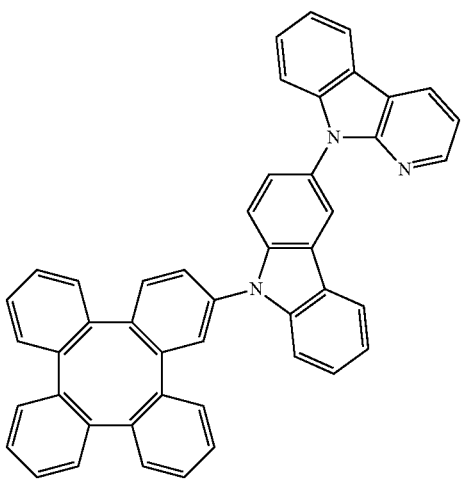
Compound 490
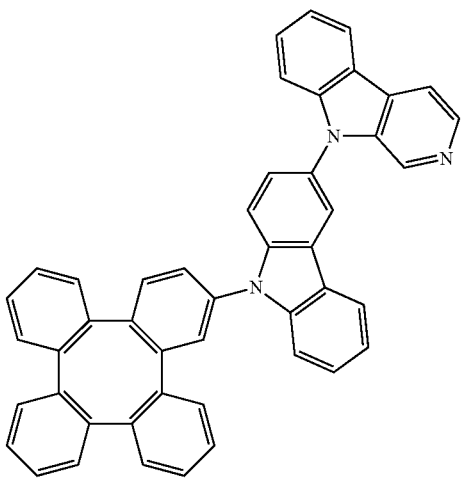
Compound 491
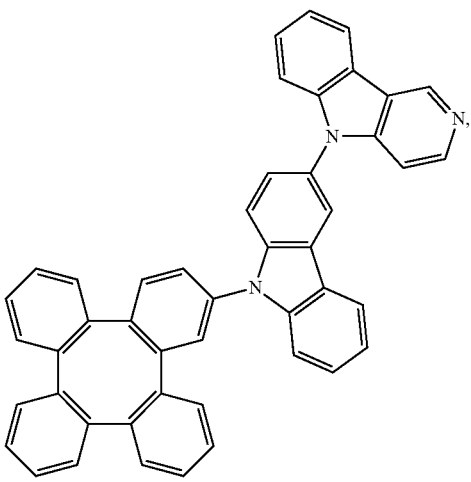

Compound 492
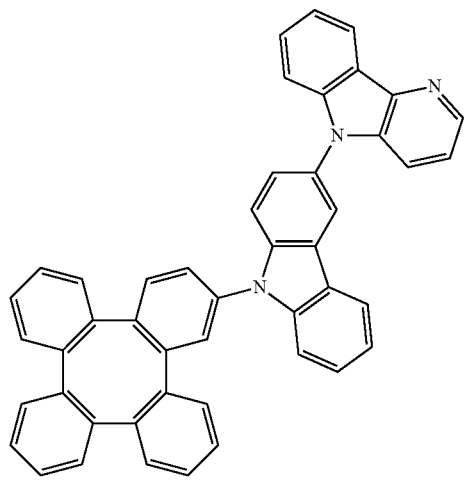
Compound 493
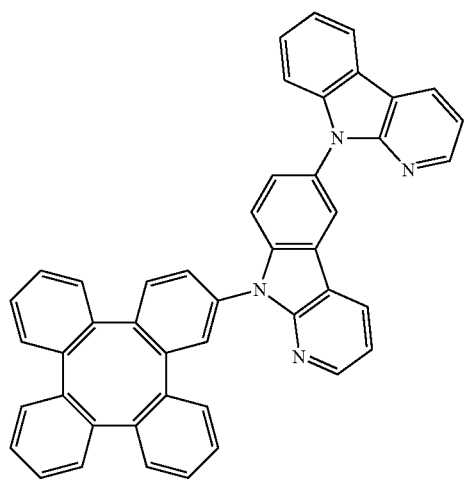
Compound 494
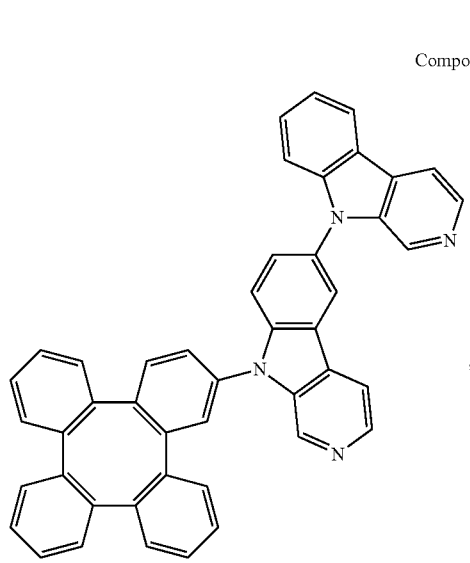
Compound 495
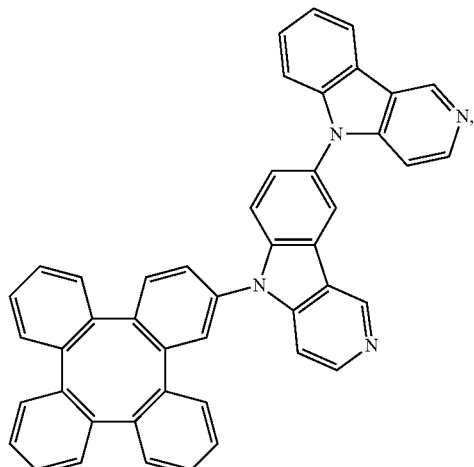
Compound 496
Compound 497
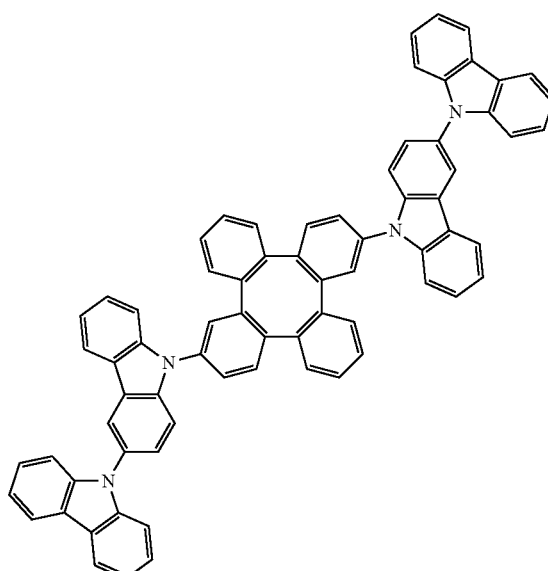

-continued

Compound 498

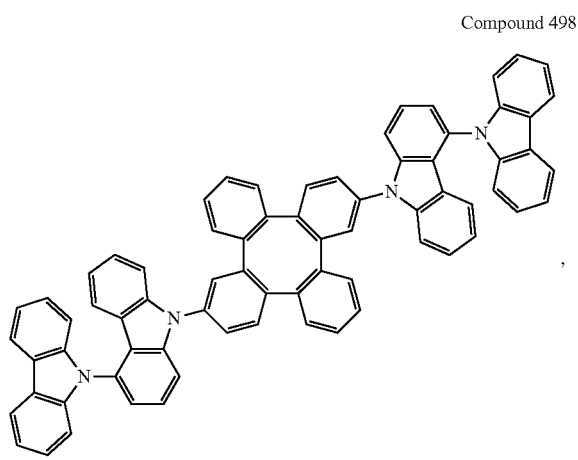

Compound 499

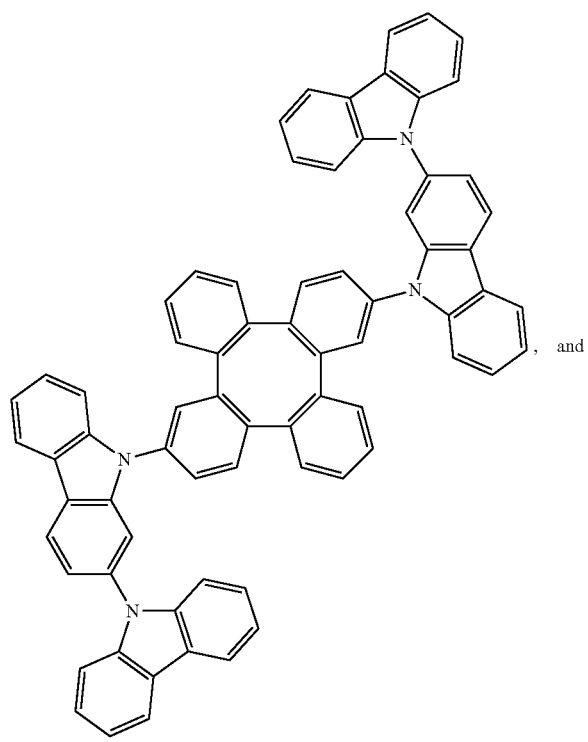
, and

Compound 500

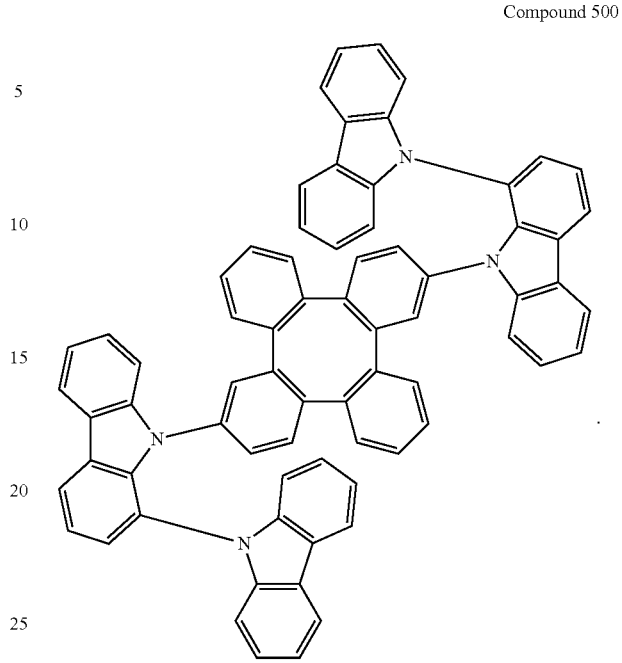

According to another aspect of the present disclosure, a device comprising one or more organic light emitting devices is disclosed. At least one of the organic light emitting devices comprising: an anode; a cathode; and an organic layer, disposed between the anode and the cathode, comprising a compound having Formula 2:

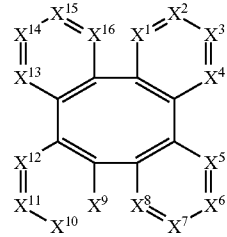

Formula 2 wherein $X^1$-$X^{16}$ are each independently selected from the group consisting of CR and N;

wherein each R is independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein at least one of $X^1$-$X^{16}$ is CR;

wherein R is

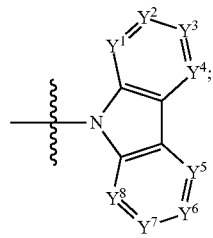

wherein $Y^1$-$Y^8$;
wherein $Y^1$ to $Y^8$ are independently selected from the group consisting of CR' and N;
wherein each R' is independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, aza-carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein at least one of $Y^1$ to $Y^8$ is CR'; and
wherein R' is a group containing at least one carbazole or aza-carbazole.

In some embodiments of the device, each of $X^1$-$X^{16}$ is CR. In some embodiments of the device, at least one of $X^1$-$X^{16}$ is N. In some embodiments of the device, the compound of Formula 2 is selected from the group consisting of Compound 470 through Compound 500.

In some embodiments of the device, the organic layer is an emissive layer and the compound of Formula 2 is a host. In some embodiments of the device, the organic layer further comprises a phosphorescent emissive dopant.

In some embodiments of the device, the organic layer further comprises a phosphorescent emissive dopant, wherein the phosphorescent emissive dopant is a transition metal complex having at least one ligand or part of the ligand if the ligand is more than bidentate, selected from the group consisting of:

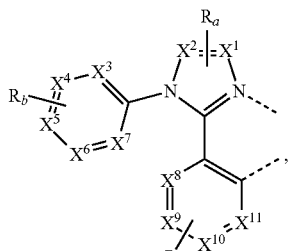

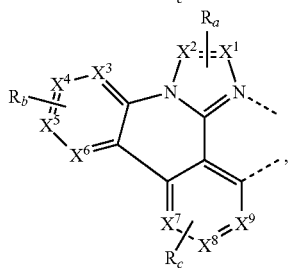

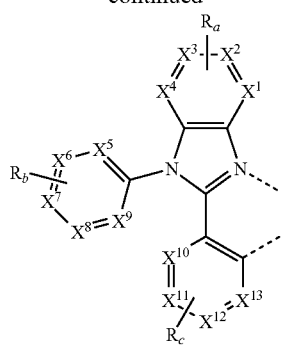

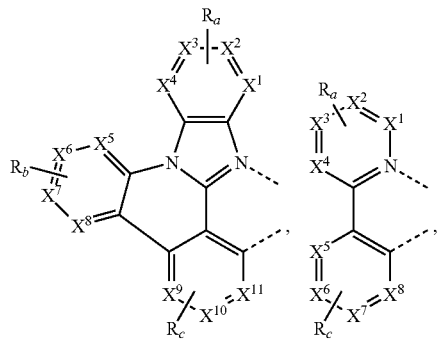

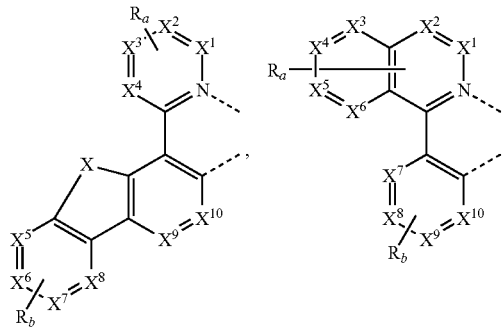

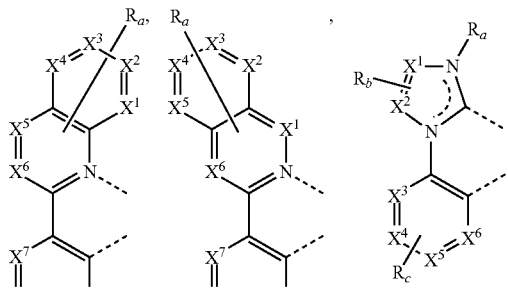

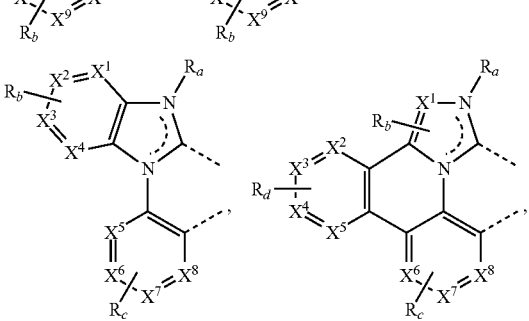

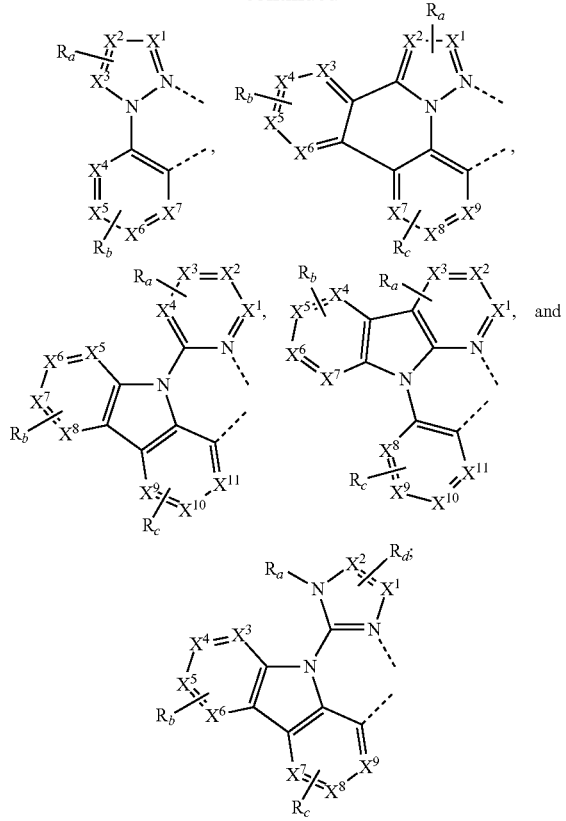

wherein each $X^1$ to $X^{13}$ are independently selected from the group consisting of carbon and nitrogen;

wherein X is selected from the group consisting of BR', NR', PR', O, S, Se, C=O, S=O, $SO_2$, CR'R'', SiR'R'', and GeR'R'';

wherein R' and R'' are optionally fused or joined to form a ring;

wherein each $R_a$, $R_b$, $R_c$, and $R_d$ may represent from mono substitution to the possible maximum number of substitution, or no substitution;

wherein R', R'', $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of $R_a$, $R_b$, $R_c$, and $R_d$ are optionally fused or joined to form a ring or form a multi-dentate ligand.

In some embodiments of the device, the organic layer is a charge carrier blocking layer and the compound having Formula 2 is a charge carrier blocking material in the organic layer.

In some embodiments of the device, the organic layer is a charge carrier transporting layer and the compound having Formula 2 is a charge carrier transporting material in the organic layer.

According to another aspect, a formulation comprising the compound of Formula 2 is disclosed. The formulation can include one or more components selected from the group consisting of a solvent, a host, a hole injection material, hole transport material, and an electron transport layer material, disclosed herein.

The OLED can be incorporated into one or more of a consumer product, an electronic component module, and a lighting panel.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compound.

Examples of aromatic amine derivatives used in HIL or HTL include, but are not limited to the following general structures:

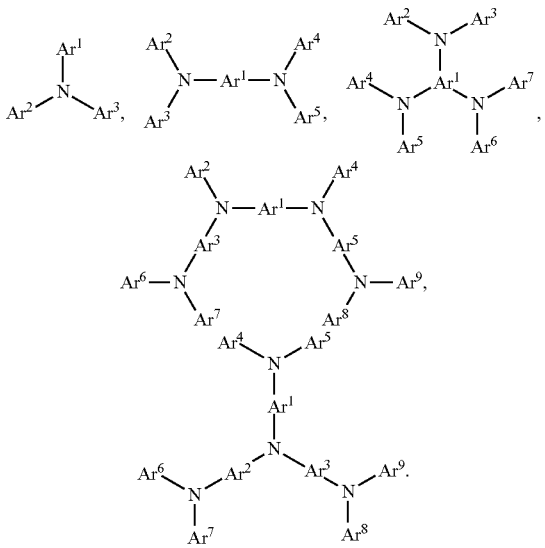

Each of $A^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $A^1$ to $Ar^9$ is independently selected from the group consisting of:

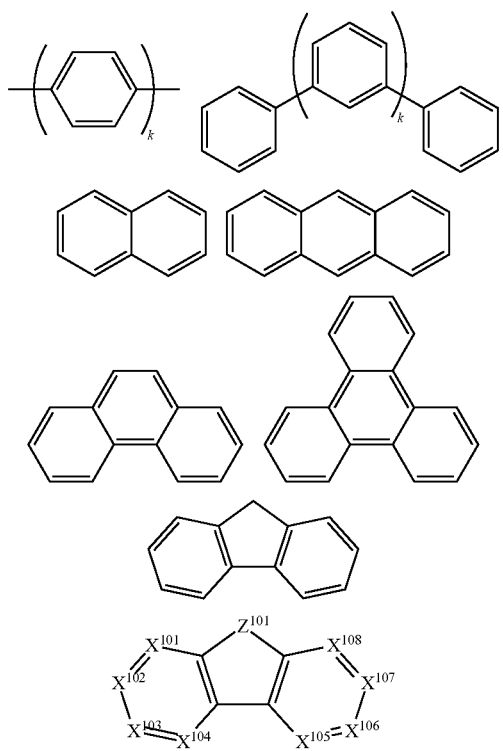

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

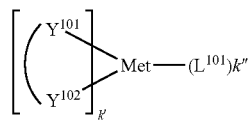

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V. Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

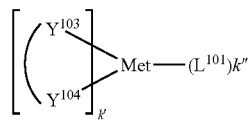

wherein Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

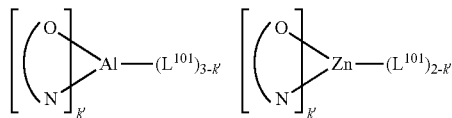

wherein (O—N) is a bidentate ligand, having metal coordinated to atoms O and N.

In another aspect, Met is selected from Ir and Pt. In a further aspect, $(Y^{103}\text{-}Y^{104})$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

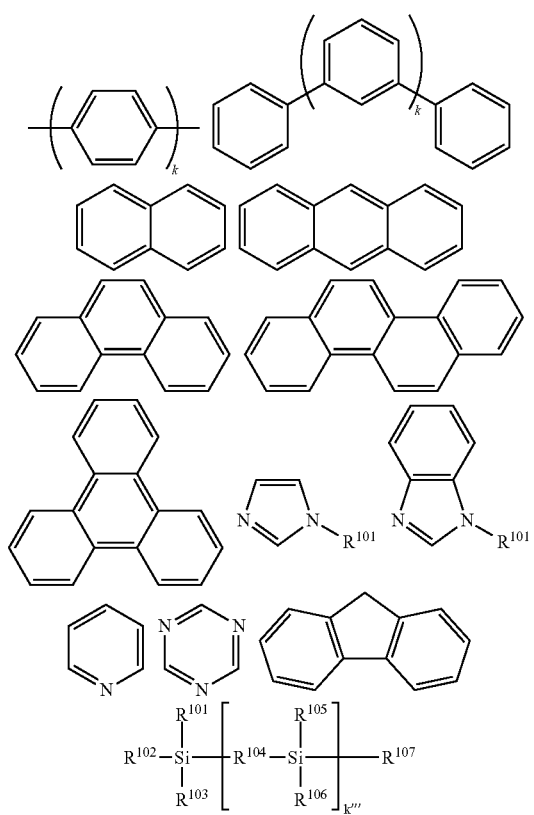

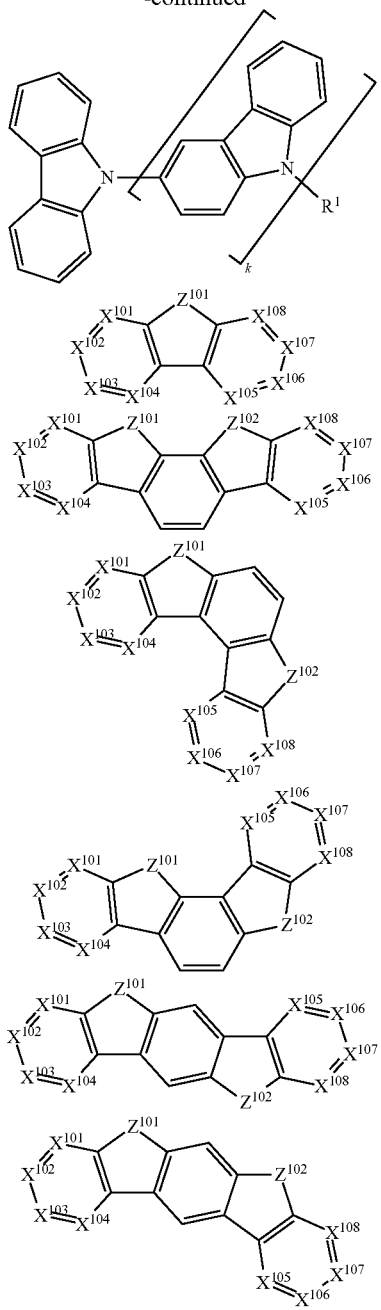

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

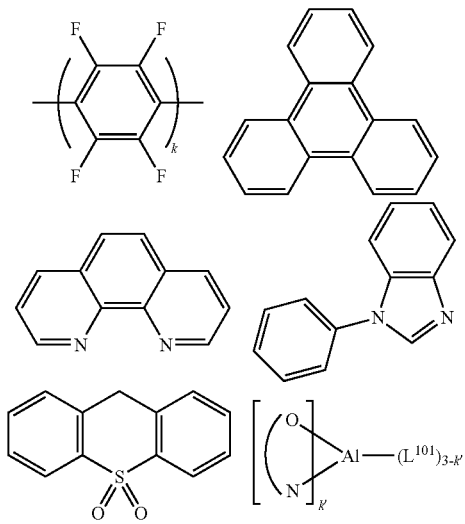

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

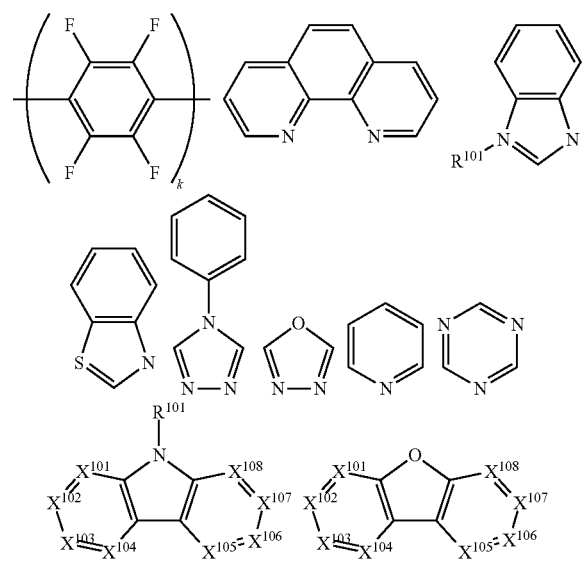

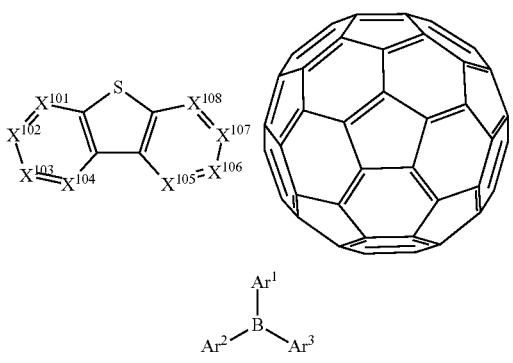

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

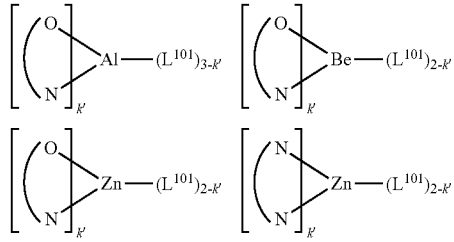

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exciton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A

| MATERIAL | EXAMPLES OF MATERIAL | PUBLICATIONS |
|---|---|---|
| Hole injection materials | | |
| Phthalocyanine and porphyrin compounds | | Appl. Phys. Lett. 69, 2160 (1996) |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | | Synth. Met. 87, 171 (1997) WO2007002683 |
| Phosphonic acid and silane SAMs | | US20030162053 |
| Triarylamine or polythiophene polymers with conductivity dopants | and | EP1725079A1 |

TABLE A-continued
| MATERIAL | EXAMPLES OF MATERIAL | PUBLICATIONS |
|---|---|---|
| | 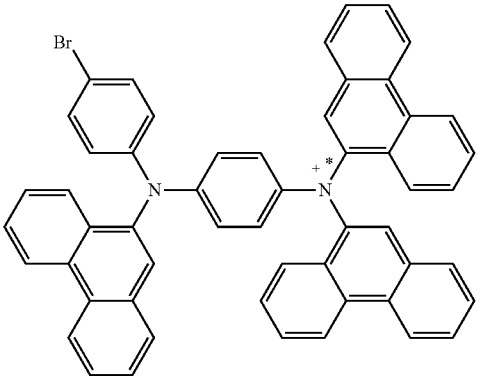 [SMILES: Brc1ccc(N(c2ccc(N(c3cc4ccccc4c4ccccc34)c3cc4ccccc4c4ccccc34)cc2)c2cc3ccccc3c3ccccc23)cc1] | |
| | 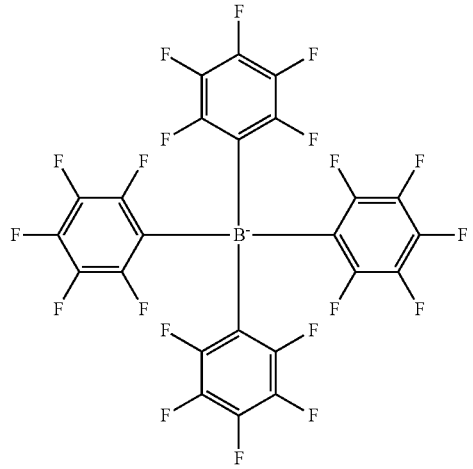 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Organic compounds with conductive inorganic compounds, such as molybdenum and tungsten oxides | 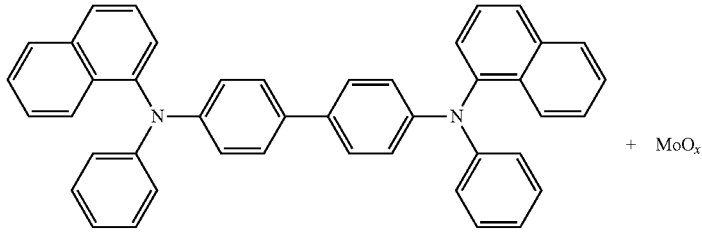 [SMILES: c1ccc(N(c2ccc(-c3ccc(N(c4ccccc4)c4cccc5ccccc45)cc3)cc2)c2cccc3ccccc23)cc1] + $MoO_x$ | US20050123751<br>SID Symposium Digest, 37, 923 (2006)<br>WO2009018009 |
| n-type semiconducting organic complexes | 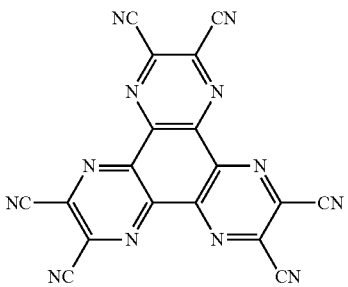 [SMILES: N#Cc1nc2c3nc(C#N)c(C#N)nc3c3nc(C#N)c(C#N)nc3c2nc1C#N] | US20020158242 |

TABLE A-continued

| MATERIAL | EXAMPLES OF MATERIAL | PUBLICATIONS |
| --- | --- | --- |
| Metal organometallic complexes | | US20060240279 |
| Cross-linkable compounds | | US20080220265 |
| Polythiophene based polymers and copolymers | | WO 2011075644<br>EP2350216 |

Hole transporting materials

| | | |
| --- | --- | --- |
| Triarylamines<br>(e.g., TPD, α-NPD) | | Appl. Phys. Lett. 51, 913 (1987) |

TABLE A-continued
| MATERIAL | EXAMPLES OF MATERIAL | PUBLICATIONS |
|---|---|---|
| | 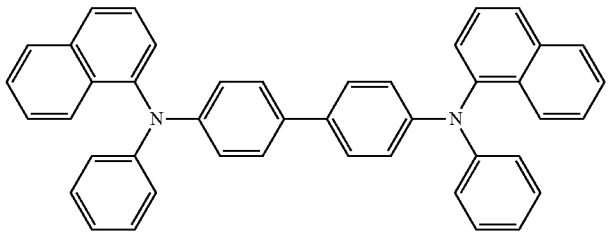 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 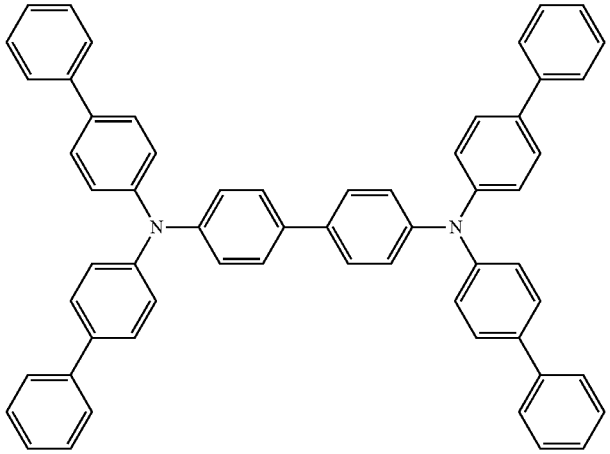 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 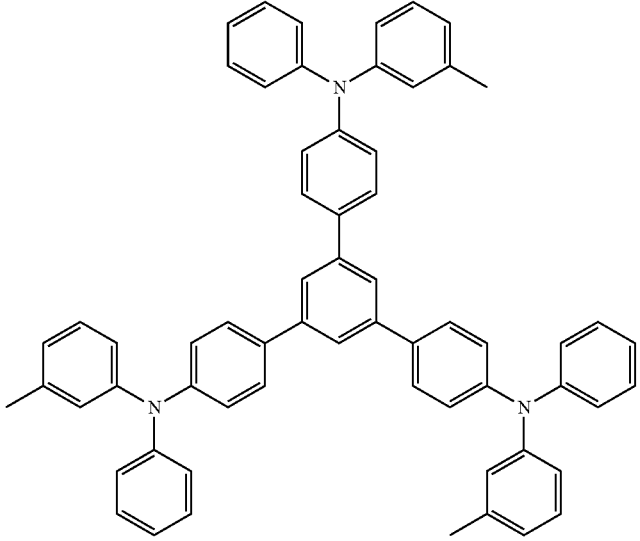 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE A-continued
| MATERIAL | EXAMPLES OF MATERIAL | PUBLICATIONS |
|---|---|---|
| | 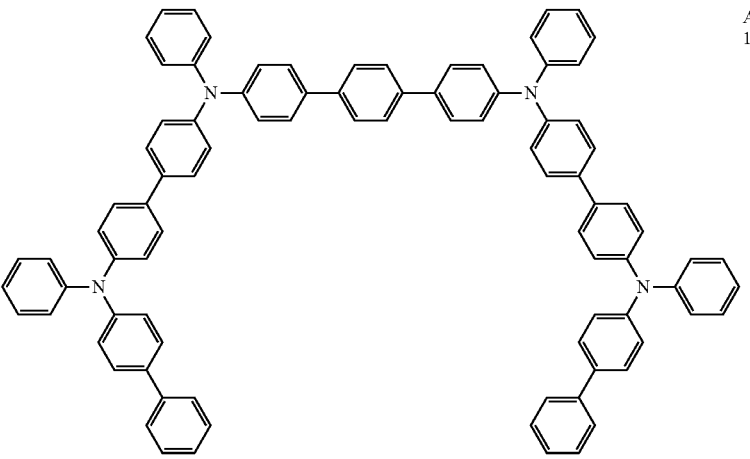 | Appl. Phys. Lett. 90, 183503 (2007) |
| | 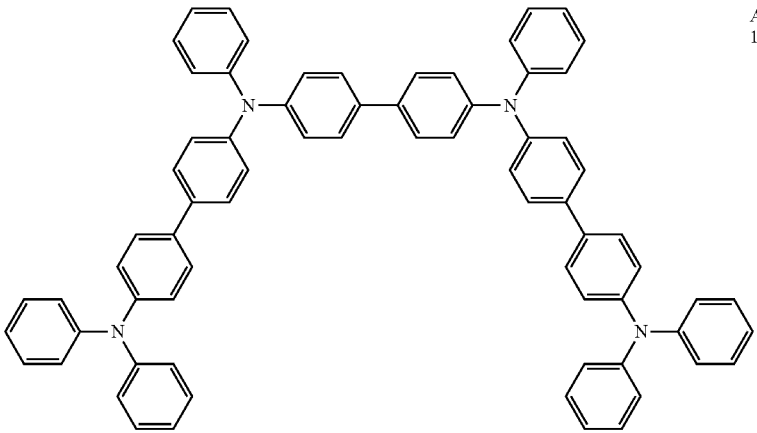 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triarylamine on spirofluorene core | 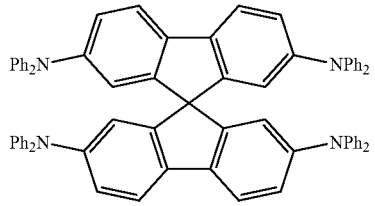 | Synth. Met. 91, 209 (1997) |
| Arylamine carbazole compounds | 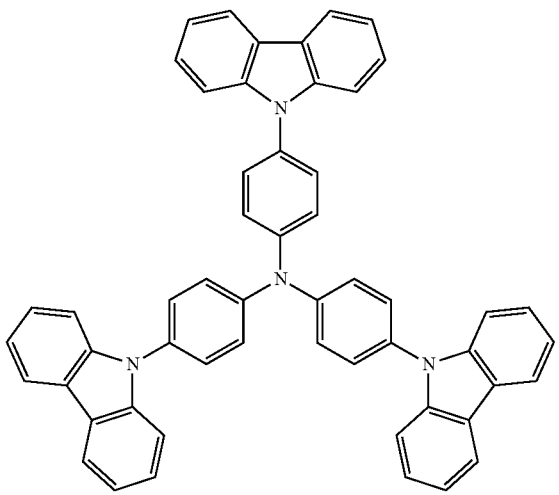 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |

TABLE A-continued
| MATERIAL | EXAMPLES OF MATERIAL | PUBLICATIONS |
| --- | --- | --- |
| Triarylamine with (di)benzothiophene/(di)benzofuran | 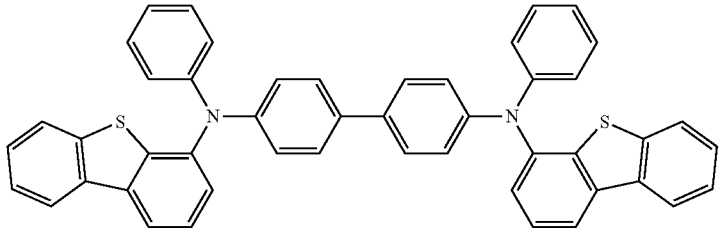 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 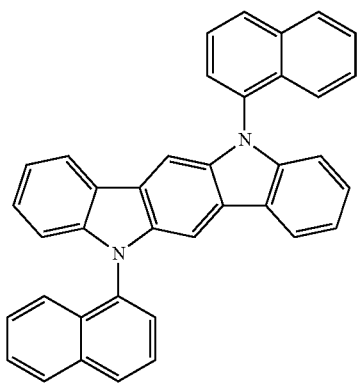 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 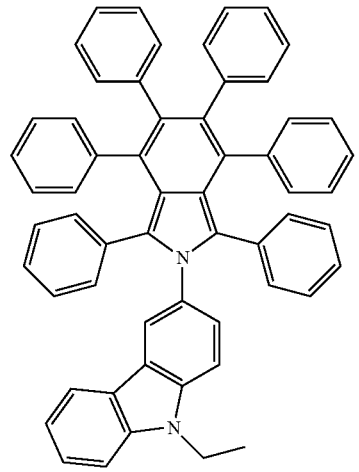 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 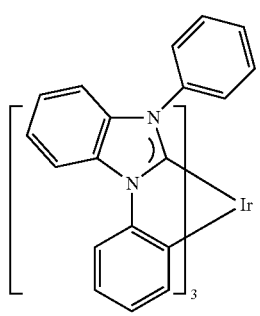 | US20080018221 |
Phosphorescent OLED host materials
Red hosts TABLE A-continued
| MATERIAL | EXAMPLES OF MATERIAL | PUBLICATIONS |
|---|---|---|
| Arylcarbazoles | 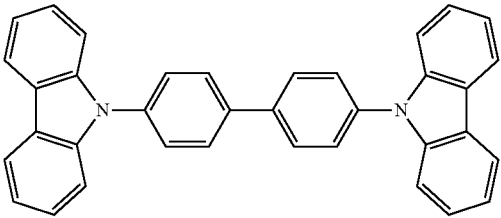 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., $Alq_3$, BAlq) | 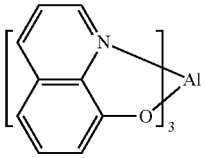 | Nature 395, 151 (1998) |
| | 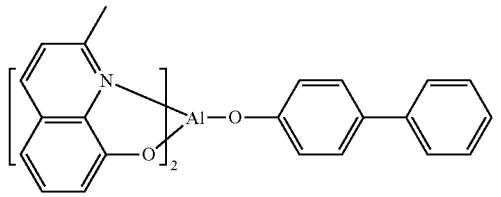 | US20060202194 |
| | 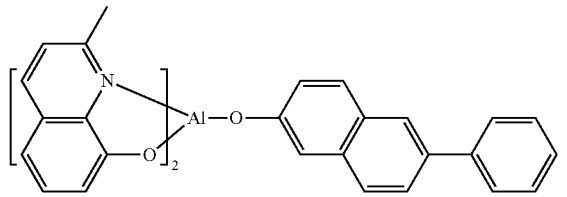 | WO2005014551 |
| | 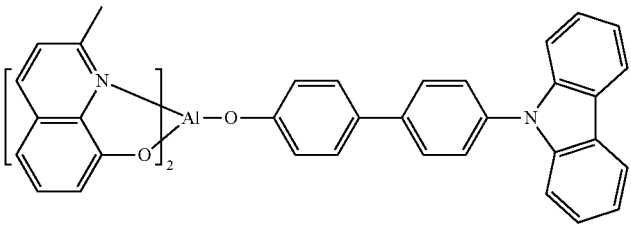 | WO2006072002 |
| Metal phenoxybenzothiazole compounds | 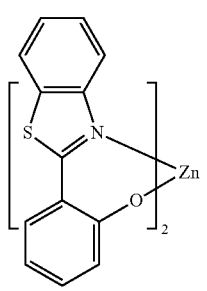 | Appl. Phys. Lett. 90, 123509 (2007) |
| Conjugated oligomers and polymers (e.g., polyfluorene) | 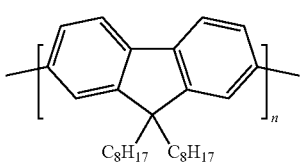 | Org. Electron. 1, 15 (2000) |

TABLE A-continued
| MATERIAL | EXAMPLES OF MATERIAL | PUBLICATIONS |
|---|---|---|
| Aromatic fused rings | 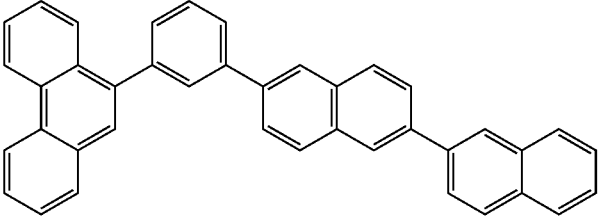 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 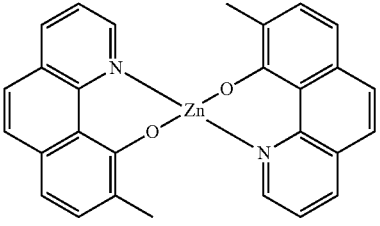 | WO2010056066 |
| Chrysene based compounds | 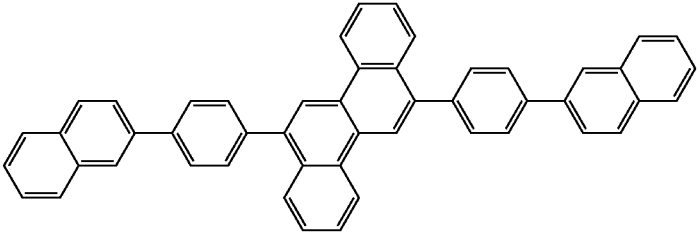 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
Green hosts
| Arylcarbazoles | 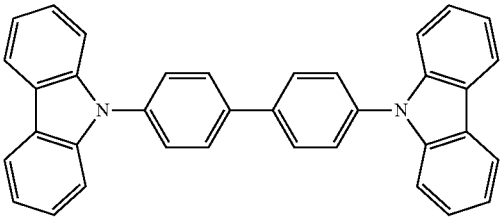 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 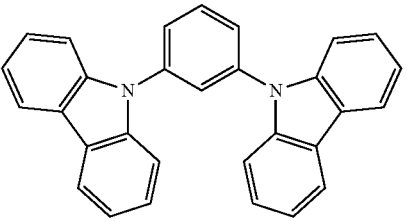 [SMILES: c1cc(-n2c3ccccc3c3ccccc32)cc(-n2c3ccccc3c3ccccc32)c1] | US20030175553 |
| | 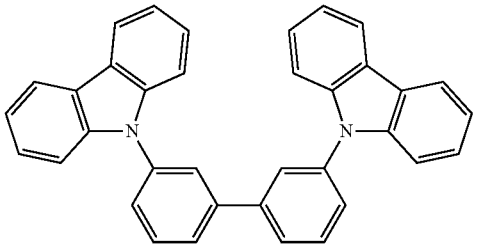 [SMILES: c1cc(-c2cccc(-n3c4ccccc4c4ccccc43)c2)cc(-n2c3ccccc3c3ccccc32)c1] | WO2001039234 |

TABLE A-continued
| MATERIAL | EXAMPLES OF MATERIAL | PUBLICATIONS |
|---|---|---|
| Aryltriphenylene compounds | 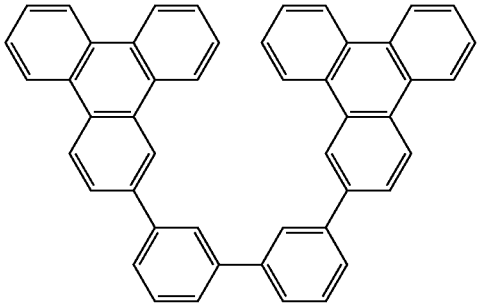 [SMILES: c1cc(-c2cccc(-c3ccc4c5ccccc5c5ccccc5c4c3)c2)cc(-c2ccc3c4ccccc4c4ccccc4c3c2)c1] | US20060280965 |
|  | 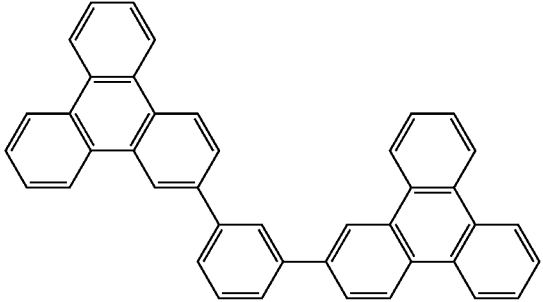 [SMILES: c1cc(-c2ccc3c4ccccc4c4ccccc4c3c2)cc(-c2ccc3c4ccccc4c4ccccc4c3c2)c1] | US20060280965 |
|  | 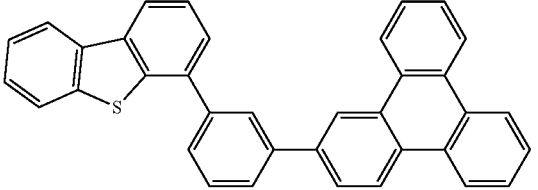 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 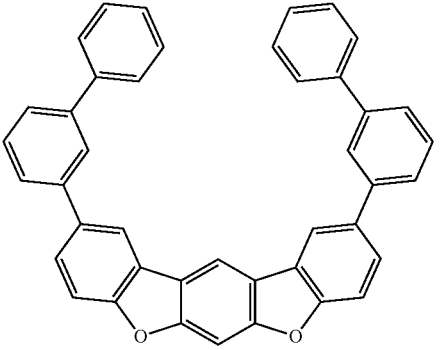 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 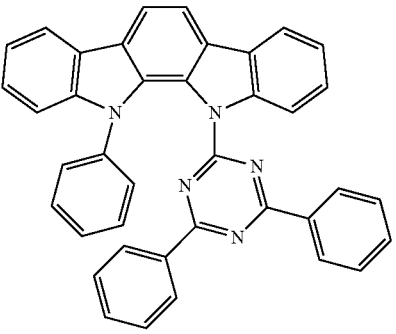 [SMILES: c1ccc(-c2nc(-c3ccccc3)nc(-n3c4ccccc4c4ccc5c6ccccc6n(-c6ccccc6)c5c43)n2)cc1] | WO2008056746 |

TABLE A-continued
| MATERIAL | EXAMPLES OF MATERIAL | PUBLICATIONS |
|---|---|---|
| | 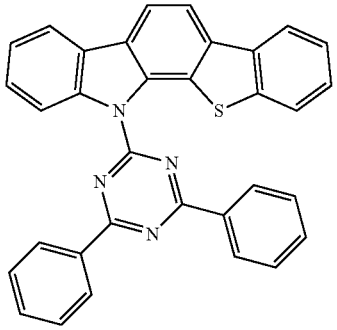 [SMILES: c1ccc(-c2nc(-c3ccccc3)nc(-n3c4ccccc4c4ccc5c6ccccc6sc5c43)n2)cc1] | WO2010107244 |
| Aza-carbazole/DBT/DBF | 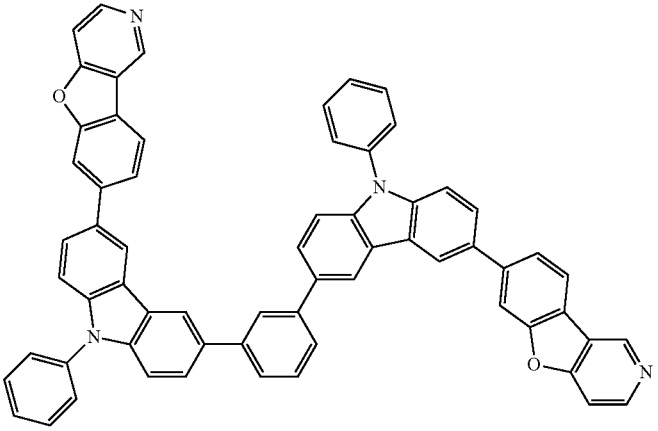 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 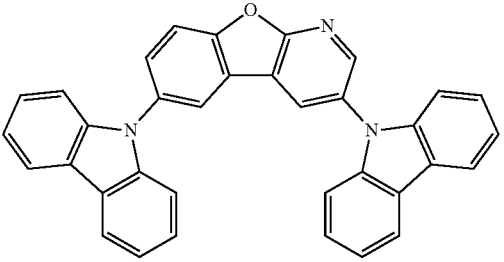 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 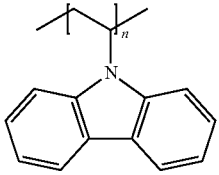 | Appl. Phys. Lett. 77, 2280 (2000) |
| Spirofluorene compounds | 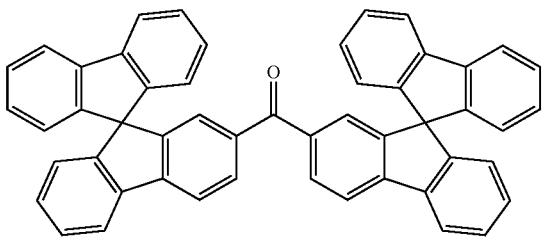 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE A-continued

| MATERIAL | EXAMPLES OF MATERIAL | PUBLICATIONS |
| --- | --- | --- |
| Metal phenoxybenzooxazole compounds | | WO2005089025 |
| | | WO2006132173 |
| | | JP200511610 |
| Spirofluorene-carbazole compounds | | JP2007254297 |
| | | JP2007254297 |

TABLE A-continued

| MATERIAL | EXAMPLES OF MATERIAL | PUBLICATIONS |
| --- | --- | --- |
| Indolocarbazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE A-continued

| MATERIAL | EXAMPLES OF MATERIAL | PUBLICATIONS |
| --- | --- | --- |
| Metal phenoxypyridine compounds | | WO2005030900 |
| Metal coordination complexes (e.g., Zn, Al with N^N ligands) | | US20040137268, US20040137267 |

Blue hosts

| | | |
| --- | --- | --- |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |

| MATERIAL | EXAMPLES OF MATERIAL | PUBLICATIONS |
|---|---|---|
| | 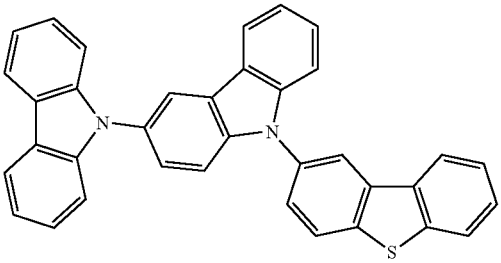 [SMILES: c1ccc2c(c1)sc1ccc(-n3c4ccccc4c4cc(-n5c6ccccc6c6ccccc65)ccc43)cc12] | WO2009086028 |
| | 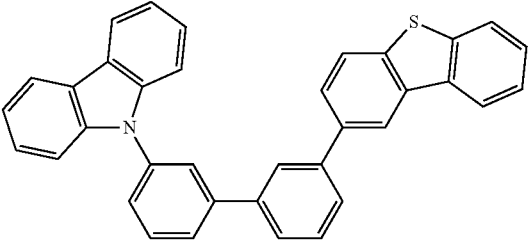 [SMILES: c1cc(-c2cccc(-n3c4ccccc4c4ccccc43)c2)cc(-c2ccc3sc4ccccc4c3c2)c1] | US20090030202, US20090017330 |
| | 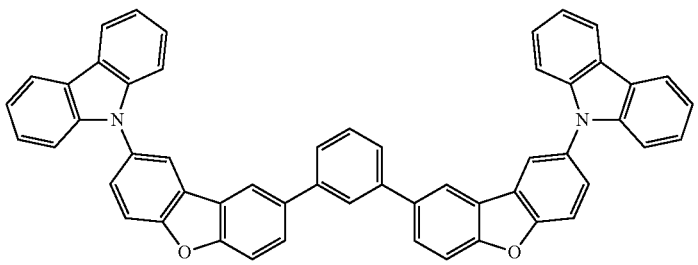 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 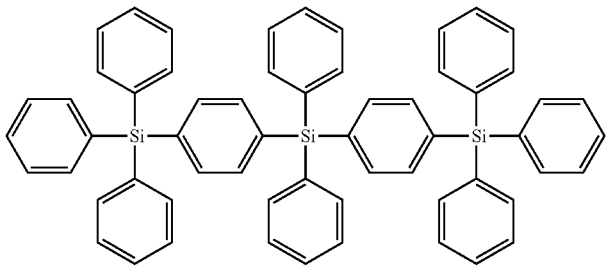 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 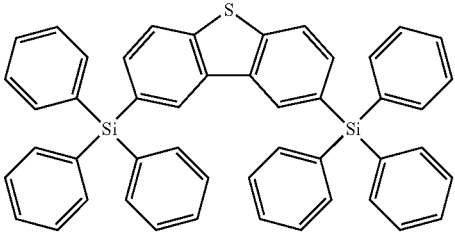 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE A-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| Carbazole linked by non-conjugated groups | | US20040115476 |
| Aza-carbazoles | | US20060121308 |
| High triplet metal organometallic complex | | U.S. Pat. No. 7,154,114 |

Phosphorescent dopants
Red dopants

| | | |
| --- | --- | --- |
| Heavy metal porphyrins (e.g., PtOEP) | | Nature 395, 151 (1998) |

TABLE A-continued

| MATERIAL | EXAMPLES OF MATERIAL | PUBLICATIONS |
| --- | --- | --- |
| Iridium(III) organometallic complexes | | Appl. Phys. Lett. 78, 1622 (2001) |
| | | US20030072964 |
| | | US20030072964 |
| | | US20060202194 |
| | | US20060202194 |

TABLE A-continued

| MATERIAL | EXAMPLES OF MATERIAL | PUBLICATIONS |
|---|---|---|
| | | US20070087321 |
| | | US20080261076<br>US20100090591 |
| | | US20070087321 |
| | | Adv. Mater. 19, 739 (2007) |
| | | WO2009100991 |

TABLE A-continued
| MATERIAL | EXAMPLES OF MATERIAL | PUBLICATIONS |
|---|---|---|
| | 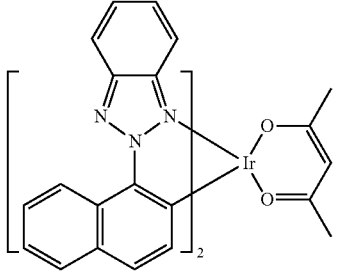 | WO2008101842 |
| | 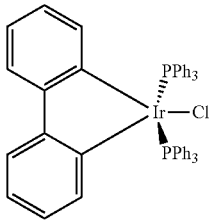 | U.S. Pat. No. 7,232,618 |
| Platinum(II) organometallic complexes | 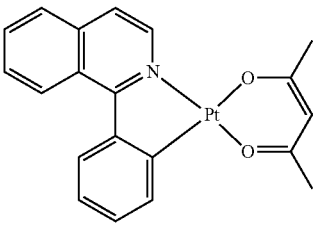 | WO2003040257 |
| | 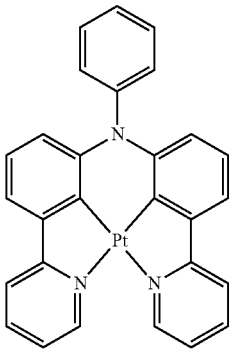 | US20070103060 |
| Osmium(III) complexes | 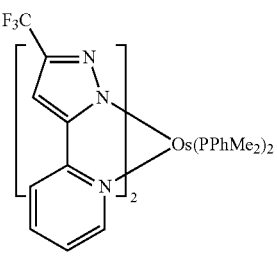 | Chem. Mater. 17, 3532 (2005) |

TABLE A-continued

| MATERIAL | EXAMPLES OF MATERIAL | PUBLICATIONS |
| --- | --- | --- |
| Ruthenium(II) complexes | | Adv. Mater. 17, 1059 (2005) |
| Rhenium (I), (II), and (III) complexes | | US20050244673 |

Green dopants

| | | |
| --- | --- | --- |
| Iridium(III) organometallic complexes | and its derivatives | Inorg. Chem. 40, 1704 (2001) |
| | | US20020034656 |

| MATERIAL | EXAMPLES OF MATERIAL | PUBLICATIONS |
|---|---|---|
| | 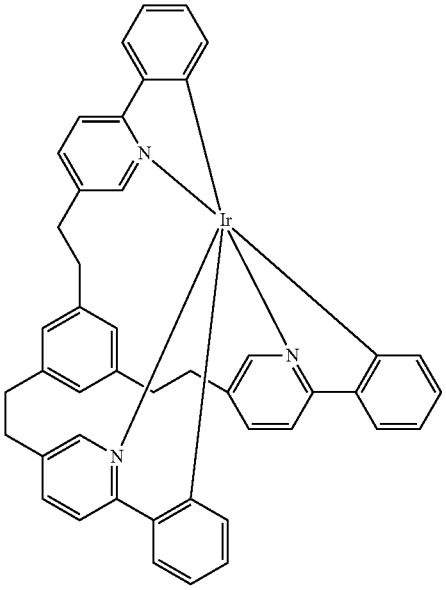 | U.S. Pat. No. 7,332,232 |
| | 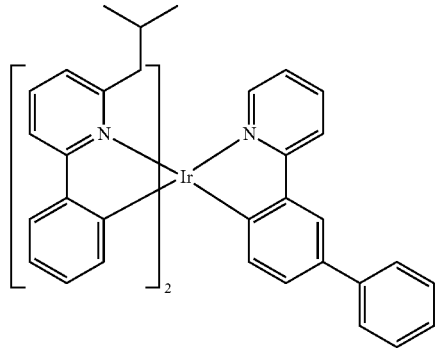 | US20090108737 |
| | 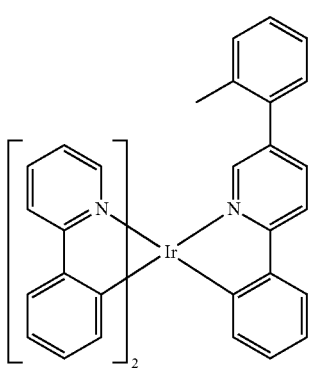 | WO2010028151 |

TABLE A-continued
| MATERIAL | EXAMPLES OF MATERIAL | PUBLICATIONS |
|---|---|---|
| | 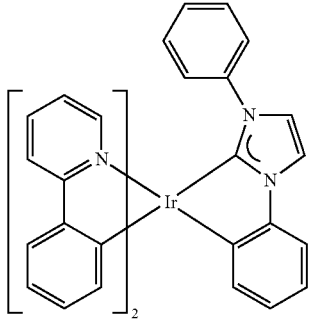 | EP1841834B |
| | 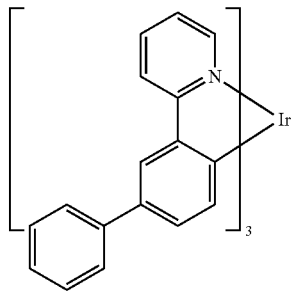 | US20060127696 |
| | 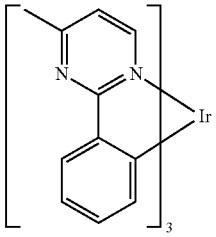 | US20090039776 |
| | 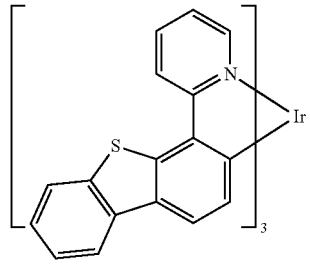 | U.S. Pat. No. 6,921,915 |
| | 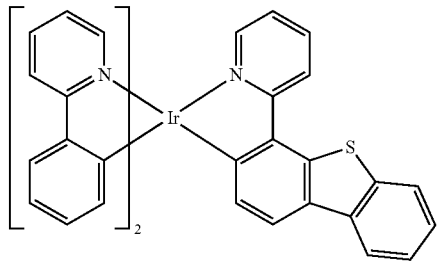 | US20100244004 |

TABLE A-continued
| MATERIAL | EXAMPLES OF MATERIAL | PUBLICATIONS |
|---|---|---|
| | 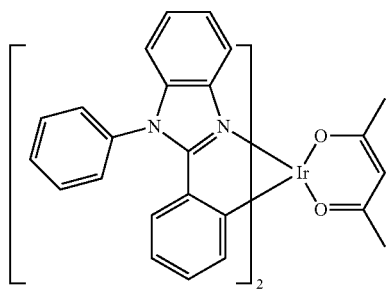 | U.S. Pat. No. 6,687,266 |
| | 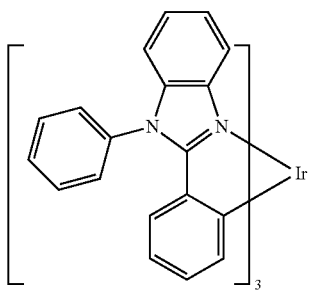 | Chem. Mater. 16, 2480 (2004) |
| | 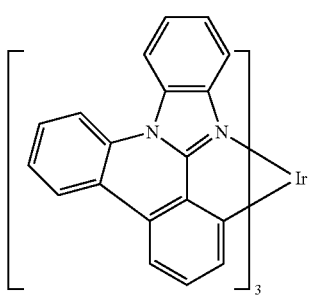 | US20070190359 |
| | 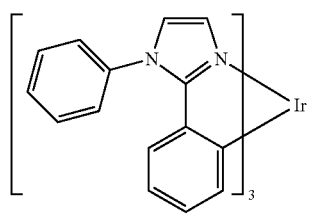 | US 20060008670<br>JP2007123392 |
| | 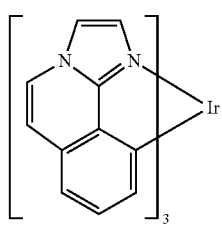 | WO2010086089,<br>WO2011044988 |
| | 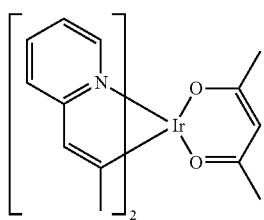 | Adv. Mater. 16, 2003 (2004) |

TABLE A-continued
| MATERIAL | EXAMPLES OF MATERIAL | PUBLICATIONS |
|---|---|---|
| | 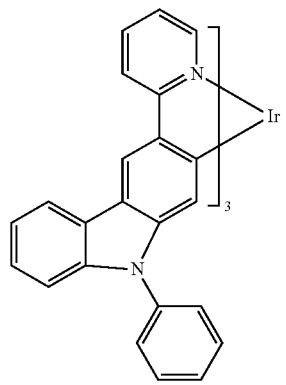 | Angew. Chem. Int. Ed. 2006, 45, 7800 |
| | 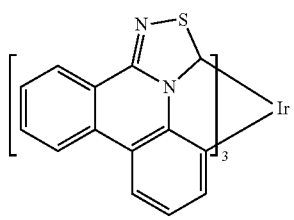 | WO2009050290 |
| | 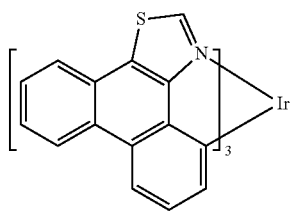 | US20090165846 |
| | 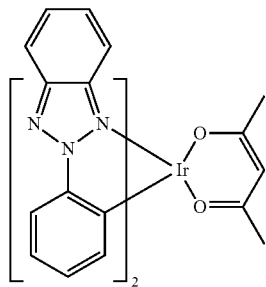 | US20080015355 |
| | 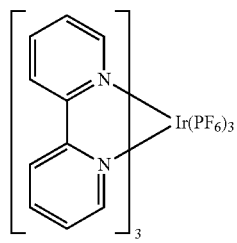 | US20010015432 |
| | 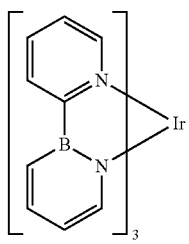 | US20100295032 |

TABLE A-continued

| MATERIAL | EXAMPLES OF MATERIAL | PUBLICATIONS |
| --- | --- | --- |
| Monomer for polymeric metal organometallic compounds | | U.S. Pat. No. 7,250,226, U.S. Pat. No. 7,396,598 |
| Pt(II) organometallic complexes, including polydentate ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

TABLE A-continued

| MATERIAL | EXAMPLES OF MATERIAL | PUBLICATIONS |
| --- | --- | --- |
|  |  | US20060263635 |
|  |  | US20060182992<br>US20070103060 |
| Cu complexes |  | WO2009000673 |
|  |  | US20070111026 |

TABLE A-continued

| MATERIAL | EXAMPLES OF MATERIAL | PUBLICATIONS |
|---|---|---|
| Gold complexes | | Chem. Commun. 2906 (2005) |
| Rhenium(III) complexes | | Inorg. Chem. 42, 1248 (2003) |
| Osmium(II) complexes | | U.S. Pat. No. 7,279,704 |
| Deuterated organometallic complexes | | US20030138657 |

TABLE A-continued

| MATERIAL | EXAMPLES OF MATERIAL | PUBLICATIONS |
|---|---|---|
| Organometallic complexes with two or more metal centers | | US20030152802 |
| | | U.S. Pat. No. 7,090,928 |
| Blue dopants | | |
| Iridium(III) organometallic complexes | | WO2002002714 |
| | | WO2006009024 |
| | | US20060251923<br>US20110057559<br>US20110204333 |

| MATERIAL | EXAMPLES OF MATERIAL | PUBLICATIONS |
|---|---|---|
| | | U.S. Pat. No. 7,393,599, WO2006056418, US20050260441, WO2005019373 |
| | | U.S. Pat. No. 7,534,505 |
| | | WO2011051404 |
| | | U.S. Pat. No. 7,445,855 |
| | | US20070190359, US20080297033 US20100148663 |

TABLE A-continued

| MATERIAL | EXAMPLES OF MATERIAL | PUBLICATIONS |
|---|---|---|
| | | U.S. Pat. No. 7,338,722 |
| | | US20020134984 |
| | | Angew. Chem. Int. Ed. 47, 4542 (2008) |
| | | Chem. Mater. 18, 5119 (2006) |
| | | Inorg. Chem. 46, 4308 (2007) |

TABLE A-continued

| MATERIAL | EXAMPLES OF MATERIAL | PUBLICATIONS |
|---|---|---|
| | | WO2005123873 |
| | | WO2005123873 |
| | | WO2007004380 |
| | | WO2006082742 |
| Osmium(II) complexes | | U.S. Pat. No. 7,279,704 |

TABLE A-continued

| MATERIAL | EXAMPLES OF MATERIAL | PUBLICATIONS |
|---|---|---|
|  | (Os(PPh₃) complex structure) | Organometallics 23, 3745 (2004) |
| Gold complexes | (Ph₂P-Au-Cl dimer structure) | Appl. Phys. Lett. 74, 1361 (1999) |
| Platinum(II) complexes | (Pt complex with pyrazolylborate structure) | WO2006098120, WO2006103874 |
| Pt tetradentate complexes with at least one metal-carbene bond | (Pt tetradentate carbene complex structure) | U.S. Pat. No. 7,655,323 |
| Exciton/hole blocking layer materials | | |
| Bathocuprine compounds (e.g., BCP, BPhen) | (BCP structure) | Appl. Phys. Lett. 75, 4 (1999) |
|  | (BPhen structure) | Appl. Phys. Lett. 79, 449 (2001) |
| Metal 8-hydroxyquinolates (e.g., BAlq) | (BAlq structure) | Appl. Phys. Lett. 81, 162 (2002) |

TABLE A-continued

| MATERIAL | EXAMPLES OF MATERIAL | PUBLICATIONS |
| --- | --- | --- |
| 5-member ring electron deficient heterocycles such as triazole, oxadiazole, imidazole, benzoimidazole | | Appl. Phys. Lett. 81, 162 (2002) |
| Triphenylene compounds | | US20050025993 |
| Fluorinated aromatic compounds | | Appl. Phys. Lett. 79, 156 (2001) |

TABLE A-continued
| MATERIAL | EXAMPLES OF MATERIAL | PUBLICATIONS |
|---|---|---|
| Phenothiazine-S-oxide | 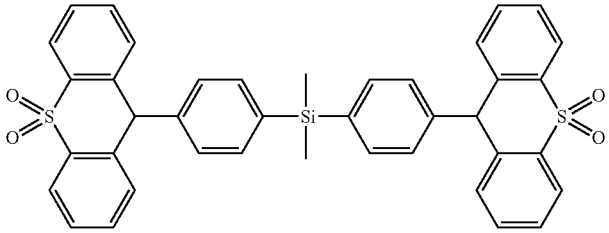 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 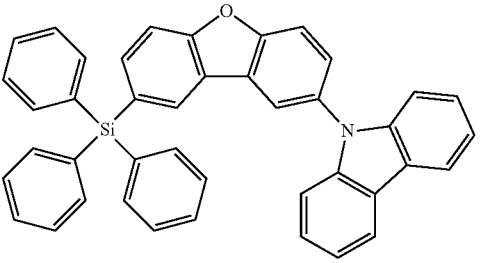 [SMILES: c1ccc([Si](c2ccccc2)(c2ccccc2)c2ccc3oc4ccc(-n5c6ccccc6c6ccccc65)cc4c3c2)cc1] | WO2010079051 |
| Aza-carbazoles | 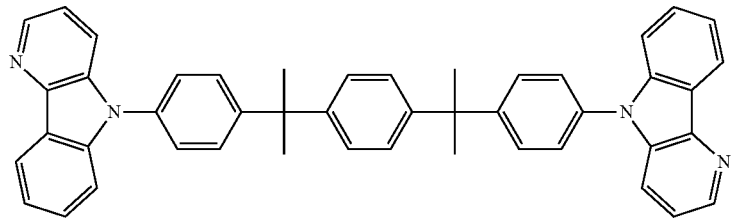 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
Electron transporting materials
| Anthracene-benzoimidazole compounds | 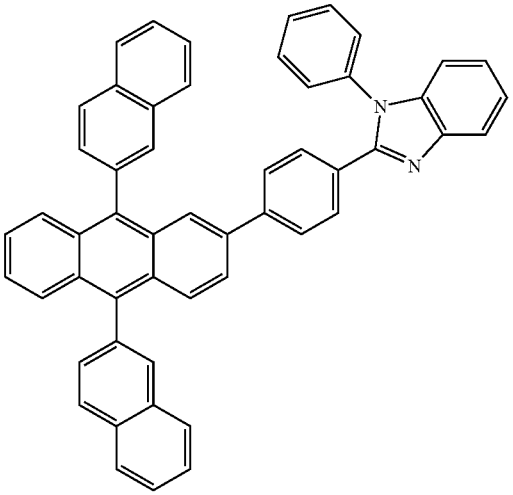 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
|---|---|---|
| | 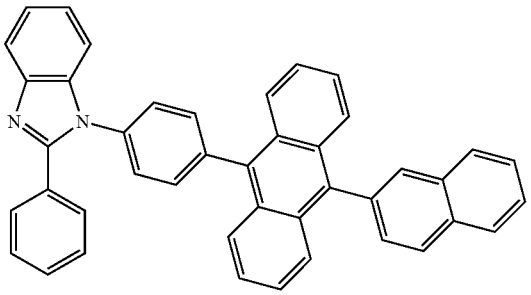 [SMILES: c1ccc(-c2nc3ccccc3n2-c2ccc(-c3c4ccccc4c(-c4ccc5ccccc5c4)c4ccccc34)cc2)cc1] | US20090179554 |

TABLE A-continued

| MATERIAL | EXAMPLES OF MATERIAL | PUBLICATIONS |
| --- | --- | --- |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) U.S. Pat. No. 7,230,107 |
| Metal hydroxybenzoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE A-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 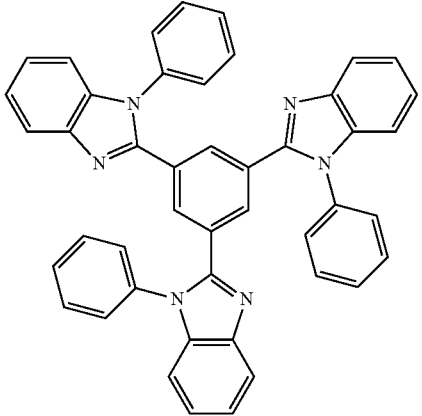 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
|  | 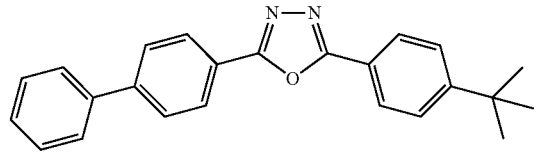 [SMILES: CC(C)(C)c1ccc(-c2nnc(-c3ccc(-c4ccccc4)cc3)o2)cc1] | Appl. Phys. Lett. 55, 1489 (1989) |
|  | 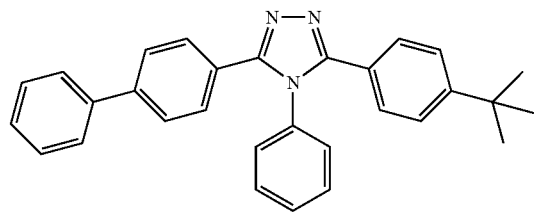 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 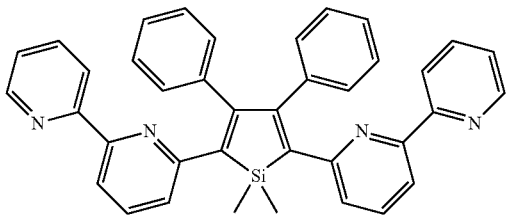 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 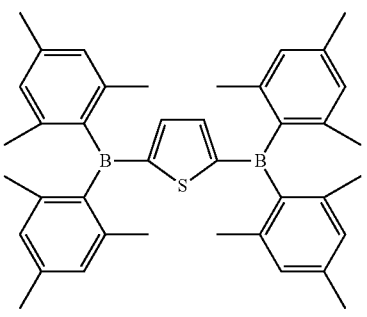 | J. Am. Chem. Soc. 120, 9714 (1998) |
| Fluorinated aromatic compounds | 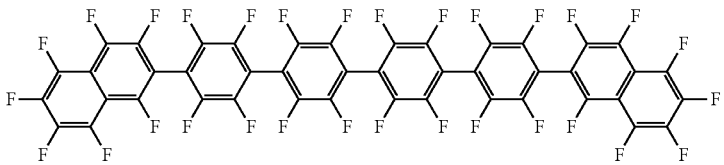 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

TABLE A-continued

| MATERIAL | EXAMPLES OF MATERIAL | PUBLICATIONS |
| --- | --- | --- |
| Fullerene (e.g., $C_{60}$) | | US20090101870 |
| Triazine complexes | | US20040036077 |
| Zn (N^N) complexes | | U.S. Pat. No. 6,528,187 |

Synthesis of 4,4,5,5-tetramethyl-2-(tetraphenylen-2-yl)-1,3,2-dioxaborolane

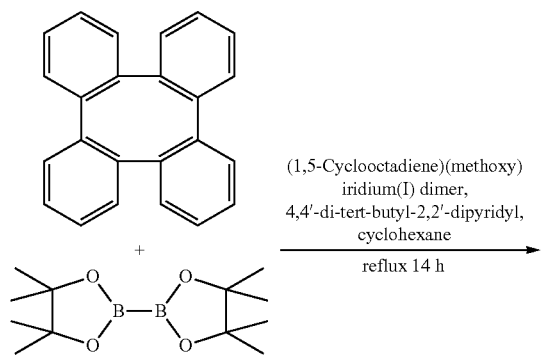

Tetraphenylene (10.6 g, 35.0 mmol) synthesized according to Liebigs Ann. Chem. 704, 91-108 (1967), bis(pinacolato)diboron (8.8 g, 35.0 mmol), 4,4'-di-tert-butyl-2,2'-dipyridyl (1.9 g, 7.0 mmol), (1,5-cyclooctadiene)(methoxy) iridium(I) dimer (2.3 g, 3.5 mmol) and anhydrous cyclohexane (250 mL) were mixed at room temperature. The reaction mixture was bubbled with nitrogen for 15 min. The resultant mixture was refluxed for 14 hours. The solvent was removed in vacuo. The residue was purified by flash column chromatography using 25%-40% of DCM in hexane (with 0.5% triethylamine). The solid obtained was then mixed with 100 mL of MeCN and sonicated for 5 min at room temperature. The solid was filtered and dried under vacuum at 60° C. to afford 4,4,5,5-tetramethyl-2-(tetraphenylen-2-yl)-1,3,2-dioxaborolane (3.2 g) as a white solid.

Synthesis of Compound 21

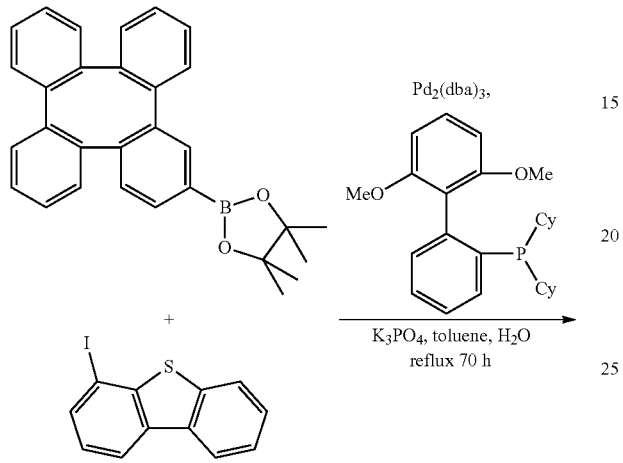

Synthesis of 2-Bromotetraphenylene

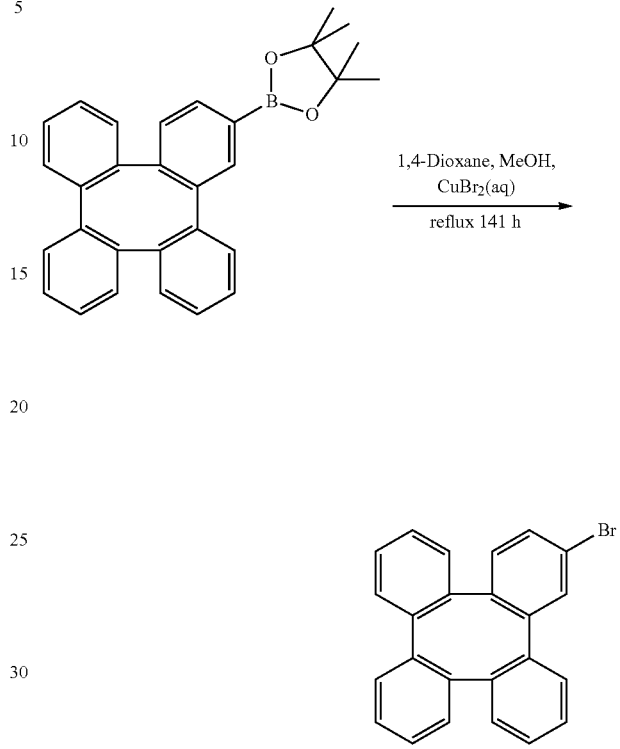

4,4,5,5-Tetramethyl-2-(tetraphenylen-2-yl)-1,3,2-dioxaborolane (2.8 g, 6.5 mmol), dioxane (150 mL), MeOH (50 mL) and $CuBr_2$ solution (9.1 g, 39 mmol in 150 mL of $H_2O$) were mixed at room temperature. The reaction mixture was bubbled with nitrogen for 15 min. The resultant mixture was refluxed for 140 hours. The reaction mixture was extracted by 50% of DCM in hexane. The extract was filtered through a silica pad and $MgSO_4$. The solvent was removed in vacuo. The residue was purified by flash column chromatography using 15% of DCM in hexane to afford 2-bromotetraphenylene (2.2 g) as a white solid.

Synthesis of Compound 1

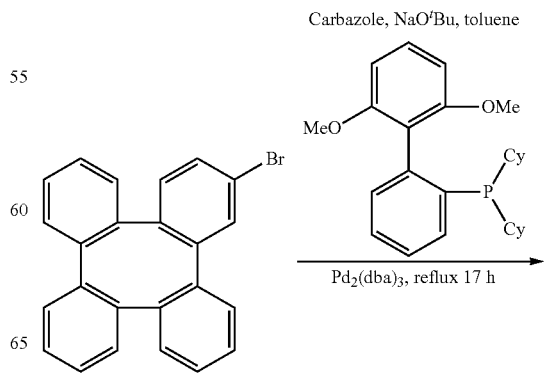

4,4,5,5-Tetramethyl-2-(tetraphenylen-2-yl)-1,3,2-dioxaborolane (1.9 g, 4.5 mmol), 4-iododibenzo[b,d]thiophene (2.0 g, 6.8 mmol), $K_3PO_4$ (1.9 g, 9.0 mmol) 2-dicyclohexylphosphino-2',6'-dimethoxybiphenyl (0.7 g, 1.8 mmol), toluene (40 mL) and water (4 mL) were mixed at room temperature. The reaction mixture was bubbled with nitrogen for 30 min. $Pd_2(dba)_3$ (0.4 g, 0.45 mmol) was added. The mixture was bubbled with nitrogen for 15 min. The resultant mixture was refluxed for 70 hours. The reaction mixture was extracted by 3 L of 50% DCM/hexane. The extract was filtered through a silica pad and $MgSO_4$. The solvent was removed in vacuo. The residue was purified by flash column chromatography using 10% then 15% of DCM in hexane. This product was mixed with 50 mL of heptane and bubbled with $N_2$ for 15 min. The resultant mixture was refluxed for 1 hour. The solid was filtered and dried under vacuum at 60° C. to afford the desired product (1.6 g) as a white solid.

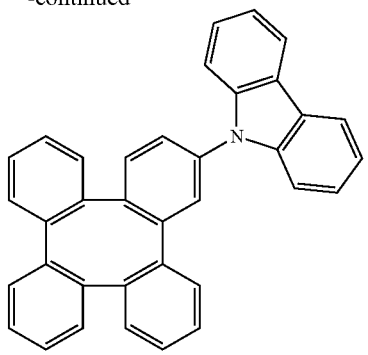

2-Bromotetraphenylene (3.1 g, 8.0 mmol), carbazole (8.0 g, 48.0 mmol), 2-dicyclohexylphosphino-2',6'-dimethoxybiphenyl (3.3 g, 8.0 mmol), sodium tert-butoxide (3.8 g, 40.0 mmol) and toluene (100 mL) were mixed at room temperature. The reaction mixture was bubbled with nitrogen for 15 min. $Pd_2(dba)_3$ (1.8 g, 2.0 mmol) was added. The mixture was bubbled with nitrogen for 15 min. The resultant mixture was refluxed for 17 hours. The reaction mixture was filtered through a silica pad and $MgSO_4$ and eluted by 50% of DCM in hexane. The solvent was removed in vacuo. This product was mixed with 600 mL of MeCN and bubbled with $N_2$ for 30 min. The resultant mixture was refluxed for 1 hour and allowed to reach room temperature. The solid was filtered and dried under vacuum at 60° C. to afford the desired product (2.5 g) as a white solid. The triplet energy of Compounds 1 and 21, measured at 77 K in dilute THF solutions, are 410 nm and 456 nm, respectively.

EXPERIMENTAL

Experiment 1

In the OLED experiment, all device examples were fabricated by high vacuum ($<10^{-7}$ Torr) thermal evaporation. The anode electrode is ~800 Å of indium tin oxide (ITO). The cathode consisted of 10 Å of LiF followed by 1,000 Å of Al. All devices were encapsulated with a glass lid sealed with an epoxy resin in a nitrogen glove box (<1 ppm of $H_2O$ and $O_2$) and a moisture getter was incorporated inside the package.

Device Example 1: The organic stack of the Device Examples in Table 1 consists of sequentially, from the ITO surface, 100 Å of LG101 (purchased from LG Chem, Korea) as the hole injection layer (HIL), 250 Å of Compound A as the primary hole transport layer (HTL1), 300 Å of Compound 1 doped with 20% of the emitter Compound B as the emissive layer (EML), 50 Å of Compound C as ETL2 and 400 Å of $Alq_3$ as ETL1.

Device Example 2 was fabricated in the same way except as Device Example 1 except that 300 Å instead of 400 Å of $Alq_3$ as ETL1 was used.

Device Example 3 was fabricated in the same way as Device Example 1 except that 50 Å of Compound E as the secondary hole transport layer (HTL2) was inserted between the HTL 1 and EML and 300 Å, instead of 400 Å, of $Alq_3$ as ETL1 was used.

Device Comparative Example 1 and Device Comparative Example 2 were fabricated in the same way as Device Example 1 except Compound C and Compound D were used as the host compounds in Device Comparative Example 1 and Device Comparative Example 2, respectively.

The device data is summarized in Table 1 below:

TABLE 1

| Device Example | HTL2 | Host 300 Å | $Alq_3$ Å | 1931 CIE CIE x | 1931 CIE CIE y | λ max [nm] | At 1,000 cd/m² Voltage [V] | At 1,000 cd/m² LE [cd/A] | At 1,000 cd/m² EQE [%] | At 1,000 cd/m² PE [lm/W] |
|---|---|---|---|---|---|---|---|---|---|---|
| Device Example 1 | none | Cmpd 1 | 400 | 0.175 | 0.393 | 474 | 5.8 | 52.2 | 23.3 | 28.2 |
| Device Example 2 | none | Cmpd 21 | 300 | 0.170 | 0.373 | 474 | 5.4 | 47.0 | 21.9 | 27.6 |
| Device Example 3 | Cmpd E (50 Å) | Cmpd 21 | 300 | 0.170 | 0.381 | 474 | 5.4 | 54.7 | 25.1 | 31.8 |
| Device Comparative Example 1 | none | Cmpd D | 400 | 0.179 | 0.408 | 474 | 5.8 | 46.5 | 20.3 | 25.2 |
| Device Comparative Example 2 | none | Cmpd C | 400 | 0.178 | 0.406 | 474 | 5.5 | 47.6 | 20.7 | 27.1 |

Some of the compounds used in the devices are:

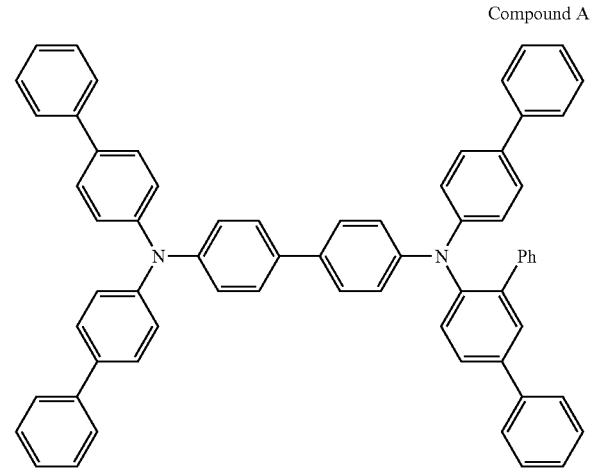

Compound A

-continued

Compound B

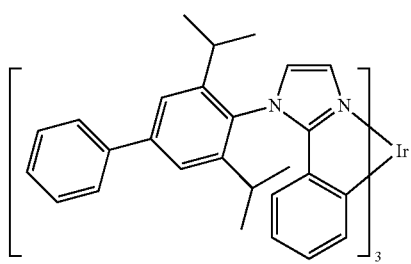

Compound C

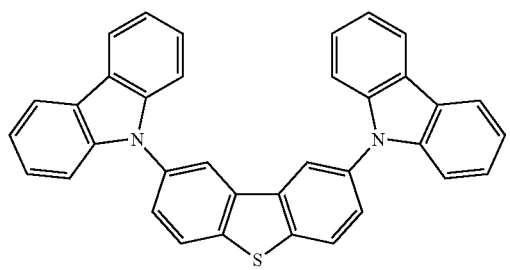

-continued

Compound D

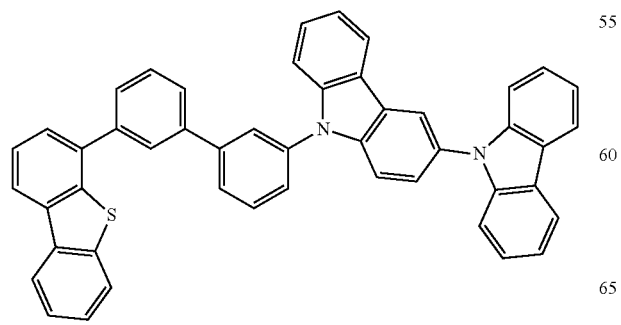

-continued

Compound E

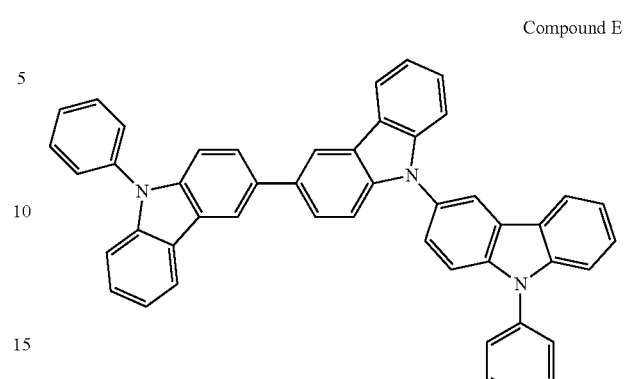

Device Example 3: The organic stack of the Device Examples in Table 2 consists of sequentially, from the ITO surface, 100 Å of LG101 as the hole injection layer (HIL), 450 Å of Compound A as the hole transport layer (HTL1), 400 Å of Compound 21 doped with 10% of the emitter Compound F as the emissive layer (EML), 50 Å of Compound Gas ETL2 and 350 Å of Alq$_3$ as ETL1.

Device Comparative Example 3 was fabricated in the same way as Device Example 3 except CBP was used as the host.

The device data is summarized in Table 2.

| Device example | Host 300 Å | 1931 CIE | | λmax [nm] | At 1,000 cd/m² | | | | LT80 at 20 mA/cm² | |
|---|---|---|---|---|---|---|---|---|---|---|
| | | CIE x | CIE y | | Voltage [V] | LE [cd/A] | EQE [%] | PE [lm/W] | L$_0$ [cd/m2] | time [h] |
| Device example 3 | Cmpd 21 | 0.321 | 0.630 | 523 | 5.9 | 63.2 | 17.6 | 33.6 | 19909 | 178 |
| Device comparative example 3 | CBP | 0.319 | 0.630 | 522 | 5.1 | 63.6 | 17.7 | 39.5 | 19382 | 69 |

Compound F

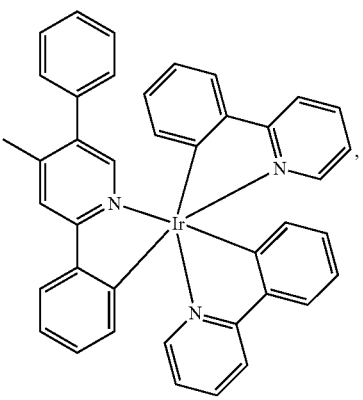

-continued

Compound G

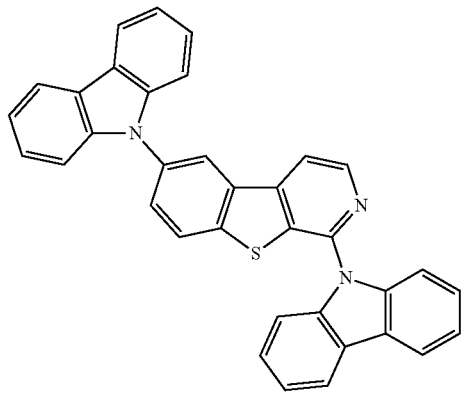

Compound H

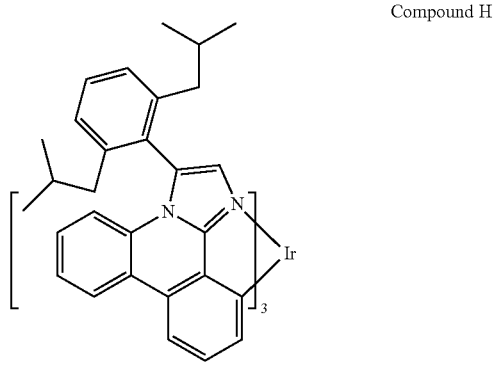

The only difference between Device Example 1 and Device Comparative Examples 1 and 2 is the host. At 1000 cd/m², Device Example 1 with Compound 1 as the host has an efficiency of 23.3% whereas Device Comparative Example 1 has an efficiency of 20.3% and Device Comparative Example 2 has an efficiency of 20.7%. Compound 1 as the host is shown to be superior to commonly used high performance hosts for blue phosphorescence OLED hosts such as Compound C and D. The increase in efficiency is presumably due to the increase of solid state triplet energy of the host in the EML because tetraphenylene acts as a sterically cumbersome block which reduces π stacking between host-host molecules and host-dopant molecules, particularly when the tetraphenylene compound has a low symmetry. The increase in efficiency can also be seen in Device Example 2 with Compound 21 as the host. Although the triplet energy of Compound 21 is not as high as the triplet energy of Compound 1, it is unexpectedly very suitable as a blue phosphorescence OLED host. The efficiency reaches 21.9%, higher than the efficiency of Device Comparative Examples 1 and 2. The efficiency can be further enhanced when a secondary hole transport layer (Compound E) is inserted between the HTL1 and EML as demonstrated in Device Example 3. A very high efficiency of 25.1% which is achieved.

Compound 21 was also tested as a host with a green phosphorescent emitter (Compound F). Device Example 3 with Compound 21 as the host has an efficiency of 17.6%. On the other hand, using a standard green phosphorescence OLED host CBP, Device Comparative Example 3 has an efficiency of 17.7%. Although the two device perform similarly, the lifetimes are very different. Device Example 3 with Compound 21 as the host shows a much superior lifetime. LT80 (the time to reach 80% of its initial luminance Lo) at J=40 mA/cm² is 178 hours compared to 69 hours of Device Comparative Example 3 with CBP as the host. The improvement is ~200%.

The device data demonstrates that OLED with tetraphenylene compounds with low symmetry as hosts can achieve high efficiency and operation stability. In particular, due to the high triplet energy of the tetraphenylene, they are especially useful in blue and green phosphorescence OLEDs.

Synthesis of Compound 470

An example of the inventive compound, Compound 470

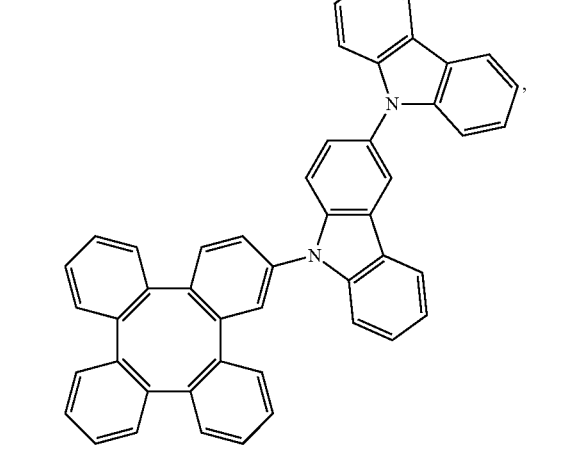

was synthesized as follows.

Synthesis of 4,4,5,5-tetramethyl-2-(tetraphenylen-2-yl)-1,3,2-dioxaborolane

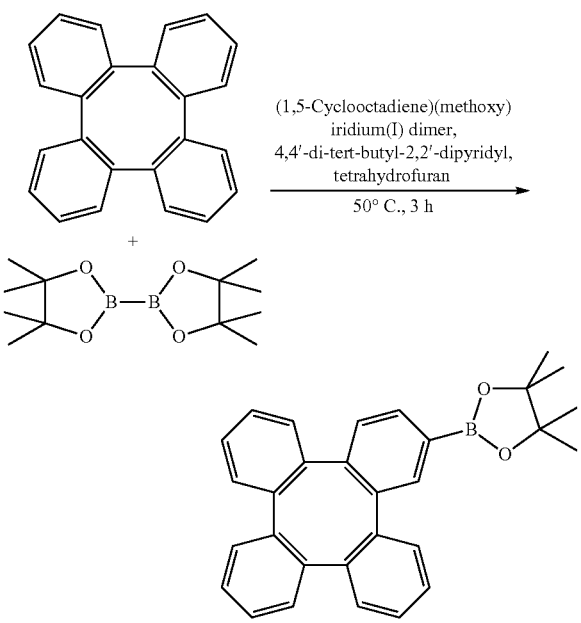

Tetraphenylene (24.3 g, 80.0 mmol), bis(pinacolato)diboron (16.3 g, 64.0 mmol), 4,4'-di-tert-butyl-2,2'-dipyridyl (1.3 g, 4.8 mmol), (1,5-Cyclooctadiene)(methoxy)iridium(I) dimer (1.6 g, 2.4 mmol) and anhydrous tetrahydrofuran (1000 mL) was mixed at room temperature. The reaction mixture was bubbled with nitrogen for 15 min. The resultant mixture was warmed at 50° C. for 3 h. The crude was filtered through a silica pad and MgSO₄ and washed with 35% DCM/hex (containing 0.5% triethylamine). The solvent was removed in vacuo and the residue was purified by flash chromatography using 25% DCM/hexane (containing 0.5% triethylamine). The solvent was removed in vacuo and the residue was re-crystallized by using acetonitrile to afford 4,4,5,5-tetramethyl-2-(tetraphenylen-2-yl)-1,3,2-dioxaborolane (14.7 g, 42% yield with respect to tetraphenylene) as a white solid.

Synthesis of 2-Bromotetraphenylene

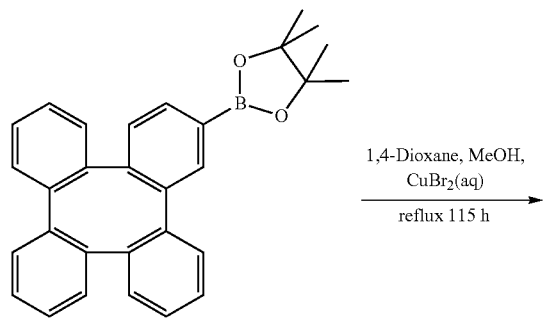

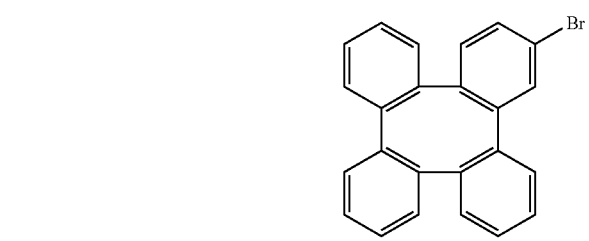

4,4,5,5-Tetramethyl-2-(tetraphenylen-2-yl)-1,3,2-dioxaborolane (11.1 g, 25.8 mmol), dioxane (250 mL), MeOH (80 mL) and CuBr₂(aq) (35.0 g, 150 mmol, 250 mL H₂O) were mixed at room temperature. The reaction mixture was bubbled with nitrogen for 15 min. The resultant mixture was refluxed for 115 h. The reaction mixture was extracted by DCM. And the extract was filtered through a silica pad and MgSO₄. The solvent was removed in vacuo. The residue was purified by flash chromatography using 10% DCM/hexane to afford 2-bromotetraphenylene (9.7 g, 98% yield) as a white solid.

Synthesis of Compound 470

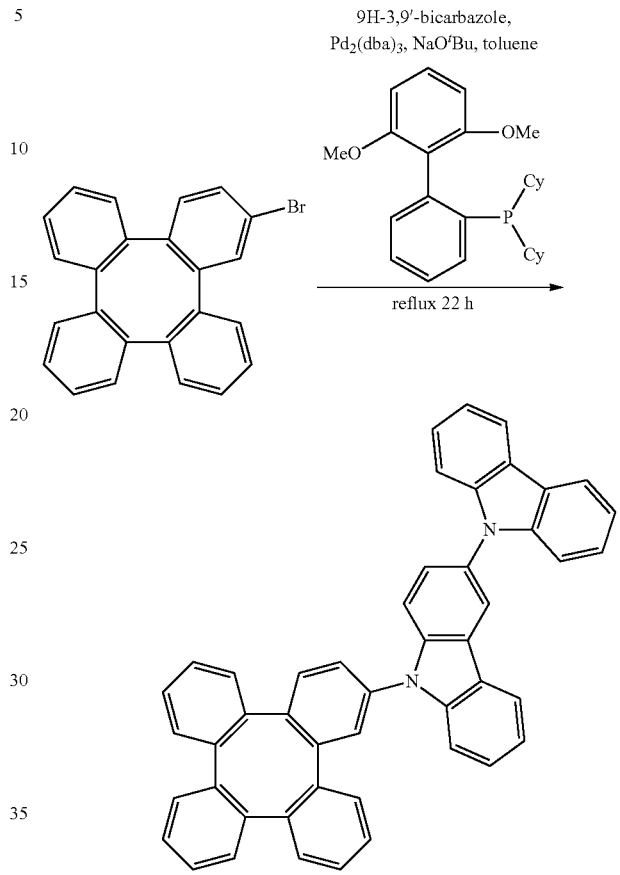

2-Bromotetraphenylene (5.3 g, 14.0 mmol), 9H-3,9'-bicarbazole (7.0 g, 21.0 mmol), Pd₂(dba)₃ (1.9 g, 2.1 mmol), 2-dicyclohexylphosphino-2',6'-dimethoxybiphenyl (3.5 g, 8.4 mmol), sodium tert-butoxide (2.7 g, 28.0 mmol) were added. The reaction mixture was bubbled with nitrogen for 15 min. and refluxed for 22 h. The crude was filtered through a silica pad and MgSO₄ and washed with 50% DCM/hexane. The solvent was removed in vacuo and the residue was purified by flash chromatography using 20% DCM/hexane to afford Compound 470 (8.0 g, 90% yield) as a white solid.

Experiment 2

In the second OLED experiment, device examples 4 and 5 were fabricated by high vacuum (<10⁻⁷ Torr) thermal evaporation. The anode electrode is ~800 Å of indium tin oxide (ITO). The cathode consisted of 10 Å of LiF followed by 1,000 Å of Al. All devices were encapsulated with a glass lid sealed with an epoxy resin in a nitrogen glove box (<1 ppm of H₂O and O₂) and a moisture getter was incorporated inside the package.

The organic stack of the Device Example 4 in Table 3 consists of sequentially, from the ITO surface, 100 Å of LG101 (purchased from LG Chem, Korea) as the hole injection layer (HIL), 250 Å of Compound A the hole transporting layer (HTL), 300 Å of Compound 470 doped with 20% of the emitter Compound B as the emissive layer (EML), 50 Å of Compound C as ETL2 and 300 Å of Alq₃ as ETL1. Device Example 5 was fabricated in the same way except the emitter in Device Example 5 was Compound H instead of Compound B.

TABLE 3

Summary of data from EXPERIMENT 2

| | | 1931 CIE | | $Em_{max}$ | At 1,000 cd/m² | | | | At 20 mA/cm² | |
| | | | | | Voltage | LE | EQE | PE | $L_0$ | $LT_{80\%}$ |
| Device | Host | x | y | [nm] | [V] | [cd/A] | [%] | [lm/W] | [cd/m²] | [h] |
|---|---|---|---|---|---|---|---|---|---|---|
| Example 4 | Cmpd 470 | 0.170 | 0.374 | 474 | 5.1 | 50.4 | 22.9 | 30.8 | 8118 | 40 |
| Example 5 | Cmpd 470 | 0.147 | 0.225 | 462 | 5.0 | 18.5 | 11.5 | 11.7 | 3374 | 8 |

The data in Table 3 shows that Compound 470 can be an excellent host in terms of device efficiency and lifetime. Device Example 4 shows that Compound 470 can host Compound B (sky blue emitter) with excellent external quantum efficiency of 22.9% and $LT_{80\%}$ of 40 hrs at J=20 mA/cm². Device Example 5 shows that Compound 470 can host Compound D (deep blue emitter) with decent external quantum efficiency of 11.5% and $LT_{80\%}$ of 8 hrs at J=20 mA/cm². The excellent efficiency may be due to the higher triplet energy of Compound 470. In addition, the non-planarity of the tetraphenylene ring may decrease molecular packing in the solid state and decrease the solid state triplet and improve mixing of the dopant in the host:dopant matrix.

We claim:

1. A compound having a formula:

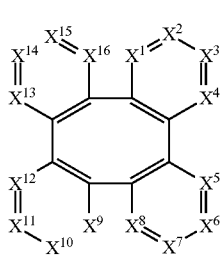

Formula 2 wherein $X^1$-$X^{16}$ are each independently selected from the group consisting of CR and N;
wherein each R is independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carboxylic acids, nitrile, isonitrile, sulfanyl, phosphino, and combinations thereof;
wherein at least one of $X^1$-$X^{16}$ is CR;
wherein R is

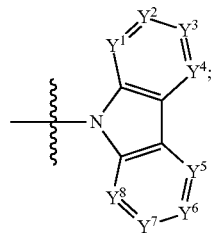

wherein $Y^1$-$Y^8$ are independently selected from the group consisting of CR' and N;
wherein each R' is independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, aza-carbazolyl, silyl, halosilyl, alkenyl, cycloalkenyl, heteroalkenyl, alkynyl, aryl, heteroaryl, acyl, carboxylic acids, nitrile, isonitrile, sulfanyl, phosphino, and combinations thereof;
wherein at least one of $Y^1$ to $Y^8$ is CR' whose R' is a group containing at least one carbazole or aza-carbazole.

2. The compound of claim 1, wherein each of $X^1$ to $X^{16}$ is CR.

3. The compound of claim 1, wherein at least one of $X^1$ to $X^{16}$ is N.

4. The compound of claim 1, wherein each of $Y^1$ to $Y^8$ is CR'.

5. The compound of claim 1, wherein at least one of $Y^1$ to $Y^8$ is N.

6. The compound of claim 1, wherein at least one of $Y^1$ to $Y^8$ is CR' whose R' is a group containing at least one carbazole.

7. The compound of claim 1, wherein at least one of $Y^1$ to $Y^8$ is CR' whose R' is a group containing at least one aza-carbazole.

8. The compound of claim 1, wherein the compound of Formula 2 is selected from the group consisting of:

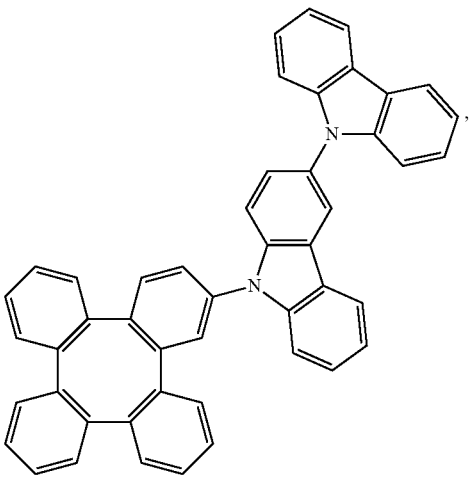

Compound 470

Compound 471
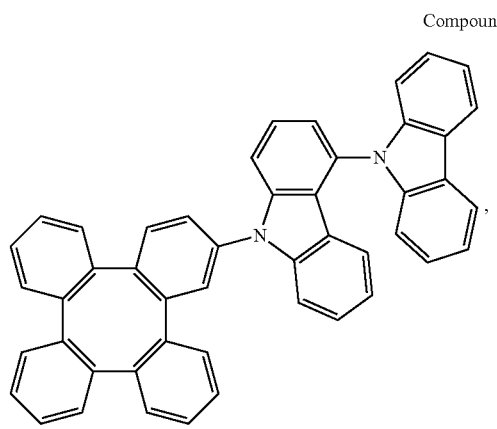
Compound 472
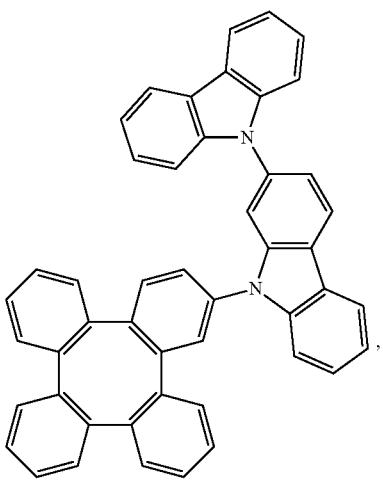
Compound 473
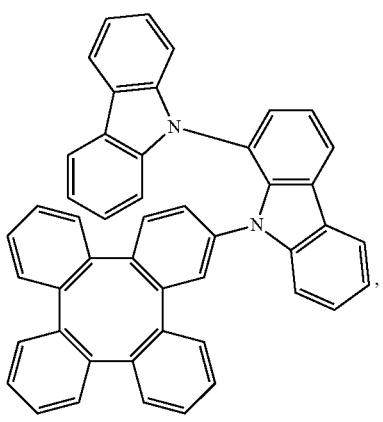
Compound 474
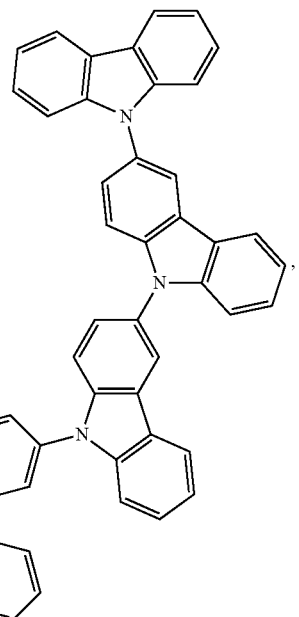
Compound 475
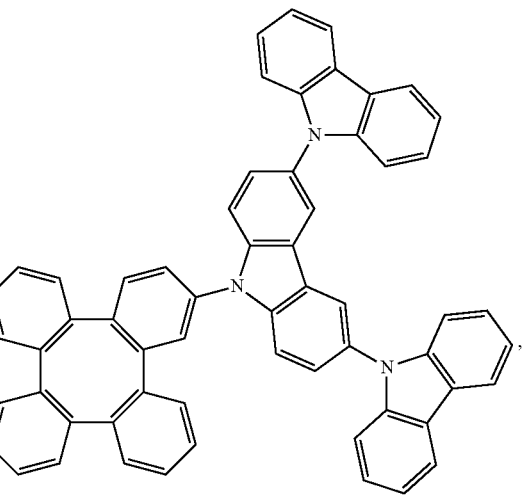
Compound 476
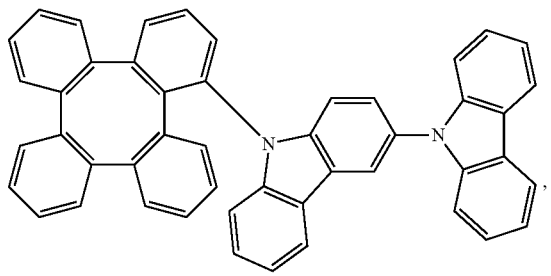

Compound 477
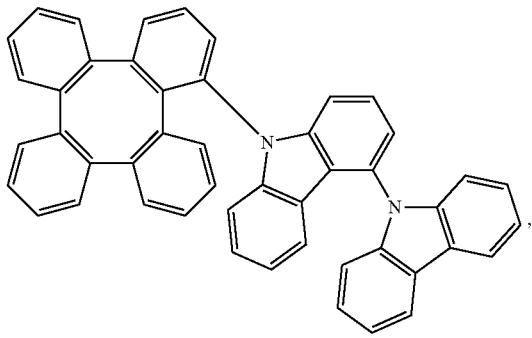
Compound 478
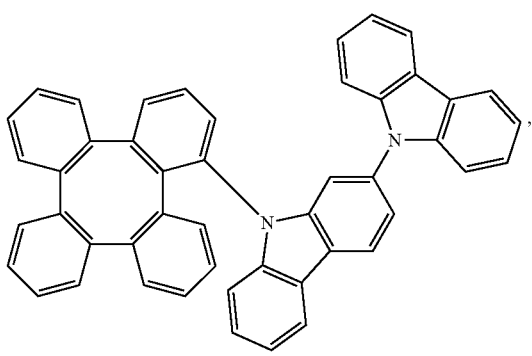
Compound 479
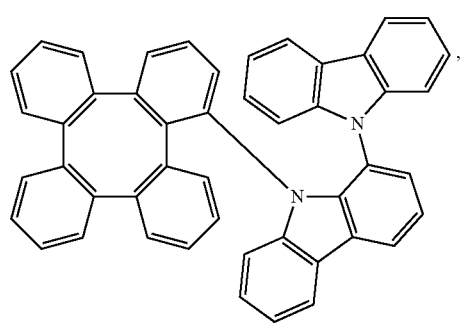
Compound 480
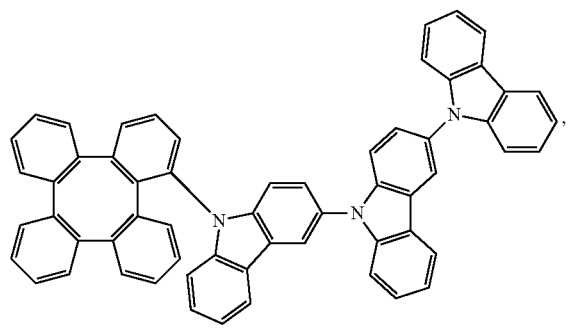
Compound 481
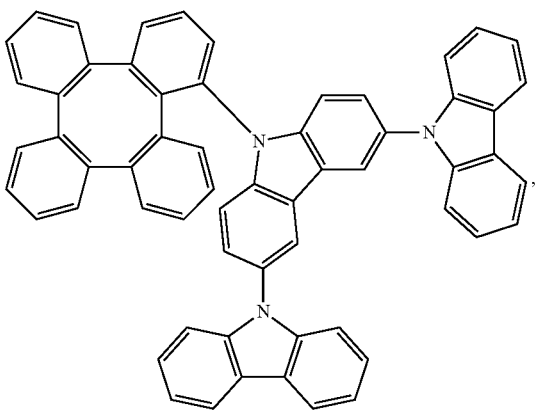
Compound 482
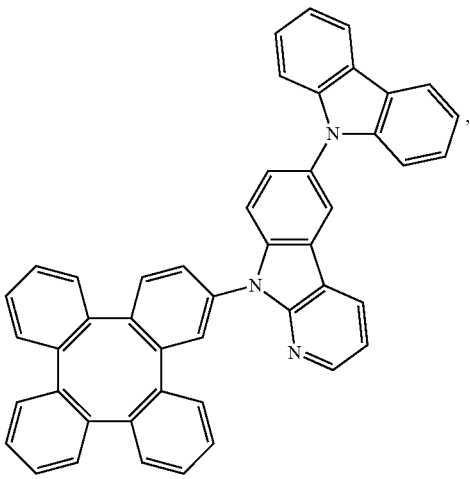
Compound 483
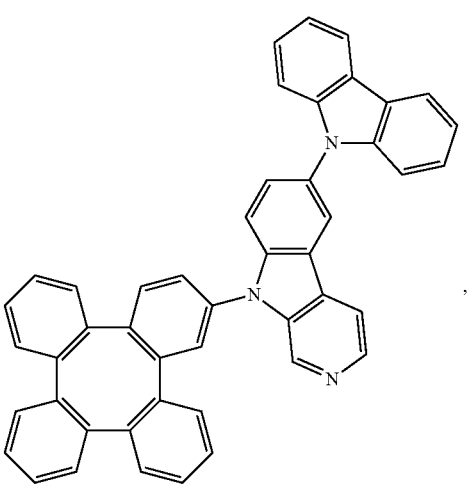

-continued
Compound 484
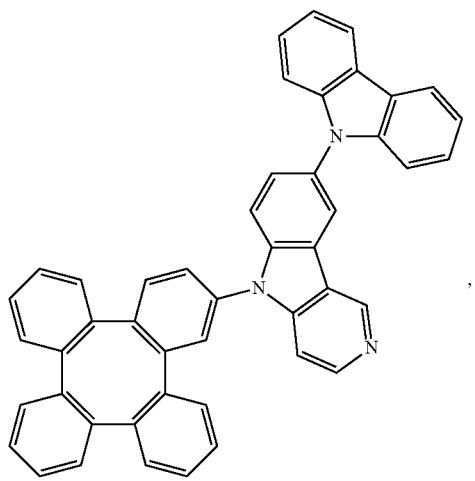
Compound 485
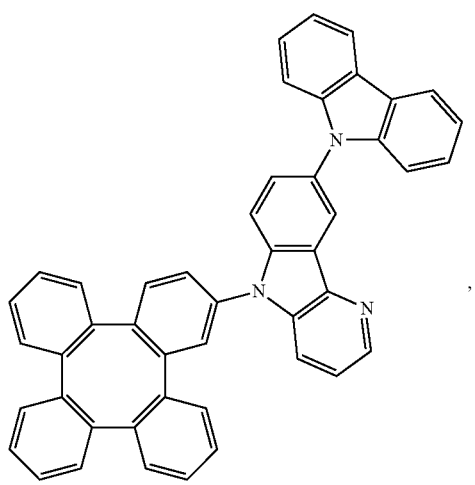
Compound 486
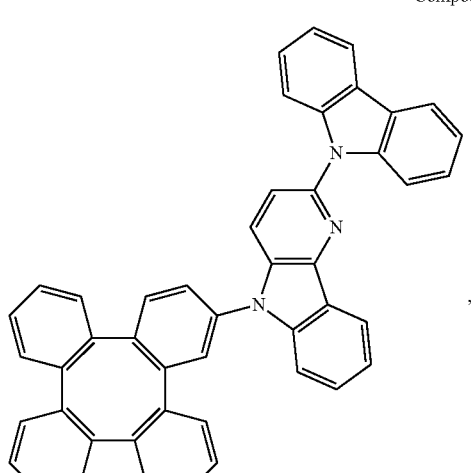
-continued
Compound 487
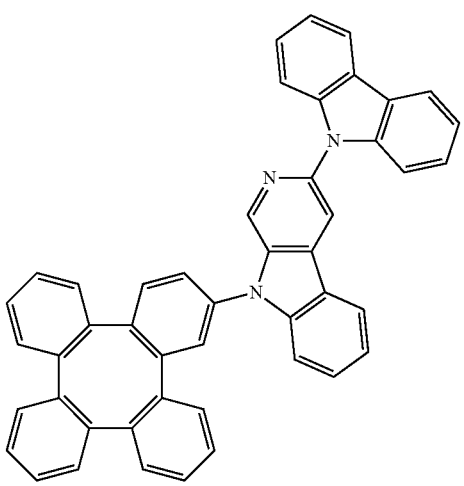
Compound 488
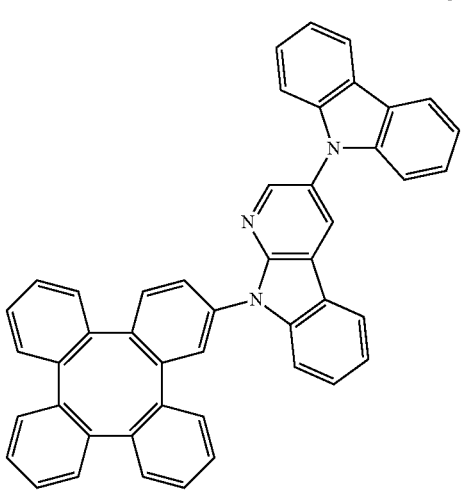
Compound 489
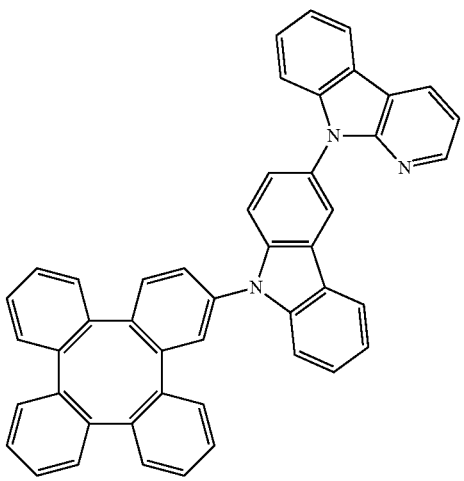

Compound 490
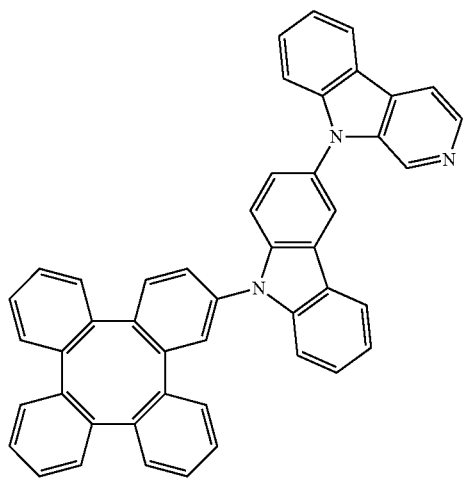
Compound 491
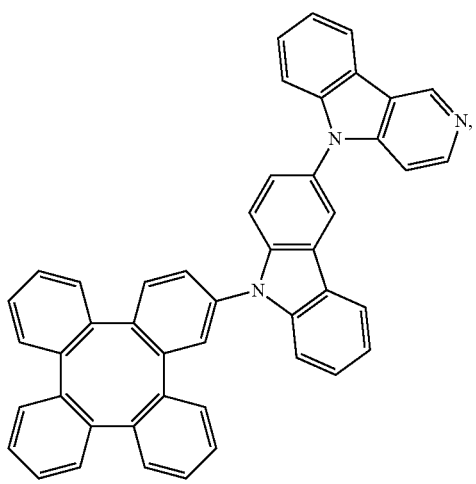
Compound 492
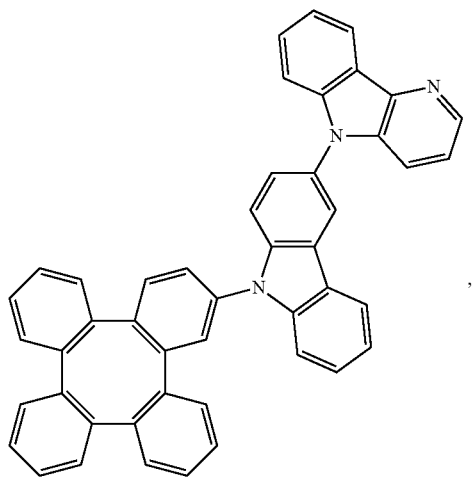 [SMILES: c1ccc2c(c1)-c1ccccc1-c1ccc(-n3c4ccccc4c4cc(-n5c6ccccc6c6ccccc65)ccc43)cc1-c1ccccc1-2]
Compound 493
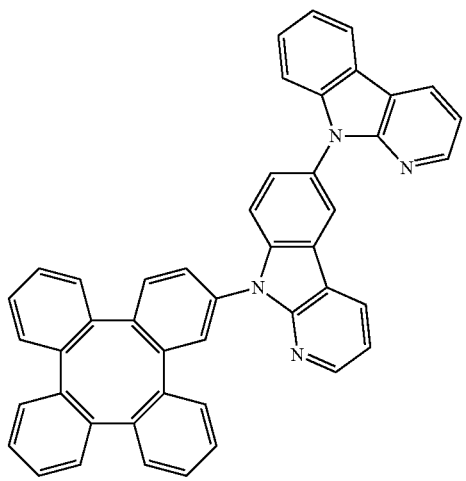
Compound 494
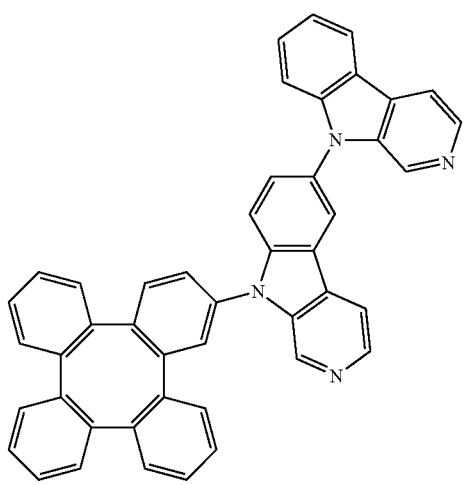
Compound 495
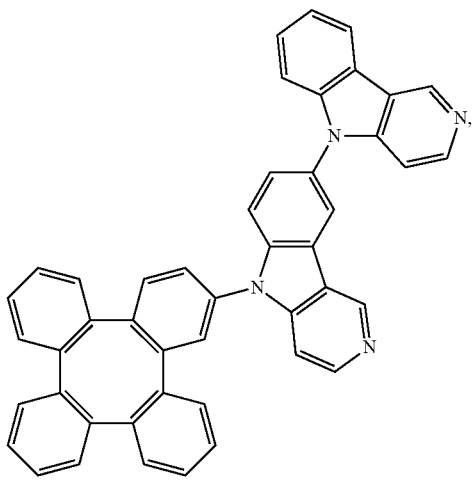

265
-continued
Compound 496
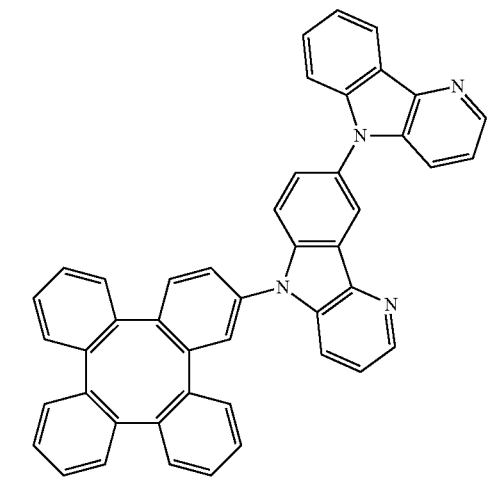
Compound 497
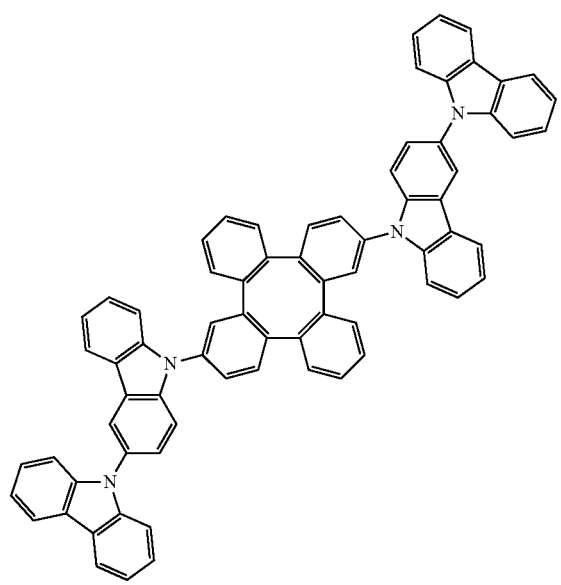
Compound 498
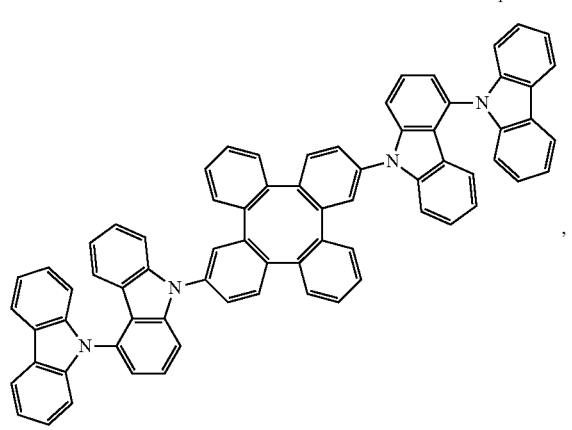
266
-continued
Compound 499
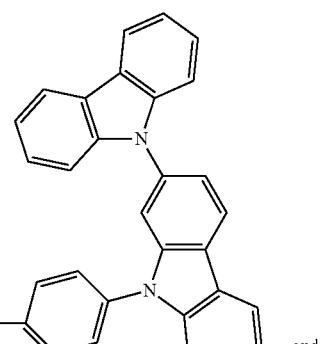
, and
Compound 500
9. A device comprising one or more organic light emitting devices, at least one of the organic light emitting devices comprising:
    an anode;
    a cathode; and
    an organic layer, disposed between the anode and the cathode, comprising a compound having a formula:

Formula 2

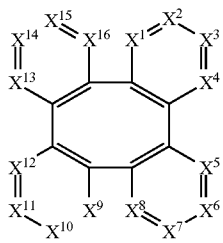

wherein $X^1$-$X^{16}$ are each independently selected from the group consisting of CR and N;

wherein each R is independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carboxylic acids, nitrile, isonitrile, sulfanyl, phosphino, and combinations thereof;

wherein at least one of $X^1$-$X^{16}$ is CR;
wherein R is

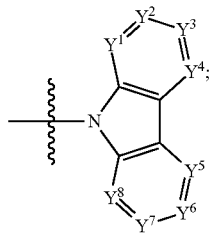

wherein $Y^1$-$Y^8$;

wherein $Y^1$ to $Y^8$ are independently selected from the group consisting of CR' and N;

wherein each R' is independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, aza-carbazolyl, silyl, halosilyl, alkenyl, cycloalkenyl, heteroalkenyl, alkynyl, aryl, heteroaryl, acyl, carboxylic acids, nitrile, isonitrile, sulfanyl, phosphino, and combinations thereof;

wherein at least one of $Y^1$ to $Y^8$ is CR'; and
wherein R' is a group containing at least one carbazole or aza-carbazole.

10. The device of claim 9, wherein each of $X^1$-$X^{16}$ is CR.

11. The device of claim 9, wherein at least one of $X^1$-$X^{16}$ is N.

12. The device of claim 9, wherein the compound of Formula 2 is selected from the group consisting of:

Compound 470

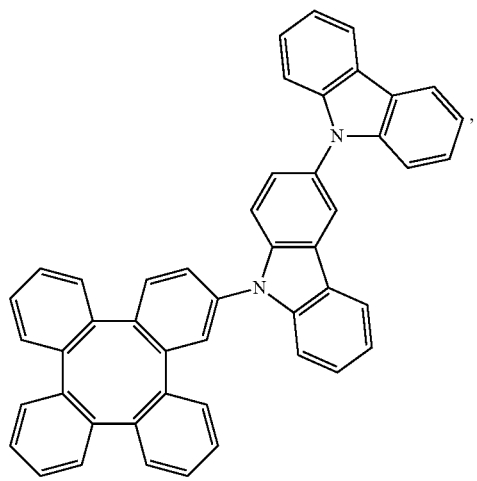

Compound 471

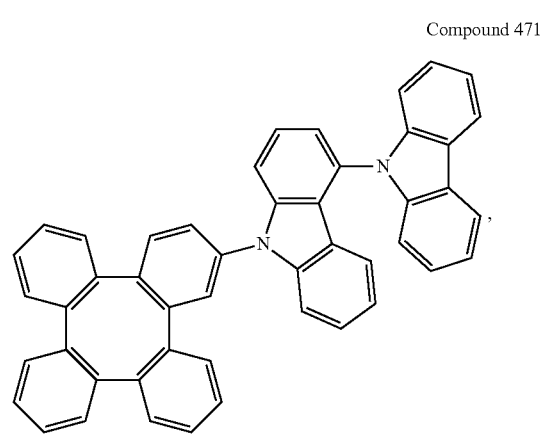

Compound 472

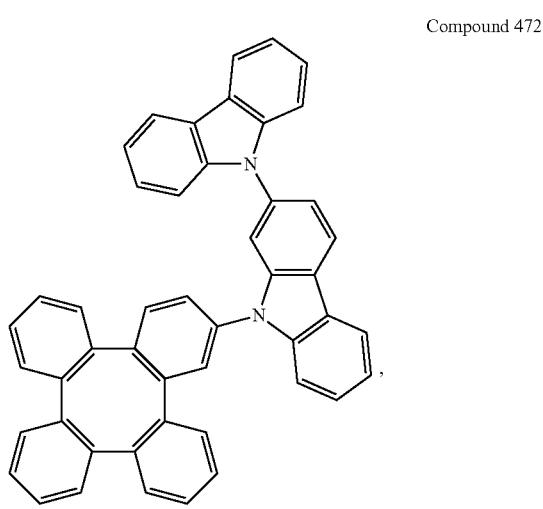

Compound 473
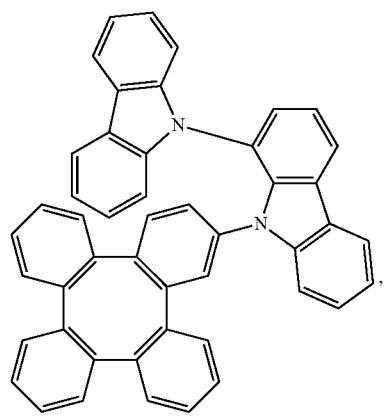
Compound 476
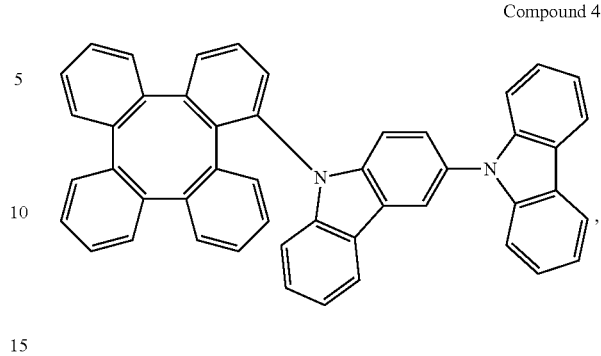
Compound 474
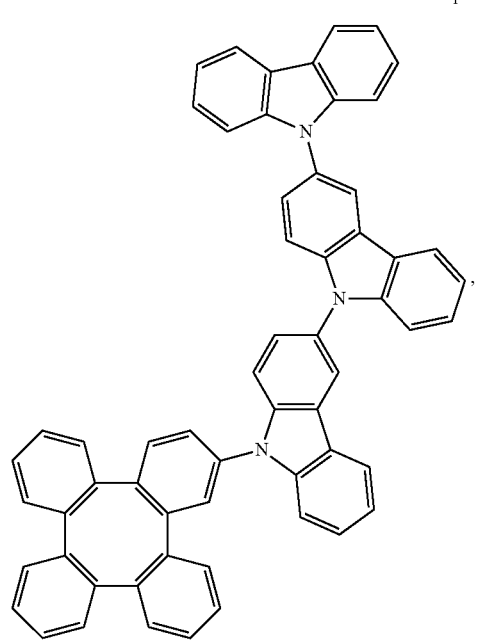
Compound 477
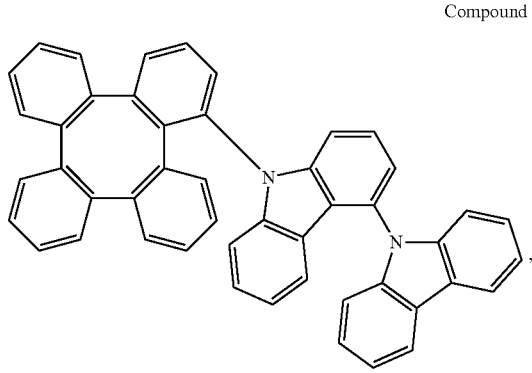
Compound 478
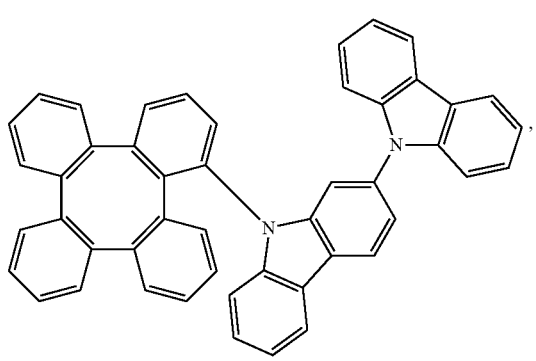
Compound 475
Compound 479
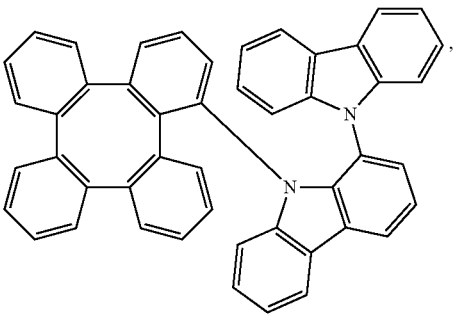

Compound 480
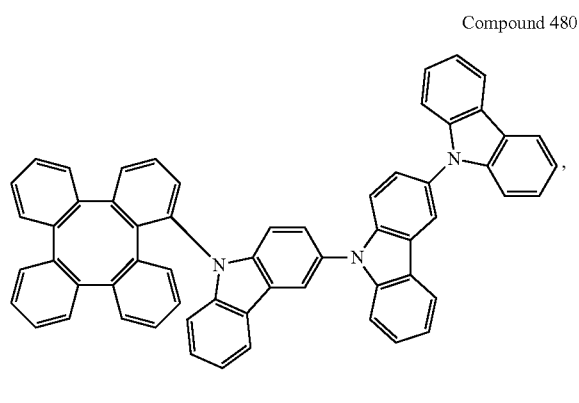
Compound 481
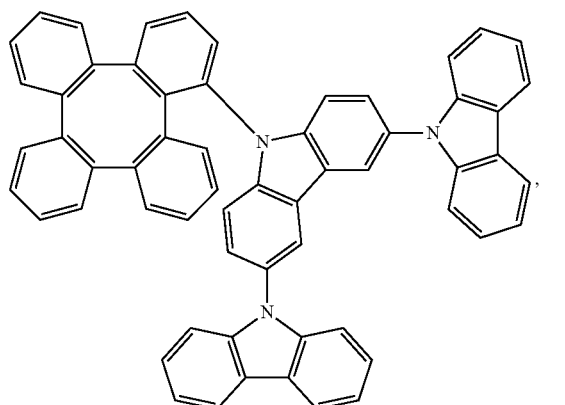
Compound 482
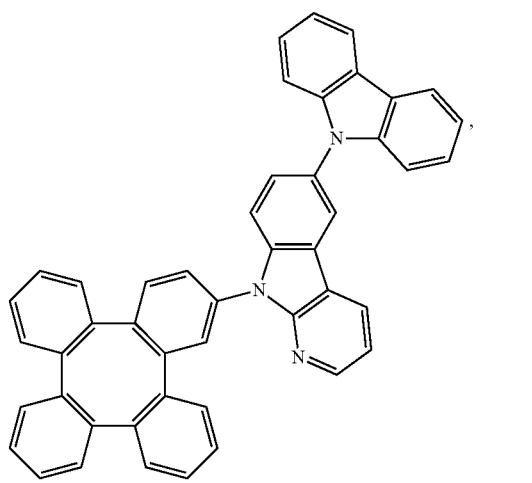
Compound 483
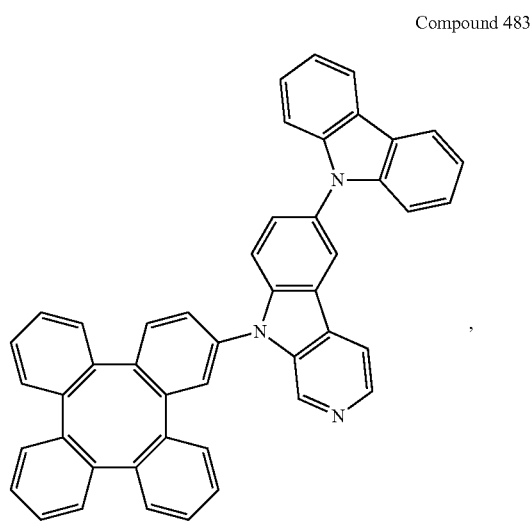
Compound 484
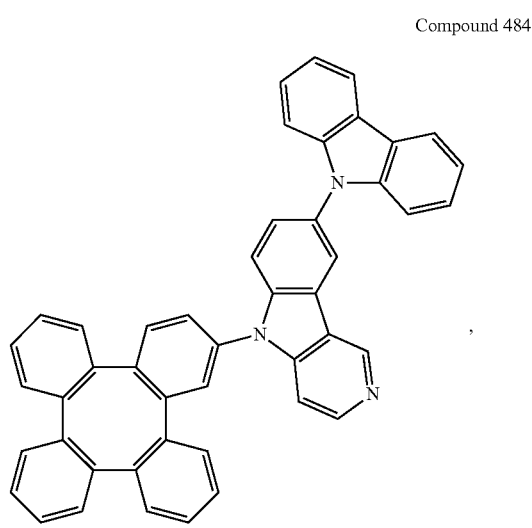
Compound 485
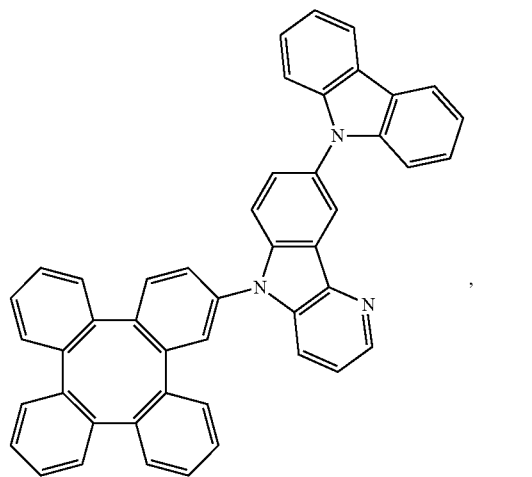

Compound 486
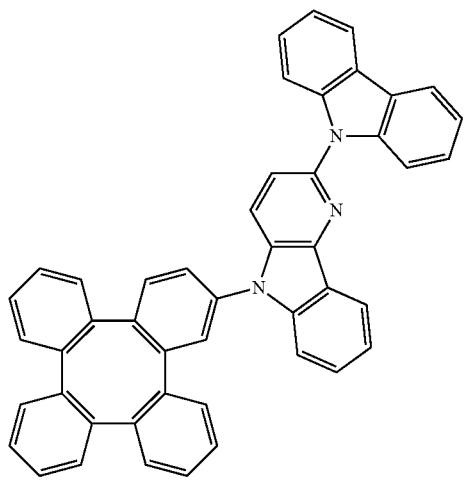
Compound 487
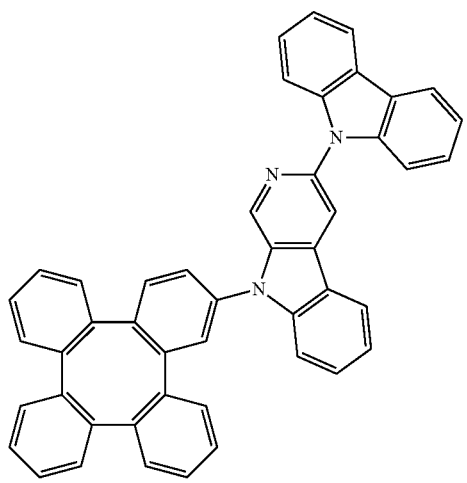
Compound 488
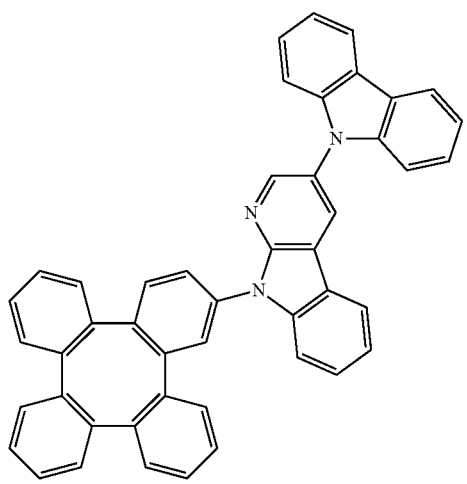
Compound 489
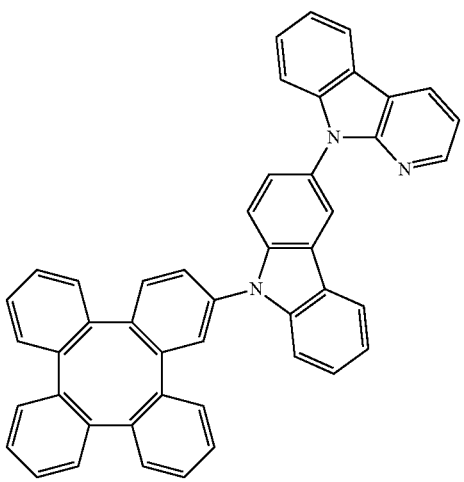
Compound 490
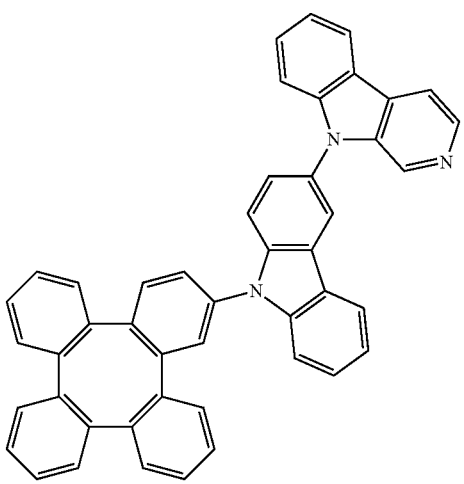
Compound 491
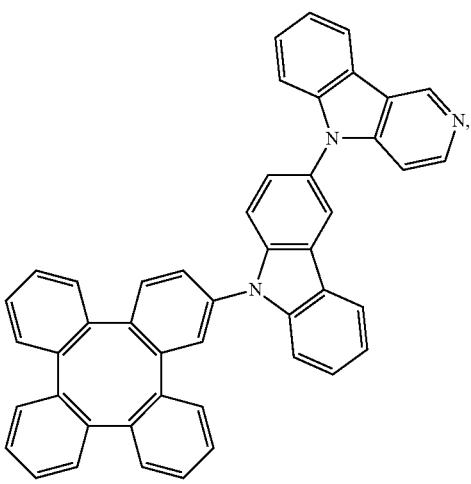

Compound 492
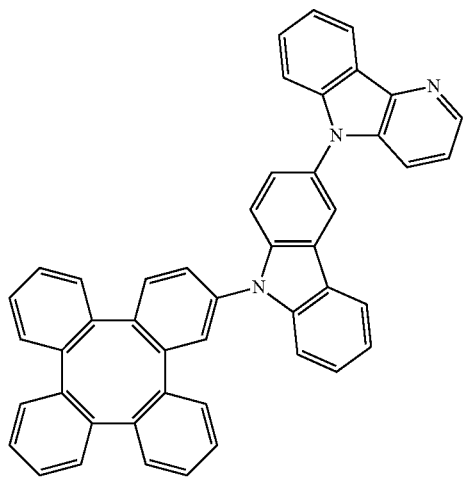
Compound 493
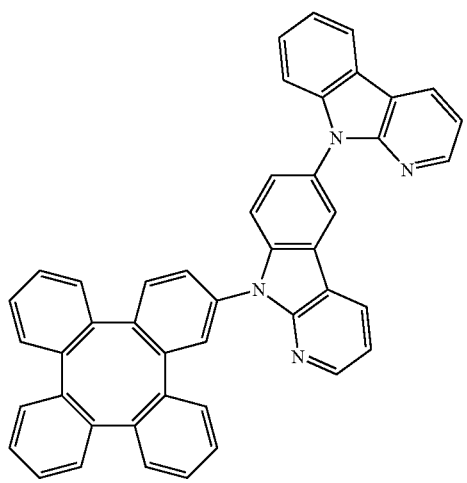
Compound 494
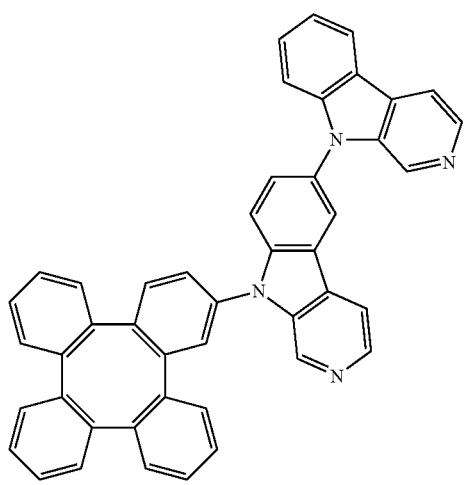
Compound 495
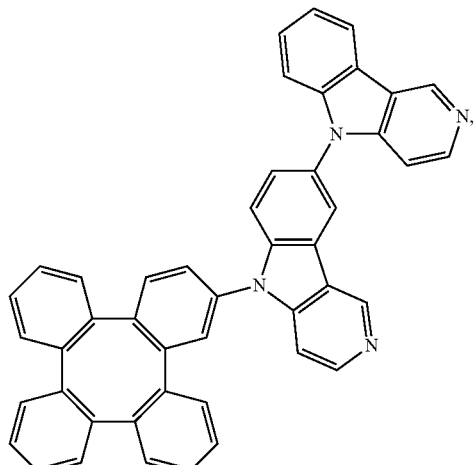
Compound 496
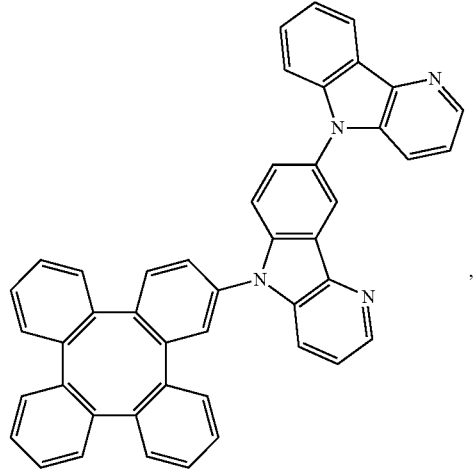
Compound 497
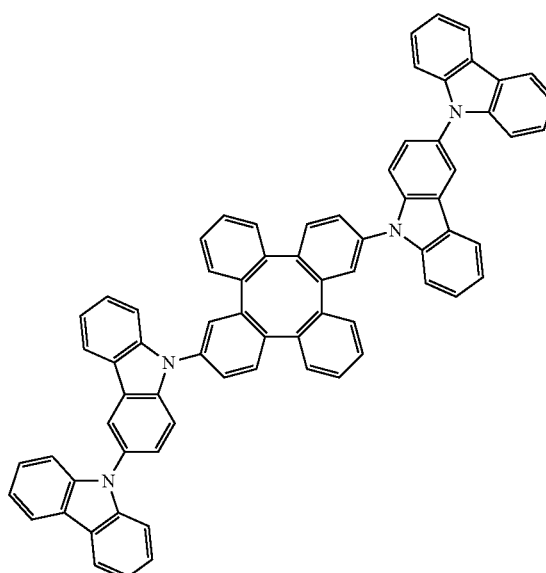

-continued

Compound 498
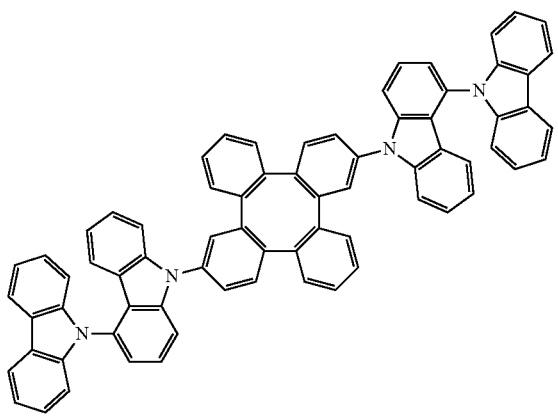

Compound 499
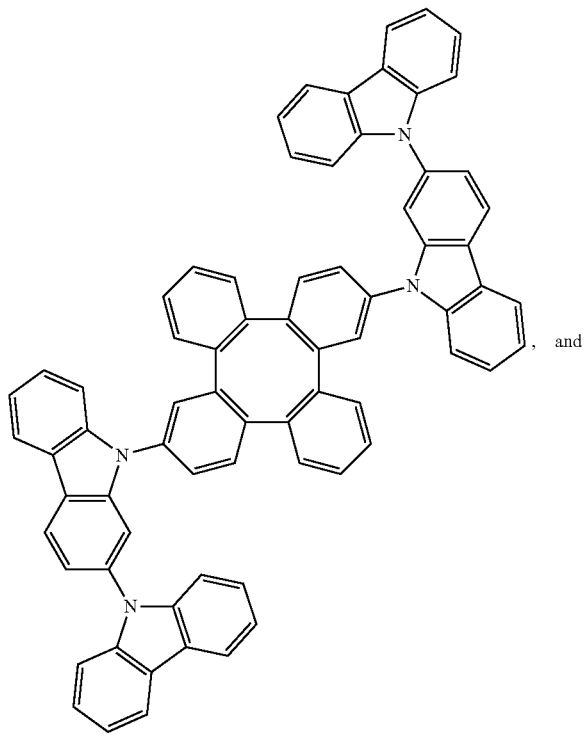
, and

-continued

Compound 500
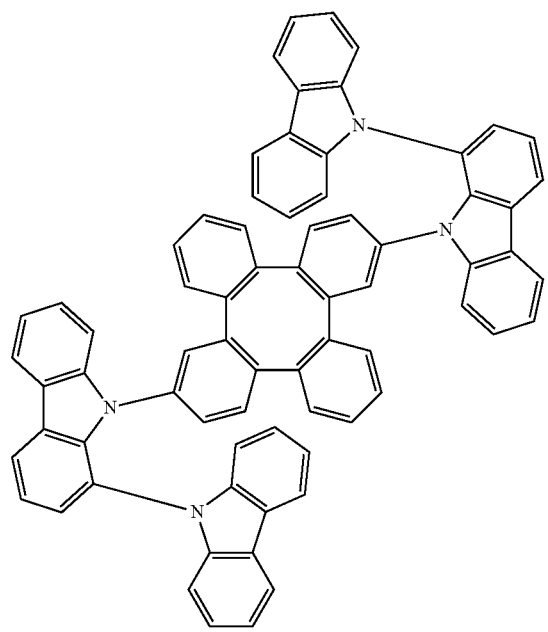

13. The device of claim 9, wherein the organic layer is an emissive layer and the compound is a host.

14. The device of claim 9, wherein the organic layer further comprises a phosphorescent emissive dopant.

15. The device of claim 9, wherein the organic layer further comprises a phosphorescent emissive dopant, wherein the phosphorescent emissive dopant is a transition metal complex having at least one ligand or part of the ligand if the ligand is more than bidentate, selected from the group consisting of:

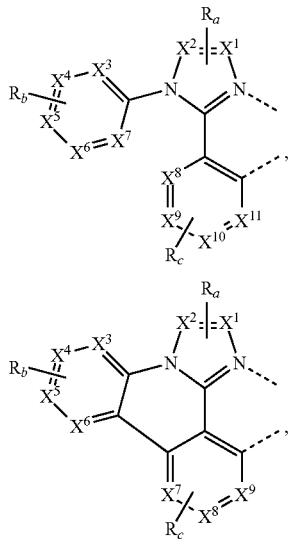

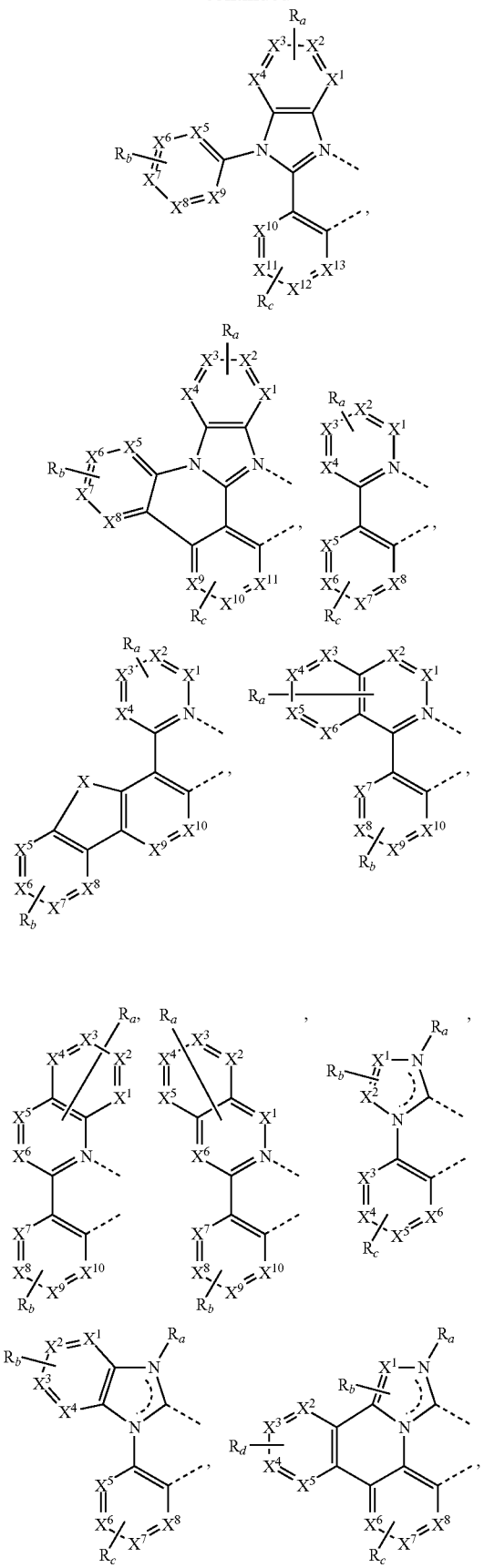

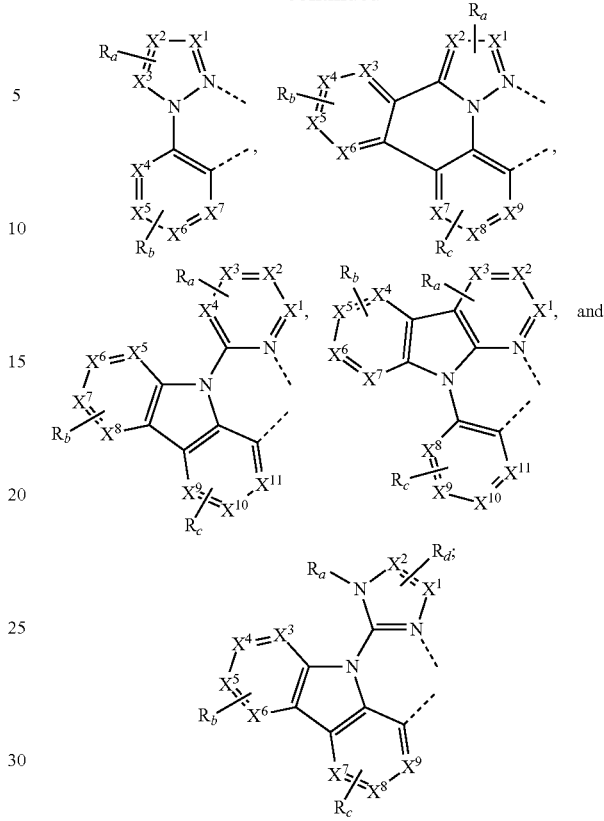

wherein each $X^1$ to $X^{13}$ are independently selected from the group consisting of carbon and nitrogen;

wherein X is selected from the group consisting of BR', NR', PR', O, S, Se, C=O, S=O, SO$_2$, CR'R'', SiR'R'', and GeR'R'';

wherein R' and R'' are optionally fused or joined to form a ring;

wherein each $R_a$, $R_b$, $R_c$, and $R_d$ may represent from mono substitution to the possible maximum number of substitution, or no substitution;

wherein R', R'', $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxylic acids, nitrile, isonitrile, sulfanyl, phosphino, and combinations thereof; and wherein any two adjacent substituents of $R_a$, $R_b$, $R_c$, and $R_d$ are optionally fused or joined to form a ring or form a multi-dentate ligand.

16. The device of claim 9, wherein the organic layer is a charge carrier blocking layer and the compound having Formula I is a charge carrier blocking material in the organic layer.

17. The device of claim 9, wherein the organic layer is a charge carrier transporting layer and the compound having Formula 2 is a charge carrier transporting material in the organic layer.

18. The device of claim 9, wherein the device is selected from the group consisting of a consumer product, an electronic component module, and a lighting panel.

19. A formulation comprising the compound in claim 1.

* * * * *